United States Patent
Joseph et al.

(10) Patent No.: US 9,617,602 B2
(45) Date of Patent: Apr. 11, 2017

(54) METHODS AND COMPOSITIONS FOR DETERMINING RESISTANCE TO ANDROGEN RECEPTOR THERAPY

(71) Applicant: Aragon Pharmaceuticals, Inc., San Diego, CA (US)

(72) Inventors: James David Joseph, San Diego, CA (US); Jeffrey H Hager, San Diego, CA (US); John Lee Sensintaffar, Poway, CA (US); Nhin Lu, San Diego, CA (US); Jing Qian, San Diego, CA (US); Nicholas D Smith, San Diego, CA (US)

(73) Assignee: ARAGON PHARMACEUTICALS, INC., San Diego, CA (US)

( * ) Notice: Subject to any disclaimer, the term of this patent is extended or adjusted under 35 U.S.C. 154(b) by 0 days.

(21) Appl. No.: 14/417,515

(22) PCT Filed: Jul. 26, 2013

(86) PCT No.: PCT/US2013/052395
§ 371 (c)(1),
(2) Date: Jan. 26, 2015

(87) PCT Pub. No.: WO2014/018926
PCT Pub. Date: Jan. 30, 2014

(65) Prior Publication Data
US 2015/0252426 A1    Sep. 10, 2015

Related U.S. Application Data

(60) Provisional application No. 61/676,842, filed on Jul. 27, 2012, provisional application No. 61/783,763, filed on Mar. 14, 2013, provisional application No. 61/829,123, filed on May 30, 2013.

(51) Int. Cl.
| | |
|---|---|
| *C12Q 1/68* | (2006.01) |
| *C07K 14/72* | (2006.01) |
| *A61K 45/06* | (2006.01) |
| *A61K 31/4166* | (2006.01) |
| *A61K 31/4439* | (2006.01) |
| *A61K 38/09* | (2006.01) |
| *C07K 16/28* | (2006.01) |
| *G01N 33/574* | (2006.01) |

(52) U.S. Cl.
CPC ........ *C12Q 1/6886* (2013.01); *A61K 31/4166* (2013.01); *A61K 31/4439* (2013.01); *A61K 38/09* (2013.01); *A61K 45/06* (2013.01); *C07K 14/721* (2013.01); *C07K 16/2869* (2013.01); *C12Q 1/6897* (2013.01); *G01N 33/57492* (2013.01); *C12Q 2600/106* (2013.01); *C12Q 2600/156* (2013.01); *C12Q 2600/158* (2013.01); *C12Q 2600/16* (2013.01); *G01N 2333/723* (2013.01)

(58) Field of Classification Search
None
See application file for complete search history.

(56) References Cited

U.S. PATENT DOCUMENTS

2003/0167999 A1* 9/2003 Donner ................ C07K 14/721
117/2
2010/0068802 A1    3/2010 Qiu et al.

FOREIGN PATENT DOCUMENTS

EP           2065474 A1    6/2009
WO    WO 01/66599 A1    9/2001

OTHER PUBLICATIONS

P10275.2 (Androgen Receptor UniprotKB Accession, GI:113830, priority to Jan. 11, 2011, 65 pages).*
Tran et al. (2009) Development of a Second-Generation Antiandrogen for Treatment of Advanced Prostate Cancer. Science, 324:787-790.*
Taplin et al. (1999) Selection for Androgen Receptor Mutations in Prostate Cancers Treated with Androgen Antagonist. Cancer Research, 59:2511-2515.*
Fisherbrand Cat. No. 05-541 (Fisherbrand Polypropylene Microtube Storage Racks, Fisher Catalog 2004/2005, p. 1241).*
Heemers et al. (2011) Identification of a Clinically Relevant Androgen-Dependent Gene Signature in Prostate Cancer. Cancer Research, 71(5):1978-1988.*

(Continued)

*Primary Examiner* — Neil P Hammell
(74) *Attorney, Agent, or Firm* — Baker & Hostetler LLP

(57) ABSTRACT

Described herein are modified androgen receptor polypeptides that are resistant to inhibition by an androgen receptor inhibitor. Described herein are compositions, combinations, and kits containing the modified androgen receptor polypeptides and methods of using the modified androgen receptor polypeptides. Also described herein are methods of using the modified androgen receptor polypeptides as screening agents for the identification and design of third-generation androgen receptor modulators. Also described herein are third-generation androgen receptor modulators that inhibit the activity of the modified androgen receptor polypeptides. Also described are pharmaceutical compositions and medicaments that include the compounds described herein, as well as methods of using such androgen receptor modulators, alone and in combination with other compounds, for treating diseases or conditions, including cancers, such as castration resistant prostate cancers, that are mediated or dependent upon androgen receptors.

31 Claims, 18 Drawing Sheets

(56) References Cited

OTHER PUBLICATIONS

Affymetrix HG U133 Plus 2.0 Annotation file (filtered excerpt, accessed from: <http://www.affymetrix.com/Auth/analysis/downloads/na26/ivt/HG-U133_Plus_2.na26.annot.csv.zip>, accessed on: Mar. 18, 2013, 1 page).*
Altschul et al., "Basic Local Alignment Search Tool", 1990, J. Mol. Biol., 215, 403-410.
Altschul et al., "Methods for assessing the statistical significance of molecular sequence features by using general scoring schemes", 1990, Proc. Natl. Acad. Sci., 87, 2264-2268.
Altschul et al., "Applications and statistics for multiple high-scoring segments in molecular sequences", 1993, Proc. Natl. Acad. Sci., 90, 5873-5877.
Altschul et al., "Gapped BLAST and PSI_BLAST: a new generation of protein database search programs", 1997, Nucleic Acids Res., 25, 3389-3402.
Balbas et al.; "Overcoming Mutation-Based Resistance to Antiandrogens with Rational Drug Design", ELife, 2013, vol. 2, 1-21.
Batzer et al., "Enhanced evolutionary PCR using oligonucleotides with inosine at the 3'- terminus", 1991, Nucleic Acid Res., 19, 5081.
Bohl et al., "Crystal Structure of the T877A Human Androgen Receptor Ligand-Binding Domain Complexed to Cyproterone Acetate Provides Insight for Ligand-Induced Conformational Changes and Structure-Based Drug Design", Journal of Biological Chemistry, Mar. 2007, vol. 282 No. 18, 13648-13655.
Carell et al., "A Solution-Phase Screening Procedure for the Isolation of Active Compunds from a Library of Molecules", 1994, Agnew. Chem. Int. Ed. Engl.,33, 2061-2064.
Cassol et al., "Rapid DNA fingerprinting to control for specimen errors in HIV testing by the polymerase chain reaction", 1992, Cell. Probes, 6, 327-331.
Chan et al., "Circulating tumor-derived nucleic acids in cancer patients: potential applications as tumor markers", 2007, Br J Cancer, 96(5), 681-685.
Chen et al., "Molecular determinants of resistance to antiandrogen therapy", 2004, Nature Medicine, 10, 33-39.
Clegg et al., "ARN-509: A Novel Antiandrogen for Prostate Cancer Treatment", 2012, Cancer Research, 72, 1494-1503.
Cong et al., "A large deletion/insertion-induced frameshift mutation of the androgen receptor gene in a family with a familial complete androgen insensitivity syndrome", 2012, Gene, 500(2), 220-223.
Cull et al., "Screening for receptor ligands using large libraries of peptides linked to the C terminus of the lac repressor", 1992, Proc. Natl. Acad. Sci., 89, 1865-1869.
Cwirla et al., "Peptides on phage: A vast library of peptides for identifying ligands", 1990, Proc. Natl. Acad. Sci., 87, 6378-6382.
Devlin et al., "Random Peptide Libraries: A Source of Specific Protein Binding Molecules", 1990, Science, 249, 404-406.
Diehl et al., "Circulating mutant DNA to assess tumor dynamics", 2008, Nat Med., 14(9), 985-990.
Dressman et al., "Transforming single DNA molecules into fluorescent magnetic particles for detection and enumeration of genetic variations", 2003, PNAS, 100, 8817-8822.
Ellwood-Yen et al., "Transgenic Mouse Model for Rapid Pharmacodynamic Evaluation of Antiandrogens", 2006, Cancer Res., 66, 10513-10516.
Felici, "Selection of Antibody Ligands from a Large Library of Oligopeptides Expresses on a Multivalent Exposition Vector", 1991, J. Mol. Biol., 222, 301-310.
Fodor, "Multiplexed biochemical assays with biological chips", Aug. 1993, Nature, 364, 555-556.
Gallop et al., "Applications of Combinatorial Technologies to Drug Discovery. 1. Background and Peptide Combinatorial Libraries", 1994, J. Med. Chem., 37, 1233-1251.
Ghali et al., "The Use of Androgen Receptor Amino/Carboxyl-Terminal Interaction Assays to Investigate Androgen Receptor Gene Mutations in Subjects with Varying Degrees of Androgen Insensitivity", 2003, J Clin Endocrinol Metab., 88(5), 2185-2193.
Gottlieb et al., "The Androgen Receptor Gene Mutations Database: 2012 Update", 2012, Human Mutation, 33(5), 887-894.
Grasso et al., "The mutational landscape of lethal castration-resistant prostate cancer", 2012, Nature, 7406, 239-243.
Guo et al., "Regulation of androgen receptor activity by tyrosine phosphorylation", 2006, Cancer Cell, 309-319.
Haapala et al., "Androgen Receptor Alterations in Prostate Cancer Relapsed During a Combined Androgen Blockade by Orchiectomy and Bicalutamide", Laboratory Investigation, Nature Publishing Group, US and CA Academy of Pathology, Dec. 2001, vol. 81 No. 12, 1647-1651.
Hacia et al., "Mutational Analysis using oligonucleotide microarrays", 1999, J Med Genet., 36(10), 730-736.
Hay et al., "The Impact of Point Mutations in the Human Androgen Receptor: Classification of Mutations on the Basis of Transcriptional Activity", Mar. 2012, PLoS One, 7(3), e32514.
Henikoff et al., "Amino acid substitution matrices from protein blocks", 1992, Proc. Natl. Acad. Sci., 89, 10915-10919.
Higgins et al., "Detection of Tumor PIK3CA Status in Metastatic Breast Cancer Using Peripheral Blood", 2012, Clin Cancer Res., 18, 3462-3469.
Hodgson et al., "Making Monoclonals in Microbes", Bio/Technology, 1991, 9, 421-425.
Horwell et al., "'Targeted' Molecular diversity: design and development of non-peptide antagonists for cholecystokinin and tachykinin receptors", 1996, Immunopharmacology, 33, 68-72.
Houghten, "The Use of Synthetic Peptide Combinatorial Libraries for the Identification of Bioactive Peptides", 1992, Biotechniques, 13, 412-421.
Hsu et al., "Androgen Receptor (AR) $NH_2$- and COOH-Terminal Interactions Result in the Differential Influences on the AR-Mediated Transactivation and Cell Growth", Feb. 2005; Mol. Endocrinol., 19(2), 350-361.
Huo et al., "Quantitative Structure-Activity Relationship Analysis of a Novel Series of Chemicals Antagonizing WT and MT AR", Chemometrics and Intelligent Laboratory Systems, Jul. 2011, vol. 107, No. 2, 283-289.
Joseph et al., "A Clinically Relevant Androgen Receptor Mutation Confers Resistance to Second-Generation Antiandrogens Enzalutamide and ARN-509", Cancer Discovery, Jun. 2013, vol. 3 No. 9,1020-1029.
Batzer et al., "Enhanced evolutionary PCR using oligonucleotides with inosine at the 3'—terminus", 1991, Nucleic Acid Res., 19, 5081.
Koochekpour, "Androgen receptor signaling and mutations in prostate cancer", 2010, Asian J. Androl., 12(5), 639-657.
Korpal et al.,"An F876L Mutation in Androgen Receptor Confers Genetic and Phenotypic Resistance to MDV3100 (Enzalutamide)", Cancer Discovery, Jul. 2013, vol. 3 No. 9, 1030-1043.
Lam, "A new type of synthetic peptide library for identifying ligand-binding activity", 1991, Nature, 354, 82-84.
Lam, "Application of combinatorial library methods in cancer research and drug discovery", Anticancer Drug Des., 1997, 12, 145-167.
Li et al., "BEAMing up for detection and quantification of rare sequence variants", 2006, Nat Methods, 3(2), 95-97.
Li et al., "BEAMing: single-molecule PCR on microparticles in water-in-oil emulsions", 2006, Nat Methods, 3(7), 551-559.
Malmberg et al., "Using Molecular Beacons to Detect Single-Nucleotide Polymorphisms with Real-Time PCR", 2001, Methods, 25, 463-471.
Michaels et al., "A robust method for detecting single-nucleotide changes as polymorphic markers by PCR", 1998, The Plant Journal, 14(3):381-385.
Ning et al., "Novel Androgen Receptor Gene Mutation in Patient With Complete Androgen Insensitivity Syndrome", 2012, Urology, 80(1), 216-218.
Ohtsuka et al., "An Alternative Approach to Deoxyoligonucleotides as Hybridizaion Probes by Insertion of Deoxyinosine at Ambiguous Codon Positions", 1985, J. Biol. Chem, 260, 2605-2608.

(56) References Cited

OTHER PUBLICATIONS

Queen et al., "A humanized antibody that binds to the interleukin 2 receptor", Proc. Natl. Acad., 86, 1989, 10029-10032.
Robins, "Androgen receptor gene polymorphisms and alterations in prostate cancer: Of humanized mice and men", 2012, Mol. Cell Endocrinol, 352(1), 26-33.
Roche et al., "A Consensus DNA-Binding Site for the Androgen Receptor", 1992, Mol. Endocrinol., 6(12), 2229-2235.
Rossolini et al., "Use of deoxyinosine-containing primers vs. degenerate primers for polymerase chain reaction based on ambiguous sequence information", 1994, Mol. Cell. Probes, 8, 91-98.
Smith et al., "Searching for Peptide Ligands with an Epitope L:ibrary", 1990, Science, 249, 386-390.
Demura et al., "Establishment and Characterization of Monoclonal Antibody Against Androgen Receptor", Journal of Steroid Biochemistry, Nov. 1989, vol. 33 No. 5, 845-851.
Tran et al., "Development of a Second-Generation Antiandrogen for Treatment of Advanced Prostate Cancer", 2009, Science, 324(5928), 787-790.
Waltering et al., "Androgen receptor (AR) aberrations in castration-resistant prostate cancer", 2012, Mol. Cell Endocrinol., 360, 38-43.

\* cited by examiner

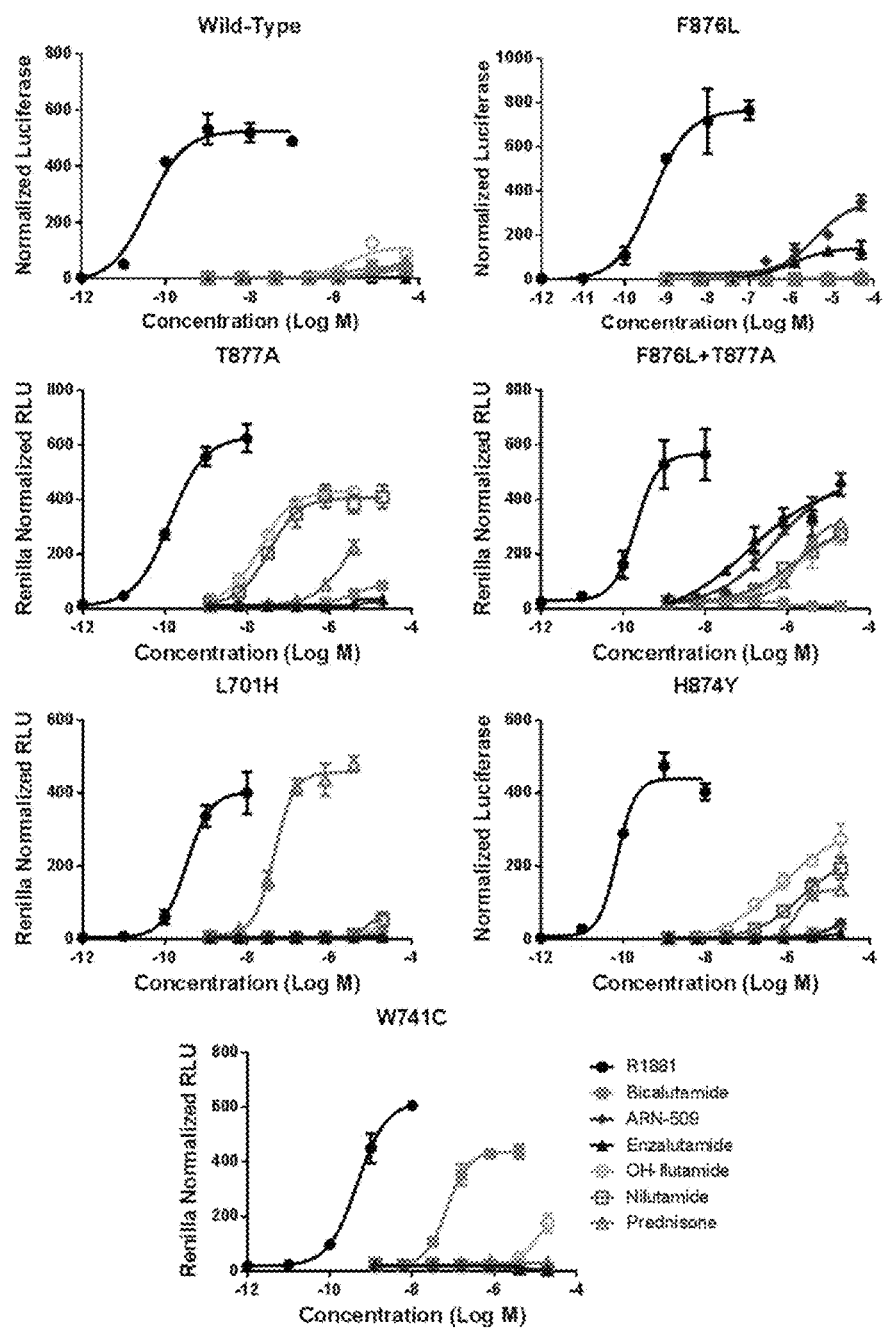

A

B

A

B

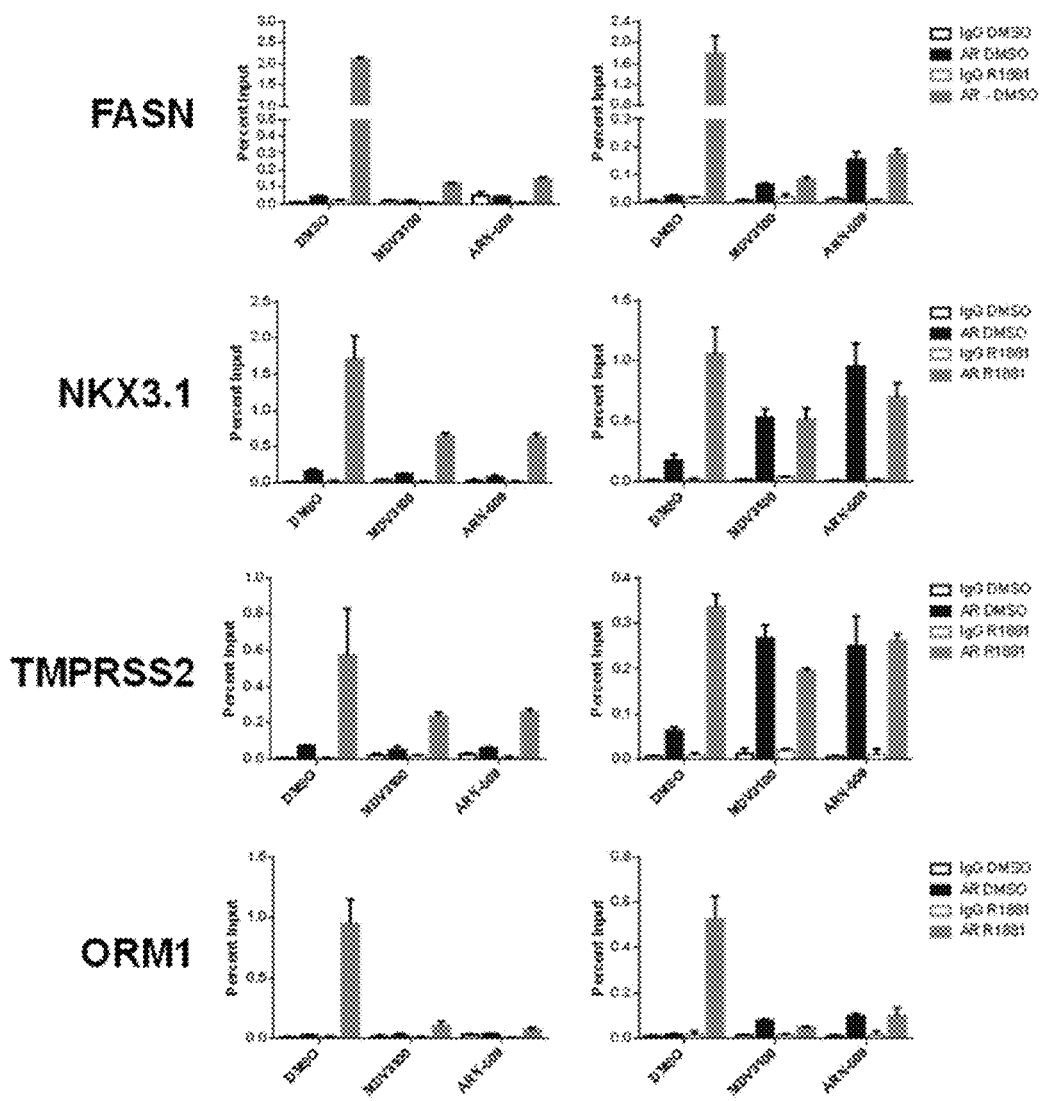

Dose Escalation Cohorts: Metastatic CRPC

Expansion Cohort: Non-Metastatic CRPC

Expansion Cohorts: Metastatic CRPC

* switched to 240 mg after 2 cycles

SEQUENCE LISTING

```
<160> NUMBER OF SEQ ID NOS: 63

<210> SEQ ID NO 1
<211> LENGTH: 919
<212> TYPE: PRT
<213> ORGANISM: Homo sapiens

<400> SEQUENCE: 1

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Leu Gln Gln Gln Gln Gln Gln Gln
    50                  55                  60

Gln Gln Gln Gln Gln Gln Gln Gln Gln Gln Gln Gln Gln Gln Glu Thr
65                  70                  75                  80

Ser Pro Arg Gln Gln Gln Gln Gln Gly Glu Asp Gly Ser Pro Gln
                85                  90                  95

Ala His Arg Arg Gly Pro Thr Gly Tyr Leu Val Leu Asp Glu Glu Gln
            100                 105                 110

Gln Pro Ser Gln Pro Gln Ser Ala Leu Glu Cys His Pro Glu Arg Gly
        115                 120                 125

Cys Val Pro Glu Pro Gly Ala Ala Val Ala Ala Ser Lys Gly Leu Pro
    130                 135                 140

Gln Gln Leu Pro Ala Pro Pro Asp Glu Asp Asp Ser Ala Ala Pro Ser
145                 150                 155                 160

Thr Leu Ser Leu Leu Gly Pro Thr Phe Pro Gly Leu Ser Ser Cys Ser
                165                 170                 175

Ala Asp Leu Lys Asp Ile Leu Ser Glu Ala Ser Thr Met Gln Leu Leu
            180                 185                 190

Gln Gln Gln Gln Gln Glu Ala Val Ser Glu Gly Ser Ser Ser Gly Arg
        195                 200                 205

Ala Arg Glu Ala Ser Gly Ala Pro Thr Ser Ser Lys Asp Asn Tyr Leu
    210                 215                 220
```

```
Gly Gly Thr Ser Thr Ile Ser Asp Asn Ala Lys Glu Leu Cys Lys Ala
225                 230                 235                 240

Val Ser Val Ser Met Gly Leu Gly Val Glu Ala Leu Glu His Leu Ser
            245                 250                 255

Pro Gly Glu Gln Leu Arg Gly Asp Cys Met Tyr Ala Pro Leu Leu Gly
        260                 265                 270

Val Pro Pro Ala Val Arg Pro Thr Pro Cys Ala Pro Leu Ala Glu Cys
    275                 280                 285

Lys Gly Ser Leu Leu Asp Asp Ser Ala Gly Lys Ser Thr Glu Asp Thr
290                 295                 300

Ala Glu Tyr Ser Pro Phe Lys Gly Gly Tyr Thr Lys Gly Leu Glu Gly
305                 310                 315                 320

Glu Ser Leu Gly Cys Ser Gly Ser Ala Ala Gly Ser Ser Gly Thr
                325                 330                 335

Leu Glu Leu Pro Ser Thr Leu Ser Leu Tyr Lys Ser Gly Ala Leu Asp
            340                 345                 350

Glu Ala Ala Ala Tyr Gln Ser Arg Asp Tyr Tyr Asn Phe Pro Leu Ala
        355                 360                 365

Leu Ala Gly Pro Pro Pro Pro Pro Pro His Pro His Ala Arg
370                 375                 380

Ile Lys Leu Glu Asn Pro Leu Asp Tyr Gly Ser Ala Trp Ala Ala
385                 390                 395                 400

Ala Ala Gln Cys Arg Tyr Gly Asp Leu Ala Ser Leu His Gly Ala Gly
        405                 410                 415

Ala Ala Gly Pro Gly Ser Gly Ser Pro Ser Ala Ala Ser Ser Ser
        420                 425                 430

Trp His Thr Leu Phe Thr Ala Glu Glu Gly Gln Leu Tyr Gly Pro Cys
        435                 440                 445

Gly Gly Gly Gly Gly Gly Gly Gly Gly Gly Gly Gly Gly
450                 455                 460

Gly Gly Gly Gly Gly Gly Gly Glu Ala Gly Ala Val Ala Pro Tyr
465                 470                 475                 480

Gly Tyr Thr Arg Pro Pro Gln Gly Leu Ala Gly Gln Glu Ser Asp Phe
            485                 490                 495

Thr Ala Pro Asp Val Trp Tyr Pro Gly Gly Met Val Ser Arg Val Pro
        500                 505                 510

Tyr Pro Ser Pro Thr Cys Val Lys Ser Glu Met Gly Pro Trp Met Asp
        515                 520                 525

Ser Tyr Ser Gly Pro Tyr Gly Asp Met Arg Leu Glu Thr Ala Arg Asp
530                 535                 540

His Val Leu Pro Ile Asp Tyr Tyr Phe Pro Pro Gln Lys Thr Cys Leu
545                 550                 555                 560

Ile Cys Gly Asp Glu Ala Ser Gly Cys His Tyr Gly Ala Leu Thr Cys
            565                 570                 575

Gly Ser Cys Lys Val Phe Phe Lys Arg Ala Ala Glu Gly Lys Gln Lys
        580                 585                 590

Tyr Leu Cys Ala Ser Arg Asn Asp Cys Thr Ile Asp Lys Phe Arg Arg
        595                 600                 605

Lys Asn Cys Pro Ser Cys Arg Leu Arg Lys Cys Tyr Glu Ala Gly Met
        610                 615                 620

Thr Leu Gly Ala Arg Lys Leu Lys Lys Leu Gly Asn Leu Lys Leu Gln
625                 630                 635                 640
```

-continued

Glu Glu Gly Glu Ala Ser Ser Thr Thr Ser Pro Thr Glu Thr Thr
            645                 650                 655

Gln Lys Leu Thr Val Ser His Ile Glu Gly Tyr Glu Cys Gln Pro Ile
        660                 665                 670

Phe Leu Asn Val Leu Glu Ala Ile Glu Pro Gly Val Val Cys Ala Gly
        675                 680                 685

His Asp Asn Asn Gln Pro Asp Ser Phe Ala Ala Leu Leu Ser Ser Leu
    690                 695                 700

Asn Glu Leu Gly Glu Arg Gln Leu Val His Val Lys Trp Ala Lys
705                 710                 715                 720

Ala Leu Pro Gly Phe Arg Asn Leu His Val Asp Asp Gln Met Ala Val
                725                 730                 735

Ile Gln Tyr Ser Trp Met Gly Leu Met Val Phe Ala Met Gly Trp Arg
                740                 745                 750

Ser Phe Thr Asn Val Asn Ser Arg Met Leu Tyr Phe Ala Pro Asp Leu
        755                 760                 765

Val Phe Asn Glu Tyr Arg Met His Lys Ser Arg Met Tyr Ser Gln Cys
        770                 775                 780

Val Arg Met Arg His Leu Ser Gln Glu Phe Gly Trp Leu Gln Ile Thr
785                 790                 795                 800

Pro Gln Glu Phe Leu Cys Met Lys Ala Leu Leu Leu Phe Ser Ile Ile
                805                 810                 815

Pro Val Asp Gly Leu Lys Asn Gln Lys Phe Phe Asp Glu Leu Arg Met
                820                 825                 830

Asn Tyr Ile Lys Glu Leu Asp Arg Ile Ile Ala Cys Lys Arg Lys Asn
        835                 840                 845

Pro Thr Ser Cys Ser Arg Arg Phe Tyr Gln Leu Thr Lys Leu Leu Asp
    850                 855                 860

Ser Val Gln Pro Ile Ala Arg Glu Leu His Gln Phe Thr Phe Asp Leu
865                 870                 875                 880

Leu Ile Lys Ser His Met Val Ser Val Asp Phe Pro Glu Met Met Ala
                885                 890                 895

Glu Ile Ile Ser Val Gln Val Pro Lys Ile Leu Ser Gly Lys Val Lys
                900                 905                 910

Pro Ile Tyr Phe His Thr Gln
        915

<210> SEQ ID NO 2
<211> LENGTH: 920
<212> TYPE: PRT
<213> ORGANISM: Homo sapiens

<400> SEQUENCE: 2

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Leu Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80

Glu Thr Ser Pro Arg Gln Gln Gln Gln Gln Gly Glu Asp Gly Ser
            85                  90                  95

```
Pro Gln Ala His Arg Arg Gly Pro Thr Gly Tyr Leu Val Leu Asp Glu
                100                 105                 110
Glu Gln Gln Pro Ser Gln Pro Gln Ser Ala Leu Glu Cys His Pro Glu
            115                 120                 125
Arg Gly Cys Val Pro Glu Pro Gly Ala Ala Val Ala Ala Ser Lys Gly
        130                 135                 140
Leu Pro Gln Gln Leu Pro Ala Pro Pro Asp Glu Asp Ser Ala Ala
145                 150                 155                 160
Pro Ser Thr Leu Ser Leu Leu Gly Pro Thr Phe Pro Gly Leu Ser Ser
                165                 170                 175
Cys Ser Ala Asp Leu Lys Asp Ile Leu Ser Glu Ala Ser Thr Met Gln
            180                 185                 190
Leu Leu Gln Gln Gln Gln Gln Glu Ala Val Ser Glu Gly Ser Ser Ser
        195                 200                 205
Gly Arg Ala Arg Glu Ala Ser Gly Ala Pro Thr Ser Ser Lys Asp Asn
    210                 215                 220
Tyr Leu Gly Gly Thr Ser Thr Ile Ser Asp Asn Ala Lys Glu Leu Cys
225                 230                 235                 240
Lys Ala Val Ser Val Ser Met Gly Leu Gly Val Glu Ala Leu Glu His
                245                 250                 255
Leu Ser Pro Gly Glu Gln Leu Arg Gly Asp Cys Met Tyr Ala Pro Leu
            260                 265                 270
Leu Gly Val Pro Pro Ala Val Arg Pro Thr Pro Cys Ala Pro Leu Ala
        275                 280                 285
Glu Cys Lys Gly Ser Leu Leu Asp Asp Ser Ala Gly Lys Ser Thr Glu
    290                 295                 300
Asp Thr Ala Glu Tyr Ser Pro Phe Lys Gly Gly Tyr Thr Lys Gly Leu
305                 310                 315                 320
Glu Gly Glu Ser Leu Gly Cys Ser Gly Ser Ala Ala Ala Gly Ser Ser
                325                 330                 335
Gly Thr Leu Glu Leu Pro Ser Thr Leu Ser Leu Tyr Lys Ser Gly Ala
            340                 345                 350
Leu Asp Glu Ala Ala Ala Tyr Gln Ser Arg Asp Tyr Tyr Asn Phe Pro
        355                 360                 365
Leu Ala Leu Ala Gly Pro Pro Pro Pro Pro Pro Pro His Pro His
    370                 375                 380
Ala Arg Ile Lys Leu Glu Asn Pro Leu Asp Tyr Gly Ser Ala Trp Ala
385                 390                 395                 400
Ala Ala Ala Ala Gln Cys Arg Tyr Gly Asp Leu Ala Ser Leu His Gly
                405                 410                 415
Ala Gly Ala Ala Gly Pro Gly Ser Gly Ser Pro Ser Ala Ala Ala Ser
            420                 425                 430
Ser Ser Trp His Thr Leu Phe Thr Ala Glu Glu Gly Gln Leu Tyr Gly
        435                 440                 445
Pro Cys Gly Gly Gly Gly Gly Gly Gly Gly Gly Gly Gly Gly Gly Gly
    450                 455                 460
Gly Gly Gly Gly Gly Gly Gly Gly Glu Ala Gly Ala Val Ala Pro
465                 470                 475                 480
Tyr Gly Tyr Thr Arg Pro Pro Gln Gly Leu Ala Gly Gln Glu Ser Asp
                485                 490                 495
Phe Thr Ala Pro Asp Val Trp Tyr Pro Gly Gly Met Val Ser Arg Val
            500                 505                 510
```

-continued

```
Pro Tyr Pro Ser Pro Thr Cys Val Lys Ser Glu Met Gly Pro Trp Met
        515                 520                 525
Asp Ser Tyr Ser Gly Pro Tyr Gly Asp Met Arg Leu Glu Thr Ala Arg
    530                 535                 540
Asp His Val Leu Pro Ile Asp Tyr Tyr Phe Pro Pro Gln Lys Thr Cys
545                 550                 555                 560
Leu Ile Cys Gly Asp Glu Ala Ser Gly Cys His Tyr Gly Ala Leu Thr
                565                 570                 575
Cys Gly Ser Cys Lys Val Phe Phe Lys Arg Ala Ala Glu Gly Lys Gln
            580                 585                 590
Lys Tyr Leu Cys Ala Ser Arg Asn Asp Cys Thr Ile Asp Lys Phe Arg
        595                 600                 605
Arg Lys Asn Cys Pro Ser Cys Arg Leu Arg Lys Cys Tyr Glu Ala Gly
    610                 615                 620
Met Thr Leu Gly Ala Arg Lys Leu Lys Lys Leu Gly Asn Leu Lys Leu
625                 630                 635                 640
Gln Glu Glu Gly Glu Ala Ser Ser Thr Thr Ser Pro Thr Glu Glu Thr
                645                 650                 655
Thr Gln Lys Leu Thr Val Ser His Ile Glu Gly Tyr Glu Cys Gln Pro
            660                 665                 670
Ile Phe Leu Asn Val Leu Glu Ala Ile Glu Pro Gly Val Val Cys Ala
        675                 680                 685
Gly His Asp Asn Asn Gln Pro Asp Ser Phe Ala Ala Leu Leu Ser Ser
    690                 695                 700
Leu Asn Glu Leu Gly Glu Arg Gln Leu Val His Val Val Lys Trp Ala
705                 710                 715                 720
Lys Ala Leu Pro Gly Phe Arg Asn Leu His Val Asp Asp Gln Met Ala
                725                 730                 735
Val Ile Gln Tyr Ser Trp Met Gly Leu Met Val Phe Ala Met Gly Trp
            740                 745                 750
Arg Ser Phe Thr Asn Val Asn Ser Arg Met Leu Tyr Phe Ala Pro Asp
        755                 760                 765
Leu Val Phe Asn Glu Tyr Arg Met His Lys Ser Arg Met Tyr Ser Gln
    770                 775                 780
Cys Val Arg Met Arg His Leu Ser Gln Glu Phe Gly Trp Leu Gln Ile
785                 790                 795                 800
Thr Pro Gln Glu Phe Leu Cys Met Lys Ala Leu Leu Leu Phe Ser Ile
                805                 810                 815
Ile Pro Val Asp Gly Leu Lys Asn Gln Lys Phe Phe Asp Glu Leu Arg
            820                 825                 830
Met Asn Tyr Ile Lys Glu Leu Asp Arg Ile Ile Ala Cys Lys Arg Lys
        835                 840                 845
Asn Pro Thr Ser Cys Ser Arg Arg Phe Tyr Gln Leu Thr Lys Leu Leu
    850                 855                 860
Asp Ser Val Gln Pro Ile Ala Arg Glu Leu His Gln Phe Thr Phe Asp
865                 870                 875                 880
Leu Leu Ile Lys Ser His Met Val Ser Val Asp Phe Pro Glu Met Met
                885                 890                 895
Ala Glu Ile Ile Ser Val Gln Val Pro Lys Ile Leu Ser Gly Lys Val
            900                 905                 910
Lys Pro Ile Tyr Phe His Thr Gln
        915                 920
```

```
<210> SEQ ID NO 3
<211> LENGTH: 369
<212> TYPE: PRT
<213> ORGANISM: Homo sapiens

<400> SEQUENCE: 3
```

| | | | | | | | | | | | | | | |
|---|---|---|---|---|---|---|---|---|---|---|---|---|---|---|
| Tyr | Tyr | Phe | Pro | Pro | Gln | Lys | Thr | Cys | Leu | Ile | Cys | Gly | Asp | Glu | Ala |
| 1 | | | | 5 | | | | | 10 | | | | | 15 | |
| Ser | Gly | Cys | His | Tyr | Gly | Ala | Leu | Thr | Cys | Gly | Ser | Cys | Lys | Val | Phe |
| | | | 20 | | | | | 25 | | | | | 30 | | |
| Phe | Lys | Arg | Ala | Ala | Glu | Gly | Lys | Gln | Lys | Tyr | Leu | Cys | Ala | Ser | Arg |
| | | | 35 | | | | | 40 | | | | | 45 | | |
| Asn | Asp | Cys | Thr | Ile | Asp | Lys | Phe | Arg | Arg | Lys | Asn | Cys | Pro | Ser | Cys |
| | 50 | | | | | 55 | | | | | 60 | | | | |
| Arg | Leu | Arg | Lys | Cys | Tyr | Glu | Ala | Gly | Met | Thr | Leu | Gly | Ala | Arg | Lys |
| 65 | | | | | 70 | | | | | 75 | | | | | 80 |
| Leu | Lys | Lys | Leu | Gly | Asn | Leu | Lys | Leu | Gln | Glu | Glu | Gly | Glu | Ala | Ser |
| | | | | 85 | | | | | 90 | | | | | 95 | |
| Ser | Thr | Thr | Ser | Pro | Thr | Glu | Glu | Thr | Thr | Gln | Lys | Leu | Thr | Val | Ser |
| | | | 100 | | | | | 105 | | | | | 110 | | |
| His | Ile | Glu | Gly | Tyr | Glu | Cys | Gln | Pro | Ile | Phe | Leu | Asn | Val | Leu | Glu |
| | | | 115 | | | | | 120 | | | | | 125 | | |
| Ala | Ile | Glu | Pro | Gly | Val | Val | Cys | Ala | Gly | His | Asp | Asn | Asn | Gln | Pro |
| | 130 | | | | | 135 | | | | | 140 | | | | |
| Asp | Ser | Phe | Ala | Ala | Leu | Leu | Ser | Ser | Leu | Asn | Glu | Leu | Gly | Glu | Arg |
| 145 | | | | | 150 | | | | | 155 | | | | | 160 |
| Gln | Leu | Val | His | Val | Val | Lys | Trp | Ala | Lys | Ala | Leu | Pro | Gly | Phe | Arg |
| | | | | 165 | | | | | 170 | | | | | 175 | |
| Asn | Leu | His | Val | Asp | Asp | Gln | Met | Ala | Val | Ile | Gln | Tyr | Ser | Trp | Met |
| | | | 180 | | | | | 185 | | | | | 190 | | |
| Gly | Leu | Met | Val | Phe | Ala | Met | Gly | Trp | Arg | Ser | Phe | Thr | Asn | Val | Asn |
| | | | 195 | | | | | 200 | | | | | 205 | | |
| Ser | Arg | Met | Leu | Tyr | Phe | Ala | Pro | Asp | Leu | Val | Phe | Asn | Glu | Tyr | Arg |
| | 210 | | | | | 215 | | | | | 220 | | | | |
| Met | His | Lys | Ser | Arg | Met | Tyr | Ser | Gln | Cys | Val | Arg | Met | Arg | His | Leu |
| 225 | | | | | 230 | | | | | 235 | | | | | 240 |
| Ser | Gln | Glu | Phe | Gly | Trp | Leu | Gln | Ile | Thr | Pro | Gln | Glu | Phe | Leu | Cys |
| | | | | 245 | | | | | 250 | | | | | 255 | |
| Met | Lys | Ala | Leu | Leu | Leu | Phe | Ser | Ile | Ile | Pro | Val | Asp | Gly | Leu | Lys |
| | | | 260 | | | | | 265 | | | | | 270 | | |
| Asn | Gln | Lys | Phe | Phe | Asp | Glu | Leu | Arg | Met | Asn | Tyr | Ile | Lys | Glu | Leu |
| | | | 275 | | | | | 280 | | | | | 285 | | |
| Asp | Arg | Ile | Ile | Ala | Cys | Lys | Arg | Lys | Asn | Pro | Thr | Ser | Cys | Ser | Arg |
| | 290 | | | | | 295 | | | | | 300 | | | | |
| Arg | Phe | Tyr | Gln | Leu | Thr | Lys | Leu | Leu | Asp | Ser | Val | Gln | Pro | Ile | Ala |
| 305 | | | | | 310 | | | | | 315 | | | | | 320 |
| Arg | Glu | Leu | His | Gln | Phe | Thr | Phe | Asp | Leu | Leu | Ile | Lys | Ser | His | Met |
| | | | | 325 | | | | | 330 | | | | | 335 | |
| Val | Ser | Val | Asp | Phe | Pro | Glu | Met | Met | Ala | Glu | Ile | Ile | Ser | Val | Gln |
| | | | 340 | | | | | 345 | | | | | 350 | | |
| Val | Pro | Lys | Ile | Leu | Ser | Gly | Lys | Val | Lys | Pro | Ile | Tyr | Phe | His | Thr |
| | | | 355 | | | | | 360 | | | | | 365 | | |
| Gln | | | | | | | | | | | | | | | |

<210> SEQ ID NO 4
<211> LENGTH: 230
<212> TYPE: PRT
<213> ORGANISM: Homo sapiens

<400> SEQUENCE: 4

```
Asp Asn Asn Gln Pro Asp Ser Phe Ala Ala Leu Leu Ser Ser Leu Asn
1               5                   10                  15

Glu Leu Gly Glu Arg Gln Leu Val His Val Val Lys Trp Ala Lys Ala
            20                  25                  30

Leu Pro Gly Phe Arg Asn Leu His Val Asp Asp Gln Met Ala Val Ile
        35                  40                  45

Gln Tyr Ser Trp Met Gly Leu Met Val Phe Ala Met Gly Trp Arg Ser
    50                  55                  60

Phe Thr Asn Val Asn Ser Arg Met Leu Tyr Phe Ala Pro Asp Leu Val
65                  70                  75                  80

Phe Asn Glu Tyr Arg Met His Lys Ser Arg Met Tyr Ser Gln Cys Val
                85                  90                  95

Arg Met Arg His Leu Ser Gln Glu Phe Gly Trp Leu Gln Ile Thr Pro
            100                 105                 110

Gln Glu Phe Leu Cys Met Lys Ala Leu Leu Leu Phe Ser Ile Ile Pro
        115                 120                 125

Val Asp Gly Leu Lys Asn Gln Lys Phe Phe Asp Glu Leu Arg Met Asn
    130                 135                 140

Tyr Ile Lys Glu Leu Asp Arg Ile Ile Ala Cys Lys Arg Lys Asn Pro
145                 150                 155                 160

Thr Ser Cys Ser Arg Arg Phe Tyr Gln Leu Thr Lys Leu Leu Asp Ser
                165                 170                 175

Val Gln Pro Ile Ala Arg Glu Leu His Gln Phe Thr Phe Asp Leu Leu
            180                 185                 190

Ile Lys Ser His Met Val Ser Val Asp Phe Pro Glu Met Met Ala Glu
        195                 200                 205

Ile Ile Ser Val Gln Val Pro Lys Ile Leu Ser Gly Lys Val Lys Pro
    210                 215                 220

Ile Tyr Phe His Thr Gln
225                 230
```

<210> SEQ ID NO 5
<211> LENGTH: 919
<212> TYPE: PRT
<213> ORGANISM: Homo sapiens

<400> SEQUENCE: 5

```
Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Leu Gln Gln Gln Gln Gln Gln Gln
    50                  55                  60

Gln Gln Gln Gln Gln Gln Gln Gln Gln Gln Gln Gln Gln Gln Glu Thr
65                  70                  75                  80

Ser Pro Arg Gln Gln Gln Gln Gln Gly Glu Asp Gly Ser Pro Gln
                85                  90                  95

Ala His Arg Arg Gly Pro Thr Gly Tyr Leu Val Leu Asp Glu Glu Gln
```

-continued

```
                100                 105                 110
Gln Pro Ser Gln Pro Gln Ser Ala Leu Glu Cys His Pro Glu Arg Gly
            115                 120                 125
Cys Val Pro Glu Pro Gly Ala Ala Val Ala Ala Ser Lys Gly Leu Pro
130                 135                 140
Gln Gln Leu Pro Ala Pro Asp Glu Asp Ser Ala Ala Pro Ser
145                 150                 155                 160
Thr Leu Ser Leu Leu Gly Pro Thr Phe Pro Gly Leu Ser Ser Cys Ser
                165                 170                 175
Ala Asp Leu Lys Asp Ile Leu Ser Glu Ala Ser Thr Met Gln Leu Leu
            180                 185                 190
Gln Gln Gln Gln Glu Ala Val Ser Glu Gly Ser Ser Ser Gly Arg
        195                 200                 205
Ala Arg Glu Ala Ser Gly Ala Pro Thr Ser Ser Lys Asp Asn Tyr Leu
        210                 215                 220
Gly Gly Thr Ser Thr Ile Ser Asp Asn Ala Lys Glu Leu Cys Lys Ala
225                 230                 235                 240
Val Ser Val Ser Met Gly Leu Gly Val Glu Ala Leu Glu His Leu Ser
                245                 250                 255
Pro Gly Glu Gln Leu Arg Gly Asp Cys Met Tyr Ala Pro Leu Leu Gly
            260                 265                 270
Val Pro Pro Ala Val Arg Pro Thr Pro Cys Ala Pro Leu Ala Glu Cys
        275                 280                 285
Lys Gly Ser Leu Leu Asp Asp Ser Ala Gly Lys Ser Thr Glu Asp Thr
        290                 295                 300
Ala Glu Tyr Ser Pro Phe Lys Gly Gly Tyr Thr Lys Gly Leu Glu Gly
305                 310                 315                 320
Glu Ser Leu Gly Cys Ser Gly Ser Ala Ala Gly Ser Ser Gly Thr
                325                 330                 335
Leu Glu Leu Pro Ser Thr Leu Ser Leu Tyr Lys Ser Gly Ala Leu Asp
            340                 345                 350
Glu Ala Ala Tyr Gln Ser Arg Asp Tyr Tyr Asn Phe Pro Leu Ala
        355                 360                 365
Leu Ala Gly Pro Pro Pro Pro Pro Pro Pro His Pro His Ala Arg
        370                 375                 380
Ile Lys Leu Glu Asn Pro Leu Asp Tyr Gly Ser Ala Trp Ala Ala Ala
385                 390                 395                 400
Ala Ala Gln Cys Arg Tyr Gly Asp Leu Ala Ser Leu His Gly Ala Gly
                405                 410                 415
Ala Ala Gly Pro Gly Ser Gly Ser Pro Ser Ala Ala Ala Ser Ser Ser
            420                 425                 430
Trp His Thr Leu Phe Thr Ala Glu Gly Gln Leu Tyr Gly Pro Cys
        435                 440                 445
Gly Gly Gly Gly Gly Gly Gly Gly Gly Gly Gly Gly Gly Gly Gly
450                 455                 460
Gly Gly Gly Gly Gly Gly Gly Glu Ala Gly Ala Val Ala Pro Tyr
465                 470                 475                 480
Gly Tyr Thr Arg Pro Pro Gln Gly Leu Ala Gly Gln Glu Ser Asp Phe
                485                 490                 495
Thr Ala Pro Asp Val Trp Tyr Pro Gly Gly Met Val Ser Arg Val Pro
            500                 505                 510
Tyr Pro Ser Pro Thr Cys Val Lys Ser Glu Met Gly Pro Trp Met Asp
            515                 520                 525
```

```
Ser Tyr Ser Gly Pro Tyr Gly Asp Met Arg Leu Glu Thr Ala Arg Asp
            530                 535                 540

His Val Leu Pro Ile Asp Tyr Phe Pro Gln Lys Thr Cys Leu
545                 550                 555                 560

Ile Cys Gly Asp Glu Ala Ser Gly Cys His Tyr Gly Ala Leu Thr Cys
                    565                 570                 575

Gly Ser Cys Lys Val Phe Phe Lys Arg Ala Ala Glu Gly Lys Gln Lys
            580                 585                 590

Tyr Leu Cys Ala Ser Arg Asn Asp Cys Thr Ile Asp Lys Phe Arg Arg
            595                 600                 605

Lys Asn Cys Pro Ser Cys Arg Leu Arg Lys Cys Tyr Glu Ala Gly Met
            610                 615                 620

Thr Leu Gly Ala Arg Lys Leu Lys Lys Leu Gly Asn Leu Lys Leu Gln
625                 630                 635                 640

Glu Glu Gly Glu Ala Ser Ser Thr Thr Ser Pro Thr Glu Glu Thr Thr
                    645                 650                 655

Gln Lys Leu Thr Val Ser His Ile Glu Gly Tyr Glu Cys Gln Pro Ile
                    660                 665                 670

Phe Leu Asn Val Leu Glu Ala Ile Glu Pro Gly Val Val Cys Ala Gly
                    675                 680                 685

His Asp Asn Asn Gln Pro Asp Ser Phe Ala Ala Leu Leu Ser Ser Leu
            690                 695                 700

Asn Glu Leu Gly Glu Arg Gln Leu Val His Val Val Lys Trp Ala Lys
705                 710                 715                 720

Ala Leu Pro Gly Phe Arg Asn Leu His Val Asp Gln Met Ala Val
                    725                 730                 735

Ile Gln Tyr Ser Trp Met Gly Leu Met Val Phe Ala Met Gly Trp Arg
            740                 745                 750

Ser Phe Thr Asn Val Asn Ser Arg Met Leu Tyr Phe Ala Pro Asp Leu
            755                 760                 765

Val Phe Asn Glu Tyr Arg Met His Lys Ser Arg Met Tyr Ser Gln Cys
770                 775                 780

Val Arg Met Arg His Leu Ser Gln Glu Phe Gly Trp Leu Gln Ile Thr
785                 790                 795                 800

Pro Gln Glu Phe Leu Cys Met Lys Ala Leu Leu Leu Phe Ser Ile Ile
                    805                 810                 815

Pro Val Asp Gly Leu Lys Asn Gln Lys Phe Phe Asp Glu Leu Arg Met
                    820                 825                 830

Asn Tyr Ile Lys Glu Leu Asp Arg Ile Ile Ala Cys Lys Arg Lys Asn
            835                 840                 845

Pro Thr Ser Cys Ser Arg Arg Phe Tyr Gln Leu Thr Lys Leu Leu Asp
            850                 855                 860

Ser Val Gln Pro Ile Ala Arg Glu Leu His Gln Leu Thr Phe Asp Leu
865                 870                 875                 880

Leu Ile Lys Ser His Met Val Ser Val Asp Phe Pro Glu Met Met Ala
                    885                 890                 895

Glu Ile Ile Ser Val Gln Val Pro Lys Ile Leu Ser Gly Lys Val Lys
                    900                 905                 910

Pro Ile Tyr Phe His Thr Gln
            915

<210> SEQ ID NO 6
<211> LENGTH: 902
```

<212> TYPE: PRT
<213> ORGANISM: Rattus norvegicus

<400> SEQUENCE: 6

```
Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Ala Ile Gln Asn Pro Gly Pro Arg His Pro Glu Ala Ala Ser Ile Ala
        35                  40                  45

Pro Pro Gly Ala Cys Leu Gln Gln Arg Gln Glu Thr Ser Pro Arg Arg
    50                  55                  60

Arg Arg Arg Gln Gln His Pro Glu Asp Gly Ser Pro Gln Ala His Ile
65                  70                  75                  80

Arg Gly Thr Thr Gly Tyr Leu Ala Leu Glu Glu Glu Gln Gln Pro Ser
                85                  90                  95

Gln Gln Gln Ser Ala Ser Glu Gly His Pro Glu Ser Gly Cys Leu Pro
            100                 105                 110

Glu Pro Gly Ala Ala Thr Ala Pro Gly Lys Gly Leu Pro Gln Gln Pro
        115                 120                 125

Pro Ala Pro Pro Asp Gln Asp Asp Ser Ala Ala Pro Ser Thr Leu Ser
    130                 135                 140

Leu Leu Gly Pro Thr Phe Pro Gly Leu Ser Ser Cys Ser Ala Asp Ile
145                 150                 155                 160

Lys Asp Ile Leu Ser Glu Ala Gly Thr Met Gln Leu Leu Gln Gln Gln
                165                 170                 175

Gln Gln Gln Gln Gln Gln Gln Gln Gln Gln Gln Gln Gln Gln Gln Gln
            180                 185                 190

Gln Gln Gln Glu Val Ile Ser Glu Gly Ser Ser Val Arg Ala Arg
            195                 200                 205

Glu Ala Thr Gly Ala Pro Ser Ser Ser Lys Asp Ser Tyr Leu Gly Gly
        210                 215                 220

Asn Ser Thr Ile Ser Asp Ser Ala Lys Glu Leu Cys Lys Ala Val Ser
225                 230                 235                 240

Val Ser Met Gly Leu Gly Val Glu Ala Leu Glu His Leu Ser Pro Gly
                245                 250                 255

Glu Gln Leu Arg Gly Asp Cys Met Tyr Ala Ser Leu Leu Gly Gly Pro
            260                 265                 270

Pro Ala Val Arg Pro Thr Pro Cys Ala Pro Leu Ala Glu Cys Lys Gly
        275                 280                 285

Leu Ser Leu Asp Glu Gly Pro Gly Lys Gly Thr Glu Glu Thr Ala Glu
    290                 295                 300

Tyr Ser Ser Phe Lys Gly Gly Tyr Ala Lys Gly Leu Glu Gly Glu Ser
305                 310                 315                 320

Leu Gly Cys Ser Gly Ser Ser Glu Ala Gly Ser Ser Gly Thr Leu Glu
                325                 330                 335

Ile Pro Ser Ser Leu Ser Leu Tyr Lys Ser Gly Ala Val Asp Glu Ala
            340                 345                 350

Ala Ala Tyr Gln Asn Arg Asp Tyr Tyr Asn Phe Pro Leu Ala Leu Ser
        355                 360                 365

Gly Pro Pro His Pro Pro Pro Thr His Pro His Ala Arg Ile Lys
    370                 375                 380

Leu Glu Asn Pro Ser Asp Tyr Gly Ser Ala Trp Ala Ala Ala Ala
385                 390                 395                 400
```

```
Gln Cys Arg Tyr Gly Asp Leu Ala Ser Leu His Gly Ser Val Ala
                405                 410                 415

Gly Pro Ser Thr Gly Ser Pro Pro Ala Thr Ala Ser Ser Trp His
            420                 425                 430

Thr Leu Phe Thr Ala Glu Glu Gly Gln Leu Tyr Gly Pro Gly Gly
        435                 440                 445

Gly Gly Ser Ser Pro Ser Asp Ala Gly Pro Val Ala Pro Tyr Gly
    450                 455                 460

Tyr Thr Arg Pro Pro Gln Gly Leu Ala Ser Gln Glu Gly Asp Phe Ser
465                 470                 475                 480

Ala Ser Glu Val Trp Tyr Pro Gly Gly Val Val Asn Arg Val Pro Tyr
                485                 490                 495

Pro Ser Pro Ser Cys Val Lys Ser Glu Met Gly Pro Trp Met Glu Asn
            500                 505                 510

Tyr Ser Gly Pro Tyr Gly Asp Met Arg Leu Asp Ser Thr Arg Asp His
        515                 520                 525

Val Leu Pro Ile Asp Tyr Tyr Phe Pro Pro Gln Lys Thr Cys Leu Ile
    530                 535                 540

Cys Gly Asp Glu Ala Ser Gly Cys His Tyr Gly Ala Leu Thr Cys Gly
545                 550                 555                 560

Ser Cys Lys Val Phe Phe Lys Arg Ala Ala Glu Gly Lys Gln Lys Tyr
                565                 570                 575

Leu Cys Ala Ser Arg Asn Asp Cys Thr Ile Asp Lys Phe Arg Arg Lys
            580                 585                 590

Asn Cys Pro Ser Cys Arg Leu Arg Lys Cys Tyr Glu Ala Gly Met Thr
        595                 600                 605

Leu Gly Ala Arg Lys Leu Lys Lys Leu Gly Asn Leu Lys Leu Gln Glu
    610                 615                 620

Glu Gly Glu Asn Ser Ser Ala Gly Ser Pro Thr Glu Asp Pro Ser Gln
625                 630                 635                 640

Lys Met Thr Val Ser His Ile Glu Gly Tyr Glu Cys Gln Pro Ile Phe
                645                 650                 655

Leu Asn Val Leu Glu Ala Ile Glu Pro Gly Val Val Cys Ala Gly His
            660                 665                 670

Asp Asn Asn Gln Pro Asp Ser Phe Ala Ala Leu Leu Ser Ser Leu Asn
        675                 680                 685

Glu Leu Gly Glu Arg Gln Leu Val His Val Val Lys Trp Ala Lys Ala
    690                 695                 700

Leu Pro Gly Phe Arg Asn Leu His Val Asp Asp Gln Met Ala Val Ile
705                 710                 715                 720

Gln Tyr Ser Trp Met Gly Leu Met Val Phe Ala Met Gly Trp Arg Ser
                725                 730                 735

Phe Thr Asn Val Asn Ser Arg Met Leu Tyr Phe Ala Pro Asp Leu Val
            740                 745                 750

Phe Asn Glu Tyr Arg Met His Lys Ser Arg Met Tyr Ser Gln Cys Val
        755                 760                 765

Arg Met Arg His Leu Ser Gln Glu Phe Gly Trp Leu Gln Ile Thr Pro
    770                 775                 780

Gln Glu Phe Leu Cys Met Lys Ala Leu Leu Leu Phe Ser Ile Ile Pro
785                 790                 795                 800

Val Asp Gly Leu Lys Asn Gln Lys Phe Phe Asp Glu Leu Arg Met Asn
                805                 810                 815
```

```
Tyr Ile Lys Glu Leu Asp Arg Ile Ile Ala Cys Lys Arg Lys Asn Pro
                820                 825                 830

Thr Ser Cys Ser Arg Arg Phe Tyr Gln Leu Thr Lys Leu Leu Asp Ser
            835                 840                 845

Val Gln Pro Ile Ala Arg Glu Leu His Gln Phe Thr Phe Asp Leu Leu
        850                 855                 860

Ile Lys Ser His Met Val Ser Val Asp Phe Pro Glu Met Met Ala Glu
865                 870                 875                 880

Ile Ile Ser Val Gln Val Pro Lys Ile Leu Ser Gly Lys Val Lys Pro
                885                 890                 895

Ile Tyr Phe His Thr Gln
                900

<210> SEQ ID NO 7
<211> LENGTH: 899
<212> TYPE: PRT
<213> ORGANISM: Mus musculus

<400> SEQUENCE: 7

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Ala Ile Gln Asn Pro Gly Pro Arg His Pro Glu Ala Ala Asn Ile Ala
        35                  40                  45

Pro Pro Gly Ala Cys Leu Gln Gln Arg Gln Glu Thr Ser Pro Arg Arg
    50                  55                  60

Arg Arg Arg Gln Gln His Thr Glu Asp Gly Ser Pro Gln Ala His Ile
65              70                  75                  80

Arg Gly Pro Thr Gly Tyr Leu Ala Leu Glu Glu Glu Gln Pro Ser
                85                  90                  95

Gln Gln Gln Ala Ala Ser Glu Gly His Pro Glu Ser Ser Cys Leu Pro
            100                 105                 110

Glu Pro Gly Ala Ala Thr Ala Pro Gly Lys Gly Leu Pro Gln Gln Pro
        115                 120                 125

Pro Ala Pro Pro Asp Gln Asp Asp Ser Ala Ala Pro Ser Thr Leu Ser
    130                 135                 140

Leu Leu Gly Pro Thr Phe Pro Gly Leu Ser Ser Cys Ser Ala Asp Ile
145                 150                 155                 160

Lys Asp Ile Leu Asn Glu Ala Gly Thr Met Gln Leu Leu Gln Gln Gln
                165                 170                 175

Gln Gln Gln Gln Gln His Gln Gln His Gln Gln His Gln Gln Gln
            180                 185                 190

Gln Glu Val Ile Ser Glu Gly Ser Ser Ala Arg Ala Arg Glu Ala Thr
        195                 200                 205

Gly Ala Pro Ser Ser Ser Lys Asp Ser Tyr Leu Gly Gly Asn Ser Thr
    210                 215                 220

Ile Ser Asp Ser Ala Lys Glu Leu Cys Lys Ala Val Ser Val Ser Met
225                 230                 235                 240

Gly Leu Gly Val Glu Ala Leu Glu His Leu Ser Pro Gly Glu Gln Leu
                245                 250                 255

Arg Gly Asp Cys Met Tyr Ala Ser Leu Leu Gly Gly Pro Pro Ala Val
            260                 265                 270

Arg Pro Thr Pro Cys Ala Pro Leu Pro Glu Cys Lys Gly Leu Pro Leu
        275                 280                 285
```

-continued

```
Asp Glu Gly Pro Gly Lys Ser Thr Glu Thr Ala Glu Tyr Ser Ser
    290                 295                 300
Phe Lys Gly Gly Tyr Ala Lys Gly Leu Glu Gly Ser Leu Gly Cys
305                 310                 315                 320
Ser Gly Ser Ser Glu Ala Gly Ser Ser Gly Thr Leu Glu Ile Pro Ser
                325                 330                 335
Ser Leu Ser Leu Tyr Lys Ser Gly Ala Leu Asp Glu Ala Ala Tyr
                340                 345                 350
Gln Asn Arg Asp Tyr Tyr Asn Phe Pro Leu Ala Leu Ser Gly Pro Pro
            355                 360                 365
His Pro Pro Pro Thr His Pro His Ala Arg Ile Lys Leu Glu Asn
    370                 375                 380
Pro Leu Asp Tyr Gly Ser Ala Trp Ala Ala Ala Ala Gln Cys Arg
385                 390                 395                 400
Tyr Gly Asp Leu Gly Ser Leu His Gly Gly Ser Val Ala Gly Pro Ser
                405                 410                 415
Thr Gly Ser Pro Pro Ala Thr Thr Ser Ser Trp His Thr Leu Phe
                420                 425                 430
Thr Ala Glu Glu Gly Gln Leu Tyr Gly Pro Gly Gly Gly Gly Ser
    435                 440                 445
Ser Ser Pro Ser Asp Ala Gly Pro Val Ala Pro Tyr Gly Tyr Thr Arg
450                 455                 460
Pro Pro Gln Gly Leu Thr Ser Gln Glu Ser Asp Tyr Ser Ala Ser Glu
465                 470                 475                 480
Val Trp Tyr Pro Gly Gly Val Val Asn Arg Val Pro Tyr Pro Ser Pro
                485                 490                 495
Asn Cys Val Lys Ser Glu Met Gly Pro Trp Met Glu Asn Tyr Ser Gly
                500                 505                 510
Pro Tyr Gly Asp Met Arg Leu Asp Ser Thr Arg Asp His Val Leu Pro
                515                 520                 525
Ile Asp Tyr Tyr Phe Pro Pro Gln Lys Thr Cys Leu Ile Cys Gly Asp
                530                 535                 540
Glu Ala Ser Gly Cys His Tyr Gly Ala Leu Thr Cys Gly Ser Cys Lys
545                 550                 555                 560
Val Phe Phe Lys Arg Ala Ala Glu Gly Lys Gln Lys Tyr Leu Cys Ala
                565                 570                 575
Ser Arg Asn Asp Cys Thr Ile Asp Lys Phe Arg Arg Lys Asn Cys Pro
            580                 585                 590
Ser Cys Arg Leu Arg Lys Cys Tyr Glu Ala Gly Met Thr Leu Gly Ala
        595                 600                 605
Arg Lys Leu Lys Lys Leu Gly Asn Leu Lys Leu Gln Glu Glu Gly Glu
610                 615                 620
Asn Ser Asn Ala Gly Ser Pro Thr Glu Asp Pro Ser Gln Lys Met Thr
625                 630                 635                 640
Val Ser His Ile Glu Gly Tyr Glu Cys Gln Pro Ile Phe Leu Asn Val
                645                 650                 655
Leu Glu Ala Ile Glu Pro Gly Val Val Cys Ala Gly His Asp Asn Asn
                660                 665                 670
Gln Pro Asp Ser Phe Ala Ala Leu Leu Ser Ser Leu Asn Glu Leu Gly
            675                 680                 685
Glu Arg Gln Leu Val His Val Val Lys Trp Ala Lys Ala Leu Pro Gly
    690                 695                 700
```

```
Phe Arg Asn Leu His Val Asp Asp Gln Met Ala Val Ile Gln Tyr Ser
705                 710                 715                 720

Trp Met Gly Leu Met Val Phe Ala Met Gly Trp Arg Ser Phe Thr Asn
            725                 730                 735

Val Asn Ser Arg Met Leu Tyr Phe Ala Pro Asp Leu Val Phe Asn Glu
        740                 745                 750

Tyr Arg Met His Lys Ser Arg Met Tyr Ser Gln Cys Val Arg Met Arg
    755                 760                 765

His Leu Ser Gln Glu Phe Gly Trp Leu Gln Ile Thr Pro Gln Glu Phe
770                 775                 780

Leu Cys Met Lys Ala Leu Leu Leu Phe Ser Ile Ile Pro Val Asp Gly
785                 790                 795                 800

Leu Lys Asn Gln Lys Phe Phe Asp Glu Leu Arg Met Asn Tyr Ile Lys
            805                 810                 815

Glu Leu Asp Arg Ile Ile Ala Cys Lys Arg Lys Asn Pro Thr Ser Cys
        820                 825                 830

Ser Arg Arg Phe Tyr Gln Leu Thr Lys Leu Leu Asp Ser Val Gln Pro
    835                 840                 845

Ile Ala Arg Glu Leu His Gln Phe Thr Phe Asp Leu Leu Ile Lys Ser
850                 855                 860

His Met Val Ser Val Asp Phe Pro Glu Met Met Ala Glu Ile Ile Ser
865                 870                 875                 880

Val Gln Val Pro Lys Ile Leu Ser Gly Lys Val Lys Pro Ile Tyr Phe
            885                 890                 895

His Thr Gln

<210> SEQ ID NO 8
<211> LENGTH: 907
<212> TYPE: PRT
<213> ORGANISM: Canis familiaris

<400> SEQUENCE: 8

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Val Ser Ala Ala
        35                  40                  45

Pro Pro Gly Ala His Leu Gln Gln Gln Gln Gln Gln Gln Gln Gln Gln
    50                  55                  60

Glu Thr Ser Pro Arg Gln Gln Gln Gln Gln Gly Asp Asp Gly
65                  70                  75                  80

Ser Pro Gln Ala Gln Ser Arg Gly Pro Thr Gly Tyr Leu Ala Leu Asp
                85                  90                  95

Glu Glu Gln Gln Pro Ser Gln Arg Ser Ala Ser Lys Gly His Pro
            100                 105                 110

Glu Ser Ala Cys Val Pro Glu Pro Gly Val Thr Ser Thr Gly Lys
            115                 120                 125

Gly Leu Gln Gln Gln Gln Pro Ala Pro Pro Asp Glu Asn Asp Ser Ala
130                 135                 140

Ala Pro Ser Thr Leu Ser Leu Leu Gly Pro Thr Phe Pro Gly Leu Ser
145                 150                 155                 160

Ser Cys Ser Thr Asp Leu Lys Asp Ile Leu Ser Glu Ala Gly Thr Met
            165                 170                 175
```

-continued

```
Gln Leu Leu Gln Gln Arg Gln Gln Gln Gln Gln Gln Gln
            180                 185                 190
Gln Gln Gln Gln Gln Gln Gln Gln Glu Val Val Ser Glu Gly
        195                 200                 205
Ser Ser Ser Gly Arg Ala Arg Glu Ala Ala Gly Ala Ser Thr Ser Ser
    210                 215                 220
Lys Asp Ser Tyr Leu Gly Gly Ser Ser Thr Ile Ser Asp Ser Ala Lys
225                 230                 235                 240
Glu Leu Cys Lys Ala Val Ser Val Ser Met Gly Leu Gly Val Glu Ala
                245                 250                 255
Leu Glu His Leu Ser Pro Gly Glu Gln Leu Arg Gly Asp Cys Met Tyr
            260                 265                 270
Ala Pro Leu Leu Gly Gly Pro Ala Val Arg Pro Cys Ala Pro Leu
        275                 280                 285
Ala Glu Cys Lys Gly Ser Leu Leu Asp Asp Gly Pro Gly Lys Gly Thr
    290                 295                 300
Glu Glu Thr Ala Glu Tyr Ser Pro Phe Lys Ala Gly Tyr Ala Lys Gly
305                 310                 315                 320
Leu Asp Gly Asp Ser Leu Gly Cys Ser Ser Ser Glu Ala Gly Gly
                325                 330                 335
Ser Gly Thr Leu Glu Met Pro Ser Thr Leu Ser Leu Tyr Lys Ser Gly
            340                 345                 350
Ala Leu Asp Glu Ala Ala Ala Tyr Gln Ser Arg Asp Tyr Tyr Asn Phe
        355                 360                 365
Pro Leu Ser Leu Gly Gly Pro Pro His Pro Pro Pro His Pro
    370                 375                 380
His Thr Arg Ile Lys Leu Glu Asn Pro Leu Asp Tyr Gly Ser Ala Trp
385                 390                 395                 400
Ala Ala Ala Ala Ala Gln Cys Arg Tyr Gly Asp Leu Ala Ser Leu His
                405                 410                 415
Gly Ala Gly Ala Ala Gly Pro Ser Ser Gly Ser Pro Ser Ala Thr Thr
            420                 425                 430
Ser Ser Ser Trp His Thr Leu Phe Thr Ala Glu Glu Gly Gln Leu Tyr
        435                 440                 445
Gly Pro Cys Gly Gly Ser Gly Gly Gly Ser Ala Gly Asp Gly Gly Ser
    450                 455                 460
Val Ala Pro Tyr Gly Tyr Thr Arg Pro Pro Gln Gly Leu Ala Gly Gln
465                 470                 475                 480
Glu Gly Asp Phe Pro Pro Pro Asp Val Trp Tyr Pro Gly Gly Val Val
                485                 490                 495
Ser Arg Val Pro Phe Pro Ser Pro Ser Cys Val Lys Ser Glu Met Gly
            500                 505                 510
Ser Trp Met Glu Ser Tyr Ser Gly Pro Tyr Gly Asp Met Arg Leu Glu
        515                 520                 525
Thr Ala Arg Asp His Val Leu Pro Ile Asp Tyr Tyr Phe Pro Pro Gln
    530                 535                 540
Lys Thr Cys Leu Ile Cys Gly Asp Glu Ala Ser Gly Cys His Tyr Gly
545                 550                 555                 560
Ala Leu Thr Cys Gly Ser Cys Lys Val Phe Phe Lys Arg Ala Ala Glu
                565                 570                 575
Gly Lys Gln Lys Tyr Leu Cys Ala Ser Arg Asn Asp Cys Thr Ile Asp
            580                 585                 590
Lys Phe Arg Arg Lys Asn Cys Pro Ser Cys Arg Leu Arg Lys Cys Tyr
```

```
                    595                 600                 605
Glu Ala Gly Met Thr Leu Gly Ala Arg Lys Leu Lys Lys Leu Gly Asn
            610                 615                 620

Leu Lys Leu Gln Glu Glu Gly Glu Ala Ser Asn Val Thr Ser Pro Thr
625                 630                 635                 640

Glu Glu Pro Thr Gln Lys Leu Thr Val Ser His Ile Glu Gly Tyr Glu
                645                 650                 655

Cys Gln Pro Ile Phe Leu Asn Val Leu Glu Ala Ile Glu Pro Gly Val
            660                 665                 670

Val Cys Ala Gly His Asp Asn Asn Gln Pro Asp Ser Phe Ala Ala Leu
        675                 680                 685

Leu Ser Ser Leu Asn Glu Leu Gly Glu Arg Gln Leu Val His Val Val
    690                 695                 700

Lys Trp Ala Lys Ala Leu Pro Gly Phe Arg Asn Leu His Val Asp Asp
705                 710                 715                 720

Gln Met Ala Val Ile Gln Tyr Ser Trp Met Gly Leu Met Val Phe Ala
                725                 730                 735

Met Gly Trp Arg Ser Phe Thr Asn Val Asn Ser Arg Met Leu Tyr Phe
            740                 745                 750

Ala Pro Asp Leu Val Phe Asn Glu Tyr Arg Met His Lys Ser Arg Met
        755                 760                 765

Tyr Ser Gln Cys Val Arg Met Arg His Leu Ser Gln Glu Phe Gly Trp
    770                 775                 780

Leu Gln Ile Thr Pro Gln Glu Phe Leu Cys Met Lys Ala Leu Leu Leu
785                 790                 795                 800

Phe Ser Ile Ile Pro Val Asp Gly Leu Lys Asn Gln Lys Phe Phe Asp
                805                 810                 815

Glu Leu Arg Met Asn Tyr Ile Lys Glu Leu Asp Arg Ile Ile Ala Cys
            820                 825                 830

Lys Arg Lys Asn Pro Thr Ser Cys Ser Arg Arg Phe Tyr Gln Leu Thr
        835                 840                 845

Lys Leu Leu Asp Ser Val Gln Pro Ile Ala Arg Glu Leu His Gln Phe
    850                 855                 860

Thr Phe Asp Leu Leu Ile Lys Ser His Met Val Ser Val Asp Phe Pro
865                 870                 875                 880

Glu Met Met Ala Glu Ile Ile Ser Val Gln Val Pro Lys Ile Leu Ser
                885                 890                 895

Gly Lys Val Lys Pro Ile Tyr Phe His Thr Gln
            900                 905

<210> SEQ ID NO 9
<211> LENGTH: 912
<212> TYPE: PRT
<213> ORGANISM: Crocuta crocuta

<400> SEQUENCE: 9

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Thr Ser Ala Ala
        35                  40                  45

Pro Pro Gly Ala Arg Leu Gln Gln Gln His Gln Gln Gln His
    50                  55                  60
```

```
Gln His Glu Thr Ser Pro Arg Arg Gln Gln Gln Gln Pro Glu Asp
 65                  70                  75                  80

Gly Ser Pro Gln Arg Pro Ser Arg Gly Pro Thr Ser Tyr Leu Ala Leu
                 85                  90                  95

Asp Glu Glu Gln Gln Pro Ser Gln His Gln Ser Ala Lys Gly His Pro
             100                 105                 110

Glu Ser Gly Cys Val Pro Glu Pro Val Ala Met Ser Arg Thr Gly Lys
         115                 120                 125

Gly Leu Glu Gln Gln Gln Pro Ala Pro Asp Glu Asp Asp Ser Ala
     130                 135                 140

Ala Pro Ser Thr Leu Ser Leu Leu Gly Pro Thr Phe Pro Gly Leu Ser
145                 150                 155                 160

Ser Cys Ser Thr Asp Leu Lys Asp Ile Leu Ser Glu Ala Gly Thr Met
                 165                 170                 175

Gln Leu Leu Gln Arg Gln Arg Gln Arg Gln Gln Gln Arg Gln Gln Gln
             180                 185                 190

Gln Gln Gln Gln Gln Gln Gln Gln Gln Gln Gln Gln Gln Gln Gln Glu
             195                 200                 205

Val Val Ser Glu Gly Ser Ser Gly Arg Ala Arg Glu Ala Ala Gly
    210                 215                 220

Ala Pro Thr Ser Ser Lys Asp Ser Tyr Leu Gly Gly Ser Ser Thr Ile
225                 230                 235                 240

Ser Asp Ser Ala Lys Glu Leu Cys Lys Ala Val Ser Val Ser Met Gly
                 245                 250                 255

Leu Gly Val Glu Ala Leu Glu His Leu Ser Pro Gly Glu Gln Leu Arg
             260                 265                 270

Gly Asp Cys Met Tyr Ala Pro Leu Leu Gly Gly Pro Pro Val Cys
    275                 280                 285

Pro Cys Ala Pro Leu Thr Glu Cys Lys Gly Ser Val Leu Asp Asp Gly
             290                 295                 300

Pro Ser Lys Gly Thr Glu Glu Thr Ala Glu Tyr Ser Pro Phe Lys Thr
305                 310                 315                 320

Gly Tyr Ala Lys Gly Leu Asp Gly Asp Ser Leu Gly Cys Ser Gly Ser
                 325                 330                 335

Ser Gln Ala Gly Gly Ser Gly Thr Leu Glu Ile Pro Ser Thr Leu Ser
             340                 345                 350

Leu Tyr Lys Ser Gly Thr Leu Asp Glu Ala Ala Ala Tyr Gln Ser Arg
             355                 360                 365

Asp Tyr Tyr Asn Phe Gln Leu Ser Leu Ala Gly Pro Pro Pro Pro
    370                 375                 380

Pro Ser Pro His Pro His Ala Arg Ile Lys Leu Glu Asn Pro Leu Asp
385                 390                 395                 400

Tyr Gly Ser Ala Trp Ala Ala Ala Ala Gln Cys Arg Tyr Gly Asp
                 405                 410                 415

Leu Ala Ser Leu His Gly Gly Ala Ala Gly Pro Gly Ser Gly Ser
             420                 425                 430

Pro Ser Ala Thr Ala Ser Ser Trp His Thr Leu Phe Thr Ala Glu
             435                 440                 445

Glu Gly Gln Leu Tyr Gly Pro Cys Gly Gly Ser Gly Gly Gly Thr
             450                 455                 460

Gly Glu Ser Val Ser Val Thr Pro Tyr Gly Tyr Thr Arg Pro Gln Gln
465                 470                 475                 480

Gly Leu Thr Gly Gln Glu Gly Asp Phe Pro Pro Pro Asp Val Trp Tyr
```

```
                485                 490                 495
Pro Gly Gly Val Val Ser Arg Met Pro Tyr Pro Ser Ala Ser Cys Val
            500                 505                 510
Lys Ser Glu Met Gly Pro Trp Met Glu Ser Tyr Ser Gly Pro Tyr Gly
            515                 520                 525
Asp Met Arg Leu Glu Thr Thr Arg Asp His Val Leu Pro Ile Asp Tyr
            530                 535                 540
Tyr Phe Pro Pro Gln Lys Thr Cys Leu Ile Cys Gly Asp Glu Ala Ser
545                 550                 555                 560
Gly Cys His Tyr Gly Ala Leu Thr Cys Gly Ser Cys Lys Val Phe Phe
                565                 570                 575
Lys Arg Ala Ala Glu Gly Lys Gln Lys Tyr Leu Cys Ala Ser Arg Asn
            580                 585                 590
Asp Cys Thr Ile Asp Lys Phe Arg Arg Lys Asn Cys Pro Pro Cys Arg
            595                 600                 605
Leu Arg Lys Cys Tyr Glu Ala Gly Met Thr Leu Gly Ala Arg Arg Leu
            610                 615                 620
Lys Lys Leu Gly Asn Leu Lys Leu Gln Glu Glu Gly Glu Ala Ser Ser
625                 630                 635                 640
Thr Thr Ser Pro Thr Glu Glu Thr Thr Gln Lys Leu Thr Val Ser His
                645                 650                 655
Ile Glu Gly Tyr Glu Cys Gln Pro Ile Phe Leu Asn Val Leu Glu Ala
            660                 665                 670
Ile Glu Pro Gly Val Val Cys Ala Gly His Asp Asn Asn Gln Pro Asp
            675                 680                 685
Ser Phe Ala Ala Leu Leu Ser Ser Leu Asn Glu Leu Gly Glu Arg Gln
            690                 695                 700
Leu Val His Val Val Lys Trp Ala Lys Ala Leu Pro Gly Phe Arg Asn
705                 710                 715                 720
Leu His Val Asp Asp Gln Met Ala Val Ile Gln Tyr Ser Trp Met Gly
                725                 730                 735
Leu Met Val Phe Ala Met Gly Trp Arg Ser Phe Thr Asn Val Asn Ser
            740                 745                 750
Arg Met Leu Tyr Phe Ala Pro Asp Leu Val Phe Asn Glu Tyr Arg Met
            755                 760                 765
His Lys Ser Arg Met Tyr Ser Gln Cys Val Arg Met Arg His Leu Ser
            770                 775                 780
Gln Glu Phe Gly Trp Leu Gln Ile Thr Pro Gln Glu Phe Leu Cys Met
785                 790                 795                 800
Lys Ala Leu Leu Leu Phe Ser Ile Ile Pro Val Asp Gly Leu Lys Asn
                805                 810                 815
Gln Lys Phe Phe Asp Glu Leu Arg Met Asn Tyr Ile Lys Asp Leu Asp
            820                 825                 830
Arg Ile Ile Ala Cys Lys Arg Lys Asn Pro Thr Ser Cys Ser Arg Arg
            835                 840                 845
Phe Tyr Gln Leu Thr Lys Leu Leu Asp Ser Val Gln Pro Ile Ala Arg
            850                 855                 860
Glu Leu His Gln Phe Thr Phe Asp Leu Leu Ile Lys Ser His Met Val
865                 870                 875                 880
Ser Val Asp Phe Pro Glu Met Met Ala Glu Ile Ile Ser Val Gln Val
                885                 890                 895
Pro Lys Ile Leu Ser Gly Lys Val Lys Pro Ile Tyr Phe His Thr Gln
            900                 905                 910
```

```
<210> SEQ ID NO 10
<211> LENGTH: 884
<212> TYPE: PRT
<213> ORGANISM: Eulemur fulvus

<400> SEQUENCE: 10

Met Glu Val Gln Leu Gly Leu Gly Arg Val Tyr Pro Arg Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Arg Leu Gln Gln Gln Glu Thr Ser Pro Pro Gln
    50                  55                  60

Gln Gln Gln Gln Gln Gly Glu Asp Gly Ser Pro Gln Ala Gln Ser
65                  70                  75                  80

Arg Gly Pro Thr Gly Tyr Leu Ala Leu Asp Glu Glu Gln Gln Pro Ser
                85                  90                  95

Gln Gln Gln Ser Ala Leu Glu Cys His Pro Glu Ser Gly Cys Val Pro
            100                 105                 110

Glu Pro Gly Ala Ala Ala Ala Ser Lys Gly Leu Gln Gln Gln Pro
        115                 120                 125

Pro Ala Pro Ser Asp Glu Asp Ser Ala Val Pro Ser Thr Leu Ser
    130                 135                 140

Leu Leu Gly Pro Thr Phe Pro Gly Leu Ser Ser Cys Ser Ala Asp Leu
145                 150                 155                 160

Lys Asp Ile Leu Ser Glu Ala Gly Thr Met Gln Leu Leu Gln Gln Gln
                165                 170                 175

Gln Gln Glu Ala Val Ser Glu Gly Ser Ser Ser Gly Arg Ala Arg Glu
            180                 185                 190

Ala Ala Gly Ala Pro Thr Ser Ser Lys Asp Ser Tyr Leu Gly Gly Thr
        195                 200                 205

Ser Thr Ile Ser Asp Ser Ala Lys Glu Leu Cys Lys Ala Val Ser Val
210                 215                 220

Ser Met Gly Leu Gly Val Glu Thr Leu Glu His Leu Ser Pro Gly Glu
225                 230                 235                 240

Gln Leu Arg Gly Asp Cys Met Tyr Ala Pro Leu Leu Gly Gly Pro Pro
                245                 250                 255

Ala Val Arg Pro Thr Pro Cys Ala Pro Leu Ala Glu Cys Lys Gly Ser
            260                 265                 270

Leu Leu Asp Asp Ser Ala Asp Lys Gly Thr Glu Glu Pro Ala Glu Tyr
        275                 280                 285

Thr Pro Phe Lys Gly Ser Tyr Thr Gln Gly Leu Glu Gly Glu Ser Leu
    290                 295                 300

Gly Cys Ser Gly Ser Ser Glu Ala Gly Ser Ser Gly Thr Leu Glu Leu
305                 310                 315                 320

Pro Ser Thr Leu Ser Leu Tyr Lys Ser Gly Ala Leu Glu Glu Ala Ala
                325                 330                 335

Ser Tyr Gln Ser Arg Asp Tyr Tyr Asn Phe Pro Leu Ala Leu Ala Gly
            340                 345                 350

Pro Pro Pro Pro Pro Leu Pro Pro His Pro His Ala Arg Ile Lys Leu
        355                 360                 365

Glu Asn Pro Leu Asp Tyr Gly Ser Ser Trp Ala Ala Ala Ala Ala Gln
```

```
          370                 375                 380

Cys Arg Phe Gly Asp Leu Ala Ser Leu His Gly Gly Ala Thr Gly
385                 390                 395                 400

Pro Gly Ser Gly Ser Pro Ser Ala Ala Ala Ser Ser Trp His Thr
                405                 410                 415

Leu Phe Thr Ala Glu Glu Gly Gln Leu Tyr Gly Pro Cys Gly Gly
            420                 425                 430

Gly Gly Gly Thr Ser Glu Ala Gly Ala Val Thr Pro Tyr Gly Tyr Ser
            435                 440                 445

Arg Pro Pro Gln Gly Leu Ala Gly Gln Glu Gly Asp Phe Pro Ala Pro
450                 455                 460

Asp Val Trp Tyr Pro Ser Gly Val Val Ser Arg Val Pro Tyr Pro Ser
465                 470                 475                 480

Pro Ser Cys Val Lys Ser Glu Met Gly Pro Trp Met Glu Ser Tyr Ser
                485                 490                 495

Gly Pro Tyr Gly Asp Val Arg Leu Glu Thr Ala Arg Asp His Val Leu
                500                 505                 510

Pro Ile Asp Tyr Tyr Phe Pro Pro Gln Lys Thr Cys Leu Ile Cys Gly
            515                 520                 525

Asp Glu Ala Ser Gly Cys His Tyr Gly Ala Leu Thr Cys Gly Ser Cys
530                 535                 540

Lys Val Phe Phe Lys Arg Ala Ala Glu Gly Lys Gln Lys Tyr Leu Cys
545                 550                 555                 560

Ala Ser Arg Asn Asp Cys Thr Ile Asp Lys Phe Arg Arg Lys Asn Cys
                565                 570                 575

Pro Ser Cys Arg Leu Arg Lys Cys Tyr Glu Ala Gly Met Thr Leu Gly
            580                 585                 590

Ala Arg Lys Leu Lys Lys Leu Gly Asn Leu Lys Leu Gln Glu Glu Gly
            595                 600                 605

Glu Ala Ser Ser Ala Thr Ser Pro Thr Glu Glu Ser Ser Gln Lys Leu
            610                 615                 620

Thr Val Ser His Ile Glu Gly Tyr Glu Cys Gln Pro Ile Phe Leu Asn
625                 630                 635                 640

Val Leu Glu Ala Ile Glu Pro Gly Val Val Cys Ala Gly His Asp Asn
                645                 650                 655

Asn Gln Pro Asp Ser Phe Ala Ala Leu Leu Ser Ser Leu Asn Glu Leu
                660                 665                 670

Gly Glu Arg Gln Leu Val His Val Val Lys Trp Ala Lys Ala Leu Pro
            675                 680                 685

Gly Phe Arg Asn Leu His Val Asp Asp Gln Met Ala Val Ile Gln Tyr
690                 695                 700

Ser Trp Met Gly Leu Met Val Phe Ala Met Gly Trp Arg Ser Phe Thr
705                 710                 715                 720

Asn Val Asn Ser Arg Met Leu Tyr Phe Ala Pro Asp Leu Val Phe Asn
                725                 730                 735

Glu Tyr Arg Met His Lys Ser Arg Met Tyr Ser Gln Cys Val Arg Met
            740                 745                 750

Arg His Leu Ser Gln Glu Phe Gly Trp Leu Gln Ile Thr Pro Gln Glu
            755                 760                 765

Phe Leu Cys Met Lys Ala Leu Leu Leu Phe Ser Ile Ile Pro Val Asp
            770                 775                 780

Gly Leu Lys Asn Gln Lys Phe Phe Asp Glu Leu Arg Met Asn Tyr Ile
785                 790                 795                 800
```

```
Lys Glu Leu Asp Arg Ile Ile Ala Cys Lys Arg Lys Asn Pro Thr Ser
                805                 810                 815

Cys Ser Arg Arg Phe Tyr Gln Leu Thr Lys Leu Leu Asp Ser Val Gln
            820                 825                 830

Pro Ile Ala Arg Glu Leu His Gln Phe Thr Phe Asp Leu Leu Ile Lys
        835                 840                 845

Ser His Met Val Ser Val Asp Phe Pro Glu Met Met Ala Glu Ile Ile
    850                 855                 860

Ser Val Gln Val Pro Lys Ile Leu Ser Gly Lys Val Lys Pro Ile Tyr
865                 870                 875                 880

Phe His Thr Gln

<210> SEQ ID NO 11
<211> LENGTH: 777
<212> TYPE: PRT
<213> ORGANISM: Lithobates catesbeiana

<400> SEQUENCE: 11

Met Glu Val His Ile Gly Leu Gly Gly Val Tyr Lys Gln Pro Pro Gly
1               5                   10                  15

Lys Met Ile Arg Gly Ala Phe Glu Asn Leu Phe Leu Ser Val Arg Glu
            20                  25                  30

Ala Leu Gln Gly Glu Arg Arg Ser Ala Ala Ser Leu Asp Thr Ser Ser
        35                  40                  45

Pro Ile Ser Ala Cys Val His Pro His Pro Thr Trp Asn Glu Pro Ser
    50                  55                  60

Thr Trp Thr Glu Val Arg Gly Thr Pro Trp Arg Glu Pro Gln Gly Ala
65                  70                  75                  80

Gln Pro Asp Pro Pro Cys Ser Pro Arg Ser Gln Ala Pro Gln Phe
                85                  90                  95

Thr Leu Ser Ser Cys Thr Thr Glu Leu Lys Glu Ile Leu Gly Glu Gln
            100                 105                 110

Gly Gly Met Pro Glu Glu Gly Asn Ser Glu Ser Ala Ser Lys Glu Gly
        115                 120                 125

Tyr Pro Glu Ser Ile Ser Asp Ser Ala Lys Glu Ile Cys Lys Ala Val
    130                 135                 140

Ser Val Ser Leu Gly Leu Ser Met Glu Ala Leu Glu His Leu Ser Ala
145                 150                 155                 160

Ala Gly Glu Trp Gln Arg Gly Asp Cys Met Phe Ala Gly Pro Pro His
                165                 170                 175

His Thr Met Gly Ala Gln Thr Cys Gln Val Ala Glu Glu Asp Lys Ser
            180                 185                 190

Asp Thr Ser Phe Ser Gln Tyr Arg Glu Gly Ala Phe Arg Arg Ala Gly
        195                 200                 205

Gln Ser Thr Tyr Ser Ala Gly Lys Ala Pro Glu Asp Gly Ser Ser Leu
    210                 215                 220

Pro Thr Glu Asp Lys Glu Gln Pro Cys Thr Asp Met Ala Leu Ser Glu
225                 230                 235                 240

Pro Gly Ser Leu Arg Ser Arg Gly Met Glu Val Met Pro Ser Leu Thr
                245                 250                 255

Leu Tyr Lys Pro Thr Ala Phe Met Glu Asp Ala Ser Ala Tyr Pro Gly
            260                 265                 270

Arg Asp Tyr Tyr Ser Phe Gln Met Ala Leu Ala Pro His Gly Arg Ile
        275                 280                 285
```

-continued

Lys Val Glu Ser Pro Ile Glu Phe Ala Gly Ser Ala Trp Gly Gly Pro
    290             295                 300

Ser Arg Tyr Ser Glu Phe Pro Gly Phe Ser His Cys Gly Pro Ser Ala
305             310                 315                 320

Asn Trp His Ser Leu Phe Glu Glu Gly Gln Ala Thr Ala Ser Tyr Thr
                325                 330                 335

Asp Ser Ser Leu Tyr Ser Tyr Pro Arg Ser His Val Pro Ala Gly Pro
            340                 345                 350

Asp Gly Glu Phe Ser Ala Glu Ala Trp Tyr Pro Ala Thr Ala Met Leu
        355                 360                 365

Gly Arg Val His Met Ala Val Pro Met Arg Pro Arg Met Thr His Gly
    370                 375                 380

Trp Thr Ala Thr Leu Gly Ile Arg Arg Arg Leu Gly Trp Thr Gly Val
385                 390                 395                 400

Glu Ser Thr Phe Tyr Pro Ile Asp Tyr Tyr Phe Pro Pro Gln Lys Pro
                405                 410                 415

Cys Leu Ser Cys Glu Asp Glu Ala Ser Gly Cys His Tyr Glu Ala Leu
            420                 425                 430

Thr Cys Gly Ser Cys Lys Val Phe Phe Lys Arg Ala Ala Glu Gly Asn
        435                 440                 445

Gln Lys Tyr Leu Cys Ala Ser Arg Asn Asp Cys Thr Ile Asp Lys Phe
    450                 455                 460

Arg Arg Lys Asn Cys Pro Ser Cys Arg Leu Arg Lys Cys Tyr Glu Ala
465                 470                 475                 480

Gly Met Thr Leu Gly Ala Arg Lys Leu Lys Lys Leu Gly Asn Leu Lys
                485                 490                 495

Ala Gln Glu Glu Leu Glu Gly Ser Pro Gly Gln Ser Glu Gly Arg Glu
            500                 505                 510

Met Pro Pro Asn Met Ser Ile Pro Gln Leu Glu Gly Tyr Ser Cys Gln
        515                 520                 525

Pro Ile Phe Leu Asn Val Leu Glu Ala Ile Glu Pro Met Val Val Cys
    530                 535                 540

Ser Gly His Asp Asn Asn Gln Pro Asp Ser Phe Ala Leu Leu Leu Ser
545                 550                 555                 560

Ser Leu Asn Glu Leu Gly Glu Arg Gln Leu Val His Val Val Lys Trp
                565                 570                 575

Ala Lys Ala Leu Pro Gly Phe Arg Asn Leu His Val Asn Asp Gln Met
            580                 585                 590

Thr Val Ile Gln Tyr Ser Trp Met Gly Leu Met Ile Phe Ala Met Gly
        595                 600                 605

Trp Arg Ser Phe Lys Asn Val Asn Ser Arg Met Leu Tyr Phe Ala Pro
    610                 615                 620

Asp Leu Val Phe Asn Glu Tyr Arg Met His Lys Ser Arg Met Tyr Ser
625                 630                 635                 640

Gln Cys Val Arg Met Arg His Leu Ser Gln Glu Phe Gly Trp Leu Gln
                645                 650                 655

Val Thr Pro Glu Glu Phe Leu Cys Asp Glu Gly Pro Ser Ala Leu Ser
            660                 665                 670

Ile Ile Pro Val Glu Gly Leu Lys Asp Gln Lys Cys Phe Asp Glu Leu
        675                 680                 685

Arg Met Asn Tyr Ile Lys Glu Leu Asp Arg Val Ile Ser Cys Lys Arg
    690                 695                 700

```
Asn Asn Pro Ala Ser Ser Pro Arg Phe Phe Asn Leu Pro Lys Leu
705                 710                 715                 720

Leu Gly Ser Val Gln Pro Ile Asp Val Asn Leu Val Gln Phe Thr Phe
            725                 730                 735

Gly Leu Phe Gly Lys Ala Gln Met Val Ser Val Asp Phe Pro Glu Met
                740                 745                 750

Met Ser Glu Ile Ile Ser Val Gln Val Pro Lys Ile Leu Ser Gly Arg
            755                 760                 765

Val Lys Pro Leu Tyr Phe His Ser Ser
        770                 775
```

<210> SEQ ID NO 12
<211> LENGTH: 895
<212> TYPE: PRT
<213> ORGANISM: Macaca fascicularis

<400> SEQUENCE: 12

```
Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Gln Gln Gln Gln Gln Gln Gln Gln Glu Thr
    50                  55                  60

Ser Pro Arg Gln Gln Gln Gln Gln Gln Gly Glu Asp Gly Ser Pro
65                  70                  75                  80

Gln Ala His Arg Arg Gly Pro Thr Gly Tyr Leu Val Leu Asp Glu Glu
                85                  90                  95

Gln Gln Pro Ser Gln Pro Gln Ser Ala Pro Glu Cys His Pro Glu Arg
            100                 105                 110

Gly Cys Val Pro Glu Pro Gly Ala Ala Val Ala Ala Gly Lys Gly Leu
        115                 120                 125

Pro Gln Gln Leu Pro Ala Pro Pro Asp Glu Asp Asp Ser Ala Ala Pro
    130                 135                 140

Ser Thr Leu Ser Leu Leu Gly Pro Thr Phe Pro Gly Leu Ser Ser Cys
145                 150                 155                 160

Ser Thr Asp Leu Lys Asp Ile Leu Ser Glu Ala Ser Thr Met Gln Leu
                165                 170                 175

Leu Gln Gln Gln Gln Gln Glu Ala Val Ser Glu Gly Ser Ser Ser Gly
            180                 185                 190

Arg Ala Arg Glu Ala Ser Gly Ala Pro Thr Ser Ser Lys Asp Asn Tyr
        195                 200                 205

Leu Gly Gly Thr Ser Thr Ile Ser Asp Ser Ala Lys Glu Leu Cys Lys
    210                 215                 220

Ala Val Ser Val Ser Met Gly Leu Gly Val Glu Ala Leu Glu His Leu
225                 230                 235                 240

Ser Pro Gly Glu Gln Leu Arg Gly Asp Cys Met Tyr Ala Pro Val Leu
                245                 250                 255

Gly Val Pro Pro Ala Val Arg Pro Thr Pro Cys Ala Pro Leu Ala Glu
            260                 265                 270

Cys Lys Gly Ser Leu Leu Asp Asp Ser Ala Gly Lys Ser Thr Glu Asp
        275                 280                 285

Thr Ala Glu Tyr Ser Pro Phe Lys Gly Gly Tyr Thr Lys Gly Leu Glu
    290                 295                 300
```

-continued

```
Gly Glu Ser Leu Gly Cys Ser Gly Ser Ala Ala Ala Gly Ser Ser Gly
305                 310                 315                 320

Thr Leu Glu Leu Pro Ser Thr Leu Ser Leu Tyr Lys Ser Gly Ala Leu
                325                 330                 335

Asp Glu Ala Ala Ala Tyr Gln Ser Arg Asp Tyr Tyr Asn Phe Pro Leu
            340                 345                 350

Ala Leu Ala Gly Pro Pro Pro Pro Pro Pro Pro His Pro His Ala
        355                 360                 365

Arg Ile Lys Leu Glu Asn Pro Leu Asp Tyr Gly Ser Ala Trp Ala Ala
        370                 375                 380

Ala Ala Ala Gln Cys Arg Tyr Gly Asp Leu Ala Ser Leu His Gly Ala
385                 390                 395                 400

Gly Ala Ala Gly Pro Gly Ser Gly Ser Pro Ser Ala Ala Ala Ser Ser
                405                 410                 415

Ser Trp His Thr Leu Phe Thr Ala Glu Glu Gly Gln Leu Tyr Gly Pro
                420                 425                 430

Cys Gly Gly Gly Gly Gly Gly Gly Gly Gly Gly Gly Ala Gly
            435                 440                 445

Glu Ala Gly Ala Val Ala Pro Tyr Gly Tyr Thr Arg Pro Pro Gln Gly
    450                 455                 460

Leu Ala Gly Gln Glu Gly Asp Phe Thr Ala Pro Asp Val Trp Tyr Pro
465                 470                 475                 480

Gly Gly Met Val Ser Arg Val Pro Tyr Pro Ser Pro Thr Cys Val Lys
                485                 490                 495

Ser Glu Met Gly Pro Trp Met Asp Ser Tyr Ser Gly Pro Tyr Gly Asp
                500                 505                 510

Met Arg Leu Glu Thr Ala Arg Asp His Val Leu Pro Ile Asp Tyr Tyr
            515                 520                 525

Phe Pro Pro Gln Lys Thr Cys Leu Ile Cys Gly Asp Glu Ala Ser Gly
            530                 535                 540

Cys His Tyr Gly Ala Leu Thr Cys Gly Ser Cys Lys Val Phe Phe Lys
545                 550                 555                 560

Arg Ala Ala Glu Gly Lys Gln Lys Tyr Leu Cys Ala Ser Arg Asn Asp
                565                 570                 575

Cys Thr Ile Asp Lys Phe Arg Arg Lys Asn Cys Pro Ser Cys Arg Leu
            580                 585                 590

Arg Lys Cys Tyr Glu Ala Gly Met Thr Leu Gly Ala Arg Lys Leu Lys
            595                 600                 605

Lys Leu Gly Asn Leu Lys Leu Gln Glu Glu Gly Glu Ala Ser Ser Thr
            610                 615                 620

Thr Ser Pro Thr Glu Glu Thr Ala Gln Lys Leu Thr Val Ser His Ile
625                 630                 635                 640

Glu Gly Tyr Glu Cys Gln Pro Ile Phe Leu Asn Val Leu Glu Ala Ile
                645                 650                 655

Glu Pro Gly Val Val Cys Ala Gly His Asp Asn Asn Gln Pro Asp Ser
            660                 665                 670

Phe Ala Ala Leu Leu Ser Ser Leu Asn Glu Leu Gly Glu Arg Gln Leu
            675                 680                 685

Val His Val Val Lys Trp Ala Lys Ala Leu Pro Gly Phe Arg Asn Leu
        690                 695                 700

His Val Asp Asp Gln Met Ala Val Ile Gln Tyr Ser Trp Met Gly Leu
705                 710                 715                 720
```

```
Met Val Phe Ala Met Gly Trp Arg Ser Phe Thr Asn Val Asn Ser Arg
                725                 730                 735

Met Leu Tyr Phe Ala Pro Asp Leu Val Phe Asn Glu Tyr Arg Met His
            740                 745                 750

Lys Ser Arg Met Tyr Ser Gln Cys Val Arg Met Arg His Leu Ser Gln
        755                 760                 765

Glu Phe Gly Trp Leu Gln Ile Thr Pro Gln Glu Phe Leu Cys Met Lys
    770                 775                 780

Ala Leu Leu Leu Phe Ser Ile Ile Pro Val Asp Gly Leu Lys Asn Gln
785                 790                 795                 800

Lys Phe Phe Asp Glu Leu Arg Met Asn Tyr Ile Lys Glu Leu Asp Arg
                805                 810                 815

Ile Ile Ala Cys Lys Arg Lys Asn Pro Thr Ser Cys Ser Arg Arg Phe
            820                 825                 830

Tyr Gln Leu Thr Lys Leu Leu Asp Ser Val Gln Pro Ile Ala Arg Glu
        835                 840                 845

Leu His Gln Phe Thr Phe Asp Leu Leu Ile Lys Ser His Met Val Ser
    850                 855                 860

Val Asp Phe Pro Glu Met Met Ala Glu Ile Ile Ser Val Gln Val Pro
865                 870                 875                 880

Lys Ile Leu Ser Gly Lys Val Lys Pro Ile Tyr Phe His Thr Gln
                885                 890                 895

<210> SEQ ID NO 13
<211> LENGTH: 895
<212> TYPE: PRT
<213> ORGANISM: Macaca mulatta

<400> SEQUENCE: 13

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Gln Gln Gln Gln Gln Gln Gln Gln Glu Thr
    50                  55                  60

Ser Pro Arg Gln Gln Gln Gln Gln Gln Gly Glu Asp Gly Ser Pro Gln
65                  70                  75                  80

Gln Ala His Arg Arg Gly Pro Thr Gly Tyr Leu Val Leu Asp Glu Glu
                85                  90                  95

Gln Gln Pro Ser Gln Pro Gln Ser Ala Pro Glu Cys His Pro Glu Arg
            100                 105                 110

Gly Cys Val Pro Glu Pro Gly Ala Ala Val Ala Ala Gly Lys Gly Leu
        115                 120                 125

Pro Gln Gln Leu Pro Ala Pro Pro Asp Glu Asp Ser Ala Ala Pro
    130                 135                 140

Ser Thr Leu Ser Leu Leu Gly Pro Thr Phe Pro Gly Leu Ser Ser Cys
145                 150                 155                 160

Ser Ala Asp Leu Lys Asp Ile Leu Ser Glu Ala Ser Thr Met Gln Leu
                165                 170                 175

Leu Gln Gln Gln Gln Gln Glu Ala Val Ser Glu Gly Ser Ser Ser Gly
            180                 185                 190

Arg Ala Arg Glu Ala Ser Gly Ala Pro Thr Ser Ser Lys Asp Asn Tyr
        195                 200                 205
```

-continued

```
Leu Glu Gly Thr Ser Thr Ile Ser Asp Ser Ala Lys Glu Leu Cys Lys
    210                 215                 220
Ala Val Ser Val Ser Met Gly Leu Gly Val Glu Ala Leu Glu His Leu
225                 230                 235                 240
Ser Pro Gly Glu Gln Leu Arg Gly Asp Cys Met Tyr Ala Pro Val Leu
                245                 250                 255
Gly Val Pro Pro Ala Val Arg Pro Thr Pro Cys Ala Pro Leu Ala Glu
            260                 265                 270
Cys Lys Gly Ser Leu Leu Asp Asp Ser Ala Gly Lys Ser Thr Glu Asp
        275                 280                 285
Thr Ala Glu Tyr Ser Pro Phe Lys Gly Tyr Thr Lys Gly Leu Glu
    290                 295                 300
Gly Glu Ser Leu Gly Cys Ser Gly Ser Ala Ala Gly Ser Ser Gly
305                 310                 315                 320
Thr Leu Glu Leu Pro Ser Thr Leu Ser Leu Tyr Lys Ser Gly Ala Leu
                325                 330                 335
Asp Glu Ala Ala Ala Tyr Gln Ser Arg Asp Tyr Tyr Asn Phe Pro Leu
            340                 345                 350
Ala Leu Ala Gly Pro Pro Pro Pro Pro Pro His Pro His Ala
        355                 360                 365
Arg Ile Lys Leu Glu Asn Pro Leu Asp Tyr Gly Ser Ala Trp Ala Ala
    370                 375                 380
Ala Ala Ala Gln Cys Arg Tyr Gly Asp Leu Ala Ser Leu His Gly Ala
385                 390                 395                 400
Gly Ala Ala Gly Pro Gly Ser Gly Ser Pro Ser Ala Ala Ala Ser Ser
                405                 410                 415
Ser Trp His Thr Leu Phe Thr Ala Glu Glu Gly Gln Leu Tyr Gly Pro
            420                 425                 430
Cys Gly Gly Gly Gly Gly Gly Gly Gly Gly Gly Gly Gly Ala Gly
        435                 440                 445
Glu Ala Gly Ala Val Ala Pro Tyr Gly Tyr Thr Arg Pro Pro Gln Gly
    450                 455                 460
Leu Ala Gly Gln Glu Gly Asp Phe Thr Ala Pro Asp Val Trp Tyr Pro
465                 470                 475                 480
Gly Gly Met Val Ser Arg Val Pro Tyr Pro Ser Pro Thr Cys Val Lys
                485                 490                 495
Ser Glu Met Gly Pro Trp Met Asp Ser Tyr Ser Gly Pro Tyr Gly Asp
            500                 505                 510
Met Arg Leu Glu Thr Ala Arg Asp His Val Leu Pro Ile Asp Tyr Tyr
    515                 520                 525
Phe Pro Pro Gln Lys Thr Cys Leu Ile Cys Gly Asp Glu Ala Ser Gly
530                 535                 540
Cys His Tyr Gly Ala Leu Thr Cys Gly Ser Cys Lys Val Phe Phe Lys
545                 550                 555                 560
Arg Ala Ala Glu Gly Lys Gln Lys Tyr Leu Cys Ala Ser Arg Asn Asp
                565                 570                 575
Cys Thr Ile Asp Lys Phe Arg Arg Lys Asn Cys Pro Ser Cys Arg Leu
            580                 585                 590
Arg Lys Cys Tyr Glu Ala Gly Met Thr Leu Gly Ala Arg Lys Leu Lys
        595                 600                 605
Lys Leu Gly Asn Leu Lys Leu Gln Glu Glu Gly Glu Ala Ser Ser Thr
    610                 615                 620
```

-continued

Thr Ser Pro Thr Glu Thr Ala Gln Lys Leu Thr Val Ser His Ile
625                 630                 635                 640

Glu Gly Tyr Glu Cys Gln Pro Ile Phe Leu Asn Val Leu Glu Ala Ile
            645                 650                 655

Glu Pro Gly Val Val Cys Ala Gly His Asp Asn Asn Gln Pro Asp Ser
                660                 665                 670

Phe Ala Ala Leu Leu Ser Ser Leu Asn Glu Leu Gly Glu Arg Gln Leu
        675                 680                 685

Val His Val Val Lys Trp Ala Lys Ala Leu Pro Gly Phe Arg Asn Leu
    690                 695                 700

His Val Asp Asp Gln Met Ala Val Ile Gln Tyr Ser Trp Met Gly Leu
705                 710                 715                 720

Met Val Phe Ala Met Gly Trp Arg Ser Phe Thr Asn Val Asn Ser Arg
                725                 730                 735

Met Leu Tyr Phe Ala Pro Asp Leu Val Phe Asn Glu Tyr Arg Met His
            740                 745                 750

Lys Ser Arg Met Tyr Ser Gln Cys Val Arg Met Arg His Leu Ser Gln
        755                 760                 765

Glu Phe Gly Trp Leu Gln Ile Thr Pro Gln Glu Phe Leu Cys Met Lys
770                 775                 780

Ala Leu Leu Leu Phe Ser Ile Ile Pro Val Asp Gly Leu Lys Asn Gln
785                 790                 795                 800

Lys Phe Phe Asp Glu Leu Arg Met Asn Tyr Ile Lys Glu Leu Asp Arg
                805                 810                 815

Ile Ile Ala Cys Lys Arg Lys Asn Pro Thr Ser Cys Ser Arg Arg Phe
            820                 825                 830

Tyr Gln Leu Thr Lys Leu Leu Asp Ser Val Gln Pro Ile Ala Arg Glu
        835                 840                 845

Leu His Gln Phe Thr Phe Asp Leu Leu Ile Lys Ser His Met Val Ser
850                 855                 860

Val Asp Phe Pro Glu Met Met Ala Glu Ile Ile Ser Val Gln Val Pro
865                 870                 875                 880

Lys Ile Leu Ser Gly Lys Val Lys Pro Ile Tyr Phe His Thr Gln
                885                 890                 895

<210> SEQ ID NO 14
<211> LENGTH: 911
<212> TYPE: PRT
<213> ORGANISM: Pan troglodyte

<400> SEQUENCE: 14

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Gln Gln Gln Gln Gln Gln Gln Gln
    50                  55                  60

Gln Gln Gln Gln Gln Gln Gln Gln Gln Gln Gln Gln Gln Gln Glu Thr
65                  70                  75                  80

Ser Pro Arg Gln Gln Gln Gln Gly Glu Asp Gly Ser Pro Gln Ala
                85                  90                  95

His Arg Arg Gly Pro Thr Gly Tyr Leu Val Leu Asp Glu Glu Gln Gln
            100                 105                 110

```
Pro Ser Gln Pro Gln Ser Ala Pro Glu Cys His Pro Glu Arg Gly Cys
            115                 120                 125

Val Pro Glu Pro Gly Ala Ala Val Ala Ser Lys Gly Leu Pro Gln
    130                 135                 140

Gln Leu Pro Ala Pro Pro Asp Glu Asp Ser Ala Ala Pro Ser Thr
145                 150                 155                 160

Leu Ser Leu Leu Gly Pro Thr Phe Pro Gly Leu Ser Ser Cys Ser Ala
                165                 170                 175

Asp Leu Lys Asp Ile Leu Ser Glu Ala Ser Thr Met Gln Leu Leu Gln
            180                 185                 190

Gln Gln Gln Gln Glu Ala Val Ser Glu Gly Ser Ser Ser Gly Arg Ala
            195                 200                 205

Arg Glu Ala Ser Gly Ala Pro Thr Ser Ser Lys Asp Asn Tyr Leu Gly
    210                 215                 220

Gly Thr Ser Thr Ile Ser Asp Ser Ala Lys Glu Leu Cys Lys Ala Val
225                 230                 235                 240

Ser Val Ser Met Gly Leu Gly Val Glu Ala Leu Glu His Leu Ser Pro
                245                 250                 255

Gly Glu Gln Leu Arg Gly Asp Cys Met Tyr Ala Pro Leu Leu Gly Val
            260                 265                 270

Pro Pro Ala Val Arg Pro Thr Pro Cys Ala Pro Leu Ala Glu Cys Lys
            275                 280                 285

Gly Ser Leu Leu Asp Asp Ser Ala Gly Lys Ser Thr Glu Asp Thr Ala
            290                 295                 300

Glu Tyr Ser Pro Phe Lys Gly Gly Tyr Thr Lys Gly Leu Glu Gly Glu
305                 310                 315                 320

Ser Leu Gly Cys Ser Gly Ser Ala Ala Gly Ser Ser Gly Thr Leu
                325                 330                 335

Glu Leu Pro Ser Thr Leu Ser Leu Tyr Lys Ser Gly Ala Leu Asp Glu
                340                 345                 350

Ala Ala Ala Tyr Gln Ser Arg Asp Tyr Tyr Asn Phe Pro Leu Ala Leu
            355                 360                 365

Ala Gly Pro Pro Pro Pro Pro Pro Pro His Pro His Ala Arg Ile
    370                 375                 380

Lys Leu Glu Asn Pro Leu Asp Tyr Gly Ser Ala Trp Ala Ala Ala
385                 390                 395                 400

Ala Gln Cys Arg Tyr Gly Asp Leu Ala Ser Leu His Gly Ala Gly Ala
            405                 410                 415

Ala Gly Pro Gly Ser Gly Ser Pro Ser Ala Ala Ala Ser Ser Ser Trp
            420                 425                 430

His Thr Leu Phe Thr Ala Glu Glu Gly Gln Leu Tyr Gly Pro Cys Gly
            435                 440                 445

Gly Gly Gly Gly Gly Gly Gly Gly Gly Gly Gly Gly Gly
450                 455                 460

Glu Ala Gly Ala Val Ala Pro Tyr Gly Tyr Thr Arg Pro Pro Gln Gly
465                 470                 475                 480

Leu Ala Gly Gln Glu Gly Asp Phe Thr Ala Pro Asp Val Trp Tyr Pro
            485                 490                 495

Gly Gly Met Val Ser Arg Val Pro Tyr Pro Ser Pro Thr Cys Val Lys
            500                 505                 510

Ser Glu Met Gly Pro Trp Met Asp Ser Tyr Ser Gly Pro Tyr Gly Asp
            515                 520                 525
```

```
Met Arg Leu Glu Thr Ala Arg Asp His Val Leu Pro Ile Asp Tyr Tyr
    530                 535                 540

Phe Pro Pro Gln Lys Thr Cys Leu Ile Cys Gly Asp Glu Ala Ser Gly
545                 550                 555                 560

Cys His Tyr Gly Ala Leu Thr Cys Gly Ser Cys Lys Val Phe Phe Lys
                565                 570                 575

Arg Ala Ala Glu Gly Lys Gln Lys Tyr Leu Cys Ala Ser Arg Asn Asp
                580                 585                 590

Cys Thr Ile Asp Lys Phe Arg Arg Lys Asn Cys Pro Ser Cys Arg Leu
            595                 600                 605

Arg Lys Cys Tyr Glu Ala Gly Met Thr Leu Gly Ala Arg Lys Leu Lys
610                 615                 620

Lys Leu Gly Asn Leu Lys Leu Gln Glu Glu Gly Glu Ala Ser Ser Thr
625                 630                 635                 640

Thr Ser Pro Thr Glu Glu Thr Thr Gln Lys Leu Thr Val Ser His Ile
                645                 650                 655

Glu Gly Tyr Glu Cys Gln Pro Ile Phe Leu Asn Val Leu Glu Ala Ile
                660                 665                 670

Glu Pro Gly Val Val Cys Ala Gly His Asp Asn Asn Gln Pro Asp Ser
                675                 680                 685

Phe Ala Ala Leu Leu Ser Ser Leu Asn Glu Leu Gly Glu Arg Gln Leu
690                 695                 700

Val His Val Val Lys Trp Ala Lys Ala Leu Pro Gly Phe Arg Asn Leu
705                 710                 715                 720

His Val Asp Asp Gln Met Ala Val Ile Gln Tyr Ser Trp Met Gly Leu
                725                 730                 735

Met Val Phe Ala Met Gly Trp Arg Ser Phe Thr Asn Val Asn Ser Arg
                740                 745                 750

Met Leu Tyr Phe Ala Pro Asp Leu Val Phe Asn Glu Tyr Arg Met His
                755                 760                 765

Lys Ser Arg Met Tyr Ser Gln Cys Val Arg Met Arg His Leu Ser Gln
770                 775                 780

Glu Phe Gly Trp Leu Gln Ile Thr Pro Gln Glu Phe Leu Cys Met Lys
785                 790                 795                 800

Ala Leu Leu Leu Phe Ser Ile Ile Pro Val Asp Gly Leu Lys Asn Gln
                805                 810                 815

Lys Phe Phe Asp Glu Leu Arg Met Asn Tyr Ile Lys Glu Leu Asp Arg
                820                 825                 830

Ile Ile Ala Cys Lys Arg Lys Asn Pro Thr Ser Cys Ser Arg Arg Phe
            835                 840                 845

Tyr Gln Leu Thr Lys Leu Leu Asp Ser Val Gln Pro Ile Ala Arg Glu
850                 855                 860

Leu His Gln Phe Thr Phe Asp Leu Leu Ile Lys Ser His Met Val Ser
865                 870                 875                 880

Val Asp Phe Pro Glu Met Met Ala Glu Ile Ile Ser Val Gln Val Pro
                885                 890                 895

Lys Ile Leu Ser Gly Lys Val Lys Pro Ile Tyr Phe His Thr Gln
                900                 905                 910
```

<210> SEQ ID NO 15
<211> LENGTH: 895
<212> TYPE: PRT
<213> ORGANISM: Papio hamadryas

<400> SEQUENCE: 15

```
Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Gln Gln Gln Gln Gln Gln Gln Gln Gln Glu
50                  55                  60

Thr Ser Pro Arg Gln Gln Gln Gln Gln Gly Glu Asp Gly Ser Pro
65                  70                  75                  80

Gln Ala His Arg Arg Gly Pro Thr Gly Tyr Leu Val Leu Asp Glu Glu
                85                  90                  95

Gln Gln Pro Ser Gln Pro Gln Ser Ala Pro Glu Cys His Pro Glu Arg
            100                 105                 110

Gly Cys Val Pro Glu Pro Gly Ala Ala Val Ala Ala Gly Lys Gly Leu
        115                 120                 125

Pro Gln Gln Leu Pro Ala Pro Pro Asp Glu Asp Asp Ser Ala Ala Pro
130                 135                 140

Ser Thr Leu Ser Leu Leu Gly Pro Thr Phe Pro Gly Leu Ser Ser Cys
145                 150                 155                 160

Ser Ala Asp Leu Lys Asp Ile Leu Ser Glu Ala Ser Thr Met Gln Leu
            165                 170                 175

Leu Gln Gln Gln Gln Gln Glu Ala Val Ser Glu Gly Ser Ser Ser Gly
            180                 185                 190

Arg Ala Arg Glu Ala Ser Gly Ala Pro Thr Ser Ser Lys Asp Asn Tyr
        195                 200                 205

Leu Gly Gly Thr Ser Thr Ile Ser Asp Ser Ala Lys Glu Leu Cys Lys
210                 215                 220

Ala Val Ser Val Ser Met Gly Leu Gly Val Glu Ala Leu Glu His Leu
225                 230                 235                 240

Ser Pro Gly Glu Gln Leu Arg Gly Asp Cys Met Tyr Ala Pro Val Leu
            245                 250                 255

Gly Val Pro Pro Ala Val Arg Pro Thr Pro Cys Ala Pro Leu Ala Glu
        260                 265                 270

Cys Lys Gly Ser Leu Leu Asp Asp Ser Ala Gly Lys Ser Thr Glu Asp
    275                 280                 285

Thr Ala Glu Tyr Ser Pro Phe Lys Gly Gly Tyr Thr Lys Gly Leu Glu
290                 295                 300

Gly Glu Ser Leu Gly Cys Ser Gly Ser Ala Ala Gly Ser Ser Gly
305                 310                 315                 320

Thr Leu Glu Leu Pro Ser Thr Leu Ser Leu Tyr Lys Ser Gly Ala Leu
            325                 330                 335

Asp Glu Ala Ala Ala Tyr Gln Ser Arg Asp Tyr Tyr Asn Phe Pro Leu
            340                 345                 350

Ala Leu Ala Gly Pro Pro Pro Pro Pro Pro His Pro His Ala
        355                 360                 365

Arg Ile Lys Leu Glu Asn Pro Leu Asp Tyr Gly Ser Ala Trp Ala Ala
    370                 375                 380

Ala Ala Ala Gln Cys Arg Tyr Gly Glu Leu Ala Ser Leu His Gly Ala
385                 390                 395                 400

Gly Ala Ala Gly Pro Gly Ser Gly Ser Pro Ser Ala Ala Ala Ser Ser
                405                 410                 415
```

```
Ser Trp His Thr Leu Phe Thr Ala Glu Gly Gln Leu Tyr Gly Pro
            420                 425                 430

Cys Gly Gly Gly Gly Gly Gly Gly Gly Gly Gly Gly Ala Gly
            435                 440                 445

Glu Ala Gly Ala Val Ala Pro Tyr Gly Tyr Thr Arg Pro Pro Gln Gly
            450                 455                 460

Leu Ala Gly Gln Glu Gly Asp Phe Thr Ala Pro Asp Val Trp Tyr Pro
465                 470                 475                 480

Gly Gly Met Val Ser Arg Val Pro Tyr Pro Ser Pro Thr Cys Val Lys
                485                 490                 495

Ser Glu Met Gly Pro Trp Met Asp Ser Tyr Ser Gly Pro Tyr Gly Asp
                500                 505                 510

Met Arg Leu Glu Thr Ala Arg Asp His Val Leu Pro Ile Asp Tyr Tyr
            515                 520                 525

Phe Pro Pro Gln Lys Thr Cys Leu Ile Cys Gly Asp Glu Ala Ser Gly
            530                 535                 540

Cys His Tyr Gly Ala Leu Thr Cys Gly Ser Cys Lys Val Phe Phe Lys
545                 550                 555                 560

Arg Ala Ala Glu Gly Lys Gln Lys Tyr Leu Cys Ala Ser Arg Asn Asp
                565                 570                 575

Cys Thr Ile Asp Lys Phe Arg Arg Lys Asn Cys Pro Ser Cys Arg Leu
            580                 585                 590

Arg Lys Cys Tyr Glu Ala Gly Met Thr Leu Gly Ala Arg Lys Leu Lys
                595                 600                 605

Lys Leu Gly Asn Leu Lys Leu Gln Glu Glu Gly Glu Ala Ser Ser Thr
610                 615                 620

Thr Ser Pro Thr Glu Glu Thr Ala Gln Lys Leu Thr Val Ser His Ile
625                 630                 635                 640

Glu Gly Tyr Glu Cys Gln Pro Ile Phe Leu Asn Val Leu Glu Ala Ile
                645                 650                 655

Glu Pro Gly Val Val Cys Ala Gly His Asp Asn Asn Gln Pro Asp Ser
                660                 665                 670

Phe Ala Ala Leu Leu Ser Ser Leu Asn Glu Leu Gly Glu Arg Gln Leu
            675                 680                 685

Val His Val Val Lys Trp Ala Lys Ala Leu Pro Gly Phe Arg Asn Leu
            690                 695                 700

His Val Asp Asp Gln Met Ala Val Ile Gln Tyr Ser Trp Met Gly Leu
705                 710                 715                 720

Met Val Phe Ala Met Gly Trp Arg Ser Phe Thr Asn Val Asn Ser Arg
                725                 730                 735

Met Leu Tyr Phe Ala Pro Asp Leu Val Phe Asn Glu Tyr Arg Met His
            740                 745                 750

Lys Ser Arg Met Tyr Ser Gln Cys Val Arg Met Arg His Leu Ser Gln
            755                 760                 765

Glu Phe Gly Trp Leu Gln Ile Thr Pro Gln Glu Phe Leu Cys Met Lys
            770                 775                 780

Ala Leu Leu Leu Phe Ser Ile Ile Pro Val Asp Gly Leu Lys Asn Gln
785                 790                 795                 800

Lys Phe Phe Asp Glu Leu Arg Met Asn Tyr Ile Lys Glu Leu Asp Arg
                805                 810                 815

Ile Ile Ala Cys Lys Arg Lys Asn Pro Thr Ser Cys Ser Arg Arg Phe
            820                 825                 830

Tyr Gln Leu Thr Lys Leu Leu Asp Ser Val Gln Pro Ile Ala Arg Glu
```

```
                    835                 840                 845
Leu His Gln Phe Thr Phe Asp Leu Leu Ile Lys Ser His Met Val Ser
    850                 855                 860
Val Asp Phe Pro Glu Met Met Ala Glu Ile Ile Ser Val Gln Val Pro
865                 870                 875                 880
Lys Ile Leu Ser Gly Lys Val Lys Pro Ile Tyr Phe His Thr Gln
                885                 890                 895

<210> SEQ ID NO 16
<211> LENGTH: 896
<212> TYPE: PRT
<213> ORGANISM: Sus scrofa

<400> SEQUENCE: 16

Met Glu Val Gln Leu Gly Leu Gly Arg Val Tyr Pro Arg Pro Pro Ser
1               5                   10                  15
Lys Thr Phe Arg Gly Ala Phe Gln Asn Leu Phe Gln Ser Val Arg Glu
                20                  25                  30
Val Ile Gln Asn Pro Gly Pro Arg His Pro Glu Ala Ala Ser Ala Ala
            35                  40                  45
Pro Pro Gly Ala Arg Leu Gln Gln Gln Gln Leu Gln Gln Gln Glu Thr
        50                  55                  60
Ser Pro Arg Arg Gln Gln Gln Gln Gln Gln Pro Ser Glu Asp Gly
65                  70                  75                  80
Ser Pro Gln Val Gln Ser Arg Gly Pro Thr Gly Tyr Leu Ala Leu Asp
                85                  90                  95
Glu Lys Gln Gln Pro Ser Gln Gln Ser Ala Pro Glu Cys His Pro
                100                 105                 110
Glu Ser Gly Cys Thr Pro Glu Pro Gly Ala Ala Ser Ala Ala Ser Lys
            115                 120                 125
Gly Leu Gln Gln Gln Pro Pro Ala Pro Pro Asp Glu Asp Asp Ser Ala
        130                 135                 140
Ala Pro Ser Thr Leu Ser Leu Leu Gly Pro Thr Phe Pro Gly Leu Ser
145                 150                 155                 160
Ser Cys Ser Thr Asp Leu Lys Asp Ile Leu Ser Glu Ala Gly Thr Met
                165                 170                 175
Gln Leu Leu Gln Gln Gln Gln Gln Gln Gln Gln Gln Gln Glu Ala Val
            180                 185                 190
Ser Glu Gly Asn Ser Ser Gly Arg Ala Arg Glu Ala Thr Gly Ala Pro
        195                 200                 205
Ile Ser Ser Lys Asp Ser Tyr Leu Gly Gly Ser Ser Thr Ile Ser Asp
        210                 215                 220
Ser Ala Lys Glu Leu Cys Lys Ala Val Ser Val Ser Met Gly Leu Gly
225                 230                 235                 240
Val Glu Ala Leu Glu His Leu Ser Pro Gly Glu Gln Leu Arg Gly Asp
                245                 250                 255
Cys Met Tyr Ala Pro Leu Leu Thr Gly Pro Pro Ser Val Arg Pro Thr
            260                 265                 270
Pro Cys Ala Pro Leu Ala Glu Cys Lys Gly Ser Leu Leu Asp Asp Gly
        275                 280                 285
Pro Gly Lys Ser Asn Glu Glu Thr Ala Glu Tyr Ser Pro Phe Lys Ala
        290                 295                 300
Gly Tyr Thr Lys Gly Leu Asp Ser Glu Ser Leu Gly Cys Ser Ser Gly
305                 310                 315                 320
```

-continued

```
Gly Glu Ala Gly Gly Ser Gly Thr Leu Glu Leu Pro Ser Ala Leu Ser
                325                 330                 335

Leu Tyr Lys Ser Gly Ala Leu Asp Asp Val Ala Ala Tyr Pro Ser Arg
            340                 345                 350

Asp Tyr Tyr Asn Phe Pro Leu Ala Leu Ala Gly Pro Pro Pro Pro
        355                 360                 365

Pro Pro Pro His Pro His Ala Arg Ile Lys Leu Glu Asn Pro Leu Asp
    370                 375                 380

Tyr Gly Ser Ala Trp Ala Ala Ala Ala Gln Cys Arg Tyr Gly Asp
385                 390                 395                 400

Leu Ala Ser Leu His Gly Gly Ala Pro Gly Pro Gly Ser Gly Ser
                405                 410                 415

Pro Ser Ala Thr Ser Ser Ser Trp His Thr Leu Phe Thr Ala Glu
            420                 425                 430

Glu Ser Gln Leu Tyr Gly Pro Cys Gly Gly Gly Gly Ser Ala
        435                 440                 445

Gly Glu Ala Gly Ala Val Ala Pro Tyr Gly Tyr Thr Arg Pro Pro Gln
    450                 455                 460

Gly Leu Ala Gly Gln Glu Gly Asp Leu Ala Ile Pro Asp Ile Trp Tyr
465                 470                 475                 480

Pro Gly Gly Val Val Ser Arg Val Pro Tyr Pro Ser Pro Ser Cys Val
                485                 490                 495

Lys Ser Glu Met Gly Pro Trp Met Glu Ser Tyr Ser Gly Pro Tyr Gly
            500                 505                 510

Asp Met Arg Leu Glu Pro Thr Arg Asp His Val Leu Pro Ile Asp Tyr
        515                 520                 525

Tyr Phe Pro Pro Gln Lys Thr Cys Leu Ile Cys Gly Asp Glu Ala Ser
    530                 535                 540

Gly Cys His Tyr Gly Ala Leu Thr Cys Gly Ser Cys Lys Val Phe Phe
545                 550                 555                 560

Lys Arg Ala Ala Glu Gly Lys Gln Lys Tyr Leu Cys Ala Ser Arg Asn
                565                 570                 575

Asp Cys Thr Ile Asp Lys Phe Arg Arg Lys Asn Cys Pro Ser Cys Arg
            580                 585                 590

Leu Arg Lys Cys Tyr Glu Ala Gly Met Thr Leu Gly Ala Arg Lys Leu
        595                 600                 605

Lys Lys Leu Gly Asn Leu Lys Leu Gln Glu Glu Gly Glu Ala Ser Ser
    610                 615                 620

Ala Thr Ser Pro Thr Glu Glu Pro Ala Gln Lys Leu Thr Val Ser His
625                 630                 635                 640

Ile Glu Gly Tyr Glu Cys Gln Pro Ile Phe Leu Asn Val Leu Glu Ala
                645                 650                 655

Ile Glu Pro Gly Val Val Cys Ala Gly His Asp Asn Gln Pro Asp
            660                 665                 670

Ser Phe Ala Ala Leu Leu Ser Ser Leu Asn Glu Leu Gly Glu Arg Gln
        675                 680                 685

Leu Val His Val Val Lys Trp Ala Lys Ala Leu Pro Gly Phe Arg Asn
    690                 695                 700

Leu His Val Asp Asp Gln Met Ala Val Ile Gln Tyr Ser Trp Met Gly
705                 710                 715                 720

Leu Met Val Phe Ala Met Gly Trp Arg Ser Phe Thr Asn Val Asn Ser
                725                 730                 735

Arg Met Leu Tyr Phe Ala Pro Asp Leu Val Phe Asn Glu Tyr Arg Met
```

```
                740                 745                 750
His Lys Ser Arg Met Tyr Ser Gln Cys Val Arg Met Arg His Leu Ser
            755                 760                 765

Gln Glu Phe Gly Trp Leu Gln Ile Thr Pro Gln Glu Phe Leu Cys Met
        770                 775                 780

Lys Ala Leu Leu Leu Phe Ser Ile Ile Pro Val Asp Gly Leu Lys Asn
785                 790                 795                 800

Gln Lys Phe Phe Asp Glu Leu Arg Met Asn Tyr Ile Lys Glu Leu Asp
                805                 810                 815

Arg Ile Ile Ala Cys Lys Arg Lys Asn Pro Thr Ser Cys Ser Arg Arg
            820                 825                 830

Phe Tyr Gln Leu Thr Lys Leu Leu Asp Ser Val Gln Pro Ile Ala Arg
        835                 840                 845

Glu Leu His Gln Phe Thr Phe Asp Leu Leu Ile Lys Ser His Met Val
    850                 855                 860

Ser Val Asp Phe Pro Glu Met Met Ala Glu Ile Ile Ser Val Gln Val
865                 870                 875                 880

Pro Lys Ile Leu Ser Gly Lys Val Lys Pro Ile Tyr Phe His Thr Gln
                885                 890                 895

<210> SEQ ID NO 17
<211> LENGTH: 709
<212> TYPE: PRT
<213> ORGANISM: Oryctolagus cuniculus

<400> SEQUENCE: 17

His His Gln Gln Gln Gln Asp Ala Ala Thr Glu Gly Ser Ser Ser Gly
1               5                   10                  15

Arg Ala Arg Arg Pro Ser Gly Ala Ser Thr Ser Ser Lys Asp Ser Tyr
            20                  25                  30

Leu Gly Ser Thr Ser Val Ile Ser Asp Ser Ala Lys Glu Leu Cys Lys
        35                  40                  45

Ala Val Ser Val Ser Leu Gly Leu Gly Val Glu Ala Leu Glu His Leu
    50                  55                  60

Ser Ser Gly Glu Gln Leu Arg Gly Asp Cys Met Tyr Ala Pro Leu Leu
65                  70                  75                  80

Gly Gly Pro Pro Val Val Arg Pro Thr Pro Cys Leu Pro Leu Val Glu
                85                  90                  95

Cys Lys Gly Ser Leu Leu Asp Asp Gly Pro Gly Lys Gly Thr Glu Glu
            100                 105                 110

Thr Ala Glu Tyr Thr Pro Phe Lys Gly Gly Tyr Asn Lys Gly Leu Glu
        115                 120                 125

Ala Glu Ser Leu Gly Cys Ser Gly Ser Gly Glu Ala Gly Ser Ser Gly
    130                 135                 140

Thr Leu Glu Leu Pro Ser Thr Leu Ser Leu Tyr Lys Ser Gly Thr Leu
145                 150                 155                 160

Asp Glu Ala Ala Ala Tyr Gln Thr Arg Asp Tyr Tyr Asn Phe Pro Leu
                165                 170                 175

Ala Leu Ala Gly Gln Pro Pro Pro His Pro Arg Ile Lys Leu
            180                 185                 190

Glu Asn Pro Leu Asp Tyr Gly Ser Ala Trp Ala Ala Ala Ala Ala Gln
        195                 200                 205

Cys Arg Tyr Gly Asp Leu Ala Ser Leu His Gly Gly Ala Ala Ala Gly
    210                 215                 220
```

-continued

Pro Gly Ser Gly Ser Pro Ser Thr Ala Ala Ser Ser Trp His Thr
225                 230                 235                 240

Leu Phe Thr Thr Glu Glu Gly Gln Leu Tyr Gly Leu Cys Gly Gly Gly
            245                 250                 255

Gly Gly Ser Gly Pro Gly Glu Ala Gly Ala Val Ala Pro Tyr Gly Tyr
        260                 265                 270

Thr Arg Pro Pro Gln Gly Leu Thr Gly Gln Glu Gly Asp Phe Pro Ala
    275                 280                 285

Pro Glu Val Trp Tyr Pro Gly Val Val Ser Arg Val Pro Tyr Pro
290                 295                 300

Asn Pro Ser Cys Val Lys Ser Glu Met Gly Pro Trp Met Glu Ser Tyr
305                 310                 315                 320

Ser Gly Pro Tyr Gly Asp Met Arg Leu Glu Thr Ala Arg Asp His Val
            325                 330                 335

Leu Pro Ile Asp Tyr Tyr Phe Pro Pro Gln Lys Thr Cys Leu Ile Cys
        340                 345                 350

Gly Asp Glu Ala Ser Gly Cys His Tyr Gly Ala Leu Thr Cys Gly Ser
    355                 360                 365

Cys Lys Val Phe Phe Lys Arg Ala Ala Glu Gly Lys Gln Lys Tyr Leu
370                 375                 380

Cys Ala Ser Arg Asn Asp Cys Thr Ile Asp Lys Phe Arg Arg Lys Asn
385                 390                 395                 400

Cys Pro Ser Cys Arg Leu Arg Lys Cys Tyr Glu Ala Gly Met Thr Leu
            405                 410                 415

Gly Ala Arg Lys Leu Lys Lys Leu Gly Asn Leu Lys Leu Gln Glu Glu
        420                 425                 430

Gly Glu Ser Ser Ser Ala Ser Ser Pro Thr Glu Asp Thr Thr Gln Lys
    435                 440                 445

Leu Thr Val Ser His Ile Glu Gly Tyr Glu Cys Gln Pro Ile Phe Leu
450                 455                 460

Asn Val Leu Glu Ala Ile Glu Pro Gly Val Val Cys Ala Gly His Asp
465                 470                 475                 480

Asn Asn Gln Pro Asp Ser Phe Ala Ala Leu Leu Ser Ser Leu Asn Glu
            485                 490                 495

Leu Gly Glu Arg Gln Leu Val His Val Val Lys Trp Ala Lys Ala Leu
        500                 505                 510

Pro Gly Phe Arg Asn Leu His Val Asp Asp Gln Met Ala Val Ile Gln
    515                 520                 525

Tyr Ser Trp Met Gly Leu Met Val Phe Ala Met Gly Trp Arg Ser Phe
530                 535                 540

Thr Asn Val Asn Ser Arg Met Leu Tyr Phe Ala Pro Asp Leu Val Phe
545                 550                 555                 560

Asn Glu Tyr Arg Met His Lys Ser Arg Met Tyr Ser Gln Cys Val Arg
            565                 570                 575

Met Arg His Leu Ser Gln Glu Phe Gly Trp Leu Gln Ile Thr Pro Gln
        580                 585                 590

Glu Phe Leu Cys Met Lys Ala Leu Leu Leu Phe Ser Ile Ile Pro Val
    595                 600                 605

Asp Gly Leu Lys Asn Gln Lys Phe Phe Asp Glu Leu Arg Met Asn Tyr
        610                 615                 620

Ile Lys Glu Leu Asp Arg Ile Ile Ala Cys Lys Arg Lys Asn Pro Thr
625                 630                 635                 640

Ser Cys Ser Arg Arg Phe Tyr Gln Leu Thr Lys Leu Leu Asp Ser Val

```
                  645                 650                 655
Gln Pro Ile Ala Arg Glu Leu His Gln Phe Thr Phe Asp Leu Leu Ile
            660                 665                 670

Lys Ser His Met Val Ser Val Asp Phe Pro Glu Met Met Ala Glu Ile
        675                 680                 685

Ile Ser Val Gln Val Pro Lys Ile Leu Ser Gly Lys Val Lys Pro Ile
    690                 695                 700

Tyr Phe His Thr Gln
705

<210> SEQ ID NO 18
<211> LENGTH: 2760
<212> TYPE: DNA
<213> ORGANISM: Homo sapiens

<400> SEQUENCE: 18
atggaagtgc agttagggct gggaagggtc taccctcggc cgccgtccaa gacctaccga      60
ggagctttcc agaatctgtt ccagagcgtg cgcgaagtga tccagaaccc gggccccagg     120
cacccagagg ccgcgagcgc agcacctccc ggcgccagtt tgctgctgct gcagcagcag     180
cagcagcagc agcagcagca gcagcagcag cagcagcagc agcagcagca gcagcagcaa     240
gagactagcc ccaggcagca gcagcagcag cagggtgagg atggttctcc ccaagcccat     300
cgtagaggcc ccacaggcta cctggtcctg atgaggaaac agcaaccttc acagccgcag     360
tcggccctgg agtgccaccc cgagagaggt tgcgtcccag agcctggagc cgccgtggcc     420
gccagcaagg ggctgccgca gcagctgcca gcacctccgg acgaggatga ctcagctgcc     480
ccatccacgt tgtccctgct gggccccact tccccggct taagcagctg ctccgctgac     540
cttaaagaca tcctgagcga ggccagcacc atgcaactcc ttcagcaaca gcagcaggaa     600
gcagtatccg aaggcagcag cagcgggaga gcgagggagg cctcgggggc tcccacttcc     660
tccaaggaca attacttagg gggcacttcg accatttctg acaacgccaa ggagttgtgt     720
aaggcagtgt cggtgtccat gggcctgggt gtggaggcgt ggagcatct gagtccaggg     780 aacagcttc gggggattg catgtacgcc ccacttttgg gagttccacc cgctgtgcgt     840
cccactcctt gtgccccatt ggccgaatgc aaaggttctc tgctagacga cagcgcaggc     900
aagagcactg aagatactgc tgagtattcc cctttcaagg gaggttacac caaagggcta     960
gaaggcgaga gcctaggctg ctctggcagc gctgcagcag ggagctccgg acacttgaa    1020 ctgccgtcta ccctgtctct ctacaagtcc ggagcactgg acgaggcagc tgcgtaccag    1080
agtcgcgact actacaactt ccactggctc tggccggac cgccgccccc tccgccgcct    1140
ccccatcccc acgctcgcat caagctggag aacccgctgg actacggcag cgcctgggcg    1200
gctgcggcgg cgcagtgccg ctatgggac ctggcgagcc tgcatggcgc gggtgcagcg    1260
ggacccggtt ctgggtcacc ctcagccgcc gcttcctcat cctggcacac tctcttcaca    1320
gccgaagaag gccagttgta tggaccgtgt ggtggtggtg ggggtggtgg cggcggcggc    1380
ggcggcggcg gcggcggcgg cggcggcggc ggcggcggcg aggcgggagc tgtagccccc    1440
tacggctaca ctcggccccc tcaggggctg gcgggccagg aaagcgactt caccgcacct    1500
gatgtgtggt accctggcgg catggtgagc agagtgccct atcccagtcc cacttgtgtc    1560
aaaagcgaaa tgggccctg gatggatagc tactccggac cttacggga catgcgtttg    1620 gagactgcca gggaccatgt tttgcccatt gactattact ttccacccca gaagacctgc    1680
ctgatctgtg gagatgaagc ttctgggtgt cactatgag ctctcacatg tggaagctgc    1740
```

```
aaggtcttct tcaaaagagc cgctgaaggg aaacagaagt acctgtgcgc cagcagaaat   1800
gattgcacta ttgataaatt ccgaaggaaa aattgtccat cttgtcgtct tcggaaatgt   1860
tatgaagcag ggatgactct gggagcccgg aagctgaaga aacttggtaa tctgaaacta   1920
caggaggaag gagaggcttc cagcaccacc agccccactg aggagacaac ccagaagctg   1980
acagtgtcac acattgaagg ctatgaatgt cagcccatct ttctgaatgt cctggaagcc   2040
attgagccag gtgtagtgtg tgctggacac gacaacaacc agcccgactc ctttgcagcc   2100
ttgctctcta gcctcaatga actgggagag agacagcttg tacacgtggt caagtgggcc   2160
aaggccttgc ctggcttccg caacttacac gtggacgacc agatggctgt cattcagtac   2220
tcctggatgg ggctcatggt gtttgccatg ggctggcgat ccttcaccaa tgtcaactcc   2280
aggatgctct acttcgcccc tgatctggtt ttcaatgagt accgcatgca caagtcccgg   2340
atgtacagcc agtgtgtccg aatgaggcac ctctctcaag agtttggatg ctccaaatc    2400 acccccagg aattcctgtg catgaaagca ctgctactct tcagcattat tccagtggat    2460
gggctgaaaa atcaaaaatt ctttgatgaa cttcgaatga actacatcaa ggaactcgat   2520
cgtatcattg catgcaaaag aaaaaatccc acatcctgct caagacgctt ctaccagctc   2580
accaagctcc tggactccgt gcagcctatt gcgagagagc tgcatcagtt cacttttgac   2640
ctgctaatca agtcacacat ggtgagcgtg gactttccgg aaatgatggc agagatcatc   2700
tctgtgcaag tgcccaagat cctttctggg aaagtcaagc ccatctattt ccacacccag   2760

<210> SEQ ID NO 19
<211> LENGTH: 2760
<212> TYPE: DNA
<213> ORGANISM: Homo sapiens

<400> SEQUENCE: 19
atggaagtgc agttagggct gggaagggtc taccctcggc cgccgtccaa gacctaccga     60
ggagctttcc agaatctgtt ccagagcgtg cgcgaagtga tccagaaccc gggccccagg    120
cacccagagg ccgcgagcgc agcacctccc ggcgccagtt tgctgctgct gcagcagcag    180
cagcagcagc agcagcagca gcagcagcag cagcagcagc agcagcagca gcagcagcaa    240
gagactagcc ccaggcagca gcagcagcag cagggtgagg atggttctcc ccaagcccat    300
cgtagaggcc ccacaggcta cctggtcctg gatgaggaac agcaaccttc acagccgcag    360
tcggccctgg agtgccaccc cgagagaggt tgcgtcccag agcctggagc cgccgtggcc    420
gccagcaagg ggctgccgca gcagctgcca gcacctccgg acgaggatga ctcagctgcc    480
ccatccacgt tgtccctgct gggccccact ttccccggct taagcagctg ctccgctgac    540
cttaaagaca tcctgagcga ggccagcacc atgcaactcc ttcagcaaca gcagcaggaa    600
gcagtatccg aaggcagcag cagcgggaga gcgagggagg cctcgggggc tcccacttcc    660
tccaaggaca attacttagg gggcacttcg accattctg acaacgccaa ggagttgtgt    720
aaggcagtgt cggtgtccat gggcctgggt gtggaggcgt tggagcatct gagtccaggg    780
gaacagcttc gggggattg catgtacgcc ccacttttgg gagttccacc cgctgtgcgt    840
cccactcctt gtgcccatt ggccgaatgc aaaggttctc tgctagacga cagcgcaggc    900
aagagcactg aagatactgc tgagtattcc cctttcaagg gaggttacac caaagggcta    960
gaaggcgaga gcctaggctg ctctggcagc gctgcagcag ggagctccgg gacacttgaa   1020
ctgccgtcta ccctgtctct ctacaagtcc ggagcactgg acgaggcagc tgcgtaccag   1080
```

```
agtcgcgact actacaactt tccactggct ctggccggac cgccgccccc tccgccgcct    1140
ccccatcccc acgctcgcat caagctggag aacccgctgg actacggcag cgcctgggcg    1200
gctgcggcgg cgcagtgccg ctatggggac ctggcgagcc tgcatggcgc gggtgcagcg    1260
ggacccggtt ctgggtcacc ctcagccgcc gcttcctcat cctggcacac tctcttcaca    1320
gccgaagaag gccagttgta tggaccgtgt ggtggtggtg ggggtggtgg cggcggcggc    1380
ggcggcggcg gcggcggcgg cggcggcggc ggcggcggcg aggcgggagc tgtagccccc    1440
tacggctaca ctcggccccc tcaggggctg gcgggccagg aaagcgactt caccgcacct    1500
gatgtgtggt accctggcgg catggtgagc agagtgccct atcccagtcc cacttgtgtc    1560
aaaagcgaaa tgggcccctg gatggatagc tactccggac cttacgggga catgcgtttg    1620
gagactgcca gggaccatgt tttgcccatt gactattact ttccacccca gaagacctgc    1680
ctgatctgtg gagatgaagc ttctgggtgt cactatggag ctctcacatg tggaagctgc    1740
aaggtcttct tcaaaagagc cgctgaaggg aaacagaagt acctgtgcgc cagcagaaat    1800
gattgcacta ttgataaatt ccgaaggaaa aattgtccat cttgtcgtct tcggaaatgt    1860
tatgaagcag ggatgactct gggagcccgg aagctgaaga aacttggtaa tctgaaacta    1920
caggaggaag gagaggcttc cagcaccacc agccccactg aggagacaac ccagaagctg    1980
acagtgtcac acattgaagg ctatgaatgt cagcccatct ttctgaatgt cctggaagcc    2040
attgagccag tgtagtgtg tgctggacac gacaacaacc agcccgactc ctttgcagcc    2100
ttgctctcta gcctcaatga actgggagag agacagcttg tacacgtggt caagtgggcc    2160 aaggcctgc ctggcttccg caacttacac gtggacgacc agatggctgt cattcagtac    2220
tcctggatgg ggctcatggt gtttgccatg ggctggcgat ccttcaccaa tgtcaactcc    2280
aggatgctct acttcgcccc tgatctggtt ttcaatgagt accgcatgca caagtcccgg    2340
atgtacagcc agtgtgtccg aatgaggcac ctctctcaag agtttggatg gctccaaatc    2400 acccccagg aattcctgtg catgaaagca ctgctactct tcagcattat tccagtggat    2460
gggctgaaaa atcaaaaatt ctttgatgaa cttcgaatga actacatcaa ggaactcgat    2520
cgtatcattg catgcaaaag aaaaaatccc acatcctgct caagacgctt ctaccagctc    2580
accaagctcc tggactccgt gcagcctatt gcgagagagc tgcatcagct cacttttgac    2640
ctgctaatca agtcacacat ggtgagcgtg gactttccgg aaatgatggc agagatcatc    2700
tctgtgcaag tgcccaagat cctttctggg aaagtcaagc ccatctattt ccacacccag    2760

<210> SEQ ID NO 20
<211> LENGTH: 20
<212> TYPE: DNA
<213> ORGANISM: Artificial Sequence
<220> FEATURE:
<223> OTHER INFORMATION: Primer Sequence

<400> SEQUENCE: 20
agagactcag aggcgaccat                                                   20

<210> SEQ ID NO 21
<211> LENGTH: 20
<212> TYPE: DNA
<213> ORGANISM: Artificial Sequence
<220> FEATURE:
<223> OTHER INFORMATION: Primer Sequence

<400> SEQUENCE: 21
atcagcaaac acagcagctc                                                   20
```

<210> SEQ ID NO 22
<211> LENGTH: 24
<212> TYPE: DNA
<213> ORGANISM: Artificial Sequence
<220> FEATURE:
<223> OTHER INFORMATION: Primer Sequence

<400> SEQUENCE: 22
agagctgttg gatgaggacc agaa                                              24

<210> SEQ ID NO 23
<211> LENGTH: 24
<212> TYPE: DNA
<213> ORGANISM: Artificial Sequence
<220> FEATURE:
<223> OTHER INFORMATION: Primer Sequence

<400> SEQUENCE: 23
aggctccaaa ggcacttgac tact                                              24

<210> SEQ ID NO 24
<211> LENGTH: 21
<212> TYPE: DNA
<213> ORGANISM: Artificial Sequence
<220> FEATURE:
<223> OTHER INFORMATION: Primer Sequence

<400> SEQUENCE: 24
gaccaagcgg gttgttattg a                                                 21

<210> SEQ ID NO 25
<211> LENGTH: 23
<212> TYPE: DNA
<213> ORGANISM: Artificial Sequence
<220> FEATURE:
<223> OTHER INFORMATION: Primer Sequence

<400> SEQUENCE: 25
tgccttgtcg gtcatatttt tca                                               23

<210> SEQ ID NO 26
<211> LENGTH: 20
<212> TYPE: DNA
<213> ORGANISM: Artificial Sequence
<220> FEATURE:
<223> OTHER INFORMATION: Primer Sequence

<400> SEQUENCE: 26
cggagaacca aacggaaagg                                                   20

<210> SEQ ID NO 27
<211> LENGTH: 19
<212> TYPE: DNA
<213> ORGANISM: Artificial Sequence
<220> FEATURE:
<223> OTHER INFORMATION: Primer Sequence

<400> SEQUENCE: 27
cttcgcccac agtgaatgc                                                    19

<210> SEQ ID NO 28
<211> LENGTH: 24
<212> TYPE: DNA
<213> ORGANISM: Artificial Sequence
<220> FEATURE:

<223> OTHER INFORMATION: Primer Sequence

<400> SEQUENCE: 28
acagcagccg gtttattgtg cttc                                    24

<210> SEQ ID NO 29
<211> LENGTH: 24
<212> TYPE: DNA
<213> ORGANISM: Artificial Sequence
<220> FEATURE:
<223> OTHER INFORMATION: Primer Sequence

<400> SEQUENCE: 29
tggcattcag tctcacacca ctgt                                    24

<210> SEQ ID NO 30
<211> LENGTH: 24
<212> TYPE: DNA
<213> ORGANISM: Artificial Sequence
<220> FEATURE:
<223> OTHER INFORMATION: Primer Sequence

<400> SEQUENCE: 30
accactcacc atcatctcaa ggca                                    24

<210> SEQ ID NO 31
<211> LENGTH: 24
<212> TYPE: DNA
<213> ORGANISM: Artificial Sequence
<220> FEATURE:
<223> OTHER INFORMATION: Primer Sequence

<400> SEQUENCE: 31
tgctcttctt tgccagatcc tcgt                                    24

<210> SEQ ID NO 32
<211> LENGTH: 20
<212> TYPE: DNA
<213> ORGANISM: Artificial Sequence
<220> FEATURE:
<223> OTHER INFORMATION: Primer Sequence

<400> SEQUENCE: 32
gccttaccct tgcagcttac                                         20

<210> SEQ ID NO 33
<211> LENGTH: 20
<212> TYPE: DNA
<213> ORGANISM: Artificial Sequence
<220> FEATURE:
<223> OTHER INFORMATION: Primer Sequence

<400> SEQUENCE: 33
gagcatgctg tccactctgt                                         20

<210> SEQ ID NO 34
<211> LENGTH: 24
<212> TYPE: DNA
<213> ORGANISM: Artificial Sequence
<220> FEATURE:
<223> OTHER INFORMATION: Primer Sequence

<400> SEQUENCE: 34
cttgcgcatt cccaagtcag atgt                                    24

```
<210> SEQ ID NO 35
<211> LENGTH: 24
<212> TYPE: DNA
<213> ORGANISM: Artificial Sequence
<220> FEATURE:
<223> OTHER INFORMATION: Primer Sequence

<400> SEQUENCE: 35
tttcctctcc ttctcgtgct gctt                                              24

<210> SEQ ID NO 36
<211> LENGTH: 20
<212> TYPE: DNA
<213> ORGANISM: Artificial Sequence
<220> FEATURE:
<223> OTHER INFORMATION: Primer Sequence

<400> SEQUENCE: 36
gagcctgcta cagatggtca                                                   20

<210> SEQ ID NO 37
<211> LENGTH: 20
<212> TYPE: DNA
<213> ORGANISM: Artificial Sequence
<220> FEATURE:
<223> OTHER INFORMATION: Primer Sequence

<400> SEQUENCE: 37
tgtctaccag caggacgaag                                                   20

<210> SEQ ID NO 38
<211> LENGTH: 20
<212> TYPE: DNA
<213> ORGANISM: Artificial Sequence
<220> FEATURE:
<223> OTHER INFORMATION: Primer Sequence

<400> SEQUENCE: 38
cctcctgaag aatcgattcc                                                   20

<210> SEQ ID NO 39
<211> LENGTH: 20
<212> TYPE: DNA
<213> ORGANISM: Artificial Sequence
<220> FEATURE:
<223> OTHER INFORMATION: Primer Sequence

<400> SEQUENCE: 39
gaggtccaca cactgaagtt                                                   20

<210> SEQ ID NO 40
<211> LENGTH: 24
<212> TYPE: DNA
<213> ORGANISM: Artificial Sequence
<220> FEATURE:
<223> OTHER INFORMATION: Primer Sequence

<400> SEQUENCE: 40
tttctgggct ggccaaacat aagc                                              24

<210> SEQ ID NO 41
<211> LENGTH: 24
<212> TYPE: DNA
<213> ORGANISM: Artificial Sequence
<220> FEATURE:
<223> OTHER INFORMATION: Primer Sequence
```

<400> SEQUENCE: 41
acacaaggta atgtgtgggt ccga                                    24

<210> SEQ ID NO 42
<211> LENGTH: 24
<212> TYPE: DNA
<213> ORGANISM: Artificial Sequence
<220> FEATURE:
<223> OTHER INFORMATION: Primer Sequence

<400> SEQUENCE: 42
cggcaggtgt ttgtgtgtgg aaat                                    24

<210> SEQ ID NO 43
<211> LENGTH: 24
<212> TYPE: DNA
<213> ORGANISM: Artificial Sequence
<220> FEATURE:
<223> OTHER INFORMATION: Primer Sequence

<400> SEQUENCE: 43
agaagacaca cagcacagca gaca                                    24

<210> SEQ ID NO 44
<211> LENGTH: 24
<212> TYPE: DNA
<213> ORGANISM: Artificial Sequence
<220> FEATURE:
<223> OTHER INFORMATION: Primer Sequence

<400> SEQUENCE: 44
tagtgaaacc agtgtgtctg ccca                                    24

<210> SEQ ID NO 45
<211> LENGTH: 24
<212> TYPE: DNA
<213> ORGANISM: Artificial Sequence
<220> FEATURE:
<223> OTHER INFORMATION: Primer Sequence

<400> SEQUENCE: 45
agcgttcagc acttctgagg tctt                                    24

<210> SEQ ID NO 46
<211> LENGTH: 21
<212> TYPE: DNA
<213> ORGANISM: Artificial Sequence
<220> FEATURE:
<223> OTHER INFORMATION: Primer Sequence

<400> SEQUENCE: 46
cgctctggtt catctgctct g                                       21

<210> SEQ ID NO 47
<211> LENGTH: 22
<212> TYPE: DNA
<213> ORGANISM: Artificial Sequence
<220> FEATURE:
<223> OTHER INFORMATION: Primer Sequence

<400> SEQUENCE: 47
tcatcaaagg tgctctcgtc tg                                      22

<210> SEQ ID NO 48
<211> LENGTH: 24

<212> TYPE: DNA
<213> ORGANISM: Artificial Sequence
<220> FEATURE:
<223> OTHER INFORMATION: Primer Sequence

<400> SEQUENCE: 48
tggagaggaa gttcagccat caga                                    24

<210> SEQ ID NO 49
<211> LENGTH: 24
<212> TYPE: DNA
<213> ORGANISM: Artificial Sequence
<220> FEATURE:
<223> OTHER INFORMATION: Primer Sequence

<400> SEQUENCE: 49
aggagagctg ctttcgctta gtct                                    24

<210> SEQ ID NO 50
<211> LENGTH: 24
<212> TYPE: DNA
<213> ORGANISM: Artificial Sequence
<220> FEATURE:
<223> OTHER INFORMATION: Primer Sequence

<400> SEQUENCE: 50
acctgctcag cctttgtctc tgat                                    24

<210> SEQ ID NO 51
<211> LENGTH: 24
<212> TYPE: DNA
<213> ORGANISM: Artificial Sequence
<220> FEATURE:
<223> OTHER INFORMATION: Primer Sequence

<400> SEQUENCE: 51
agatccaggc ttgcttactg tcct                                    24

<210> SEQ ID NO 52
<211> LENGTH: 24
<212> TYPE: DNA
<213> ORGANISM: Artificial Sequence
<220> FEATURE:
<223> OTHER INFORMATION: Primer Sequence

<400> SEQUENCE: 52
attctgggtt gggagtgcaa ggaa                                    24

<210> SEQ ID NO 53
<211> LENGTH: 24
<212> TYPE: DNA
<213> ORGANISM: Artificial Sequence
<220> FEATURE:
<223> OTHER INFORMATION: Primer Sequence

<400> SEQUENCE: 53
aggagacatg cccaggatga aaca                                    24

<210> SEQ ID NO 54
<211> LENGTH: 24
<212> TYPE: DNA
<213> ORGANISM: Artificial Sequence
<220> FEATURE:
<223> OTHER INFORMATION: Primer Sequence

<400> SEQUENCE: 54

-continued

| | |
|---|---|
| actaggcagg acattgacat ccca | 24 |

<210> SEQ ID NO 55
<211> LENGTH: 24
<212> TYPE: DNA
<213> ORGANISM: Artificial Sequence
<220> FEATURE:
<223> OTHER INFORMATION: Primer Sequence

<400> SEQUENCE: 55

| | |
|---|---|
| acagtaaacc tctccacaca tggc | 24 |

<210> SEQ ID NO 56
<211> LENGTH: 24
<212> TYPE: DNA
<213> ORGANISM: Artificial Sequence
<220> FEATURE:
<223> OTHER INFORMATION: Primer Sequence

<400> SEQUENCE: 56

| | |
|---|---|
| tatgacaccc agggctttcg ttca | 24 |

<210> SEQ ID NO 57
<211> LENGTH: 24
<212> TYPE: DNA
<213> ORGANISM: Artificial Sequence
<220> FEATURE:
<223> OTHER INFORMATION: Primer Sequence

<400> SEQUENCE: 57

| | |
|---|---|
| taacgttccc tgcgcgttta caga | 24 |

<210> SEQ ID NO 58
<211> LENGTH: 18
<212> TYPE: DNA
<213> ORGANISM: Artificial Sequence
<220> FEATURE:
<223> OTHER INFORMATION: Primer Sequence

<400> SEQUENCE: 58

| | |
|---|---|
| tcccaaatcc tgacccca | 18 |

<210> SEQ ID NO 59
<211> LENGTH: 20
<212> TYPE: DNA
<213> ORGANISM: Artificial Sequence
<220> FEATURE:
<223> OTHER INFORMATION: Primer Sequence

<400> SEQUENCE: 59

| | |
|---|---|
| accacacagc ccctaggaga | 20 |

<210> SEQ ID NO 60
<211> LENGTH: 21
<212> TYPE: DNA
<213> ORGANISM: Artificial Sequence
<220> FEATURE:
<223> OTHER INFORMATION: Primer Sequence

<400> SEQUENCE: 60

| | |
|---|---|
| acagggtggc ccaaatagaa c | 21 |

<210> SEQ ID NO 61
<211> LENGTH: 21
<212> TYPE: DNA
<213> ORGANISM: Artificial Sequence

```
<220> FEATURE:
<223> OTHER INFORMATION: Primer Sequence

<400> SEQUENCE: 61
cctgtcttgg acaagcggag a                                              21

<210> SEQ ID NO 62
<211> LENGTH: 24
<212> TYPE: DNA
<213> ORGANISM: Artificial Sequence
<220> FEATURE:
<223> OTHER INFORMATION: Primer Sequence

<400> SEQUENCE: 62
gggtcatttc caccacctca aaca                                           24

<210> SEQ ID NO 63
<211> LENGTH: 24
<212> TYPE: DNA
<213> ORGANISM: Artificial Sequence
<220> FEATURE:
<223> OTHER INFORMATION: Primer Sequence

<400> SEQUENCE: 63
ggagaaaggc cttacagtag tctc                                           24
```

METHODS AND COMPOSITIONS FOR DETERMINING RESISTANCE TO ANDROGEN RECEPTOR THERAPY

CROSS REFERENCE TO RELATED APPLICATIONS

This application is a national stage application of Patent Application No. PCT/US2013/052395, filed Jul. 26, 2013, which claims the benefit of U.S. Provisional Application No. 61/676,842, filed Jul. 27, 2012, 61/783,763, filed on Mar. 14, 2013 and 61/829,123, filed on May 30, 2013, which are incorporated herein by reference in their entireties.

INCORPORATION BY REFERENCE OF SEQUENCE LISTING SUBMITTED AS A TEXT FILE VIA EFS-WEB

The instant application contains a Sequence Listing, which has been submitted as a computer readable text file in ASCII format via EFS-Web and is hereby incorporated in its entirety by reference herein.

BACKGROUND OF THE INVENTION

The androgen receptor ("AR") is a ligand-activated transcriptional regulatory protein that mediates induction of a variety of biological effects through its interaction with endogenous androgens. Endogenous androgens include steroids such as testosterone and dihydrotestosterone. Testosterone is converted to dihydrotestosterone by the enzyme 5 alpha-reductase in many tissues.

The actions of androgens with androgen receptors have been implicated in a number of diseases or conditions, such as androgen dependent cancers, virilization in women, and acne, among others. Compounds that diminish the effects of androgen signaling via the androgen receptor and/or lower the concentrations of androgen receptors find use in the treatment of diseases or conditions in which androgen receptors play a role.

SUMMARY OF THE INVENTION

Described herein, in certain embodiments, is a method for selecting a subject for therapy with a third-generation androgen receptor antagonist, comprising: (a) obtaining a sample containing a nucleic acid molecule encoding an androgen receptor polypeptide from the subject; (b) testing the sample to determine whether the encoded androgen receptor polypeptide is modified at an amino acid position corresponding to amino acid position 876 of the amino acid sequence set forth in SEQ ID NO: 1; and (c) characterizing the subject as a candidate for therapy with a third-generation androgen receptor antagonist if the subject has the modification.

Described herein, in certain embodiments, is a method for determining whether a subject is or will become resistant to therapy with a first- or second-generation androgen receptor antagonist, comprising: (a) obtaining a sample containing a nucleic acid molecule encoding an androgen receptor polypeptide from the subject; (b) testing the sample to determine whether the encoded androgen receptor polypeptide is modified at an amino acid position corresponding to amino acid position 876 of the amino acid sequence set forth in SEQ ID NO: 1; and (c) characterizing the subject as resistant or will become resistant to therapy with a first- or second-generation androgen receptor antagonist if the subject has the modification.

Described herein, in certain embodiments, is a method for detecting a modified androgen receptor that is resistant to inhibition with a first- or second-generation androgen receptor antagonist in a subject, comprising: (a) obtaining a sample containing a nucleic acid molecule encoding an androgen receptor polypeptide from the subject; (b) testing the sample to determine whether the encoded androgen receptor polypeptide is modified at an amino acid position corresponding to amino acid position 876 of the amino acid sequence set forth in SEQ ID NO: 1; and (c) characterizing the androgen receptor as resistant to inhibition with a first- or second-generation androgen receptor antagonist if the subject has the modification.

Described herein, in certain embodiments, is a method for monitoring whether a subject receiving a first- or second-generation androgen receptor antagonist for treatment of a cancer has developed or will develop resistance to the therapy, comprising: (a) obtaining a sample containing a nucleic acid molecule encoding an androgen receptor polypeptide from the subject; (b) testing the sample to determine whether the encoded androgen receptor polypeptide is modified at an amino acid position corresponding to amino acid position 876 of the amino acid sequence set forth in SEQ ID NO: 1; and (c) characterizing the subject as resistant or will become resistant to therapy with a first- or second-generation androgen receptor antagonist if the subject has the modification.

Described herein, in certain embodiments, is a method for optimizing the therapy of a subject receiving a first- or second-generation androgen receptor antagonist for treatment of a cancer, comprising: (a) obtaining a sample containing a nucleic acid molecule encoding an androgen receptor polypeptide from the subject; (b) testing the sample to determine whether the encoded androgen receptor polypeptide is modified at an amino acid position corresponding to amino acid position 876 of the amino acid sequence set forth in SEQ ID NO: 1; and (c) discontinuing treatment with the a second-generation androgen receptor antagonist if the subject has the modification or continuing treatment with a first- or second-generation androgen receptor antagonist if the subject does not have the modification.

In some embodiments, the method further comprises discontinuing treatment with the first- or second-generation androgen receptor antagonist if the subject has the modification. In some embodiments, the method further comprises continuing treatment with a first- or second-generation androgen receptor antagonist if the subject does not have the modification. In some embodiments, the method further comprises administering third-generation androgen receptor antagonist that inhibits the modified receptor if the subject has the modification.

In some embodiments, the modified AR polypeptide comprises a substitution or a deletion of the amino acid at amino acid position 876 in the androgen receptor polypeptide. In some embodiments, the modified AR polypeptide comprises a substitution of phenylalanine to an amino acid selected from among leucine, isoleucine, valine, alanine, glycine, methionine, serine, threonine, cysteine, tryptophan, lysine, arginine, histidine, proline, tyrosine, asparagine, glutamine, aspartic acid and glutamic acid at amino acid position 876 of the androgen receptor polypeptide. In some embodiments, the modified AR polypeptide comprises a substitution of phenylalanine to an amino acid selected from among glycine, alanine, valine, leucine, and isoleucine at amino acid position 876 of the androgen receptor polypeptide. In some embodiments, the modified AR polypeptide comprises a substitution of phenylalanine to leucine at amino acid position 876 of the androgen receptor polypeptide. In some embodiments, the modified AR polypeptide comprises a deletion of nucleic acid encoding amino acid position 876 of the androgen receptor polypeptide.

In some embodiments of the method, the nucleic acid sample contains RNA or DNA. In some embodiments of the method, the nucleic acid sample is genomic DNA. In some embodiments, the method further comprises isolating mRNA from the RNA sample. In some embodiments, the nucleic acid is isolated from a tumor cell sample from the subject. In some embodiments, the sample is a tumor biopsy sample, a blood sample, a serum sample, a lymph sample, or a bone marrow aspirate. In some embodiments, the sample contains circulating tumor cells. In some embodiments, the sample contains disseminated tumor cells.

In some embodiments of the method, testing comprises performing polymerase chain reaction (PCR) amplification of nucleic acid encoding amino acid position 876 of the androgen receptor polypeptide. In some embodiments, PCR amplification comprises using a pair of oligonucleotide primers that flank the region encoding amino acid position 876 of the androgen receptor polypeptide. In some embodiments, the method comprises sequencing the amplified nucleic acid.

In some embodiments, testing comprises contacting the nucleic acid with a sequence specific nucleic acid probe, wherein the sequence specific nucleic acid probe: (a) binds to nucleic acid encoding a modified receptor that is modified at amino acid position 876; and (b) does not bind to nucleic acid encoding the wild-type receptor having phenylalanine at amino acid position 876.

In some embodiments, the first- or second-generation androgen receptor antagonist inhibits a wild-type androgen receptor polypeptide by competitive antagonism. In some embodiments, the second-generation androgen receptor antagonist is selected from among ARN-509, enzalutamide (MDV3100), and RD162.

In some embodiments, the subject has a disease or disorder selected from among cancer, an inflammatory disorder or a proliferative disorder. In some embodiments, the subject has cancer. In some embodiments, the subject has an AR-mediated cancer. In some embodiments, the cancer is a prostate cancer, a breast cancer, liver (i.e. hepatocellular) cancer, or a bladder cancer. In some embodiments, the cancer is prostate cancer. In some embodiments, the subject has a castration resistant prostate cancer. In some embodiments, the subject has a solid tumor.

In some embodiments, the subject is treated with the first- or second-generation androgen receptor antagonist prior to obtaining the sample. In some embodiments, the subject is responsive the treatment with the first- or second-generation androgen receptor antagonist when it is first administered.

Described herein, in certain embodiments, is a method for screening compounds that antagonize a modified androgen receptor, comprising: (a) expressing a modified androgen receptor in a cell, wherein the modified androgen receptor is modified at an amino acid position corresponding to amino acid position 876 of the amino acid sequence set forth in SEQ ID NO: 1; (b) contacting the cell with a test compound; and (c) detecting the level of androgen receptor activity in the cell, wherein a decrease in activity indicates that the compound antagonizes the modified AR. In some embodiments, the test compound exhibits full antagonist activity toward the modified AR. In some embodiments, the test compound does not exhibit agonist activity toward the modified AR. Described herein, in certain embodiments, is a third-generation androgen receptor inhibitor identified by the methods. In some embodiments, the modification of the AR polypeptide used in the method is a substitution or deletion of the amino acid at position 876 of the androgen receptor polypeptide. In some embodiments, the modification of the AR polypeptide used in the method is a substitution of phenylalanine to an amino acid selected from among leucine, isoleucine, valine, alanine, glycine, methionine, serine, threonine, cysteine, tryptophan, lysine, arginine, histidine, proline, tyrosine, asparagine, glutamine, aspartic acid and glutamic acid at amino acid position 876 of the androgen receptor polypeptide. In some embodiments, the modification of the AR polypeptide used in the method is a substitution of phenylalanine to an amino acid selected from among glycine, alanine, valine, leucine, and isoleucine at amino acid position 876 of the androgen receptor polypeptide. In some embodiments, the modification of the AR polypeptide used in the method is a substitution of phenylalanine to leucine at amino acid position 876 of the androgen receptor polypeptide.

In some embodiments, the cell employed in the method is deficient for the expression of wild-type androgen receptor, expresses a low level of wild-type androgen receptor, or expresses a modified AR receptor. In some embodiments, the cell is a selected from among HeLa, CV1, COS7, HepG2, HEK-293, DU145, PC3, TSY-PR1, LNCaP, CWR, VCaP and LAPC4. In some embodiments, the cell comprises a reporter gene operably linked to an androgen responsive promoter. In some embodiments, the activity of the AR polypeptide is determined by analyzing the expression of the reporter gene. In some embodiments, the promoter comprises androgen response element. In some embodiments, the androgen response element is 4×ARE or a probasin element. In some embodiments, the promoter is a probasin, a prostate specific antigen, MMTV LTR, FASN, STEAP4, TMPRSS2, ORM1, or NKX3.1 promoter. In some embodiments, the reporter gene encodes a protein selected from among a luciferase, a fluorescent protein, a bioluminescent protein, or an enzyme.

Described herein, in certain embodiments, is an isolated androgen receptor polypeptide or a variant thereof having androgen receptor activity comprising a modification at an amino acid position corresponding to amino acid position 876 of the amino acid sequence set forth in SEQ ID NO: 1, wherein the modification confers resistance to an androgen receptor antagonist on the modified androgen receptor polypeptide or variant. In some embodiments, the modification comprises substitution of the amino acid at position 876 compared to a wild-type androgen receptor set forth in SEQ ID NO: 1. In some embodiments, the substitution is F876L. In some embodiments, the modification comprises a deletion of amino acid position 876. In some embodiments, the modified AR polypeptide has the sequence of amino acids set forth in SEQ ID NO: 5.

In some embodiments, the modified AR polypeptide comprises a substitution of the amino acid at position 876 compared to a wild-type androgen receptor set forth in SEQ ID NO: 1 and one or more additional amino acid substitutions. In some embodiments, the modified AR polypeptide comprises a substitution at amino acid at position 876 that is F876L. In some embodiments, the modified AR polypeptide comprises one or more additional amino acid substitutions selected from among one or more amino acid substitutions associated with castration resistant prostate cancer. In some embodiments, the one or more additional amino acid substitutions is selected from among one or more substitutions at amino acid positions 701, 741, 874 and 877 compared to a wild-type androgen receptor set forth in SEQ ID NO: 1. In some embodiments, the one or more additional amino acid substitutions is selected from among T877A, W741C, W741L, W741R, L701H and H874Y.

In some embodiments, the modified AR polypeptide comprises a sequence of amino acids set forth in SEQ ID NO: 5 or a variant that has at least or at least about 60%, 70%, 75%, 80%, 85%, 90%, 95%, 96%, 97%, 98%, 99% or more sequence identity with the polypeptide having the sequence set forth in SEQ ID NO: 5, wherein the amino acid at position 876 is not phenylalanine.

Described herein, in certain embodiments, is an isolated nucleic acid molecule encoding the modified androgen receptor polypeptide provided herein. In some embodiments, the nucleic acid is a DNA or an RNA molecule. In some embodiments, the nucleic acid comprises the sequence of nucleic acids set forth in SEQ ID NO: 19 or a variant that has at least or at least about 60%, 70%, 75%, 80%, 85%, 90%, 95%, 96%, 97%, 98%, 99% or more sequence identity with the polypeptide having the sequence set forth in SEQ ID NO: 19, wherein the nucleic acid codon encoding amino acid at position 876 does not encode phenylalanine.

Described herein, in certain embodiments, is a vector, comprising a nucleic acid molecule encoding the modified androgen receptor polypeptide provided herein. In some embodiments, the vector is a viral or plasmid vector. In some embodiments, the nucleic acid is operably linked to a promoter. In some embodiments, the promoter is a constitutive or an inducible promoter. Described herein, in certain embodiments, is a host cell, comprising the vector. In some embodiments, the cell is a prokaryotic cell or a eukaryotic cell. Described herein, in certain embodiments, is a mutant AR polypeptide expressed by the host cell.

Described herein, in certain embodiments, is a pharmaceutical composition comprising a third-generation androgen receptor inhibitor identified by the methods provided herein. Described herein, in certain embodiments, is a method of treatment comprising administering to a subject in need thereof a therapeutically effective amount of the pharmaceutical composition, wherein the composition comprises a suitable pharmaceutical carrier. In some embodiments, the subject has cancer. In some embodiments, the subject has an AR-mediated cancer. In some embodiments, the cancer is a prostate cancer, breast cancer, liver (i.e. hepatocellular) cancer or bladder cancer. In some embodiments, the cancer is a castration resistant prostate cancer. In some embodiments, the subject expresses a mutant AR. In some embodiments, the mutant AR comprises a substitution or a deletion of the amino acid at amino acid position 876 in the androgen receptor polypeptide. In some embodiments, the substitution is F876L.

Described herein, in certain embodiments, is a kit comprising the mutant AR polypeptide provided herein. Described herein, in certain embodiments, is a kit comprising the isolated nucleic acid encoding a mutant AR polypeptide provided herein. Described herein, in certain embodiments, is a kit comprising one or more reagents for the detection of a mutant AR polypeptide comprising a modification at amino acid position 876. Described herein, in certain embodiments, is a kit comprising one or more reagents for the detection of nucleic acid encoding a mutant AR polypeptide comprising a modification at amino acid position 876. In some embodiments, the modification is an amino acid substitution that is F876L.

Described herein, in certain embodiments, is a microchip comprising the mutant AR polypeptide provided herein or a nucleic acid encoding modified AR polypeptide provided herein. In some embodiments, the modified AR polypeptide comprises a modification at amino acid 876. In some embodiments, the modification is an amino acid substitution that is F876L.

Described herein, in certain embodiments, is a an isolated antibody that binds to a modified androgen receptor polypeptide provided herein, wherein the antibody does not bind to or binds with lower affinity to a wild-type AR polypeptide having the sequence of amino acids set forth in SEQ ID NO: 1. In some embodiments, the modified AR polypeptide comprises a modification at amino acid 876. In some embodiments, the modification is an amino acid substitution that is F876L.

Other objects, features and advantages of the polypeptides, nucleic acids, compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Certain Terminology

Figure 1A:
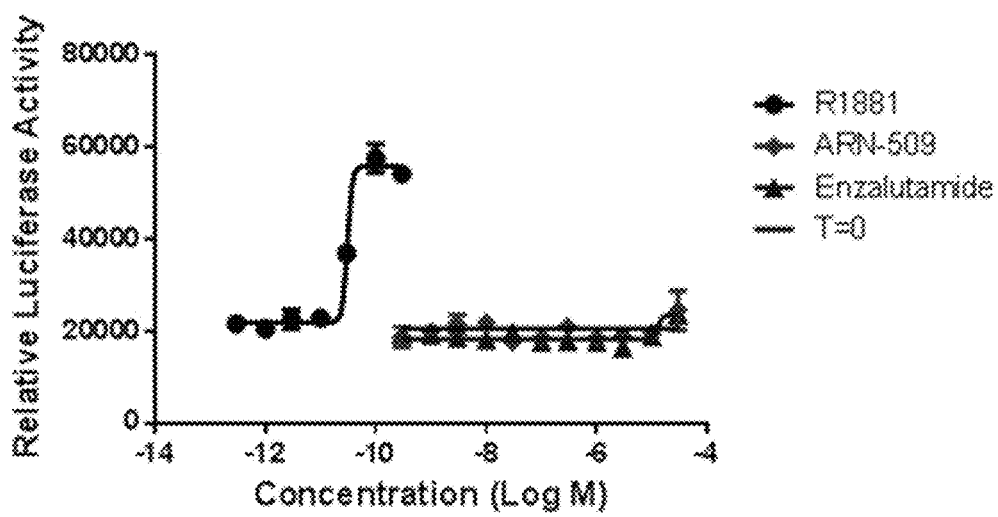
FIG. 1 illustrates ARN-509 and enzalutamide resistance. (A) LNCaP and LNCaP ARN-509r1 cell proliferation. LNCaP and LNCaP ARN-509r1 cells were cultured in the presence of hormone depleted medium for 2 days followed by ligand addition. Proliferation is quantified by CellTiter-Glo® (Promega Corp.) luminescence based viability assay after 7 day compound treatment. (B) Agonist proliferation assay of LNCaP/AR-Luc, LNCaP/AR-Luc ENZr2 and LNCaP ARN-509r2 cell lines. Cells were cultured in the presence of hormone depleted medium for 2 days followed by ligand treatment for 7 days. Proliferation is quantified by CellTiter-Glo® luminescence based viability assay. (C) Antagonist proliferation assay of parental and $2^{nd}$ generation anti-androgen resistant cell lines. Cells were cultured in the presence of hormone depleted medium for 2 days followed by ligand treatment in the presence of R1881 (final concentration=100 pM). Proliferation is quantified by CellTiter-Glo luminescence based viability assay. (D) Schematic representation of AR domain structure showing amino acids that when mutated display altered ligand activity in CRPC.
Figure 1A:
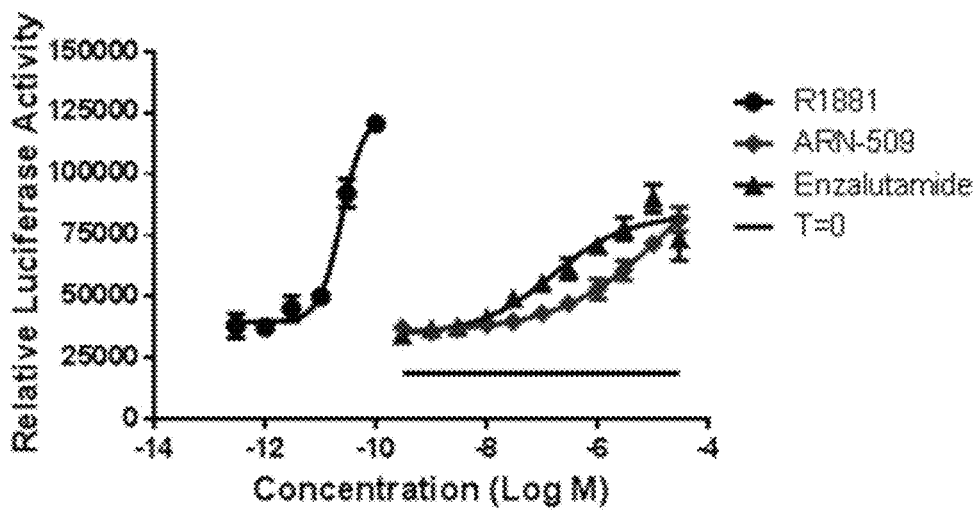

Unless defined otherwise, all technical and scientific terms used herein have the same meaning as is commonly understood by one of skill in the art to which the claimed subject matter belongs. All patents, patent applications, published applications and publications, GENBANK sequences, websites and other published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information. Generally, the procedures for cell culture, cell infection, antibody production and molecular biology methods are methods commonly used in the art. Such standard techniques can be found, for example, in reference manual, such as, for example, Sambrook et al. (2000) and Ausubel et al. (1994).

As used herein, the singular forms "a," "an" and "the" include plural referents unless the context clearly dictates otherwise. In this application, the use of the singular includes the plural unless specifically stated otherwise. As used herein, the use of "or" means "and/or" unless stated otherwise. Furthermore, use of the term "including" as well as other forms (e.g., "include", "includes", and "included") is not limiting.

As used herein, ranges and amounts can be expressed as "about" a particular value or range. About also includes the exact amount. Hence "about 5 µg" means "about 5 µg" and also "5 µg." Generally, the term "about" includes an amount that would be expected to be within experimental error.

As used herein, an androgen receptor (AR) polypeptide refers to any androgen receptor protein or polypeptide, including, but not limited to, a recombinantly produced protein, a synthetically produced protein, a native androgen receptor protein, and an androgen receptor protein extracted from cells or tissues. An AR polypeptide includes related polypeptides from different species including, but not limited to animals of human and non-human origin. AR polypeptides of non-human origin include, but are not limited to, non-human primate (e.g. chimpanzee and ape), murine (e.g., mouse and rat), canine (dog), feline (cat), leporine (rabbit), avian (bird), bovine (cow), ovine (sheep), porcine (pig), equine (horse), piscine (fish), ranine (frog) and other mammalian or non-mammalian AR polypeptides. Exemplary AR polypeptides include, for example, SEQ ID NOS: 1-17. An androgen receptor polypeptide includes wild-type androgen receptor, allelic variant isoforms, somatic mutations including those found in tumors, synthetic molecules from nucleic acids, protein isolated from human tissue and cells, and modified forms thereof. The androgen receptor polypeptides provided herein can be further modified by modification of the primary amino acid sequence, by deletion, addition, or substitution of one or more amino acids. An androgen receptor polypeptide includes any AR polypeptide or a portion thereof having AR activity, including for example, fusion polypeptides of an AR ligand binding domain to a heterologous DNA binding domain.

As used herein, a mutant androgen receptor (AR) polypeptide, a mutant AR protein, a modified AR polypeptide, or a modified AR protein or are used interchangeably herein and refer to an androgen receptor polypeptide that is modified at one or more amino acid positions. Exemplary modifications include, but are not limited to, substitutions, deletions or additions of amino acids.

As used herein, the term "anti-androgen" refers to a group of hormone receptor antagonist compounds that are capable of preventing or inhibiting the biologic effects of androgens on normally responsive tissues in the body.

As used herein, the term "AR inhibitor" or "AR antagonist" are used interchangeably herein and refer to an agent that inhibits or reduces at least one activity of an AR polypeptide. Exemplary AR activities include, but are not limited to, co-activator binding, DNA binding, ligand binding, or nuclear translocation.

As used herein, a "full antagonist" refers to an antagonist which, at an effective concentration, essentially completely inhibits an activity of an AR polypeptide. As used herein, a "partial antagonist" refers an antagonist that is capable of partially inhibiting an activity of an AR polypeptide, but that, even at a highest concentration is not a full antagonist. By 'essentially completely' is meant at least about 80%, at least about 90%, at least about 95%, at least about 96%, at least about 97%, at least about 98% at least about 99%, or greater inhibition of the activity of an AR polypeptide.

As used herein, the term "third-generation AR inhibitor" or "third-generation AR antagonist" are used interchangeably herein and refer to an agent that inhibits at least one activity of an AR polypeptide containing one or more amino acid modifications that confers resistance to inhibition by a second-generation AR antagonist, such as, for example, ARN-509 (CAS No. 956104-40-8), enzalutamide (also known as MDV3100; CAS No: 915087-33-1), or RD162 (CAS No. 915087-27-3). In some embodiments, a third-generation AR inhibitor inhibits at least one activity of a wild-type AR polypeptide, such as, but not limited to, co-activator binding, DNA binding, ligand binding, or nuclear translocation. In some embodiments, a third-generation AR inhibitor inhibits an activity of a mutant AR polypeptide that is also inhibited by a first- or second-generation AR inhibitor.

As used herein, the term "second-generation AR inhibitor" or "second-generation AR antagonist" are used interchangeably herein and refer to an agent that exhibits full antagonist activity of a wild-type AR polypeptide, but does not exhibit full antagonist activity of an AR polypeptide containing one or more amino acid modifications that confers resistance to inhibition, such as a modification at amino acid position 876 in the AR polypeptide. In some embodiments, the second-generation AR inhibitor does not exhibit full antagonist activity on an AR polypeptide having an amino acid substitution that is F876L. In some embodiments, the second-generation AR inhibitor induces activity of AR (i.e. is an AR agonist) at concentrations that are equivalent or higher than the concentration required to inhibit a wild-type AR. Second-generation AR inhibitors differ from first-generation AR inhibitors, such as bicalutamide and flutamide, in that second-generation AR inhibitors act as full antagonists in cells expressing elevated levels of AR, such as for example, in castration resistant prostate cancers (CRPC). First-generation AR inhibitors, such as bicalutamide and flutamide, act as agonists in CRPC. Exemplary second-generation AR inhibitors include ARN-509, enzalutamide and RD162. In some embodiments, a second-generation AR inhibitor is an agonist of a mutant AR polypeptide provided herein. In some embodiments, a second-generation AR inhibitor binds to an AR polypeptide at or near the ligand binding site of the AR polypeptide.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogs of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (e.g., phosphorothioates, phosphoroamidates). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions are achieved by generating sequences in which the third position of one or more selected (or all) codons is substituted with mixed-base and/or deoxyinosine residues (Batzer et al. (1991) *Nucleic Acid Res.* 19:5081; Ohtsuka et al. (1985) *J. Biol. Chem.* 260:2605-2608; and Cassol et al. (1992) *Mol. Cell. Probes* 6, 327-331; and Rossolini et al. (1994) *Mol. Cell. Probes* 8:91-98).

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to agents that have the same basic chemical structure as a naturally occurring amino acid, i.e., an α carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes.

The terms "polypeptide", "peptide" and "protein" are used interchangeably herein to refer to a polymer of amino acid residues. The terms apply to naturally occurring amino acid polymers as well as amino acid polymers in which one or more amino acid residues is a non-naturally occurring amino acid, e.g., an amino acid analog. The terms encompass amino acid chains of any length, including full length proteins, wherein the amino acid residues are linked by covalent peptide bonds.

As used herein, modification refers to modification of a sequence of amino acids of a polypeptide or a sequence of nucleotides in a nucleic acid molecule and includes deletions, insertions, and replacements of amino acids and nucleotides, respectively.

To determine the percent homology of two amino acid sequences or of two nucleic acids, the sequences can be aligned for optimal comparison purposes (e.g., gaps are introduced in the sequence of a first amino acid or nucleic acid sequence for optimal alignment with a second amino or nucleic acid sequence). The amino acid residues or nucleotides at corresponding amino acid positions or nucleotide positions can then be compared. When a position in the first sequence is occupied by the same amino acid residue or nucleotide as the corresponding position in the second sequence, then the molecules are identical at that position. The percent homology between the two sequences is a function of the number of identical positions shared by the sequences (i.e., % identity=# of identical positions/total # of positions (e.g., overlapping positions)×100). In some embodiments the two sequences are the same length.

To determine percent homology between two sequences, the algorithm of Karlin and Altschul (1990) Proc. Natl. Acad. Sci. USA 87:2264-2268, modified as in Karlin and Altschul (1993) Proc. Natl. Acad. Sci. USA 90:5873-5877 is used. Such an algorithm is incorporated into the NBLAST and XBLAST programs of Altschul, et al. (1990) J. Mol. Biol. 215:403-410. BLAST nucleotide searches are performed with the NBLAST program, score=100, wordlength=12 to obtain nucleotide sequences homologous to a nucleic acid molecules described or disclose herein. BLAST protein searches are performed with the XBLAST program, score=50, wordlength=3. To obtain gapped alignments for comparison purposes, Gapped BLAST is utilized as described in Altschul et al. (1997) Nucleic Acids Res. 25:3389-3402. When utilizing BLAST and Gapped BLAST programs, the default parameters of the respective programs (e.g., XBLAST and NBLAST) are used. See the website of the National Center for Biotechnology Information for further details (on the World Wide Web at ncbi.nlm.nih.gov). Proteins suitable for use in the methods described herein also includes proteins having between 1 to 15 amino acid changes, e.g., 1, 2, 3, 4, 5, 6, 7, 8, 9, 10, 11, 12, 13, 14, or 15 amino acid substitutions, deletions, or additions, compared to the amino acid sequence of any protein described herein. In other embodiments, the altered amino acid sequence is at least 75% identical, e.g., 77%, 80%, 82%, 85%, 88%, 90%, 91%, 92%, 93%, 94%, 95%, 96%, 97%, 98%, 99%, or 100% identical to the amino acid sequence of any protein described herein. Such sequence-variant proteins are suitable for the methods described herein as long as the altered amino acid sequence retains sufficient biological activity to be functional in the compositions and methods described herein. Where amino acid substitutions are made, the substitutions should be conservative amino acid substitutions. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. Those of skill in this art recognize that, in general, single amino acid substitutions in non-essential regions of a polypeptide do not substantially alter biological activity (see, e.g., Watson et al. Molecular Biology of the Gene, 4th Edition, 1987, The Benjamin/Cummings Pub. co., p. 224). The BLOSUM62 table is an amino acid substitution matrix derived from about 2,000 local multiple alignments of protein sequence segments, representing highly conserved regions of more than 500 groups of related proteins (Henikoff et al (1992) Proc. Natl. Acad. Sci. USA, 89:10915-10919). Accordingly, the BLOSUM62 substitution frequencies are used to define conservative amino acid substitutions that, in some embodiments, are introduced into the amino acid sequences described or disclosed herein. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

As used herein, corresponding residues refers to residues that occur at aligned loci. Related or variant polypeptides are aligned by any method known to those of skill in the art. Such methods typically maximize matches, and include methods such as using manual alignments and by using the numerous alignment programs available (for example, BLASTP) and others known to those of skill in the art. By aligning the sequences of polypeptides, one skilled in the art can identify corresponding residues, using conserved and identical amino acid residues as guides. Corresponding positions also can be based on structural alignments, for example by using computer simulated alignments of protein structure. In other instances, corresponding regions can be identified.

As used herein, an allelic variant or allelic variation references to a polypeptide encoded by a gene that differs from a reference form of a gene (i.e. is encoded by an allele). Typically the reference form of the gene encodes a wild-type form and/or predominant form of a polypeptide from a population or single reference member of a species. Typically, allelic variants, which include variants between and among species, have at least 80%, 90% or greater amino acid identity with a wild-type and/or predominant form from the same species; the degree of identity depends upon the gene and whether comparison is interspecies or intraspecies. Generally, intraspecies allelic variants have at least about 80%, 85%, 90% or 95% identity or greater with a wild-type and/or predominant form, including 96%, 97%, 98%, 99% or greater identity with a wild-type and/or predominant form of a polypeptide.

As used herein, species variants refer to variants of the same polypeptide between and among species. Generally, interspecies variants have at least about 60%, 70%, 80%, 85%, 90%, or 95% identity or greater with a wild-type and/or predominant form from another species, including 96%, 97%, 98%, 99% or greater identity with a wild-type and/or predominant form of a polypeptide.

As used herein, the terms "treat," "treating" or "treatment," and other grammatical equivalents, include alleviating, abating or ameliorating one or more symptoms of a disease or condition, ameliorating, preventing or reducing the appearance, severity or frequency of one or more additional symptoms of a disease or condition, ameliorating or preventing the underlying metabolic causes of one or more symptoms of a disease or condition, inhibiting the disease or condition, such as, for example, arresting the development of the disease or condition, relieving the disease or condition, causing regression of the disease or condition, relieving a condition caused by the disease or condition, or inhibiting the symptoms of the disease or condition either prophylactically and/or therapeutically. In a non-limiting example, for prophylactic benefit, a third-generation AR inhibitor compound disclosed herein is administered to an individual at risk of developing a particular disorder, predisposed to developing a particular disorder, or to an individual reporting one or more of the physiological symptoms of a disorder. In some embodiments, a third-generation AR inhibitor compound disclosed herein is administered to a subject following treatment with one or more therapeutic agents. In some embodiments, a third-generation AR inhibitor compound disclosed herein is administered to a subject in combination with treatment with one or more therapeutic agents.

As used herein, prevention or prophylaxis refers to the reduction in the risk of developing a disease or condition.

The terms "effective amount", "therapeutically effective amount" or "pharmaceutically effective amount" as used herein, refer to an amount of an AR inhibitor compound that is sufficient to treat a disorder. In some embodiments, the result is a reduction in and/or alleviation of the signs, symptoms, or causes of a disorder, or any other desired alteration of a biological system. For example, an "effective amount" for therapeutic uses is the amount of the composition comprising an AR inhibitor compound disclosed herein required to provide a clinically significant decrease in a disorder. An appropriate "effective" amount in any individual case is determined using any suitable technique, (e.g., a dose escalation study).

The term "pharmaceutically acceptable" as used herein, refers to a material, (e.g., a carrier or diluent), which does not abrogate the biological activity or properties of an AR inhibitor compound described herein, and is relatively non-toxic (i.e., the material is administered to an individual without causing undesirable biological effects or interacting in a deleterious manner with any of the components of the composition in which it is contained).

As used herein, a control refers to a sample that is substantially identical to the test sample, except that it is not treated with a test parameter, or, if it is a plasma sample, it can be from a normal volunteer not affected with the condition of interest. A control also can be an internal control.

As used herein, the terms "subject", "individual" and "patient" are used interchangeably. None of the terms are to be interpreted as requiring the supervision of a medical professional (e.g., a doctor, nurse, physician's assistant, orderly, hospice worker). As used herein, the subject can be any animal, including mammals (e.g., a human or non-human animal) and non-mammals. In one embodiment of the methods and compositions provided herein, the mammal is a human.

As used herein, "contacting" refers to refers to the act of touching, making contact, or of bringing substances into immediate proximity. "Contacting" can be achieved by mixing the components in a fluid or semi-fluid mixture.

Overview: AR Function and Drug Resistance in Cancer

Androgen receptor (AR) is a member of the steroid and nuclear receptor superfamily. Among this large family of proteins, only five vertebrate steroid receptors are known and include the androgen receptor, estrogen receptor, progesterone receptor, glucocorticoid receptor, and mineralocorticoid receptor. AR is a soluble protein that functions as an intracellular transcription factor. AR function is regulated by the binding of androgens, which initiates sequential conformational changes of the receptor that affect receptor-protein interactions and receptor-DNA interactions.

AR is mainly expressed in androgen target tissues, such as the prostate, skeletal muscle, liver, and central nervous system (CNS), with the highest expression level observed in the prostate, adrenal gland, and epididymis. AR in certain instance is activated by the binding of endogenous androgens, including testosterone and 5α-dihydrotestosterone (5α-DHT).

AR is a 110 kD nuclear receptor that, upon activation by androgens, mediates transcription of target genes that modulate growth and differentiation of prostate epithelial cells. AR is encoded by the AR gene located on the X chromosome at Xq11-12. Similar to the other steroid receptors, unbound AR is mainly located in the cytoplasm and associated with a complex of heat shock proteins (HSPs) through interactions with the ligand-binding domain. Upon agonist binding, AR goes through a series of conformational changes: the heat shock proteins dissociate from AR, and the transformed AR undergoes dimerization, phosphorylation, and translocation to the nucleus, which is mediated by the nuclear localization signal. The translocated receptor then binds to the androgen response element (ARE), which is characterized by the two hexameric six-nucleotide half-site consensus sequence 5'-TGTTCT-3' arranged as inverted repeats spaced by three random nucleotides and is located in the promoter or enhancer region of AR gene targets. Recruitment of other transcription co-regulators (including co-activators and co-repressors) and transcriptional machinery further ensures the appropriate modulation of AR-regulated gene expression. These processes are initiated by the ligand-induced conformational changes in the ligand-binding domain.

AR signaling is crucial for the development and maintenance of male reproductive organs including the prostate gland, as genetic males harboring loss of function AR mutations and mice engineered with AR defects do not develop prostates. This dependence of prostate cells on AR signaling continues even upon neoplastic transformation. Androgen depletion (e.g. using gonadotropin-releasing hormone (GnRH) agonists) continues to be the mainstay of prostate cancer treatment. However, androgen depletion is usually effective for a limited duration and prostate cancer evolves to regain the ability to grow despite low levels of circulating androgens.

Prostate cancer is the most prevalent cancer in men. Prostate cancer represents approximately 29 percent of all new cancer cases diagnosed and 10 percent of cancer deaths in males. In addition, American men over their lifetime have a roughly 17 percent chance of developing invasive prostate cancer. At initial diagnosis, a large percentage of prostate cancers have low to medium risk, meaning that the 10 year mortality risk is relatively low (up to 24%) with little intervention. However, advanced and metastatic prostate cancers have mean survival of 2.5-3 years and are subject to aggressive treatment including surgery and chemical castration therapy.

Given that most prostate cancer cells depend on AR for their proliferation and survival, treatment generally consists of administration of agents that block production of testosterone (e.g. GnRH agonists), alone or in combination with anti-androgens (e.g. bicalutamide), which antagonize the effect of any residual testosterone. Unfortunately, while often initially successful as evidenced by a drop in prostate specific antigen (PSA) and regression of visible tumor if present, metastatic tumors inevitably become resistant to hormonal therapy at which stage no curative treatment exists.

Prostate cancers resistant to hormonal therapies are currently referred to as 'castration resistant', implying that they have progressed beyond the point at which drugs targeting any point on the androgen axis would have any clinical utility. Pre-clinical and clinical evidence indicate that the AR is a viable therapeutic target even in castration resistant cancers. AR mutations have been reported to occur in up to 33 percent of prostate cancer cases and are most commonly observed following treatment in the AR dependent castration resistant state. Mutations have been found that alter ligand specificity and potency and that result in ligand independent receptor activity. The specific mutations vary widely but appear to be dependent upon treatment regimen. Additionally, upregulation of the AR itself has been associated with progression to the castration resistant state in both patients and animal models.

Two agents, abiraterone acetate (Zytiga; CAS No. 154229-19-3) and MDV3100 (enzalutamide; CAS No. 915087-33-7), have recently been employed in late stage clinical testing for the treatment of men with castration-resistant prostate cancer (CRPC). Abiraterone acetate targets 7-α-hydroxylase/17,20-lyase (CYP17A), thereby inhibiting residual androgen biosynthesis. MDV3100 is an anti-androgen discovered in a screen for potent anti-androgens lacking agonist activity in context of AR overexpression. The clinical efficacies of MDV3100 and abiraterone acetate support the hypothesis that AR continues to promote growth and survival of castration resistant prostate cancer. Unfortunately, similar to first-generation androgen ablation therapies, prolonged treatment with abiraterone acetate or second-generation AR antagonists ultimately results in resistance.

Resistance to abiraterone acetate and MDV3100 has been observed in both models of prostate cancer and in patients. Preliminary data suggests that, similar to castration resistant prostate cancer, second-generation anti-androgen resistance develops through multiple mechanisms and AR is thought to remain a therapeutic target in this setting. In both xenograft models and in patients, CYP17A upregulation and the presence of picogram levels of androgens have been noted in resistant populations. CYP17A upregulation presumably promotes resistance via AR activation by intratumoral androgen synthesis. In other cases, resistance correlates with increased AR levels as well as nuclear localization. Additionally, numerous cellular signaling pathways known to activate AR in the absence of endogenous ligands may promote second-generation therapy resistance. The observation that tumors with high levels of activated Src respond poorly to MDV3100 and abiraterone acetate treatment supports this hypothesis. To date, no AR mutations have been described that confer resistance to MDV3100, ARN-509 or abiraterone.

ARN-509 is a synthetic thiohydantoin compound discovered using structure-activity relationship (SAR)-guided medicinal chemistry to identify nonsteroidal anti-androgens that retain full antagonist activity in the setting of increased AR expression. ARN-509 exhibits anti-tumor activity in castration-sensitive and resistant xenograft models of prostate cancer and anti-androgenic effects in dogs that phenocopy castration.

Identification of AR Inhibitor-Resistant Cell Lines and a Mutant AR Polypeptide

Described herein are working examples demonstrating the production of drug resistant cell lines. In some embodiments, the methods provided are employed for the generation of a cell line that is resistant to inhibition by a second-generation-AR antagonist, such as, but not limited to, ARN-509, enzalutamide (MDV3100) or RD162. In some embodiments, the methods provided are employed for the generation of a cell line that is resistant to inhibition by an AR antagonist that inhibits androgen production and exhibits binding an AR receptor. In some embodiments, the AR antagonist that inhibits androgen production is a CYP17A inhibitor and exhibits binding to AR. In some embodiments, the AR antagonist that inhibits androgen production and exhibits AR binding is galeterone (TOK001) or abiraterone acetate. In some embodiments, the AR antagonist that inhibits androgen production and exhibits AR binding is TAK-700.

As described herein, resistant cell lines were generated in vivo in a castration resistant prostate cancer (CRPC) cell xenograft and in vitro in androgen responsive prostate cancer cell lines by exposure to increasing concentrations of the anti-androgen drugs ARN-509 or MDV3100. In cell proliferation and transcriptional assays, the cell lines segregated into two distinct classes.

Class 1 cell lines expressed a higher level of AR compared to their parental cell lines and proliferated in the absence of added androgens. Ligand-independent growth of the class 1 cells was unaltered in the presence of ARN-509, MDV3100 or bicalutamide. The synthetic androgen, R1881, inhibited proliferation in the class 1 cells and is antagonized by either MDV3100 or ARN-509, indicating that AR in these cell lines still binds to MDV3100 and ARN-509.

Class 2 resistant cell lines remained androgen dependent for growth similar to their parental cell lines. While ARN-509 and MDV3100 inhibited proliferation of the parental cell line, both compounds exhibited agonist activity and stimulated proliferation of the class 2 cell lines. Analysis of the nucleic acid encoding AR in the class 2 cell lines revealed that the cell lines expressed a mutant AR with a mutation in the ligand binding domain. The mutation was a thymidine (T) to cytosine (C) missense mutation that resulted in an amino acid substitution of phenylalanine at position 876 of the wild-type AR for leucine (F876L).

As described herein, in the examples, mutations in the AR gene have been identified in plasma samples from prostate cancer patients undergoing ARN-509 Phase 1/2 clinical studies. The mutations identified include a thymidine (T) to cytosine (C) missense mutation at position 2988 (first position of the codon encoding phenylanine), and a cytosine (C) to alanine (A) missense mutation at position 2990 (third position of the codon encoding phenylalanine) in an amino acid substitution of phenylalanine at position 876 of the wild-type AR for leucine (F876L). The patients identified as having these mutations also exhibited increasing levels of prostate specific antigen (PSA) over the course of the study indicating increasing resistance to treatment.

Described herein are mutant AR polypeptides that contain an amino acid substitution of phenylalanine at position 876 of the wild-type AR for leucine (F876L) and nucleic acids encoding the polypeptides. Also described herein are methods of producing the mutant AR nucleic acids and polypeptides described herein. Also described herein are compositions, combinations and kits containing the mutant AR nucleic acids and polypeptides described herein. Also provided are methods of using the mutant AR polypeptides for identifying mutant AR interacting molecules, including androgen inhibitors, including third-generation AR inhibitor compounds. Also provided are compositions containing the mutant AR interacting molecules, including pharmaceutical compositions thereof. Also provided are methods of treatment using the identified mutant AR interacting molecules.

As described herein, identification of a mutation at position 876 in the AR, such as for example F876L, allows for the design and screening of inhibitors effective for inhibition of a mutant AR having one or more resistance mutations. Such inhibitors are useful in clinical and therapeutic applications. In some embodiments, the inhibitors are useful for the treatment of a cancer, such as for example, an AR-mediated cancer, such as, for example, a prostate cancer, breast cancer, liver (i.e. hepatocellular) cancer, or bladder cancer, such as for example, a drug resistant prostate, breast, liver (i.e. hepatocellular), or bladder cancer.

As described herein, in some embodiments, subjects are screened for the identification of a mutation at position 876 in AR, such as for example F876L. In some embodiments, identification of such a mutation allows for the prescription of a cancer treatment or modification of a cancer treatment. In some embodiments, identification of such a mutation is used to stratify subjects for a particular therapy, such as for example, therapy with an inhibitor that inhibits the activity of the mutant AR (i.e. a third-generation AR inhibitor). In some embodiments, identification of such a mutation is used to characterize a subject as having a high risk of relapse of a disease or condition, such as, for example, a prostate cancer, breast cancer, liver (i.e. hepatocellular) cancer, or bladder cancer. In some embodiments, identification of such a mutation is used to characterize a subject as lacking responsiveness to particular AR inhibitor, such as for example ARN-509, MDV3100, or RD162. In some embodiments, identification of such a mutation is used to characterize a subject as lacking responsiveness to an AR inhibitor that is a CYP17A inhibitor, such as, for example galeterone (TOK001), TAK-700 or abiraterone acetate.

Mutant AR Polypeptides

Provided herein are mutant AR polypeptides. In some embodiments, the mutant AR polypeptides provided herein exhibit androgen receptor activity. For example, the mutant AR polypeptides bind to androgen response elements and promote the expression of AR-responsive genes. In some embodiments, the mutant AR polypeptides contain one or more amino acid substitutions that confers resistance to full antagonism by an anti-androgen. In some embodiments, the mutant AR polypeptides contain one or more amino acid substitutions that confers resistance to full antagonism by a second-generation AR inhibitor, such as, but not limited to, ARN-509, enzalutamide (MDV3100) or RD162. In some embodiments, the mutant AR polypeptides contain one or more amino acid substitutions that confers resistance to inhibition by ARN-509. In some embodiments, the mutant AR polypeptides contain one or more amino acid substitutions that confers resistance to inhibition by enzalutamide (MDV3100). In some embodiments, the mutant AR polypeptides contain one or more amino acid substitutions that confers resistance to inhibition by RD162.

In some embodiments, treatment of a mutant AR polypeptide provided herein with a second-generation AR inhibitor induces AR activity. For example, the second-generation AR inhibitor acts as an agonist of the mutant AR polypeptide. In some embodiments, treatment of a mutant AR polypeptide provided herein with ARN-509 induces AR activity. In some embodiments, treatment of a mutant AR polypeptide provided herein with enzalutamide (MDV3100) induces AR activity. In some embodiments, treatment of a mutant AR polypeptide provided herein with RD162 induces AR activity.

In some embodiments, the mutant AR polypeptide comprises a modification at a position corresponding to amino acid position 876 of the wild-type AR polypeptide set forth in SEQ ID NO: 1 (Accession No. P10275) or a corresponding position in the wild-type AR polypeptide set forth in SEQ ID NO: 2 (Accession No. NP_000035.2). In some embodiments, the modification is a substitution of the amino acid phenylalanine at the position corresponding to amino acid position 876 of the wild-type AR polypeptide set forth in SEQ ID NO: 1. In some embodiments, the mutant androgen receptor (AR) polypeptide does not comprise phenylalanine at the position corresponding to amino acid position 876 of the wild-type AR polypeptide set forth in SEQ ID NO: 1.

In some embodiments, the modification is a substitution of the amino acid phenylalanine at the position corresponding to amino acid position 876 of the wild-type AR polypeptide set forth in SEQ ID NO: 1, and the substituted amino acid is selected from among leucine, isoleucine, valine, alanine, glycine, methionine, serine, threonine, cysteine, tryptophan, lysine, arginine, histidine, proline, tyrosine, asparagine, glutamine, aspartic acid and glutamic acid. In some embodiments, the mutant androgen receptor (AR) polypeptide comprises a leucine, isoleucine, valine, alanine, glycine, methionine, serine, threonine, cysteine, tryptophan, lysine, arginine, histidine, proline, tyrosine, asparagine, glutamine, aspartic acid or glutamic acid at the position corresponding to amino acid position 876 of the wild-type AR polypeptide set forth in SEQ ID NO: 1. In some embodiments, the modification is a substitution of the amino acid phenylalanine at the position corresponding to amino acid position 876 of the wild-type AR polypeptide set forth in SEQ ID NO: 1, and the substituted amino acid is selected from among leucine, isoleucine, valine, alanine, glycine, methionine and tryptophan. In some embodiments, the mutant androgen receptor (AR) polypeptide comprises a leucine, isoleucine, valine, alanine, glycine, methionine or tryptophan at the position corresponding to amino acid position 876 of the wild-type AR polypeptide set forth in SEQ ID NO: 1. In some embodiments, the modification is a substitution of the amino acid phenylalanine to leucine at the position corresponding to amino acid position 876 of the wild-type AR polypeptide set forth in SEQ ID NO: 1. In some embodiments, the mutant AR polypeptide comprises a leucine at the position corresponding to amino acid 876 of the wild-type AR polypeptide set forth in SEQ ID NO: 1.

In some embodiments, the modification comprises a deletion of the amino acid phenylalanine at the position corresponding to amino acid position 876 of the wild-type AR polypeptide set forth in SEQ ID NO: 1.

In some embodiments, the mutant AR polypeptide comprises a sequence of amino acids set forth in SEQ ID NO: 5. In some embodiments the mutant AR polypeptide comprises a polypeptide having a leucine at the position corresponding to amino acid position 876 and having 65%, 70%, 75%, 80%, 85%, 90%, 95%, 96%, 97%, 98%, or 99% amino acid sequence identity to the polypeptide having the sequence set forth in SEQ ID NO: 5. In some embodiments the mutant AR polypeptide comprises a polypeptide not having a phenylalanine at the position corresponding to amino acid position 876 and having 65%, 70%, 75%, 80%, 85%, 90%, 95%, 96%, 97%, 98%, or 99% amino acid sequence identity to the polypeptide having the sequence set forth in SEQ ID NO: 5.

In some embodiments, the mutant AR polypeptide comprises a modification at amino acid position 876 and a modification at one or more additional amino acid positions.

In some embodiments, the mutant AR polypeptide comprises a modification at amino acid position 876 and a modification at 1, 2, 3, 4, 5, 6, 7, 8, 9, 10, 11, 12, 13, 14, 15, 16, 17, 18, 19, 20 or more amino acid positions. In some embodiments, the mutant AR polypeptide comprises a modification at position 876 and a modification at one additional amino acid position. In some embodiments, the mutant AR polypeptide comprises a leucine at amino acid position 876 and a modification at 1, 2, 3, 4, 5, 6, 7, 8, 9, 10, 11, 12, 13, 14, 15, 16, 17, 18, 19, 20 or more additional amino acid positions. In some embodiments, the mutant AR polypeptide comprises a leucine at position 876 and a modification at one additional amino acid position. In some embodiments, the modification at amino acid position 876 is a substitution that is F876L.

In some embodiments, the mutant AR polypeptide comprises a modification at position 876 and a modification at an additional amino acid position that confers resistance to a first- or second-generation AR antagonist or an AR antagonist that inhibits androgen production. In some embodiments, the modification at the amino acid position in addition to the modification at amino acid 876 increases the resistance of the AR polypeptide to a first- or second-generation AR antagonist or an AR antagonist that inhibits androgen production compared to an AR polypeptide comprising the modification at amino acid position 876 alone. In some embodiments, the modification at amino acid position 876 is a substitution that is F876L.

In some embodiments, the mutant AR polypeptide comprises a modification at position 876 and a modification selected from among AR modifications described in, for example, Grasso et al. (2012) *Nature* 487(7406):239-43; Ning et al. (2012) *Urology* 80(1):216-8; Cong et al. (2012) *Gene* 500(2):220-3; Hay et al. (2012) *PLoS One* 2012; 7(3):e32514; Koochekpour (2010) Asian J Androl. 12(5): 639-57; Waltering et al. (2012) *Mol Cell Endocrinol.* 2012 Jan. 8. [Epub ahead of print]; Robbins (2012) *Mol Cell Endocrinol.* 352(1-2):26-33; or Gottlieb et al. (2012) *Hum Mutat.* 33(5):887-94. In some embodiments, the modification at amino acid position 876 is a substitution that is F876L.

In some embodiments, the mutant AR polypeptide comprises a modification at position 876 and a modification selected from among AR modifications associated with castration resistant prostate cancer. In some embodiments, the modification associated with castration resistant prostate cancer is an amino acid substitution such as, for example, T877A, W741C, W741L, W741R, L701H or H874Y. In some embodiments, the modification at amino acid position 876 is a substitution that is F876L.

In some embodiments, the mutant AR polypeptide comprises a modification at amino acid position 876 and a modification at amino acid position 877. In some embodiments, the mutant AR polypeptide comprises a leucine at position 876 and a modification at amino acid position 877. In some embodiments, the modification at amino acid position 877 is a substitution of the amino acid threonine. In some embodiments, the substituted amino acid at amino acid position 877 is selected from among leucine, isoleucine, valine, alanine, phenylalanine, glycine, methionine, serine, cysteine, tryptophan, lysine, arginine, histidine, proline, tyrosine, asparagine, glutamine, aspartic acid and glutamic acid. In some embodiments, the substituted amino acid at amino acid position 877 is alanine. In some embodiments, the mutant AR polypeptide comprises a modification at position 876 and an alanine at amino acid position 877. In some embodiments, the mutant AR polypeptide comprises a leucine at position 876 and an alanine at amino acid position 877.

In some embodiments, the mutant AR polypeptide comprises a modification at position 876 and a modification at amino acid position 741. In some embodiments, the mutant AR polypeptide comprises a leucine at position 876 and a modification at amino acid position 741. In some embodiments, the modification at amino acid position 741 is a substitution of the amino acid tryptophan. In some embodiments, the substituted amino acid at amino acid position 741 is selected from among leucine, isoleucine, valine, alanine, phenylalanine, glycine, methionine, serine, threonine, cysteine, lysine, arginine, histidine, proline, tyrosine, asparagine, glutamine, aspartic acid and glutamic acid. In some embodiments, the substituted amino acid at amino acid position 741 is leucine, cysteine or arginine. In some embodiments, the mutant AR polypeptide comprises a modification at position 876 and a leucine at amino acid position 741. In some embodiments, the mutant AR polypeptide comprises a modification at position 876 and a cysteine at amino acid position 741. In some embodiments, the mutant AR polypeptide comprises a modification at position 876 and an arginine at amino acid position 741. In some embodiments, the mutant AR polypeptide comprises a leucine at position 876 and a leucine at amino acid position 741. In some embodiments, the mutant AR polypeptide comprises a leucine at position 876 and a cysteine at amino acid position 741. In some embodiments, the mutant AR polypeptide comprises a leucine at position 876 and an arginine at amino acid position 741.

In some embodiments, the mutant AR polypeptide comprises a modification at position 876 and a modification at amino acid position 701. In some embodiments, the mutant AR polypeptide comprises a leucine at position 876 and a modification at amino acid position 701. In some embodiments, the modification at amino acid position 701 is a substitution of the amino acid leucine. In some embodiments, the substituted amino acid at amino acid position 701 is selected from among isoleucine, valine, alanine, phenylalanine, glycine, methionine, histidine, serine, threonine, cysteine, lysine, arginine, tryptophan, proline, tyrosine, asparagine, glutamine, aspartic acid and glutamic acid. In some embodiments, the substituted amino acid at amino acid position 701 is histidine. In some embodiments, the mutant AR polypeptide comprises a modification at position 876 and a histidine at amino acid position 701. In some embodiments, the mutant AR polypeptide comprises a leucine at position 876 and a histidine at amino acid position 701.

In some embodiments, the mutant AR polypeptide comprises a modification at position 876 and a modification at amino acid position 874. In some embodiments, the mutant AR polypeptide comprises a leucine at position 876 and a modification at amino acid position 874. In some embodiments, the modification at amino acid position 874 is a substitution of the amino acid histidine. In some embodiments, the substituted amino acid at amino acid position 874 is selected from among leucine, isoleucine, valine, alanine, phenylalanine, glycine, methionine, serine, threonine, cysteine, lysine, arginine, tryptophan, proline, tyrosine, asparagine, glutamine, aspartic acid and glutamic acid. In some embodiments, the substituted amino acid at amino acid position 874 is tyrosine. In some embodiments, the mutant AR polypeptide comprises a modification at position 876 and a tyrosine at amino acid position 874. In some embodiments, the mutant AR polypeptide comprises a leucine at position 876 and a tyrosine at amino acid position 874.

In some embodiments, the mutant AR polypeptide is an AR polypeptide variant that comprises a modification at position 876 and one or more additional amino acid positions relative to the wild-type AR polypeptide set forth in SEQ ID NO: 1. Exemplary variants include, for example, species variants, allelic variants, RNA splicing variants and variants that contain conservative and non-conservative amino acid mutations. In some embodiments, the AR polypeptide variant comprises a polyglutamine tract of about 6 consecutive glutamine residues to about 39 consecutive glutamine residues. In some embodiments, the AR polypeptide variant comprises a polyglutamine tract of about 16 consecutive glutamine residues to about 29 consecutive glutamine residues. In some embodiments, the AR polypeptide variant comprises a polyglutamine tract of about 21 consecutive glutamine residues. In some embodiments, the AR polypeptide variant comprises a polyglutamine tract of about 22 consecutive glutamine residues. In some embodiments, the AR polypeptide variant comprises a polyglutamine tract of about 23 consecutive glutamine residues. In some embodiments, the AR polypeptide variant comprises a polyglycine tract of about 10 consecutive glycine residues to about 27 consecutive glycine residues. In some embodiments, the AR polypeptide variant comprises a polyglycine tract of about 23 consecutive glycine residues. In some embodiments, the AR polypeptide variant comprises a polyglycine tract of about 24 consecutive glycine residues.

In some embodiments, the mutant AR polypeptide comprises a portion of the mutant AR polypeptide set forth in SEQ ID NO: 5. In some embodiments, the portion exhibits an activity of an AR polypeptide. In some embodiments, the mutant AR polypeptide comprises the DNA binding domain of an AR polypeptide and the ligand binding domain of the AR polypeptide comprising the modification at amino acid position 876 of the mutant AR polypeptide set forth in SEQ ID NO: 5. In some embodiments, the mutant AR polypeptide consists essentially of the DNA binding domain of an AR polypeptide and the ligand binding domain of the AR polypeptide comprising the modification at amino acid position 876 of the mutant AR polypeptide set forth in SEQ ID NO: 5. In some embodiments, the mutant AR polypeptide comprises the sequence of amino acids from about amino acid position 554 to about amino acid position 919 of the mutant AR polypeptide set forth in SEQ ID NO: 5. In some embodiments, the mutant AR polypeptide comprises the ligand binding domain of the mutant AR polypeptide. In some embodiments, the mutant AR polypeptide consists essentially of the ligand binding domain of the mutant AR polypeptide. In some embodiments, the mutant AR polypeptide comprises the sequence of amino acids from about amino acid position 554 to about amino acid position 919.

In some embodiments, an AR polypeptide is a fusion protein comprising the ligand binding domain of an AR polypeptide comprising the modification at amino acid position 876 of the wild-type AR polypeptide set forth in SEQ ID NO: 1 linked to a heterologous polypeptide. In some embodiments, the modification is an amino acid substitution that is F876L. Methods for the generation of fusion proteins are known in the art and include standard recombinant DNA techniques. For example, in some embodiments, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In some embodiments, the fusion gene can be synthesized by conventional techniques including automated DNA synthesizers. In some embodiments, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992). In some embodiments, expression vectors are commercially available that encode a fusion moiety (e.g., a GST polypeptide). A nucleic acid encoding a modified AR polypeptide can be cloned into such an expression vector such that the fusion moiety is linked in-frame to the modified AR polypeptide.

In some embodiments, an AR polypeptide is a fusion protein comprising the ligand binding domain of an AR polypeptide comprising a modification at amino acid position 876 of the wild-type AR polypeptide set forth in SEQ ID NO: 1 linked to a heterologous DNA binding domain. In some embodiments, an AR polypeptide is a fusion protein comprising the ligand binding domain of a mutant AR polypeptide set forth in SEQ ID NO: 5 linked to a heterologous DNA binding domain. In some embodiments the heterologous DNA binding domain is GAL4 DNA binding domain. In some embodiments the heterologous DNA binding domain is LexA DNA binding domain. In some embodiments, the ligand binding domain of an AR polypeptide comprising a modification at amino acid position 876 of the wild-type AR polypeptide set forth in SEQ ID NO: 1 linked to a heterologous DNA binding domain via a peptide linker. In some embodiments, an AR polypeptide is a fusion protein comprising the ligand binding domain of a mutant AR polypeptide set forth in SEQ ID NO: 5 linked to a heterologous DNA binding domain via a peptide linker.

In some embodiments, an AR polypeptide is a fusion protein comprising the ligand binding domain of an AR polypeptide comprising a modification at amino acid position 876 of the wild-type AR polypeptide set forth in SEQ ID NO: 1 linked to a heterologous peptide for use in an protein interaction assay, such as, but not limited to a yeast two hybrid assay, a mammalian cell based two hybrid (M2H) system, a Förster (Fluorescence) Resonance Energy Transfer (FRET) assay, a Bioluminescence Resonance Energy Transfer (BRET), or a Homogeneous Time Resolved Fluorescence (HTRF®) assay. In some embodiments, an AR polypeptide is a fusion protein comprising the ligand binding domain of a mutant AR polypeptide set forth in SEQ ID NO: 5 linked to a heterologous peptide for use in an protein interaction assay, such as, but not limited to a yeast two hybrid assay, a mammalian cell based two hybrid (M2H) system, a Förster (Fluorescence) Resonance Energy Transfer (FRET) assay, a Bioluminescence Resonance Energy Transfer (BRET), or a Homogeneous Time Resolved Fluorescence (HTRF®) assay.

In some embodiments, the ligand binding domain of an AR polypeptide comprising a modification at amino acid position 876 of the wild-type AR polypeptide set forth in SEQ ID NO: 1 linked to a detectable polypeptide. In some embodiments, the ligand binding domain of a mutant AR polypeptide set forth in SEQ ID NO: 5 is linked to a detectable polypeptide. In some embodiments, the ligand binding domain of an AR polypeptide comprising a modification at amino acid position 876 of the wild-type AR polypeptide set forth in SEQ ID NO: 1 linked to a fluorescent protein, such as, but limited to, a green (GFP), red (RFP), cyan (CFP), yellow (YFP), or blue (BFP) fluorescent protein. In some embodiments, the ligand binding domain of a mutant AR polypeptide set forth in SEQ ID NO: 5 is linked to a fluorescent protein, such as, but limited to, a green (GFP), red (RFP), cyan (CFP), yellow (YFP), or blue (BFP) fluorescent protein. In some embodiments, the ligand binding domain of an AR polypeptide comprising a modification at amino acid position 876 of the wild-type AR polypeptide set forth in SEQ ID NO: 1 linked to a bioluminescent protein. In some embodiments, the ligand binding domain of a mutant AR polypeptide set forth in SEQ ID NO: 5 is linked to a bioluminescent protein. In some embodiments, the ligand binding domain of an AR polypeptide comprising a modification at amino acid position 876 of the wild-type AR polypeptide set forth in SEQ ID NO: 1 linked to a peptide tag. In some embodiments, the ligand binding domain of a mutant AR polypeptide set forth in SEQ ID NO: 5 is linked to a peptide tag. In some embodiments, the peptide tag is an epitope tag recognized by a tag-specific antibody. In some embodiments the tag is an epitope tag, such as, but not limited to a c-myc, V-5, hemagglutinin (HA), FLAG. In some embodiments the tag is an affinity tag, such as, but not limited to, biotin, strep-tag, chitin binding protein (CBP), maltose binding protein (MBP), glutathione-S-transferase (GST), or a poly(His) tag.

Nucleic Acids

Provided herein are nucleic acids encoding mutant AR polypeptides. Provided herein are nucleic acids encoding any of the mutant AR polypeptides described herein. Methods for deducing nucleic acids that encode particular polypeptides are known in the art and involve standard molecular biology techniques. Exemplary nucleic acids encoding mutant AR polypeptides provided herein are provided. It is understood that due to the degeneracy of the genetic code multiple variants nucleic acids exist that encode the same polypeptide. Nucleic acids that encode the mutant AR polypeptides provided herein encompass such variants.

In some embodiments, the nucleic acid encoding mutant AR polypeptides comprises a modification relative to a nucleic acid encoding a wild-type AR polypeptide. In some embodiments, the nucleic acid encoding a mutant AR polypeptide comprises a modification where the encoded polypeptide comprises a substitution of the amino acid phenylalanine at the position corresponding to amino acid position 876 of the wild-type AR polypeptide set forth in SEQ ID NO: 1. In some embodiments, the nucleic acid encoding a mutant AR polypeptide comprises a modification where encoded polypeptide does not comprise phenylalanine at the position corresponding to amino acid position 876 of the wild-type AR polypeptide set forth in SEQ ID NO: 1.

In some embodiments the nucleic acid modification is a missense mutation or a deletion of one or more codons that encode the polypeptide. In some embodiments, the modification is a missense mutation that changes the nucleic acid codon that encodes phenylalanine at amino position 876 of the AR polypeptide. In some embodiments, the nucleic acid codon that encodes phenylalanine at amino position 876 of the AR polypeptide is TTC or TTT. In some embodiments, the nucleic acid codon that encodes phenylalanine at amino position 876 of the AR polypeptide is TTC. In some embodiments, the nucleic acid codon that encodes phenylalanine at amino position 876 of the AR polypeptide is TTT. In some embodiments, the modification changes the nucleic acid codon that encodes phenylalanine at amino position 876 of the AR polypeptide from TTC to a nucleic acid codon that encodes leucine. In some embodiments, the modification changes the nucleic acid codon that encodes phenylalanine at amino position 876 of the AR polypeptide from TTT to a nucleic acid codon that encodes leucine. In some embodiments, the nucleic acid codon that encodes leucine is selected from among TTA, TTG, CTT, CTC, CTA or CTG.

In some embodiments, the modification is a missense mutation that comprises a substitution of Thymine (T) for Cytosine (C). In some embodiments, the modification changes the nucleic acid codon that encodes phenylalanine at amino position 876 of the AR polypeptide from TTC to CTC.

In some embodiments, the modification is a missense mutation that comprises a substitution of Thymine (T) for Adenosine (A). In some embodiments, the modification changes the nucleic acid codon that encodes phenylalanine at amino position 876 of the AR polypeptide from TTT to TTA.

In some embodiments, the modification is a missense mutation that comprises a substitution of Thymine (T) for Guanine (G). In some embodiments, the modification changes the nucleic acid codon that encodes phenylalanine at amino position 876 of the AR polypeptide from TTT to TTG.

In some embodiments, the modification comprises a missense mutation that comprises a substitution of Thymine (T) for Cytosine (C) at the first position of the codon that encodes F876 of the AR polypeptide and a second missense mutation that comprises a substitution of Thymine (T) for Adenosine (A) at the third position of the codon that encodes F876 of the AR polypeptide. In some embodiments, the modification changes the nucleic acid codon that encodes phenylalanine at amino position 876 of the AR polypeptide from TTT to CTA.

In some embodiments, the modification comprises a missense mutation that comprises a substitution of Thymine (T) for Cytosine (C) at the first position of the codon that encodes F876 of the AR polypeptide and a second missense mutation that comprises a substitution of Thymine (T) for Guanine (G) at the third position of the codon that encodes F876 of the AR polypeptide. In some embodiments, the modification changes the nucleic acid codon that encodes phenylalanine at amino position 876 of the AR polypeptide from TTT to CTG.

In some embodiments the nucleic acid encoding the mutant AR polypeptide comprises a sequence of nucleotides set forth in SEQ ID NO: 19. In some embodiments the nucleic acid encoding the mutant AR polypeptide comprises a nucleic acid having 65%, 70%, 75%, 80%, 85%, 90%, 95%, 96%, 97%, 98%, or 99% nucleotide acid sequence identity to the nucleic acid having the sequence of nucleotides set forth in SEQ ID NO: 19, where the encoded mutant AR comprises a modification relative to the wild-type AR polypeptide at a position corresponding to amino acid position 876. In some embodiments the nucleic acid encoding the mutant AR polypeptide comprises a nucleic acid having 65%, 70%, 75%, 80%, 85%, 90%, 95%, 96%, 97%, 98%, or 99% nucleotide acid sequence identity to the nucleic acid having the sequence of nucleotides set forth in SEQ ID NO: 19, where the encoded mutant AR does not comprise a phenylalanine at the position corresponding to amino acid position 876. In some embodiments the nucleic acid encoding the mutant AR polypeptide comprises a nucleic acid having 65%, 70%, 75%, 80%, 85%, 90%, 95%, 96%, 97%, 98%, or 99% nucleotide acid sequence identity to the nucleic acid having the sequence of nucleotides set forth in SEQ ID NO: 19, where the encoded mutant AR comprises a leucine at the position corresponding to amino acid position 876.

In some embodiments, the nucleic acid provided herein encoding a mutant AR polypeptide is an isolated nucleic acid. In some embodiments, the nucleic acid provided herein encoding a mutant AR polypeptide is a DNA molecule. In some embodiments, the nucleic acid provided herein encoding a mutant AR polypeptide is a cDNA molecule. In some embodiments, the nucleic acid provided herein encoding a mutant AR polypeptide is an RNA molecule. In some embodiments, the nucleic acid provided herein encoding a mutant AR polypeptide is an inhibitory RNA molecule (i.e. RNAi). In some embodiments, the nucleic acid provided herein is a nucleic acid molecule that is complementary, or binds to, an nucleic acid encoding a mutant AR polypeptide.

In some embodiments, the nucleic acid provide herein is an oligonucleotide that encodes a portion of the mutant AR polypeptide. In some embodiments the nucleic acid provided herein is an oligonucleotide that encodes a portion of the mutant AR polypeptide that contains a nucleotide codon encoding the amino acid corresponding to amino acid position 876. In some embodiments, the codon encodes an amino acid that is not phenylalanine. In some embodiments, the codon encodes an amino acid that is leucine.

In some embodiments, the nucleic acid provided herein is a vector that comprises nucleic acid encoding any of the mutant AR polypeptides provided herein. In some embodiments, the nucleic acid provided herein is a vector that comprises nucleic acid encoding any of the mutant AR polypeptides provided herein is an expression vector. In some embodiments, the nucleic acid provided herein is a vector that comprises nucleic acid encoding any of the mutant AR polypeptides provided herein is operably linked to a promoter for the expression of the mutant AR polypeptides.

In some embodiments, the vector is a plasmid vector. In some embodiments, the vector is a viral vector. In some embodiments, the viral vector is a DNA or RNA viral vector. Exemplary viral vectors include, but are not limited to, a vaccinia, adenovirus, adeno-associated virus (AAV), retrovirus, or herpesvirus vector.

Production of Nucleic Acids and Polypeptides

In some embodiments, an isolated nucleic acid molecule encoding a mutant AR polypeptide provided herein is inserted into an expression vector and expressed in a host cell or a non-cell extract. In some embodiments, an isolated nucleic acid molecule encoding a mutant AR polypeptide provided herein is operatively linked to a promoter for expression of the encoding polypeptide in a cell or non-cell extract. In some embodiments, the promoter is a constitutive promoter. In some embodiments, the promoter is an inducible promoter.

In some embodiments, the nucleic acid molecule encoding a mutant AR polypeptide provided herein is "exogenous" to a cell, which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., 1989 and Ausubel et al., 1996, both incorporated herein by reference.

Methods for the expression of a protein in a cell are well known in the art and include, for example, expression in cells, such as animal and plant cells. Exemplary animal cells for the expression of mutant AR polypeptides provided herein include but are not limited to bacteria, yeast, insect cells, and mammalian cells, such as for example, human, primate, rodent, bovine, and ovine cells. In some embodiments, the nucleic acid encoding the mutant AR is integrated into the genome of the host cell.

In some embodiments, a method for the expression of a mutant AR polypeptide provided herein comprises culturing a host cell containing an expression vector encoding a mutant AR polypeptide such that the mutant AR polypeptide is produced by the cell. In some methods, the nucleic acid encoding the mutant polypeptide is connected to nucleic acid encoding a signal sequence such that the signal sequence is expressed as a fusion peptide with the mutant AR polypeptide. In some embodiments the signal sequence allows for the secretion of the mutant AR polypeptide by the host cell.

In some embodiments the mutant AR polypeptide is isolated from a host cell expressing the mutant polypeptide. In some embodiments an extract is prepared from the host cell and the mutant AR polypeptide is isolated by purification methods such as but not limited to chromatography or immunoaffinity with an antibody that is specific for AR polypeptides or specific to the mutant AR polypeptide in particular.

Antibodies

In some embodiments the antibody binds to a mutant AR polypeptide provided herein, and binds with less affinity or does not bind to a wild-type AR polypeptide. In some embodiments the antibody binds to a mutant AR polypeptide in the presence of a second-generation inhibitor, such as, but not limited to ARN-509, enzalutamide (MDV3100) or RD162.

In some embodiments, mutant AR polypeptide provided herein are detected using antibodies that specifically recognize the mutant AR polypeptides, but do not recognize wild-type AR polypeptides. In some embodiments, mutant AR polypeptide provided herein are detected using antibodies that specifically recognize a mutant AR polypeptide having a leucine at amino acid position 876, but do not recognize wild-type AR polypeptides. In some embodiments, antibodies are raised against one or more allelic forms of the mutant AR polypeptide provided herein. Techniques for using a specific protein or an oligopeptide as an antigen to elicit antibodies that specifically recognize epitopes on the peptide or protein are well known. In one embodiment, the DNA sequence of the desired allelic form of the target gene is cloned by insertion into an appropriate expression vector and translated into protein in a prokaryotic or eukaryotic host cell. The protein can be recovered and used as an antigen to elicit the production of specific antibodies. In another embodiment, the DNA of the desired allelic form of the target gene is amplified by PCR technology and is subsequently translated in vitro into protein to be used as the antigen to elicit the production of specific antibodies. In another embodiment, the DNA sequence of the alternative alleles is used as a basis for the generation of synthetic peptides representing the amino acid sequence of the alleles for use as the antigen to elicit the production of specific antibodies.

In some embodiments, antibodies are generated either by standard monoclonal antibody techniques or generated through recombinant based expression systems. See generally, Abbas, Lichtman, and Pober, Cellular and Molecular Immunology, W. B. Saunders Co. (1991). The term "antibodies" is meant to include intact antibody molecules as well as antibody fragments or derivatives, such as Fab and F(ab')2, which are capable of specifically binding to antigen. The antibodies so produced preferentially bind only the mutant protein produced in the allelic form which was used as an antigen to create the antibody. Methods of generating allele-specific antibodies are also described in U.S. Pat. No. 6,200,754 and U.S. Pat. No. 6,054,273, the entire contents of which are incorporated herein by reference.

In some embodiments, the antibody provided herein is a humanized antibody. A "humanised antibody" refers to a type of engineered antibody having its CDRs derived from a non-human donor immunoglobulin, the remaining immunoglobulin-derived parts of the molecule being derived from one or more human immunoglobulin(s). In some embodiments, framework support residues are altered to preserve binding affinity (see, e.g., Queen et al. Proc. Natl. Acad Sci USA, 86:10029-10032 (1989), Hodgson et al. Bio/Technology, 9:421 (1991)). In some embodiments, a suitable human acceptor antibody is one selected from a conventional database, e.g., the KABAT® database, Los Alamos database, and Swiss Protein database, by homology to the nucleotide and amino acid sequences of the donor antibody. In some embodiments, a human antibody characterized by a homology to the framework regions of the donor antibody (on an amino acid basis) is suitable to provide a heavy chain constant region and/or a heavy chain variable framework region for insertion of the donor CDRs. In some embodiments, a suitable acceptor antibody capable of donating light chain constant or variable framework regions is selected in a similar manner. In some embodiments, the acceptor antibody heavy and light chains originate from the same acceptor antibody. In some embodiments, the acceptor antibody heavy and light chains originate from the different acceptor antibodies. The prior art describes several ways of producing such humanized antibodies—see, for example, EP-A-0239400 and EP-A-054951.

In some embodiments, antibodies specific for mutant AR polypeptide provided herein can be used to detect the presence of a mutant AR polypeptide provided herein in a sample, e.g., an assay sample, a cell sample, a cell extract, a biological sample, or a patient sample, using techniques known in the art. These techniques include, for example, Western blot, immunohistochemistry, indirect immunofluorescence, and antibody microarray. In some embodiments, antibodies which specifically recognize mutant AR polypeptide are third-generation AR inhibitors. In some embodiments, the ability of an antibody which specifically recognizes a mutant AR polypeptide to inhibit the biological activity of the mutant AR polypeptide can be determined using the methods described herein for identifying third-generation AR inhibitors.

Diagnostic Assays for Detecting Mutant AR Polypeptides and Nucleic Acids Encoding Mutant AR Polypeptides Provided herein are diagnostic methods that involve the detection of a mutant AR polypeptide in a subject or a nucleic acid encoding a mutant AR polypeptide in a subject. In some embodiments, the subject has an AR-mediated disease or condition. In some embodiments, the diagnostic methods are employed for the screening subjects having a cancer that is resistant to therapy with an anti-androgen, such as a first- or second-generation AR antagonist, identifying subjects for the treatment with anti-androgen, such as a first- or second-generation AR antagonist, monitoring the therapy of subjects receiving an anti-androgen therapy, such as a first- or second-generation AR antagonist, optimizing the therapy of subjects receiving an anti-androgen therapy, such as a first- or second-generation AR antagonist, and combinations thereof. In some embodiments, the methods comprises selecting a subject for therapy with a third-generation AR antagonist. In some embodiments, the methods further comprise administering to the subject a third-generation AR antagonist as described herein. In some embodiments, the mutant AR polypeptide detected comprises a modification at a position corresponding to amino acid position 876 of the wild-type AR polypeptide set forth in SEQ ID NO: 1. In some embodiments, the mutant AR polypeptide detected comprises a substitution of the amino acid phenylalanine to leucine at the position corresponding to amino acid position 876 of the wild-type AR polypeptide set forth in SEQ ID NO: 1. In some embodiments, a subject having a mutant AR polypeptide comprising a modification at amino acid position 876 is resistant to inhibition with a first- or a second-generation antagonist.

In some embodiments, a subject having a mutant AR polypeptide comprising a modification at amino acid position 876 is resistant to inhibition with a first- or a second-generation antagonist. In some embodiments, a subject having a mutant AR polypeptide comprising a modification at amino acid position 876 is resistant to inhibition with a first- and a second-generation antagonist. In some embodiments, a subject having a mutant AR polypeptide comprising a leucine at amino acid position 876 is resistant to inhibition with a first- or a second-generation antagonist. In some embodiments, a subject having a mutant AR polypeptide comprising a leucine at amino acid position 876 is resistant to inhibition with a first- and a second-generation antagonist. In some embodiments, a subject having a mutant AR polypeptide comprising a modification at amino acid position 876 is resistant to inhibition with a CYP17A inhibitor that binds to AR, such as for example, galeterone (TOK001), TAK-700 or abiraterone acetate. In some embodiments, a subject having a mutant AR polypeptide comprising a modification at amino acid position 876 is resistant to inhibition with a CYP17A inhibitor that binds to AR, such as for example, galeterone (TOK001), TAK-700 or abiraterone acetate.

In some embodiments, provided is a method for detecting a modified AR that is resistant to inhibition with a second-generation AR antagonist in a subject, comprising: (a) obtaining a sample containing a nucleic acid molecule encoding an AR polypeptide from the subject; (b) testing the sample to determine whether the encoded AR polypeptide is modified at an amino acid position corresponding to amino acid position 876 of the amino acid sequence set forth in SEQ ID NO: 1; and (c) characterizing the AR as resistant to inhibition with a second-generation AR antagonist if the subject has the modification. In some embodiments, the method further comprises administration of a third-generation AR antagonist provided herein for inhibition of the mutant AR. In some embodiments, the subject has cancer. In some embodiments, the subject has a prostate cancer. In some embodiments, the subject has a castration resistant prostate cancer.

In some embodiments, provided is a method for detecting a modified AR that is resistant to inhibition with a first-generation AR antagonist in a subject, comprising: (a) obtaining a sample containing a nucleic acid molecule encoding an AR polypeptide from the subject; (b) testing the sample to determine whether the encoded AR polypeptide is modified at an amino acid position corresponding to amino acid position 876 of the amino acid sequence set forth in SEQ ID NO: 1; and (c) characterizing the AR as resistant to inhibition with a first-generation AR antagonist if the subject has the modification. In some embodiments, the method further comprises administration of a third-generation AR antagonist provided herein for inhibition of the mutant AR. In some embodiments, the subject has cancer. In some embodiments, the subject has a prostate cancer. In some embodiments, the subject has a castration resistant prostate cancer.

In some embodiments, provided is a method for detecting a modified AR that is resistant to inhibition with an AR antagonist that is a CYP17A inhibitor in a subject, comprising: (a) obtaining a sample containing a nucleic acid molecule encoding an AR polypeptide from the subject; (b) testing the sample to determine whether the encoded AR polypeptide is modified at an amino acid position corresponding to amino acid position 876 of the amino acid sequence set forth in SEQ ID NO: 1; and (c) characterizing the AR as resistant to inhibition with an AR antagonist that is a CYP17A inhibitor if the subject has the modification. In some embodiments, the method further comprises administration of a third-generation AR antagonist provided herein for inhibition of the mutant AR. In some embodiments, the subject has cancer. In some embodiments, the subject has a prostate cancer. In some embodiments, the subject has a castration resistant prostate cancer. In some embodiments the CYP17A inhibitor is galeterone (TOK001), TAK-700 or abiraterone acetate.

In some embodiments, provided is a method for selecting a subject for therapy with a second-generation AR antagonist, comprising (a) obtaining a sample containing a nucleic acid molecule encoding an AR polypeptide from the subject; (b) testing the sample to determine whether the encoded AR polypeptide is modified at an amino acid position corresponding to amino acid position 876 of the amino acid sequence set forth in SEQ ID NO: 1; and (c) characterizing the subject as a candidate for therapy with a second-generation AR antagonist if the subject does not have the modification. In some embodiments, the method further comprises administration of a third-generation AR antagonist provided herein for inhibition of the mutant AR. In some embodiments, the subject has cancer. In some embodiments, the subject has a prostate cancer. In some embodiments, the subject has a castration resistant prostate cancer.

In some embodiments, provided is a method for selecting a subject for therapy with a first-generation AR antagonist, comprising (a) obtaining a sample containing a nucleic acid molecule encoding an AR polypeptide from the subject; (b) testing the sample to determine whether the encoded AR polypeptide is modified at an amino acid position corresponding to amino acid position 876 of the amino acid sequence set forth in SEQ ID NO: 1; and (c) characterizing the subject as a candidate for therapy with a first-generation AR antagonist if the subject does not have the modification. In some embodiments, the method further comprises administration of a third-generation AR antagonist provided herein for inhibition of the mutant AR. In some embodiments, the subject has cancer. In some embodiments, the subject has a prostate cancer. In some embodiments, the subject has a castration resistant prostate cancer.

In some embodiments, provided is a method for selecting a subject for therapy with an AR antagonist that is a CYP17A inhibitor, comprising (a) obtaining a sample containing a nucleic acid molecule encoding an AR polypeptide from the subject; (b) testing the sample to determine whether the encoded AR polypeptide is modified at an amino acid position corresponding to amino acid position 876 of the amino acid sequence set forth in SEQ ID NO: 1; and (c) characterizing the subject as a candidate for therapy with an AR antagonist that is a CYP17A inhibitor if the subject does not have the modification. In some embodiments, the method further comprises administration of a third-generation AR antagonist provided herein for inhibition of the mutant AR. In some embodiments, the subject has cancer. In some embodiments, the subject has a prostate cancer. In some embodiments, the subject has a castration resistant prostate cancer. In some embodiments the CYP17A inhibitor is galeterone (TOK001), TAK-700 or abiraterone acetate.

In some embodiments, provided is a method for selecting a subject for therapy with a third-generation AR antagonist, comprising (a) obtaining a sample containing a nucleic acid molecule encoding an AR polypeptide from the subject; (b) testing the sample to determine whether the encoded AR polypeptide is modified at an amino acid position corresponding to amino acid position 876 of the amino acid sequence set forth in SEQ ID NO: 1; and (c) characterizing the subject as a candidate for therapy with a third-generation AR antagonist if the subject has the modification. In some embodiments, the method further comprises administration of a third-generation AR antagonist provided herein for inhibition of the mutant AR. In some embodiments, the subject has cancer. In some embodiments, the subject has a prostate cancer. In some embodiments, the subject has a castration resistant prostate cancer.

In some embodiments, provided is a method for determining whether a subject is or is likely to become resistant to therapy with a second-generation AR antagonist, comprising: (a) obtaining a sample containing a nucleic acid molecule encoding an AR polypeptide from the subject; (b) testing the sample to determine whether the encoded AR polypeptide is modified at an amino acid position corresponding to amino acid position 876 of the amino acid sequence set forth in SEQ ID NO: 1; and (c) characterizing the subject as resistant or is likely to become resistant to therapy with a second-generation AR antagonist if the subject has the modification. In some embodiments, the method further comprises administration of a third-generation AR inhibitor provided herein for inhibition of the mutant AR. In some embodiments, the subject has cancer. In some embodiments, the subject has a prostate cancer. In some embodiments, the subject has a castration resistant prostate cancer.

In some embodiments, provided is a method for determining whether a subject is or is likely to become resistant to therapy with a first-generation AR antagonist, comprising: (a) obtaining a sample containing a nucleic acid molecule encoding an AR polypeptide from the subject; (b) testing the sample to determine whether the encoded AR polypeptide is modified at an amino acid position corresponding to amino acid position 876 of the amino acid sequence set forth in SEQ ID NO: 1; and (c) characterizing the subject as resistant or is likely to become resistant to therapy with a first-generation AR antagonist if the subject has the modification. In some embodiments, the method further comprises administration of a third-generation AR inhibitor provided herein for inhibition of the mutant AR. In some embodiments, the subject has cancer. In some embodiments, the subject has a prostate cancer. In some embodiments, the subject has a castration resistant prostate cancer.

In some embodiments, provided is a method for determining whether a subject is or is likely to become resistant to therapy with an AR antagonist that is a CYP17A inhibitor, comprising: (a) obtaining a sample containing a nucleic acid molecule encoding an AR polypeptide from the subject; (b) testing the sample to determine whether the encoded AR polypeptide is modified at an amino acid position corresponding to amino acid position 876 of the amino acid sequence set forth in SEQ ID NO: 1; and (c) characterizing the subject as resistant or is likely to become resistant to therapy with an AR antagonist that is a CYP17A inhibitor if the subject has the modification. In some embodiments, the method further comprises administration of a third-generation AR inhibitor provided herein for inhibition of the mutant AR. In some embodiments, the subject has cancer. In some embodiments, the subject has a prostate cancer. In some embodiments, the subject has a castration resistant prostate cancer. In some embodiments the CYP17A inhibitor is galeterone (TOK001), TAK-700 or abiraterone acetate.

In some embodiments, provided is a method for monitoring whether a subject receiving a second-generation AR antagonist for treatment of a cancer has developed or will develop resistance to the therapy, comprising (a) obtaining a sample containing a nucleic acid molecule encoding an AR polypeptide from the subject; (b) testing the sample to determine whether the encoded AR polypeptide is modified at an amino acid position corresponding to amino acid position 876 of the amino acid sequence set forth in SEQ ID NO: 1; and (c) characterizing the subject as resistant or will become resistant to therapy with a second-generation AR antagonist if the subject has the modification. In some embodiments, the method further comprises administration of a third-generation AR antagonist provided herein for inhibition of the mutant AR. In some embodiments, the subject has cancer. In some embodiments, the subject has a prostate cancer. In some embodiments, the subject has a castration resistant prostate cancer.

In some embodiments, provided is a method for monitoring whether a subject receiving a first-generation AR antagonist for treatment of a cancer has developed or will develop resistance to the therapy, comprising (a) obtaining a sample containing a nucleic acid molecule encoding an AR polypeptide from the subject; (b) testing the sample to determine whether the encoded AR polypeptide is modified at an amino acid position corresponding to amino acid position 876 of the amino acid sequence set forth in SEQ ID NO: 1; and (c) characterizing the subject as resistant or will become resistant to therapy with a first-generation AR antagonist if the subject has the modification. In some embodiments, the method further comprises administration of a third-generation AR antagonist provided herein for inhibition of the mutant AR. In some embodiments, the subject has cancer. In some embodiments, the subject has a prostate cancer. In some embodiments, the subject has a castration resistant prostate cancer.

In some embodiments, provided is a method for monitoring whether a subject receiving an AR antagonist that is a CYP17A inhibitor for treatment of a cancer has developed or will develop resistance to the therapy, comprising (a) obtaining a sample containing a nucleic acid molecule encoding an AR polypeptide from the subject; (b) testing the sample to determine whether the encoded AR polypeptide is modified at an amino acid position corresponding to amino acid position 876 of the amino acid sequence set forth in SEQ ID NO: 1; and (c) characterizing the subject as resistant or will become resistant to therapy with an AR antagonist that is a CYP17A inhibitor if the subject has the modification. In some embodiments, the method further comprises administration of a third-generation AR antagonist provided herein for inhibition of the mutant AR. In some embodiments, the subject has cancer. In some embodiments, the subject has a prostate cancer. In some embodiments, the subject has a castration resistant prostate cancer. In some embodiments the CYP17A inhibitor is galeterone (TOK001), TAK-700 or abiraterone acetate.

In some embodiments, provided is a method for optimizing the therapy of a subject receiving a second-generation AR antagonist for treatment of a cancer, comprising: (a) obtaining a sample containing a nucleic acid molecule encoding an AR polypeptide from the subject; (b) testing the sample to determine whether the encoded AR polypeptide is modified at an amino acid position corresponding to amino acid position 876 of the amino acid sequence set forth in SEQ ID NO: 1; and (c) discontinuing treatment with the second-generation AR antagonist if the subject has the modification or continuing treatment with the second-generation AR antagonist if the subject does not have the modification.

In some embodiments, provided is a method for optimizing the therapy of a subject receiving a first-generation AR antagonist for treatment of a cancer, comprising: (a) obtaining a sample containing a nucleic acid molecule encoding an AR polypeptide from the subject; (b) testing the sample to determine whether the encoded AR polypeptide is modified at an amino acid position corresponding to amino acid position 876 of the amino acid sequence set forth in SEQ ID NO: 1; and (c) discontinuing treatment with the first-generation AR antagonist if the subject has the modification or continuing treatment with the first-generation AR antagonist if the subject does not have the modification.

In some embodiments, provided is a method for optimizing the therapy of a subject receiving an AR antagonist that is a CYP17A inhibitor for treatment of a cancer, comprising: (a) obtaining a sample containing a nucleic acid molecule encoding an AR polypeptide from the subject; (b) testing the sample to determine whether the encoded AR polypeptide is modified at an amino acid position corresponding to amino acid position 876 of the amino acid sequence set forth in SEQ ID NO: 1; and (c) discontinuing treatment with the AR antagonist that is a CYP17A inhibitor if the subject has the modification or continuing treatment with the AR antagonist that is a CYP17A inhibitor if the subject does not have the modification. In some embodiments the CYP17A inhibitor is galeterone (TOK001), TAK-700 or abiraterone acetate.

In some embodiments, the modified AR is resistant to full antagonism by a second-generation AR antagonist, such as, for example, ARN-509, enzalutamide (MDV3100) or RD162. In some embodiments, a second-generation AR antagonist, such as, for example, ARN-509, enzalutamide (MDV3100) or RD162 exhibits agonist activity toward the modified AR. In some embodiments, the modified AR is resistant to full antagonism by a first-generation AR antagonist. In some embodiments, the modified AR is resistant to full antagonism by an AR antagonist that is a CYP17A.

In some embodiments, the subject has an AR dependent or AR mediated disease or condition. In some embodiments, the AR dependent or AR mediated disease or condition is benign prostate hyperplasia, hirsutism, acne, adenomas and neoplasms of the prostate, benign or malignant tumor cells containing the AR, hyperpilosity, seborrhea, endometriosis, polycystic ovary syndrome, androgenic alopecia, hypogonadism, osteoporosis, suppression of spermatogenesis, libido, cachexia, anorexia, androgen supplementation for age related decreased testosterone levels, prostate cancer, breast cancer, bladder cancer, liver cancer, endometrial cancer, uterine cancer, hot flashes, Kennedy's disease, muscle atrophy and weakness, skin atrophy, bone loss, anemia, arteriosclerosis, cardiovascular disease, loss of energy, loss of well-being, type 2 diabetes or abdominal fat accumulation.

In some embodiments, the subject has cancer. In some embodiments, the subject has a solid tumor. In some embodiments, the cancer is a prostate cancer, a breast cancer, a liver cancer, or a bladder cancer. In some embodiments, the cancer is a prostate cancer.

In some embodiments, the sample is from any tissue or fluid from an organism. Samples include, but are not limited, to whole blood, dissociated bone marrow, bone marrow aspirate, pleural fluid, peritoneal fluid, central spinal fluid, abdominal fluid, pancreatic fluid, cerebrospinal fluid, brain fluid, ascites, pericardial fluid, urine, saliva, bronchial lavage, sweat, tears, ear flow, sputum, hydrocele fluid, semen, vaginal flow, milk, amniotic fluid, and secretions of respiratory, intestinal or genitourinary tract. In particular embodiments, the sample is a tumor biopsy sample. In particular embodiments, the sample is from a fluid or tissue that is part of, or associated with, the lymphatic system or circulatory system. In some embodiments, the sample is a blood sample that is a venous, arterial, peripheral, tissue, cord blood sample. In particular embodiments, the sample is a serum sample. In some embodiments, the sample contains one or more circulating tumor cells (CTCs). In some embodiments, the sample contains one or more disseminated tumor cells (DTC, e.g. in a bone marrow aspirate sample).

Methods for the isolation of nucleic acids and proteins from cells contained in tissue and fluid samples are well-known in the art. In particular embodiments, the nucleic acid sample obtained from the subject is isolated from cells contained in a tumor biopsy from the subject. In particular embodiments, the nucleic acid sample obtained from the subject is isolated from cells in a bone marrow aspirate. In particular embodiments, the nucleic acid sample obtained from the subject is isolated from cells contained serum sample. In particular embodiments, the nucleic acid sample obtained from the subject is isolated from cells contained lymph sample.

In some embodiments, the samples are obtained from the subject by any suitable means of obtaining the sample using well-known and routine clinical methods. Procedures for obtaining fluid samples from a subject are well known. For example, procedures for drawing and processing whole blood and lymph are well-known and can be employed to obtain a sample for use in the methods provided. Typically, for collection of a blood sample, an anti-coagulation agent (e.g. EDTA, or citrate and heparin or CPD (citrate, phosphate, dextrose) or comparable substances) is added to the sample to prevent coagulation of the blood. In some examples, the blood sample is collected in a collection tube that contains an amount of EDTA to prevent coagulation of the blood sample.

In some embodiments, the sample is a tissue biopsy and is obtained, for example, by needle biopsy, CT-guided needle biopsy, aspiration biopsy, endoscopic biopsy, bronchoscopic biopsy, bronchial lavage, incisional biopsy, excisional biopsy, punch biopsy, shave biopsy, skin biopsy, bone marrow biopsy, and the Loop Electrosurgical Excision Procedure (LEEP). Typically, a non-necrotic, sterile biopsy or specimen is obtained that is greater than 100 mg, but which can be smaller, such as less than 100 mg, 50 mg or less, 10 mg or less or 5 mg or less; or larger, such as more than 100 mg, 200 mg or more, or 500 mg or more, 1 gm or more, 2 gm or more, 3 gm or more, 4 gm or more or 5 gm or more. The sample size to be extracted for the assay depends on a number of factors including, but not limited to, the number of assays to be performed, the health of the tissue sample, the type of cancer, and the condition of the patient. In some embodiments, the tissue is placed in a sterile vessel, such as a sterile tube or culture plate, and is optionally immersed in an appropriate media. Typically, the cells are dissociated into cell suspensions by mechanical means and/or enzymatic treatment as is well known in the art. Typically, the cells are collected and then subjected to standard procedures for the isolation of nucleic acid for the assay.

In some embodiments, the samples are obtained from the subject at regular intervals, such as, for example, one day, two days, three days, four days, five days, six days, one week, two weeks, weeks, four weeks, one month, two months, three months, four months, five months, six months, one year, daily, weekly, bimonthly, quarterly, biyearly or yearly. In some embodiments, the collection of samples is performed at a predetermined time or at regular intervals relative to treatment with one or more anti-cancer agents. In some embodiments, the collection of samples is performed at a predetermined time or at regular intervals relative to treatment with an AR antagonist, such as a first- or second-generation AR antagonist. For example, a sample is collected at a predetermined time or at regular intervals prior to, during, or following treatment or between successive treatments. In particular examples, a sample is obtained from the subject prior to administration of an anti-cancer therapy and then again at regular intervals after treatment has been effected. In particular examples, a sample is obtained from the subject prior to administration of an AR antagonist, such as a first- or second-generation AR antagonist, therapy and then again at regular intervals after treatment has been effected. In some embodiments, the AR antagonist is selected from among bicalutamide, flutamide, ARN-509, enzalutamide (MDV3100), and RD162. In some embodiments, the AR antagonist is a CYP17A inhibitor. In some embodiments, the CYP17A inhibitor is selected from among galeterone (TOK001), TAK-700 or abiraterone acetate.

The volume of a fluid sample can be any volume that is suitable for the detection of an AR mutant in the methods provided. In some examples, the volume for the fluid sample is dependent on the particular assay method used. For example, particular assay methods can require a larger or smaller fluid sample volumes depending on factors such as, but not limited to, the capacity of the device or method used and level of throughput of the assay method. In some examples a fluid sample is diluted in an appropriate medium prior to application of the assay method. In some examples, a fluid sample is obtained from a subject and a portion or aliquot of the sample is used in the assay method. The portion or aliquot can be diluted in an appropriate medium prior to application of the assay method.

In some embodiments, the sample is obtained from a subject that is mammal. Exemplary mammalian subjects include, but are not limited to primates, such as humans, apes and monkeys; rodents, such as mice, rats, rabbits, and ferrets; ruminants, such as goats, cows, deer, and sheep; horses, pigs, dogs, cats, and other animals. In some embodiments, the sample is obtained from a patient. In some examples, the patient is a human patient.

In some embodiments, the nucleic acid sample obtained from the subject is a genomic nucleic acid sample. In some embodiments, the nucleic acid sample obtained from the subject is an RNA sample. In some embodiments, mRNA is isolated from the total RNA in an RNA sample. In some embodiments, the RNA sample is reverse transcribed into cDNA.

In some embodiments, testing comprises sequencing the nucleic acid sample. In some embodiments, the nucleic acid encoding AR in a nucleic acid sample is amplified by a method such as polymerase chain reaction (PCR) using sequence specific primers. In some embodiments, the amplified PCR fragment is sequenced.

In some embodiments, the samples is a plasma or serum sample containing circulating tumor DNA (ctDNA), RNA (ctRNA) or microRNA (see e.g. Chan et al. (2007) *Br J Cancer.* 96(5):681-5). In some embodiments, the DNA encoding the mutant AR is assessed by BEAMing (beads, amplification, emulsion, magnetic) PCR sequencing method (see, e.g. Li et al. (2006) *Nat Methods.* 3(2):95-7; Li et al. (2006) *Nat Methods.* 3(7):551-9; and Diehl et al. (2008) *Nat Med.* 14(9): 985-990). BEAMing is a technique in which individual DNA molecules are attached to magnetic beads in water-in-oil emulsions and then subjected to compartmentalized PCR amplification. The mutational status of DNA bound to beads is then determined by hybridization to fluorescent allele-specific probes for mutant or wild-type AR. Flow cytometry is then used to quantify the level of mutant DNA present in the plasma or serum (see e.g. Higgins et al. (2012) *Clin Cancer Res* 18: 3462-3469).

In some embodiments, testing comprises detection of the mutation with a sequence specific oligonucleotide probe that is specific for nucleic acid that encodes the mutant AR but not the wild-type AR. In some embodiments, single nucleotide changes are detectable PCR using PCR-based cleaved amplified polymorphic sequences (CAPS) markers which create restriction sites in the mutant sequences (Michaels et al (1998) *Plant J.* 14(3):381-5) or sequence specific hairpin probes attached to detectable moieties, such as, but not limited to, a fluorophore (Mhlanga and Malmberg (2001) *Methods* 25:463-471).

In some embodiments, the presence of DNA encoding the mutant AR is assessed using an oligonucleotide array (see e.g. Hastia et al. (1999) *J Med Genet.* 36(10):730-6). In some embodiments, the oligonucleotide array is contained on a microchip.

In some embodiments, single nucleotide changes are detectable using microchips. In some embodiments, nucleic acid encoding a mutant AR polypeptide provided herein or a portion thereof that contains nucleic acid encoding the amino acid at position 876 that is not phenylalanine. In some embodiments, nucleic acid encoding a mutant AR polypeptide provided herein or a portion thereof that contains nucleic acid encoding leucine at amino acid position 876.

In some embodiments, testing comprises detection of the mutation with an antibody specific for the mutant AR polypeptide. In some embodiments, the method of detecting a mutant AR polypeptide comprises obtaining a sample from a subject, wherein the sample comprises an AR polypeptide and testing the sample for the presence of a mutant AR polypeptide by contacting the sample with an antibody that is specific for binding to the mutant AR polypeptide, and does not bind or bind with decreased affinity for the wild-type AR polypeptide. In some embodiments, the mutant AR specific antibody is conjugated to a detectable molecule, such as a fluorescent moiety, a radiolabel, an enzyme, a detectable substrate, or a peptide or molecule that binds to a second detectable protein (e.g. a secondary antibody). In some embodiments, binding of the mutant AR specific antibody is detected by assaying for the detectable molecule. In some embodiments, binding of the mutant AR specific antibody is detected by using a secondary (e.g. anti-IgG) antibody. In some embodiments, the sample is a tumor biopsy sample, a bone marrow aspirate, a blood sample, a serum sample, or a lymph sample.

Identification of Molecules that Interact with Mutant Androgen Receptor

Provided herein are methods of using the mutant AR polypeptides for screening of compounds that inhibit the mutant receptor (i.e. third-generation AR inhibitor compounds). In some embodiments, the methods are employed for the identification of third-generation AR inhibitor compounds for the treatment of cancer. In some embodiments, the methods are employed for the identification of third-generation AR inhibitor compounds for the treatment of resistant cancers, such as prostate cancer resistant to treatment with second-generation AR antagonists, such as ARN-509, enzalutamide (MDV3100) or RD162.

In some embodiments, a method for identifying third-generation AR inhibitor compounds comprises (a) expressing a mutant AR polypeptide provided herein in a cell, (b) contacting the cell with a test compound, and (c) detecting the level of AR activity in the cell. In some embodiments, the cell is contacted with an AR agonist prior to or at the same time as contacting the cell with the test compound. In some embodiments the cell is contacted with an AR agonist about 1 hour, 2, hours, 3 hours, 4 hours, 5 hours, 6 hours, 8 hours, 10 hours, 12 hours, 14 hours, 16 hours, 18 hours, 20 hours, 22 hours, 24 hours or longer prior to contacting the cell with the test compound. In some embodiments the cell is contacted with an AR agonist at the same time as the cell is contacted with test compound. In some embodiments, the AR agonist is selected from among methyltrienolone (R1881), DHT, mibolerone (Mb) and testosterone. In some embodiments, the mutant AR polypeptide comprises an amino acid substitution at a position corresponding to amino acid position 876 of the wild-type AR polypeptide set forth in SEQ ID NO: 1. In some embodiments, the mutant AR polypeptide does not contain a phenylalanine at amino acid position 876 in the polypeptide. In some embodiments, the mutant AR polypeptide contains a leucine at amino acid position 876 in the polypeptide.

In some embodiments, a cell line that can be transfected with nucleic acid encoding the mutant AR polypeptide and in which AR activity can be monitored is used. In some embodiments, the cell does not express the wild-type AR. In some embodiments, the cell expresses a low level of wild-type AR. In some embodiments, the cell expresses an endogenous mutant AR polypeptide. In some embodiments, the endogenous mutant AR polypeptide comprises a modification at an amino acid corresponding to amino acid 877 of a wild-type AR polypeptide. In some embodiments, the endogenous mutant AR polypeptide comprises a modification that is a substitution of Threonine to Alanine at amino acid position 877 (T877A). In some embodiments, the mutant AR polypeptide comprises a modification at an amino acid corresponding to amino acid 874 of a wild-type AR polypeptide. In some embodiments, the mutant AR polypeptide comprises a modification that is a substitution of Histidine to Tyrosine at amino acid position 874 (H874Y). In some embodiments, the cell is a selected from among HeLa, CV1, COS7, HepG2, HEK-293, DU145, PC3, and TSY-PR1. In some embodiments, the cell line is a prostate cancer cell line. In some embodiments, the cell line is selected from among CWR, LNCaP, VCaP and LAPC4.

In some embodiments, the cell stably expresses the mutant AR polypeptide. In some embodiments, the nucleic acid encoding the mutant AR is integrated into the genome of the cell.

In some embodiments, the level of AR activity is detected using a reporter gene operably linked to an AR-responsive promoter. In some embodiments, the AR-responsive promoter comprises one or more androgen response elements (AREs) to which the mutant AR polypeptide binds. In some embodiments, the promoter is selected from among a probasin (Pb), a prostate specific antigen (PSA), mouse mammary tumor virus long terminal repeat (MMTV LTR), fatty acid synthase (FASN), six transmembrane epithelial antigen of the prostate 4 (STEAP4), transmembrane protease, serine 2

(TMPRSS2), alpha-1-acid glycoprotein 1 (ORM1), or human homeobox gene NKX3.1 promoter. In some embodiments, the promoter is a synthetic promoter containing one or more AREs.

In some embodiments, the AR-responsive promoter is operably linked to a suitable reporter gene that encodes a detectable protein. Exemplary detectable proteins include, but are not limited to, luciferase, fluorescent proteins, bioluminescent proteins, β-galactosidase, alkaline phosphatase, and chloramphenicol acetyltransferase. In some embodiments, a decrease in the expression of the reporter gene following exposure to the test compound compared to a suitable control indicates that the test compound is effective for inhibition of the mutant AR polypeptide. In some embodiments, the control is basal expression of the reporter gene prior to exposure of the cell to the test compound. In some embodiments the expression of the reporter gene is assayed using a cell extract prepared from the test cells.

In some embodiments, the level of AR activity is detected by measuring the expression of one or more endogenous androgen responsive genes in a cell. In some embodiments, the androgen responsive gene is upregulated (i.e. induced) in response to androgen treatment. In some embodiments, the androgen responsive gene is downregulated (i.e. repressed) in response to androgen treatment. Exemplary androgen responsive genes include, but are not limited to, prostate specific antigen (PSA), prostate specific membrane antigen (PSMA), prostasin, snail homolog 2 (SLUG), transmembrane protease, serine 2 (TMPRSS2), six transmembrane epithelial antigen of prostate family member 4 (STEAP4), FK506 binding protein 5 (FKBP5), orosomucoid 1/alpha-1-acid glycoprotein 1 (ORM1), solute carrier family 35 (SLC35F2/NOV), insulin-like growth factor I (IGF-1) IGF binding protein-3 and -5, CCAAT-enhancer binding protein-δ, phosphatase and tensin homolog deleted on chromosome 10 (PTEN), FASN, NKX3.1, AMIGO2, BDNF, CAMK2N1, HPGD, NCAPD3, PLD1, IL-15, IL-18, and ERBB2/HER2.

In some embodiments, the level of AR activity is detected by measuring the expression of one or more endogenous genes that are induced by exposure to an androgen or an AR agonist. In some embodiments, a decrease in the expression of one or more androgen inducible genes following exposure to the test compound compared to a suitable control indicates that the test compound is effective for inhibition of the mutant AR polypeptide. Exemplary androgen inducible genes include but are not limited to, prostate specific antigen (PSA), prostasin, snail homolog 2 (SLUG), transmembrane protease, serine 2 (TMPRSS2), six transmembrane epithelial antigen of prostate family member 4 (STEAP4), FK506 binding protein 5 (FKBP5), and orosomucoid 1/alpha-1-acid glycoprotein 1 (ORM1). In some embodiments, expression of the inducible gene is assessed in the presence of an AR agonist. In some embodiments, the cells are contacted with an androgen agonist prior to or simultaneously with the test compound.

In some embodiments, the level of AR activity is detected by measuring the expression of one or more endogenous genes that are repressed by exposure to an androgen or an AR agonist. In some embodiments, an increase in or failure to repress the expression of one or more androgen repressed genes following exposure to the test compound compared to a suitable control indicates that the test compound is effective for inhibition of the mutant AR polypeptide. In some embodiments, the control is basal expression of the gene prior to exposure of the cell to the test compound. Exemplary androgen repressed genes include, but are not limited to, prostate specific membrane antigen (PSMA), solute carrier family 35 (SLC35F2/NOV), IGF binding protein-3 and -5, CCAAT-enhancer binding protein-δ, phosphatase and tensin homolog deleted on chromosome 10 (PTEN), IL-15, IL-18, and ERBB2/HER2. In some embodiments, expression of the repressible gene is assessed in the presence of an AR agonist. In some embodiments, the cells are contacted with an androgen agonist prior to or simultaneously with the test compound.

Methods to measure the expression of endogenous genes is well-known in the art. Exemplary methods for the measurement of gene expression include, but are not limited to protein analytical methods such as, for example, immunohistochemistry, immunoblotting (e.g. Western analysis), chromatography, and nucleic acids analytical methods, such as, for example, polymerase chain reaction (PCR), quantitative PCR (qPCR), real time PCR (RT-PCR), Northern analysis.

In some embodiments, the activity of a mutant AR polypeptide is measured using an assay such as, but not limited to, a AR coactivator binding assay (e.g. immunoprecipitation assays, two-hybrid assays, Förster (fluorescence) resonance energy transfer assays, for example, LanthaScreen™ TR-FRET androgen receptor coactivator assay), a AR conformational profiling assay (see, e.g., Joseph et al. (2009) *PNAS* 106(29):12178-12183), an AR DNA binding assay (see, e.g., Roche et al. (1992) *Mol. Endocrinol.* 6(12):2229-35), chromatin immunoprecipitation, N/C terminal interaction assay (see, e.g., Hsu et al. (2005) *Mol. Endocrinology* 19(2) 350-361 and Ghali et al. (2003) *J Clin Endocrinol Metab.* 88(5):2185-93).

In some embodiments, a method for identifying third-generation AR inhibitor compounds comprises selecting a potential third-generation AR inhibitor compound using computer-assisted modeling with a three-dimensional crystal or solution structure of a mutant AR polypeptide provided herein. In some embodiments, the mutant AR polypeptide comprises an amino acid substitution at a position corresponding to amino acid position 876 of the wild-type AR polypeptide set forth in SEQ ID NO: 1. In some embodiments, the mutant AR polypeptide does not contain a phenylalanine at amino acid position 876 in the polypeptide. In some embodiments, the mutant AR polypeptide contains a leucine at amino acid position 876 in the polypeptide. In some embodiments, the method comprises contacting the mutant AR polypeptide with the test compound and detecting the interaction of the test compound with the mutant AR polypeptide. In some embodiments, a test compound that interacts with the mutant AR polypeptide is identified as a candidate third-generation AR inhibitor compound.

In some embodiments, a test compound for use in the methods provided is a member of a library of compounds. In some embodiments, generation of a library of test compounds is by any suitable method for the production of chemical compounds. A "library of test compounds" refers to a panel comprising a multiplicity of test compounds. An exemplary approach for the synthesis of molecular libraries of small organic molecules has been described (Carell et al. (1994). Angew. Chem. Int. Ed. Engl. 33:2059; Carell et al. (1994) Angew. Chem. Int. Ed. Engl. 33:2061). In some embodiments the test compounds provided herein are obtained using any of the numerous approaches in combinatorial library methods known in the art, including: biological libraries; spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:145). Other exemplary methods for the synthesis of molecular libraries are found in the art, for example in: Erb et al. (1994). Proc. Natl. Acad. Sci. USA 91:11422; Horwell et al. (1996) Immunopharmacology 33:68-; and in Gallop et al. (1994); J. Med. Chem. 37:1233-. In some embodiments, libraries of compounds are presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner USP '409), plasmids (Cull et al. (1992) Proc Natl Acad Sci USA 89:1865-1869) or on phage (Scott and Smith (1990) Science 249:386-390); (Devlin (1990) Science 249:404-406); (Cwirla et al. (1990) Proc. Natl. Acad. Sci. 87:6378-6382); (Felici (1991) J. Mol. Biol. 222:301-310). In some embodiments, combinatorial polypeptides are produced from a cDNA library. Exemplary compounds that can be screened for activity include, but are not limited to, peptides, nucleic acids, carbohydrates, small organic molecules, and natural product extract libraries.

AR Inhibitors Identified by the Screening Methods

The third-generation AR inhibitors identified using the screening methods provided herein are AR modulators. In some embodiments, the third-generation AR inhibitor inhibits or reduces at least one activity of an AR polypeptide. Exemplary AR activities include, but are not limited to, co-activator binding, DNA binding, ligand binding, or nuclear translocation. In some embodiments, the third-generation AR inhibitor inhibits an activity of an AR polypeptide by about 10%, 20%, 30%, 40%, 50%, 60%, 70%, 80%, 85%, 90%, 95%, 98% or 100% compared to the activity of the AR polypeptide in the absence of the inhibitor. In some embodiments, the third-generation AR inhibitor compounds identified using the methods provided herein are AR inverse agonists, AR antagonists, AR degraders, AR trafficking modulators and/or AR DNA-binding inhibitors. In some embodiments, a third-generation AR inhibitor compounds identified using the methods provided herein is an AR inverse agonist. In some embodiments, the third-generation AR inhibitor compounds identified using the methods provided herein are AR antagonists. In some embodiments, the third-generation AR inhibitor compounds identified using the methods provided herein are AR degraders. In some embodiments, the third-generation AR inhibitor compounds identified using the methods provided herein are AR trafficking modulators. In some embodiments, the third-generation AR inhibitor compounds identified using the methods provided herein are AR DNA-binding inhibitors. In some embodiments, the AR inhibitor inhibits at least one activity of a wild-type AR polypeptide. In some embodiments, the AR inhibitor inhibits at least one activity of a mutant AR polypeptide.

In some embodiments, the third-generation AR inhibitor compound identified using the methods provided herein has minimal pro-convulsant activity and/or minimal impact on seizure threshold. In some embodiments, the third-generation AR inhibitor compound identified using the methods provided herein displays minimal modulation of the GABA-gated chloride channel. In some embodiments, the third-generation AR inhibitor compound identified using the methods provided herein displays minimal binding to the GABA-gated chloride channel. In some embodiments, the third-generation AR inhibitor compound identified using the methods provided herein has minimal antagonism of the GABA-gated chloride channel. In some embodiments, the third-generation AR inhibitor compound identified using the methods provided herein is an AR modulator with minimal interaction with a GABA-gated chloride channel. In some embodiments, the third-generation AR inhibitor compound identified using the methods provided herein is an AR modulator with minimal interaction with the $GABA_A$-gated chloride channel. In some embodiments, the third-generation AR inhibitor compound identified using the methods provided herein is an AR modulator with minimal interaction with the $GABA_A$-gated chloride channel and or minimal blood-brain barrier penetration. GABA assays are known and include, but are not limited to, those described in Ashok K. Mehta and Maharaj K. Ticku "Characterization of the Picrotoxin Site of $GABA_A$ Receptors" *Current Protocols in Pharmacology* (2000) 1.18.1-1.18.17; Copyright © 2000 by John Wiley & Sons, Inc., which is herein incorporated by reference.

In some embodiments, a third-generation AR inhibitor compound identified using the methods provided herein inhibits AR nuclear translocation. In some embodiments, a third-generation AR inhibitor compound identified using the methods provided herein inhibits AR DNA binding to androgen response elements. In some embodiments, a third-generation AR inhibitor compound identified using the methods provided herein inhibits coactivator recruitment at an AR responsive promoter. In some embodiments, a third-generation AR inhibitor compound identified using the methods provided herein exhibits no agonist activity in AR-overexpressing prostate cancer cells.

In some embodiments, a third-generation AR inhibitor compound identified using the methods provided herein inhibits growth of castration sensitive and castration resistant prostate cancer xenograft models. In some embodiments, a third-generation AR inhibitor compound identified using the methods provided herein inhibits growth of castration sensitive and castration resistant prostate cancer xenograft models expressing wild-type AR. In some embodiments, a third-generation AR inhibitor compound identified using the methods provided herein inhibits growth of castration sensitive and castration resistant prostate cancer xenograft models expressing a mutant AR having a F876L mutation. In some embodiments, a third-generation AR inhibitor compound identified using the methods provided herein inhibits growth of castration sensitive and castration resistant prostate cancer xenograft models expressing the wild-type AR and a mutant AR having a F876L mutation. In some embodiments, a third-generation AR inhibitor compound identified using the methods provided herein inhibits growth of castration sensitive and castration resistant prostate cancer xenograft models expressing a mutant AR having a T877A mutation (e.g. xenograft tumors formed from LNCaP cells). In some embodiments, a third-generation AR inhibitor compound identified using the methods provided herein inhibits growth of castration sensitive and castration resistant prostate cancer xenograft models expressing the wild-type AR and a mutant AR having a T877A mutation (e.g. xenograft tumors formed from LNCaP/AR cells). In some embodiments, a third-generation AR inhibitor compound identified using the methods provided herein inhibits growth of castration sensitive and castration resistant prostate cancer xenograft models expressing a mutant AR having a T877A mutation and a mutant AR having a F876L mutation.

Pharmaceutical Compositions

In some embodiments, provided is a pharmaceutical composition comprising a therapeutically effective amount of a third-generation AR inhibitor identified using the screening methods provided herein. In some embodiments, provided is a use of a third-generation AR inhibitor identified using the screening methods provided herein for the preparation of a medicament.

In some embodiments, the pharmaceutical composition comprising a third-generation AR inhibitor also contains at least one pharmaceutically acceptable inactive ingredient. In some embodiments, the pharmaceutical composition comprising a third-generation AR inhibitor is formulated for intravenous injection, subcutaneous injection, oral administration, or topical administration. In some embodiments, the pharmaceutical composition comprising a third-generation AR inhibitor is a tablet, a pill, a capsule, a liquid, a suspension, a gel, a colloid, a dispersion, a suspension, a solution, an emulsion, an ointment, or a lotion.

Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

Provided herein are pharmaceutical compositions a third-generation AR inhibitor, or a pharmaceutically acceptable salt thereof, and at least one pharmaceutically acceptable inactive ingredient. In some embodiments, the third-generation AR inhibitor described herein is administered as pharmaceutical compositions in which the third-generation AR inhibitor is mixed with other active ingredients, as in combination therapy. In other embodiments, the pharmaceutical compositions include other medicinal or pharmaceutical agents, carriers, adjuvants, preserving, stabilizing, wetting or emulsifying agents, solution promoters, salts for regulating the osmotic pressure, and/or buffers. In yet other embodiments, the pharmaceutical compositions include other therapeutically valuable substances.

A pharmaceutical composition, as used herein, refers to a mixture of a the third-generation AR inhibitor or a pharmaceutically acceptable salt thereof, with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to a subject, such as a mammal.

A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the pharmaceutical composition further comprises one or more additional therapeutically active agents, including, but not limited to, corticosteroids, anti-emetic agents, analgesics, anti-cancer agents, anti-inflammatory agents, kinase inhibitors, HSP90 inhibitors, and histone deacetylase (HDAC) inhibitors.

In some embodiments, provided is a pharmaceutical composition comprising a therapeutically effective amount of a mutant AR polypeptide provided herein. In some embodiments, provided is a pharmaceutical composition comprising a therapeutically effective amount of a nucleic acid encoding a mutant AR polypeptide provided herein.

Therapeutic Methods

In some embodiments, the third-generation AR inhibitor compounds identified using the methods provided herein are administered for the treatment of a disease or condition. In some embodiments, described herein is a method of treating an AR dependent or AR mediated disease or condition in mammal comprising administering to the mammal a therapeutically effective amount of a third-generation AR inhibitor compound identified using the methods provided herein, or a pharmaceutically acceptable salt thereof.

In some embodiments, provided is a method comprising administering a third-generation AR inhibitor compound identified using the methods provided herein to a subject (e.g. a human) having a disease or condition that is AR meditated or AR dependent. In some embodiments, provided is a use of a third-generation AR inhibitor compound identified using the methods provided herein for the preparation of medicament for the treatment of a disease or condition that is AR meditated or AR dependent. In some embodiments, provided is a third-generation AR inhibitor compound identified using the methods provided herein for the treatment of a disease or condition that is AR meditated or AR dependent. In some embodiments, the subject (e.g. a human) is currently receiving one or more additional therapeutically active agents other than the third-generation AR inhibitor compound.

In some embodiments, the method further comprises administering one or more additional therapeutically active agents other than a third-generation AR inhibitor compound identified using the methods provided herein. In some embodiments, the one or more additional therapeutically active agents other than a third-generation AR inhibitor compound identified using the methods provided herein are selected from: hormones, hormone receptor agonists or antagonists, corticosteroids, anti-emetic agents, analgesics, anti-cancer agents, anti-inflammatory agents, kinase inhibitors, HSP90 inhibitors, histone deacetylase (HDAC) inhibitors. In some embodiments, third-generation AR inhibitor compound is administered prior to, simultaneously, following, or intermittently with the one or more additional therapeutically active agents other than the third-generation AR inhibitor compound.

In some embodiments, the subject is administered a gonadotropin-releasing hormone (GnRH) agonist or antagonist in combination with third-generation AR inhibitor compound provided herein. In some embodiments, a GnRH receptor agonist such as leuprolide, bruserelin and goserelin is administered to a subject in combination with third-generation AR inhibitor compound provided herein. GnRH receptor agonists cause an initial surge in hormone production (i.e. "clinical flare") followed by the inhibition of lutenizing hormone production, which in turn causes a suppression of testosterone and dihydrotestosterone, on which continued growth of prostate cancer cells depend. In some embodiments, the subject is administered a gonadotropin-releasing hormone (GnRH) agonist or antagonist in combination with third-generation AR inhibitor compound provided herein for the treatment of an AR dependent or AR mediated disease or condition such as a prostate, breast, bladder or hepatocellular cancer. In some embodiments, the subject is administered a gonadotropin-releasing hormone (GnRH) agonist or antagonist in combination with third-generation AR inhibitor compound provided herein for the treatment of a castration resistant prostate cancer (CRPC). In some embodiments, the subject is administered a third-generation AR inhibitor compound provided herein to reduce or inhibit the initial surge in hormone production caused by treatment with a GnRH receptor agonist. In some embodiments, third-generation AR inhibitor compound is administered prior to, simultaneously, following, or intermittently with a GnRH receptor agonist or antagonist.

In some embodiments, the AR dependent or AR mediated disease or condition is benign prostate hyperplasia, hirsutism, acne, adenomas and neoplasms of the prostate, benign or malignant tumor cells containing the androgen receptor, hyperpilosity, seborrhea, endometriosis, polycystic ovary syndrome, androgenic alopecia, hypogonadism, osteoporosis, suppression of spermatogenesis, libido, cachexia, anorexia, androgen supplementation for age related decreased testosterone levels, prostate cancer, breast cancer, endometrial cancer, uterine cancer, bladder cancer, hepatocellular cancer, hot flashes, and Kennedy's disease, muscle atrophy and weakness, skin atrophy, bone loss, anemia, arteriosclerosis, cardiovascular disease, loss of energy, loss of well-being, type 2 diabetes or abdominal fat accumulation. In some embodiments, the AR dependent or AR mediated disease or condition is an AR dependent or AR mediated cancer, such as, for example, a prostate, breast, bladder or liver (i.e. hepatocellular) cancer.

In some embodiments, described herein is a method of treating cancer in a mammal comprising administering to the mammal a therapeutically effective amount of a third-generation AR inhibitor compound identified using the methods provided herein, or a pharmaceutically acceptable salt thereof. In some embodiments, the cancer is a hormone dependent cancer. In some embodiments, the hormone dependent cancer is an AR dependent cancer. In some embodiments, the cancer is prostate cancer. In some embodiments, the cancer is castration resistant prostate cancer. In some embodiments, the method of treating cancer further comprises administering to the mammal at least one additional anti-cancer agent.

In some embodiments, a third-generation AR inhibitor compound identified using the methods provided herein is used to treat prostate cancer in a mammal, wherein the mammal has not received treatment with an anti-cancer agent. In some embodiments, a third-generation AR inhibitor compound identified using the methods provided herein is used to treat prostate cancer in a mammal, wherein the mammal has not received treatment with a chemotherapeutic compound.

In some embodiments, a third-generation AR inhibitor compound identified using the methods provided herein is used to treat prostate cancer in a mammal, wherein the mammal has been administered one or more anti-cancer agents. Exemplary anti-cancer agents include, but are not limited to, hormonal therapeutic agents, including, but not limited to first- and second-generation AR antagonists (e.g. bicalutamide, flutamide, ARN-509, enzalutamide (MDV3100) and RD162) and compounds that inhibit hormone (e.g. androgen) production, such as, for example, galeterone (TOK001), TAK-700 or abiraterone acetate, chemotherapeutic compounds, anti-metabolites, anti-cancer antibodies, surgery, radiation, and hyperthermal therapy. In some embodiments, a third-generation AR inhibitor compound identified using the methods provided herein is used to treat prostate cancer in a mammal, wherein the mammal has been administered one or more chemotherapeutic compounds. In some embodiments, a third-generation AR inhibitor compound identified using the methods provided herein is used to treat prostate cancer in a mammal, wherein the mammal has been treated by surgery. In some embodiments, a third-generation AR inhibitor compound identified using the methods provided herein is used to treat prostate cancer in a mammal, wherein the mammal has been treated with radiation therapy. In some embodiments, a third-generation AR inhibitor compound identified using the methods provided herein is used to treat prostate cancer in a mammal, wherein the mammal has been treated with a hyperthermal therapy.

In some embodiments, a third-generation AR inhibitor compound identified using the methods provided herein is used to treat prostate cancer in a mammal, wherein the mammal has been administered one or more cycles of treatment with an anti-cancer agent.

In some embodiments, described herein is a method of treating cancer in a mammal comprising administering to the mammal a therapeutically effective amount of a third-generation AR inhibitor compound identified using the methods provided herein, or a pharmaceutically acceptable salt thereof, wherein the compound is an AR inverse agonist, AR antagonist, an AR degrader, an AR trafficking modulator, an AR DNA-binding inhibitor, or combinations thereof.

In some embodiments, described herein is a method of treating cancer in a mammal comprising administering to the mammal a therapeutically effective amount of a third-generation AR inhibitor compound identified using the methods provided herein, or a pharmaceutically acceptable salt thereof, wherein the compound is an AR inverse agonist.

In some embodiments, described herein is a method of treating cancer in a mammal comprising administering to the mammal a therapeutically effective amount of a third-generation AR inhibitor compound identified using the methods provided herein, or a pharmaceutically acceptable salt thereof, wherein the compound is an AR antagonist.

In some embodiments, described herein is a method of treating cancer in a mammal comprising administering to the mammal a therapeutically effective amount of a third-generation AR inhibitor compound identified using the methods provided herein, or a pharmaceutically acceptable salt thereof, wherein the compound is an AR degrader.

In some embodiments, described herein is a method of treating cancer in a mammal comprising administering to the mammal a therapeutically effective amount of a third-generation AR inhibitor compound identified using the methods provided herein, or a pharmaceutically acceptable salt thereof, wherein the compound is an AR trafficking modulator.

In some embodiments, described herein is a method of treating cancer in a mammal comprising administering to the mammal a therapeutically effective amount of a third-generation AR inhibitor compound identified using the methods provided herein, or a pharmaceutically acceptable salt thereof, wherein the compound is an AR DNA-binding inhibitor.

In some embodiments, described herein is a method of treating cancer in a mammal comprising administering to the mammal a therapeutically effective amount of a third-generation AR inhibitor compound identified using the methods provided herein, or a pharmaceutically acceptable salt thereof, wherein the compound is an AR protein synthesis inhibitor.

In some embodiments, the cancer is prostate cancer. In some embodiments, the cancer is castration resistant prostate cancer. In some embodiments, the prostate cancer is an ARN-509-resistant prostate cancer. In some embodiments, the prostate cancer is an enzalutamide (MDV3100)-resistant prostate cancer. In some embodiments, the prostate cancer is an RD162-resistant prostate cancer. In some embodiments, the prostate cancer is an abiraterone acetate-resistant prostate cancer. In some embodiments, the prostate cancer is a galeterone (TOK001)-resistant prostate cancer. In some embodiments, the prostate cancer is a TAK-700-resistant prostate cancer.

Pharmaceutical formulations described herein are administerable to a subject in a variety of ways by multiple administration routes, including but not limited to, oral, parenteral (e.g., intravenous, subcutaneous, intramuscular), buccal, topical or transdermal administration routes. The pharmaceutical formulations described herein include, but are not limited to, aqueous liquid dispersions, self-emulsifying dispersions, solid solutions, liposomal dispersions, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations. In some embodiments, a third-generation AR inhibitor compound identified using the methods provided herein is administered orally. In some embodiments, a third-generation AR inhibitor compound identified using the methods provided herein is administered intravenously.

In some embodiments, a third-generation AR inhibitor compound identified using the methods provided herein is administered topically. In such embodiments, a third-generation AR inhibitor compound identified using the methods provided herein is formulated into a variety of topically administrable compositions, such as solutions, suspensions, lotions, gels, pastes, shampoos, scrubs, rubs, smears, medicated sticks, medicated bandages, balms, creams or ointments. Such pharmaceutical compounds can contain solubilizers, stabilizers, tonicity enhancing agents, buffers and preservatives. In one aspect, the anti-androgen compound identified using the methods provided herein is administered topically to the skin.

In another aspect is the use of a third-generation AR inhibitor compound identified using the methods provided herein in the manufacture of a medicament for treating a disease, disorder or conditions in which the activity of AR contributes to the pathology and/or symptoms of the disease or condition. In one aspect, the disease or condition is any of the diseases or conditions specified herein.

In any of the aforementioned aspects are further embodiments in which: (a) the effective amount of the third-generation AR inhibitor compound identified using the methods provided herein is systemically administered to the mammal; and/or (b) the effective amount of the third-generation AR inhibitor compound is administered orally to the mammal; and/or (c) the effective amount of the third-generation AR inhibitor compound is intravenously administered to the mammal; and/or (d) the effective amount of the third-generation AR inhibitor compound is administered by injection to the mammal; and/or (e) the effective amount of the third-generation AR inhibitor compound is administered topically to the mammal; and/or (f) the effective amount of the third-generation AR inhibitor compound is administered non-systemically or locally to the mammal.

In any of the aforementioned aspects are further embodiments comprising single administrations of the effective amount of the third-generation AR inhibitor compound identified using the methods provided herein, including further embodiments in which (i) the third-generation AR inhibitor compound is administered once; (ii) the third-generation AR inhibitor compound is administered to the mammal multiple times over the span of one day; (iii) continually; or (iv) continuously.

In any of the aforementioned aspects are further embodiments comprising multiple administrations of the effective amount of a third-generation AR inhibitor compound identified using the methods provided herein, including further embodiments in which (i) the third-generation AR inhibitor compound is administered continuously or intermittently: as in a single dose; (ii) the time between multiple administrations is every 6 hours; (iii) the third-generation AR inhibitor compound is administered to the mammal every 8 hours; (iv) the third-generation AR inhibitor compound is administered to the mammal every 12 hours; (v) the third-generation AR inhibitor compound is administered to the mammal every 24 hours. In further or alternative embodiments, the method comprises a drug holiday, wherein the administration of the third-generation AR inhibitor compound is temporarily suspended or the dose of the compound being administered is temporarily reduced; at the end of the drug holiday, dosing of the compound is resumed. In some embodiments, the length of the drug holiday varies from 2 days to 1 year.

Also provided is a method of reducing AR activation in a mammal comprising administering to the mammal a third-generation AR inhibitor compound identified using the methods provided herein. In some embodiments, the method comprises reducing AR activation in prostate cells in the mammal. In some embodiments, the method comprises reducing AR activation in non-prostate cells. In some embodiments, the method of reducing AR activation comprises reducing the binding of androgens to the androgen receptor. In some embodiments, the method of reducing AR activation comprises reducing AR concentration in a cell.

In some cases disclosed herein is the use of a third-generation AR inhibitor compound identified using the methods provided herein in the manufacture of a medicament for the treatment of diseases or conditions that are AR dependent or AR mediated. In some embodiments, the disease or condition is prostate cancer. In some embodiments, the AR dependent or AR mediated disease or condition is described herein.

In some cases disclosed herein is the use of a third-generation AR inhibitor compound identified using the methods provided herein in the treatment or prevention of diseases or conditions that are AR dependent or AR mediated. In some embodiments, the AR dependent or AR mediated disease or condition is described herein.

In any of the embodiments disclosed herein, the mammal is a human. In some embodiments, the third-generation AR inhibitor compound provided herein is administered to a human.

In some embodiments, the third-generation AR inhibitor compound provided herein is used to diminish, reduce, or eliminate the activity of AR.

In some embodiments, the third-generation AR inhibitor compounds identified by the methods disclosed herein are selective AR modulators. In some embodiments, the third-generation AR inhibitor compounds identified by the methods disclosed herein have high specificity for the AR and have desirable, tissue-selective pharmacological activities. Desirable, tissue-selective pharmacological activities include, but are not limited to, AR antagonist activity in prostate cells and no AR antagonist activity in non-prostate cells. In some embodiments, the third-generation AR inhibitor compounds disclosed herein are anti-androgens that display negligible or no AR agonist activity.

In some embodiments, presented herein are third-generation AR inhibitor compounds identified by the methods disclosed herein selected from active metabolites, tautomers, pharmaceutically acceptable solvates, pharmaceutically acceptable salts or prodrugs of an AR inhibitor compound identified using the methods provided herein.

In some embodiments, the pharmaceutical composition comprising third-generation AR inhibitor compounds is administered in combination with one or more additional therapeutic agents, including, but not limited to, corticosteroids, anti-emetic agents, analgesics, anti-cancer agents, anti-inflammatory agents, kinase inhibitors, HSP90 inhibitors, and histone deacetylase (HDAC) inhibitors. In some embodiments, the pharmaceutical composition comprising third-generation AR inhibitor compounds is administered in combination with an anti-cancer agent including, but not limited to, a hormonal therapeutic agent, including, but not limited to a first- and second-generation AR antagonists (e.g. bicalutamide, flutamide, ARN-509, enzalutamide (MDV3100) and RD162), a compound that inhibits hormone (e.g. androgen) production, such as a CYP17A inhibitor, including, for example, galeterone (TOK001), TAK-700 or abiraterone acetate, chemotherapeutic compounds, antimetabolites, anti-cancer antibodies, surgery, radiation, and hyperthermal therapy. In some embodiments, the third-generation AR inhibitor compound and the additional therapeutic agent is administered in the same composition. In some embodiments, the third-generation AR inhibitor compound and the additional therapeutic agent are administered as separate compositions. In some embodiments, the third-generation AR inhibitor compound and the additional therapeutic agent are administered simultaneously, sequentially, or intermittently. In some embodiments, the third-generation AR inhibitor compound and the additional therapeutic agent are administered by the same route of administration. In some embodiments, the third-generation AR inhibitor compound and the additional therapeutic agent are administered by different routes of administration.

Kits/Articles of Manufacture

For use in the diagnostic and therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from any acceptable material including, e.g., glass or plastic.

In some embodiments, the kits provided herein are for use in detecting nucleic acid encoding a mutant AR polypeptide in a subject or for detecting a mutant AR polypeptide in a subject (i.e. a diagnostic kit). In some embodiments the kits are employed for selecting patients for treatment with a third-generation AR antagonist, for identifying subjects as resistant or likely to become resistant to a first- or second-generation AR antagonist, for monitoring the development of resistance to a first- or second-generation AR antagonist therapy, or combinations thereof. The kits provided herein contain one or more reagents for the detection of the nucleic acid encoding a mutant AR polypeptide, for the detection of mutant AR polypeptides, for detection of AR activity in cells from the subject, or combinations thereof. Exemplary reagents include but are not limited to, buffers, PCR reagents, antibodies, substrates for enzymatic staining, chromagens or other materials, such as slides, containers, microtiter plates, and optionally, instructions for performing the methods. Those of skill in the art will recognize many other possible containers and plates and reagents that can be used for contacting the various materials. Kits also can contain control samples, such as for example, nucleic acids or proteins, such as for example a mutant AR polypeptide provided herein or nucleic acids encoding a mutant AR polypeptide provided herein. In some embodiments, kits contain one or more set of oligonucleotide primers for detection of endogenous androgen gene expression.

In some embodiments, the container(s) can comprise one or more first- or second-generation AR antagonists or third-generation AR inhibitor compounds identified by the methods described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

Articles of manufacture, which include packaging material, a third-generation AR inhibitor compound identified using the methods provided herein within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for reducing, diminishing or eliminating the effects of androgen receptors, or for the treatment, prevention or amelioration of one or more symptoms of a disease or condition that would benefit from a reduction or elimination of androgen receptor activity, are provided.

Production of Anti-Androgen Resistant Cell Lines

Provided herein are methods for producing prostate cancer cell lines resistant to treatment with an AR antagonist. In some embodiments, the prostate cancer cell lines are resistant to treatment with ARN-509. In some embodiments, the prostate cancer cell lines are resistant to treatment with enzalutamide (MDV3100). In some embodiments, the resistant cell lines generated by the method provided express a higher level of AR compared to the parental cell line used to generate the resistant cell line. In some embodiments, the resistant cell lines generated by the method express about 1.5, 2, 2.5, 3, 3.5, 4, 4.5, 5, 5.5, 6, 6.5, 7, 7.5, 8, 8.5, 9, 9.5, 10 times or greater the amount of AR compared to the parental cell line. In some embodiments, the resistant cell lines express a mutant AR protein.

In some embodiments, the method comprises contacting a prostate cancer cell line (i.e. parental cell line) with an AR antagonist and culturing the cells for a predetermined period of time. In some embodiments, the method comprises culturing the cells in increasing concentrations of the AR antagonist for a predetermined period of time. In some embodiments, the concentration of the AR antagonist ranges from about 0.1 µM to about 100 µM, such as, for example, 1 µM to about 10 µM. In some embodiments, the cells are cultured at 0.8 µM, 1.5 µM, 3 µM and 6 µM of the AR antagonist. In some embodiments, the concentration of the AR antagonist is increased 2, 3, 4, 5, 6, 7, 8, 9, 10 or more times. In some embodiments, the concentration of the AR antagonist is increased 3 times. In some embodiments, the cells are cultured in the presence of the AR antagonist 1 day, 2 days, 3, days, 4 days, 5 days, 6 days, 1 week, 2 weeks, 3 weeks, 4 weeks, 1 month, 1.5 months, 2 months, 2.5 months, 3 months or more. In some embodiments, the cells are divided and re-plated every 2 days, every 3 days, every 4 days, every 5 days, every 6 days, every week or longer. In some embodiments, the culture media containing the AR antagonist is refreshed every day, every 2 days, every 3 days, every 4 days, every 5 days, every 6 days, every week or longer. In some embodiments, the AR antagonist is a second-generation antagonist. In some embodiments, the AR antagonist is ARN-509. In some embodiments, the AR antagonist is enzalutamide (MDV3100).

In some embodiments, the prostate cancer cell line is a human prostate adenocarcinoma cell line. In some embodiments, the prostate cancer cell line is an LNCaP cell line. In some embodiments, the prostate cancer cell line overexpresses the androgen receptor. In some embodiments, the prostate cancer cell line is LNCaP/AR(cs) or LNCaP/AR(cs)-Luc.

EXAMPLES

These examples are provided for illustrative purposes only and not to limit the scope of the claims provided herein.

Example 1

Generation of Drug Resistant Cell Line In Vivo

Cell lines resistant to treatment with the anti-AR compound ARN-509 were generated in vivo in mice bearing castration resistant human prostate adenocarcinoma (LNCaP/AR(cs)) xenograft tumors. The LNCaP/AR(cs) cell line over-expresses the androgen receptor (AR) 3-5 fold over the parental LNCaP cell line mimicking castration resistant prostate cancer (Chen et al. (2004) *Nature Medicine* 10:33-39).

LNCaP-AR(cs) xenograft tumors were grown in castrated six week old male SCID Hairless Outbred mice (SHO, Charles Rivers Laboratories). $1 \times 10^6$ LNCaP-ARcs cells in 50% serum-free RPMI and 50% Matrigel™ were subcutaneously injected (100 µl/animal) on the right flank of 10 mice 3-5 days post castration. Tumor size was monitored daily. When tumors reached an average volume of ~200 mm$^3$ (approximately 60 days post-injection), the animals began treatment with vehicle alone (n=1) or 30 mg/kg ARN-509 (n=9) by QD dosing regimen (i.e. orally in 15% Vitamin E-TPGS and 65% of a 0.5% w/v carboxymethyl cellulose (CMC) solution in 20 mM citrate buffer (pH 4.0)). Initially, treatment with ARN-509 induced tumor regression. Following approximately 75 days of dosing, a single tumor resumed growth and progressed to a size greater than at treatment initiation. Once the resistant tumor reached ~800 mm$^3$, the mouse was euthanized and the tumor was harvested. Tumor cells were manually dispersed by homogenization with a 3 mL syringe. Tumor cells were cultured in RPMI plus 10% FBS and 10 µM ARN-509. One resistant cell line was generated by this method.

Example 2

Generation of Drug Resistant Cell Lines In Vitro

Cell lines resistant to treatment with the anti-AR compounds ARN-509 and MDV3100 were generated in vitro using LNCaP human prostate adenocarcinoma cell lines. LNCaP (ATCC), LNCaP/AR(cs) (Guo et al. (2006) Cancer Cell 0:309-19) and LNCaP/AR-Luc (Tran et al. *Science* (2009) 324(5928):787-90; Ellwood-Yen et al. (2006) Cancer Res. 66:10513-6) were maintained in RPMI 1640 supplemented with 10% FBS (Hyclone). LNCaP (ATCC), LNCaP/AR(cs) or LNCaP/AR(cs)-Luc cells were cultured in increasing concentrations of either ARN-509 or MDV3100 over a course of 6 months. Initially, 50 mL of cells were seeded into a 225 cm$^2$ cell culture flask at a concentration of approximately 80,000 cells/mL and grown in RPMI plus 10% FBS in the presence of 800 nM ARN-509 or MDV3100. Medium and drug were changed semiweekly and the cells were passaged in 75 cm$^2$ cell culture flasks as needed. The concentration of each compound was increased several times from about 1.5 µM to about 6 µM as the growth rate of the drug-treated cells increased to that of the untreated control cells. After approximately 6 months of drug selection, the cells were maintained in RPMI plus 10% FBS and 6 µM ARN-509 or MDV3100. Following selection, 10 independent ARN-509 and MDV3100 resistant cell lines were obtained. Two lines were derived from LNCaP (ATCC) cells selected in the presence of ARN-509. Four cell lines were derived from LNCaP/AR(cs), two following treatment with ARN-509 and two following treatment with MDV3100. LNCaP/AR(cs)-Luc cells were used to derive 4 resistant cell lines, two from ARN-509 treatment and two from MDV3100 treatment.

Example 3

Proliferation Assays to Test Drug Resistance

Cell proliferation assays were performed to test resistance of the cell lines to ARN-509 and MDV3100 treatment.

Proliferation assays were performed on all ARN-509 and MDV3100 resistant cell lines by seeding 16 µL/well of cells at a density of 50,000 cells per mL in phenol-red-free RPMI 1640 (with 5% CSS) into 384-well cell culture plate (Flat Clear Bottom Black Polystyrene TC-Treated 384 Well plates (Corning)) and incubated for 2 days at 37° C. For agonist assays, 11 point semi-log dilutions of each compound were made in culture medium and 16 μL of each dilution was added to the cells. ARN-509, MDV3100 and bicalutamide were run at a final concentration ranging from $3.16 \times 10^{-5}$ M to $3.18 \times 10^{-10}$ M, while the synthetic androgen methyltrienolone (R1881) was run at a final concentration range of $3.16 \times 10^{-8}$ M to $3.18 \times 10^{-13}$ M. For the antagonist mode assay, the compounds were diluted in culture medium also containing 200 pM R1881 (PerkinElmer, Waltham, Mass.) (final [R1881]=100 pM) and then added to the cells (16 μL). After 7 days, 16 μL of CellTiter-Glo® Luminescent Cell Viability Assay (Promega, Madison, Wis.) was added directly to the cell cultures and Relative Luminescence Units (RLUs) measured according to the manufacturer's instructions.

In the agonist mode assay, percent viability of the samples was calculated as: % viability=100×([RLU sample−RLU medium without cells]/[RLU 1881 treated cells−RLU medium without cells]) (Table 1A). In the antagonist mode assay, the percent viability of the samples was calculated as: % viability=100×([RLU sample−RLU Day 0]/[RLU R1881 treated cells−RLU Day 0]) (Table 1B).

TABLE 1A

Agonist Proliferation Assay (% Viability)

|  | R1881 | Bicalutamide | MDV3100 | ARN-509 |
|---|---|---|---|---|
| LNCaP | 100.0 | + | + | + |
| LNCaP/AR(cs) | 100.0 | + | + | + |
| Class 1 | 100.0 | ++ | ++ | ++ |
| Class 2 | 100.0 | + | ++ | ++ |

'+' = <30,
'++' = >30
[R1881] = 0.1 nM,
[Antagonists] = 10 μM

TABLE 1B

Antagonist Proliferation Assay (% Viability)

|  | R1881 | Bicalutamide | MDV3100 | ARN-509 |
|---|---|---|---|---|
| LNCaP | 100.0 | + | + | + |
| LNCaP/AR(cs) | 100.0 | + | + | + |
| Class 1 | 100.0 | ++ | ++ | ++ |
| Class 2 | 100.0 | ++ | ++ | ++ |

'+' = <30,
'++' = >30
[R1881] = 0.1 nM,
[Antagonists] = 10 μM

In the proliferation assays, both ARN-509 and enzalutamide were full proliferative antagonists in all three LNCaP parental cell lines (Table 1A, FIG. 1A). The resistant cell lines segregated into two distinct classes. Unlike their parental cell lines, the first class of ARN-509- and MDV3100-resistant cells (Class 1) proliferate in the absence of added androgens. The ligand independent growth of the cells is unaltered in the presence of ARN-509, MDV3100 or bicalutamide. The synthetic androgen, R1881, inhibits proliferation in the class 1 cells at high concentrations. This growth inhibitory activity of R1881 is antagonized by either MDV3100 or ARN-509, indicating that AR is still capable of binding MDV3100 and ARN-509 in these cell lines.

Class 1 resistant cell lines included the one cell line derived from the LNCaP-AR(cs) xenograft tumor, the 2 cell lines derived from LNCaP/AR(cs) cell selected in the presence of ARN-509, the 2 cell lines derived from LNCaP/AR (cs) cells selected in the presence of MDV3100, the 2 cell lines derived from LNCaP/AR(cs)-Luc selected in the presence of ARN-509, and one of the cell lines derived from LNCaP/AR(cs)-Luc selected in the presence of MDV3100.

The second class of MDV3100- and ARN-509-resistant cell lines (Class 2) remains androgen dependent for growth, similar to their parental cell lines. However, unlike their activity on the parental cell lines, ARN-509 and MDV3100 can stimulate proliferation in the class 2 cell lines. Bicalutamide, however, did not stimulate proliferation in the class 2 cell lines. Class 2 resistant cell lines included the two cell lines derived from LNCaP cells selected in the presence of ARN-509 (LNCaP ARN-509r1 and LNCaP ARN-509r2) and one of the cell lines derived from LNCaP/AR(cs)-Luc selected in the presence of MDV3100 (LNCaP ENZr2).

Figure 1B:
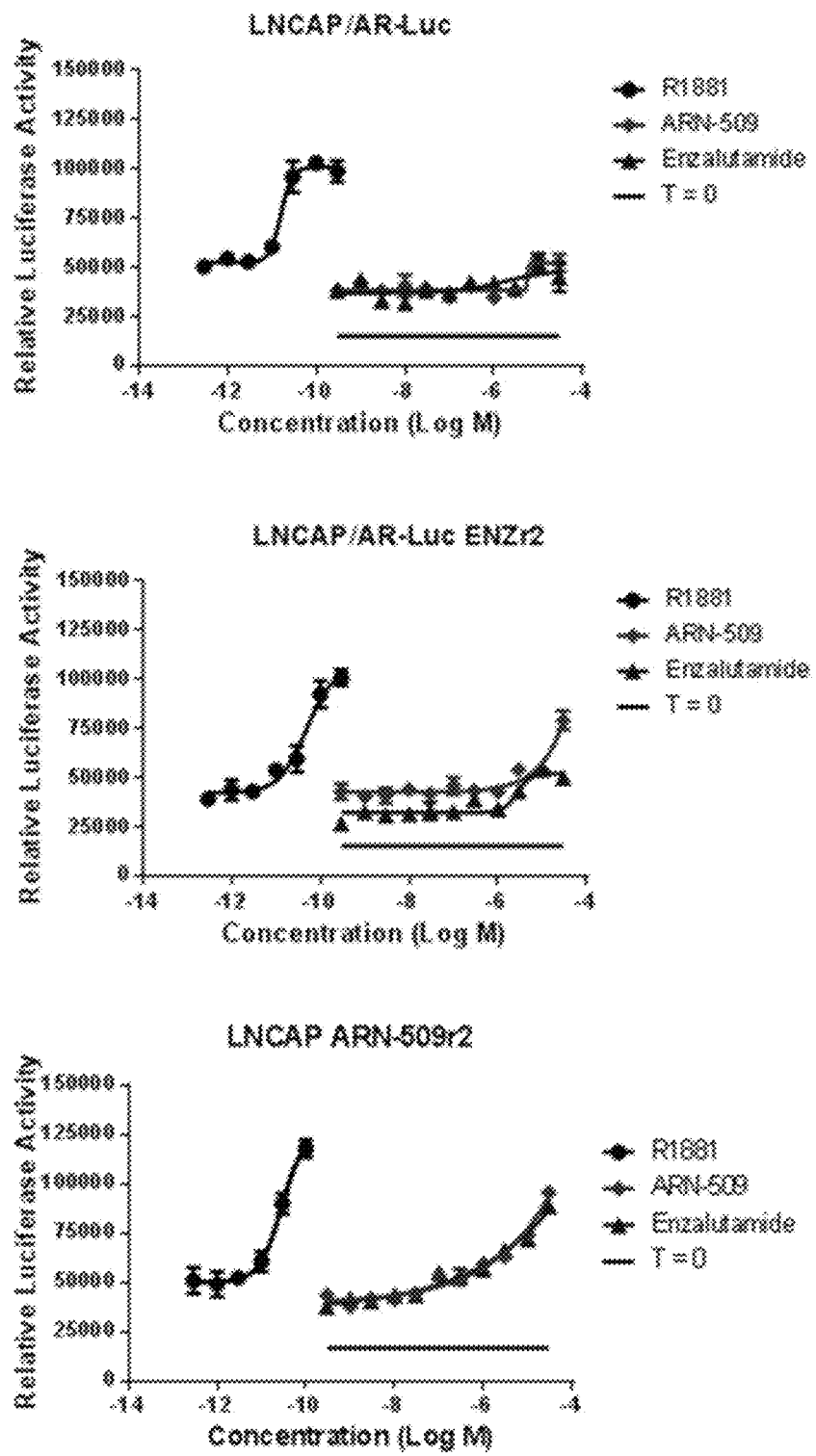
Figure 1C:
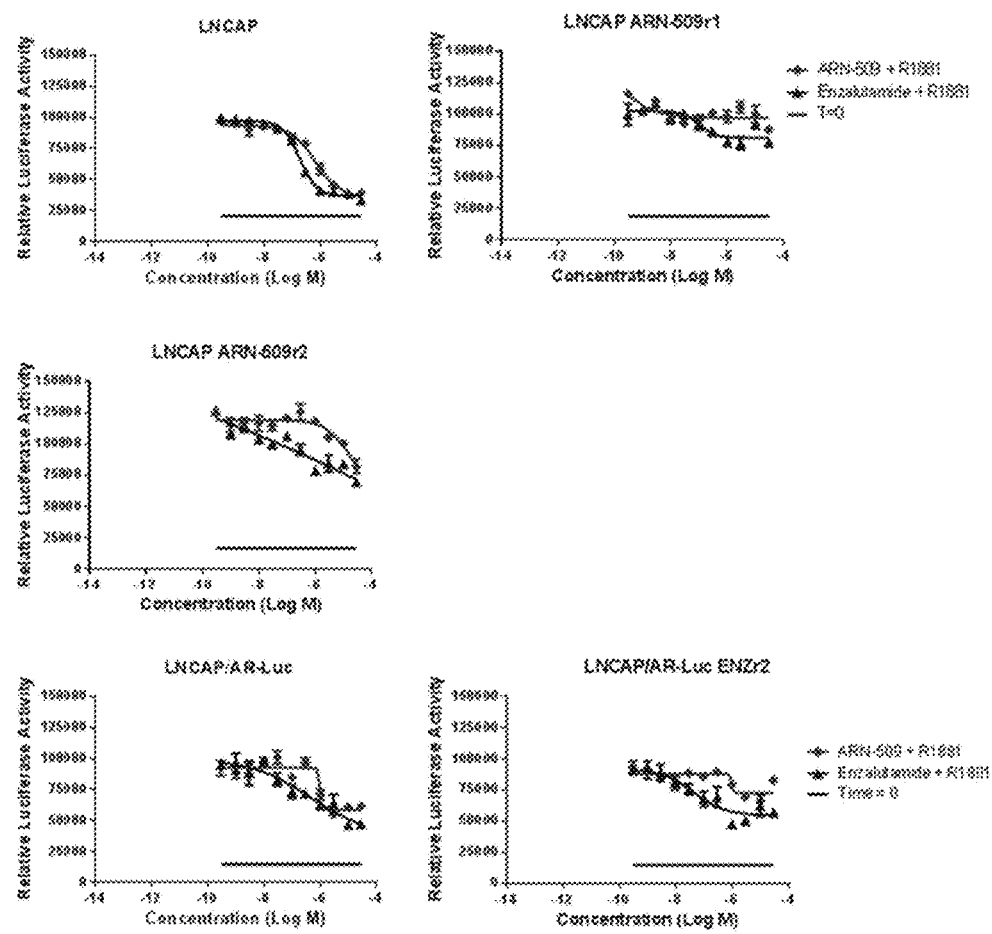

The partial agonist activity was independent of the compound utilized for selection; ARN-509 and enzalutamide displayed partial agonist activity in all three cell lines regardless of the compound used to derive the resistance variants. Consistent with proliferative activity, ARN-509 or enzalutamide only partially antagonized androgen dependent growth of these resistant lines (Table 1B, FIG. 1B,C).

Example 4

Transcriptional Reporter Assays to Test Drug Resistance

Transcriptional reporter assays using an ARE response element operatively linked to a reporter gene were performed to test resistance of the cells to ARN-509, MDV3100, and bicalutamide treatment.

Transcriptional reporter assays were performed on all resistant cell lines by seeding 100 μL of cells at a density of 250,000 cells/mL into 96-well cell culture plates in RPMI 1640 supplemented with 5% charcoal stripped serum and allowed to attach overnight at 37° C.

With the exception of the LNCaP/AR(cs)-Luc cells that contain an integrated androgen responsive reporter, cells were transiently transfected using Lipofectin® (Life Technologies) according to the manufacturer's protocol. For LNCaP and LNCaP/AR(cs) cells, triplicate transfections were performed using 428 ng reporter vector (pGL4 Pb-Luciferase (the rat probasin promoter in pGL4 (Promega, Madison, Wis.))), 50 ng pRL-CMV (normalization vector, Promega, Madison, Wis.) and 0.7 μL Lipofectin®. Following transfection, the cells were incubated for 4 hours.

Cells were then treated with the test compounds ARN-509, MDV3100 and bicalutamide. For agonist assays, the compounds were serially diluted and 50 μL of compound plus RPMI 1640 plus 5% charcoal stripped FBS was added to the cells. For antagonist assays, the compounds were serially diluted and 50 μL of compound with RPMI plus 3 nM R1881 supplemented with 5% charcoal stripped serum was added to the cells. Following 48 hour incubation the medium was removed and the cells were lysed in 40 μL of lysis buffer (25 mM Tris Phosphate, 2 mM CDTA, 10% Glycerol, 0.5% Triton X-100, 2 mM DTT). Firefly luciferase activity was measured immediately following the addition of 40 μL luciferase buffer (20 mM tricine, 0.1 mM EDTA, 1.07 mM $(MgCo_3)_4$ $Mg(OH)_2 \cdot 5H_2O$, 2.67 mM $MgSO_4$, 33.3 mM DTT, 270 μM Coenzyme A, 470 μM luciferin, 530 μM ATP).

Renilla luciferase was measured following the addition of 40 µL coelenterazine buffer (1.1 M NaCl, 2.2 mM $Na_2EDTA$, 0.22 M $K_xPO_4$ (pH 5.1), 0.44 mg/mL BSA, 1.3 mM $NaN_3$, 1.43 µM coelenterazne, final pH adjusted to 5.0).

The two classes of ARN-509- and MDV3100-resistant cell lines identified in the proliferation assays also exhibited distinct properties in the transcriptional assays. In transient transfection assays using the pGL4 Pb-Luciferase reporters or in assays using the integrated probasin-luciferase reporter (i.e. LNCaP/AR(cs)-Luc-derived cells), ARN-509 and MDV3100 were effective antagonists in the androgen-independent class 1 resistant cells as evidenced by a decrease in luciferase activity relative to no treatment controls (Table 2). Bicalutamide, however, exhibited an increased agonist activity in class 1 resistant cells compared to the parental cells. In class 2 resistant cells, MDV3100 was a weak partial agonist in the probasin-luciferase reporter assay, while bicalutamide and ARN-509 displayed no agonist activity.

TABLE 2A

Agonist Transcriptional Reporter Assay (% Max Activity)

|  | R1881 | Bicalutamide | MDV3100 | ARN-509 |
| --- | --- | --- | --- | --- |
| LNCaP | >90 | + | + | + |
| LNCaP/AR(cs) | >90 | + | + | + |
| Class 1 | >90 | ++ | + | + |
| Class 2 | >90 | + | ++ | + |

'+' = <5,
'++' = >5
[R1881] = 10 nM,
[Antagonists] = 50 µM

TABLE 2B

Antagonist Transcriptional Reporter Assay (% Max Activity)

|  | R1881 | Bicalutamide | MDV3100 | ARN-509 |
| --- | --- | --- | --- | --- |
| LNCaP | >90 | + | + | + |
| LNCaP/AR(cs) | >90 | + | + | + |

TABLE 2B-continued

Antagonist Transcriptional Reporter Assay (% Max Activity)

|  | R1881 | Bicalutamide | MDV3100 | ARN-509 |
| --- | --- | --- | --- | --- |
| Class 1 | >90 | ++ | + | ++ |
| Class 2 | >90 | + | ++ | + |

'+' = <5,
'++' = >5
[R1881] = 10 nM,
[Antagonists] = 50 µM

Example 5

Endogenous Gene Transcriptional Assays

The effects of R1881, MDV3100 and bicalutamide treatment on endogenous gene transcription was examined.

Endogenous gene transcriptional assays were performed on all resistant lines by plating 0.5 mL of cells at a density of 500,000 cells/mL in 24-well plates in RPMI containing 5% charcoal stripped FBS (hormone depleted) and growing the cells for 3 days at 37° C. Cells were then treated for 24 h with 10 nM R1881, 30 µM MDV3100 or 30 µM bicalutamide.

Total RNA was isolated using the Aurum™ total RNA isolation kit (BIO-RAD, Hercules, Calif.). RNA (1 µg) was reverse transcribed using the iScript cDNA synthesis kit (BIO-RAD, Hercules, Calif.) to produce cDNA. Real-time PCR was performed using the Applied Biosystems 7900HT instrument and SYBR Green PCR Master Mix (Applied Biosystems, Foster City, Calif.). PCR reactions were performed in 6 µL according to the manufacturer's protocol and a thermocycle protocol of 95° C. for 10 minutes followed by 40 cycles of 95° C. for 15 seconds and 58° C. for 1 minute. Androgen responsive gene (PSA, SLUG, TMPRSS2, STEAP4, FKBP5, ORM1, NOV, FASN, NKX3.1, AMIGO2, BDNF, CAMK2N1, HPGD, NCAPD3, PLD1) expression was normalized to GAPDH expression and expressed relative to vehicle treatment of the parental cell line. Relative expression results are provided in Table 3A. Primers employed for PCR are listed in Table 3B.

Similar compound and class selective agonist activities were observed on endogenous androgen-responsive genes, but in the context of the endogenous genes the transcriptional activity of MDV3100 is more evident (Table 3). In class 1 resistant cells, bicalutamide displays robust transcriptional activity and MDV3100 is a weak transcriptional agonist. In contrast, in class 2 resistant cell lines, bicalutamide is a weak transcriptional agonist while MDV3100 displays robust transcriptional agonist activity on the genes tested.

TABLE 3A

Endogenous Gene Transcriptional Activity (Fold Vehicle)

|  |  | PSA | SLUG | TMPRSS2 | STEAP4 | FKBP5 | ORM1 | NOV |
| --- | --- | --- | --- | --- | --- | --- | --- | --- |
| LNCaP | DMSO | 1.0 | 1.0 | 1.0 | 1.0 | 1.0 | 1.0 | 1.0 |
|  | R1881 | ++ | +++ | ++ | ++++ | ++ | +++ | -- |
|  | Bicalutamide | + | + | + | + | + | - | + |
|  | MDV3100 | + | + | + | - | + | + | + |
| LNCaP/AR(cs) | DMSO | 1.0 | 1.0 | 1.0 | 1.0 | 1.0 | 1.0 | 1.0 |
|  | R1881 | +++ | +++ | ++ | ++++ | ++ | ++++ | -- |
|  | Bicalutamide | ++ | + | + | ++ | + | +++ | + |
|  | MDV3100 | + | + | + | + | + | + | + |
| Class 1 | DMSO | 1.0 | 1.0 | 1.0 | 1.0 | 1.0 | 1.0 | 1.0 |
|  | R1881 | ++ | +++ | + | ++++ | +++ | ++++ | -- |
|  | Bicalutamide | + | +++ | + | +++ | ++ | ++ | + |
|  | MDV3100 | + | + | + | + | + | + | + |

TABLE 3A-continued

| | | \multicolumn{7}{c|}{Endogenous Gene Transcriptional Activity (Fold Vehicle)} |
| --- | --- | --- | --- | --- | --- | --- | --- | --- |
| | | PSA | SLUG | TMPRSS2 | STEAP4 | FKBP5 | ORM1 | NOV |
| Class 2 | DMSO | 1.0 | 1.0 | 1.0 | 1.0 | 1.0 | 1.0 | 1.0 |
| | R1881 | +++ | +++ | ++ | ++++ | +++ | ++++ | -- |
| | Bicalutamide | + | + | + | + | + | + | + |
| | MDV3100 | +++ | +++ | ++ | +++ | ++ | +++ | - |

[R1881] = 10 nM, [Antagonists] = 30 µM
-- <0.1, - = 0.1-1, + = 1-10, ++ = 10-50, +++ = 50-500, ++++ >500

TABLE 3B

Transcriptional Real-time PCR Oligonucleotide Sequence

| Gene | Forward Primer Sequence | Reverse Primer Sequence |
| --- | --- | --- |
| AMIGO2 | AGAGACTCAGAGGCGACCAT (SEQ ID NO: 20) | ATCAGCAAACACAGCAGCTC (SEQ ID NO: 21) |
| BDNF | AGAGCTGTTGGATGAGGACCAGAA (SEQ ID NO: 22) | AGGCTCCAAAGGCACTTGACTACT (SEQ ID NO: 23) |
| CAMK2N1 | GACCAAGCGGGTTGTTATTGA (SEQ ID NO: 24) | TGCCTTGTCGGTCATATTTTTCA (SEQ ID NO: 25) |
| FKBP5 | CGGAGAACCAAACGGAAAGG (SEQ ID NO: 26) | CTTCGCCCACAGTGAATGC (SEQ ID NO: 27) |
| HPGD | ACAGCAGCCGGTTTATTGTGCTTC (SEQ ID NO: 28) | TGGCATTCAGTCTCACACCACTGT (SEQ ID NO: 29) |
| NCAPD3 | ACCACTCACCATCATCTCAAGGCA (SEQ ID NO: 30) | TGCTCTTCTTTGCCAGATCCTCGT (SEQ ID NO: 31) |
| NOV | GCCTTACCCTTGCAGCTTAC (SEQ ID NO: 32) | GAGCATGCTGTCCACTCTGT (SEQ ID NO: 33) |
| ORM1 | CTTGCGCATTCCCAAGTCAGATGT (SEQ ID NO: 34) | TTTCCTCTCCTTCTCGTGCTGCTT (SEQ ID NO: 35) |
| PLD1 | GAGCCTGCTACAGATGGTCA (SEQ ID NO: 36) | TGTCTACCAGCAGGACGAAG (SEQ ID NO: 37) |
| PSA | CCTCCTGAAGAATCGATTCC (SEQ ID NO: 38) | GAGGTCCACACACTGAAGTT (SEQ ID NO: 39) |
| SLUG | TTTCTGGGCTGGCCAAACATAAGC (SEQ ID NO: 40) | ACACAAGGTAATGTGTGGGTCCGA (SEQ ID NO: 41) |
| STEAP4 | CGGCAGGTGTTTGTGTGTGGAAAT (SEQ ID NO: 42) | AGAAGACACACAGCACAGCAGACA (SEQ ID NO: 43) |
| TMPRSS2 | TAGTGAAACCAGTGTGTCTGCCCA (SEQ ID NO: 44) | AGCGTTCAGCACTTCTGAGGTCTT (SEQ ID NO: 45) |
| FASN | CGCTCTGGTTCATCTGCTCTG (SEQ ID NO: 46) | TCATCAAAGGTGCTCTCGTCTG (SEQ ID NO: 47) |
| NKX3.1 | TGGAGAGGAAGTTCAGCCATCAGA (SEQ ID NO: 48) | AGGAGAGCTGCTTTCGCTTAGTCT (SEQ ID NO: 49) |

In a separate experiment, gene expression of the following genes were analyzed in LNCaP, LNCaP/AR(cs), LNCaP/AR-Luc, LNCaP ARN-509r1, LNCaP ARN-509r2 and LNCaP/AR-Luc ENZr2 cells: PLD, CAM2KN, NOV, BDNF, AMIGO2, FASN, TMPRSS2, NKX3.1, PSA, FKBP5, HPGD, NCAPD3, SLUG, STEAP4, and ORM. Cells were cultured for 3 days in hormone depleted medium followed by treatment with vehicle, 1 nM R1881 or 30 µM compound. Gene expression was normalized to GAPDH as described above. Results are presented in Tables 4A and 4B.

TABLE 4A

| | \multicolumn{12}{c|}{LNCaP, LNCaP/AR(cs) and resistant line transcription} |
| --- | --- | --- | --- | --- | --- | --- | --- | --- | --- | --- | --- | --- |
| | \multicolumn{4}{c|}{LNCaP} | \multicolumn{4}{c|}{LNCaP/AR(cs)} | \multicolumn{4}{c|}{LNCaP ARN-509r1} |
| Gene | Vehicle | ARN-509 | ENZ | R1881 | Vehicle | ARN-509 | ENZ | R1881 | Vehicle | ARN-509 | ENZ | R1881 |
| AMIGO2 | 1.00 | 1.12 | 1.20 | 0.68 | 1.00 | 0.72 | 1.13 | 0.54 | 1.00 | 0.62 | 0.99 | 0.21 |
| BDNF | 1.00 | 1.09 | 0.85 | 0.40 | 1.00 | 0.85 | 1.13 | 0.48 | 1.00 | 0.90 | 1.58 | 0.31 |
| CAM2KN1 | 1.00 | 1.17 | 1.39 | 0.13 | 1.00 | 0.80 | 1.11 | 0.05 | 1.00 | 0.37 | 0.59 | 0.01 |
| FASN | 1.00 | 1.34 | 1.24 | 5.58 | 1.00 | 0.75 | 1.19 | 7.11 | 1.00 | 1.04 | 1.53 | 3.12 |
| FKBP5 | 1.00 | 0.99 | 1.04 | 54.95 | 1.00 | 0.99 | 1.71 | 97.01 | 1.00 | 2.58 | 9.45 | 53.45 |
| HPGD | 1.00 | 1.48 | 1.78 | 100.43 | 1.00 | 1.18 | 2.01 | 183.55 | 1.00 | 2.36 | 10.20 | 61.39 |
| NCAPD3 | 1.00 | 1.16 | 1.20 | 104.69 | 1.00 | 0.91 | 1.22 | 93.05 | 1.00 | 1.29 | 3.12 | 90.51 |
| NKX3.1 | 1.00 | 0.90 | 1.66 | 30.06 | 1.00 | 1.13 | 2.51 | 8.82 | 1.00 | 6.54 | 11.55 | 8.11 |
| NOV | 1.00 | 1.73 | 2.57 | 0.15 | 1.00 | 1.04 | 1.27 | 0.04 | 1.00 | 1.40 | 1.39 | 0.03 |
| ORM1 | 1.00 | 0.71 | 1.13 | 873.10 | 1.00 | 0.84 | 3.58 | 3444.31 | 1.00 | 15.89 | 205.07 | 1296.13 |
| PLD1 | 1.00 | 1.09 | 0.70 | 0.02 | 1.00 | 1.04 | 0.65 | 0.02 | 1.00 | 0.33 | 0.24 | 0.03 |

TABLE 4A-continued

LNCaP. LNCaP/AR(cs) and resistant line transcription

| | | | | | | | | | | | |
|---|---|---|---|---|---|---|---|---|---|---|---|
| PSA | 1.00 | 0.66 | 1.69 | 47.84 | 1.00 | 1.43 | 2.69 | 19.16 | 1.00 | 32.67 | 57.68 | 85.63 |
| SLUG | 1.00 | 1.27 | 2.35 | 129.79 | 1.00 | 1.03 | 2.06 | 89.88 | 1.00 | 4.66 | 42.52 | 164.28 |
| STEAP4 | 1.00 | 0.78 | 1.54 | 639.15 | 1.00 | 0.90 | 1.95 | 1314.23 | 1.00 | 3.03 | 32.22 | 1184.45 |
| TMPRSS2 | 1.00 | 0.77 | 1.68 | 22.16 | 1.00 | 1.06 | 2.36 | 17.51 | 1.00 | 10.20 | 23.75 | 37.27 |

| | LNCaP | | | | LNCaP ARN-509r2 | | | |
|---|---|---|---|---|---|---|---|---|
| Gene | Vehicle | ARN-509 | ENZ | R1881 | Vehicle | ARN-509 | ENZ | R1881 |
| AMIGO2 | 1.00 | 1.12 | 1.20 | 0.68 | 1.00 | 0.67 | 0.63 | 0.55 |
| BDNF | 1.00 | 1.09 | 0.85 | 0.40 | 1.00 | 1.04 | 0.77 | 0.47 |
| CAM2KN1 | 1.00 | 1.17 | 1.39 | 0.13 | 1.00 | 0.46 | 0.38 | 0.02 |
| FASN | 1.00 | 1.34 | 1.24 | 5.58 | 1.00 | 0.98 | 0.93 | 4.82 |
| FKBP5 | 1.00 | 0.99 | 1.04 | 54.95 | 1.00 | 8.00 | 3.41 | 48.50 |
| HPGD | 1.00 | 1.48 | 1.78 | 100.43 | 1.00 | 1.49 | 4.56 | 59.30 |
| NCAPD3 | 1.00 | 1.16 | 1.20 | 104.69 | 1.00 | 1.13 | 1.35 | 54.95 |
| NKX3.1 | 1.00 | 0.90 | 1.66 | 30.06 | 1.00 | 3.73 | 6.28 | 10.20 |
| NOV | 1.00 | 1.73 | 2.57 | 0.15 | 1.00 | 1.39 | 0.71 | 0.07 |
| ORM1 | 1.00 | 0.71 | 1.13 | 873.10 | 1.00 | 3.94 | 23.75 | 625.99 |
| PLD1 | 1.00 | 1.09 | 0.70 | 0.02 | 1.00 | 0.81 | 0.29 | 0.02 |
| PSA | 1.00 | 0.66 | 1.69 | 47.84 | 1.00 | 1.91 | 2.48 | 7.89 |
| SLUG | 1.00 | 1.27 | 2.35 | 129.79 | 1.00 | 1.31 | 9.58 | 77.17 |
| STEAP4 | 1.00 | 0.78 | 1.54 | 639.15 | 1.00 | 1.45 | 4.69 | 377.41 |
| TMPRSS2 | 1.00 | 0.77 | 1.68 | 22.16 | 1.00 | 3.07 | 4.86 | 15.14 |

TABLE 4B

LNCaP/AR-Luc and LNCaP/AR-Luc ENZr2 transcription

| | LNCaP/AR-Luc | | | | LNCaP/AR-Luc ENZr2 | | | |
|---|---|---|---|---|---|---|---|---|
| Gene | Vehicle | ARN-509 | ENZ | R1881 | Vehicle | ARN-509 | ENZ | R1881 |
| AMIGO2 | 1.00 | 1.13 | 1.44 | 0.54 | 1.00 | 0.99 | 0.78 | 0.49 |
| BDNF | 1.00 | 1.17 | 1.08 | 0.18 | 1.00 | 0.56 | 0.44 | 0.12 |
| CAM2KN1 | 1.00 | 1.13 | 1.51 | 0.11 | 1.00 | 0.65 | 0.57 | 0.11 |
| FASN | 1.00 | 1.08 | 1.40 | 3.48 | 1.00 | 1.72 | 1.20 | 4.44 |
| FKBP5 | 1.00 | 1.16 | 1.46 | 20.82 | 1.00 | 2.46 | 3.03 | 23.43 |
| HPGD | 1.00 | 1.88 | 2.51 | 2.41 | 1.00 | 1.22 | 1.61 | 1.39 |
| NCAPD3 | 1.00 | 1.09 | 1.33 | 17.27 | 1.00 | 1.38 | 1.39 | 31.12 |
| NKX3.1 | 1.00 | 1.14 | 1.68 | 11.24 | 1.00 | 4.82 | 5.21 | 10.13 |
| NOV | 1.00 | 2.55 | 1.95 | 0.47 | 1.00 | 1.21 | 1.20 | 0.27 |
| ORM1 | 1.00 | 1.27 | 1.39 | 7.89 | 1.00 | 15.24 | 17.88 | 347.29 |
| PLD1 | 1.00 | 1.45 | 1.33 | 0.15 | 1.00 | 0.46 | 0.74 | 0.21 |
| PSA | 1.00 | 0.60 | 0.44 | 2.10 | 1.00 | 4.59 | 3.48 | 16.91 |
| SLUG | 1.00 | 1.13 | 2.73 | 48.84 | 1.00 | 5.98 | 12.30 | 160.90 |
| STEAP4 | 1.00 | 0.88 | 1.23 | 20.25 | 1.00 | 1.66 | 4.38 | 79.89 |
| TMPRSS2 | 1.00 | 0.74 | 1.35 | 3.46 | 1.00 | 4.44 | 4.23 | 7.73 |

Example 6

Assays for Mechanisms of Resistance

Array CGH, mRNA expression profiling and sequence analysis of patient derived prostate cancer tumors as well as many animal and in vitro models have implicated multiple pathways in the progression to the castration resistant state. Three of the most commonly activated pathways indentified in castration resistant prostate cancer are the PI3K, Raf and AR pathways. In this example, Akt and Erk phosphorylation was evaluated by Western blot to assess the activation states of the PI3K and Raf pathway respectively.

To evaluate the mode of drug resistance in the class 1 and class 2 cell lines, Western analysis was performed to assess AR protein levels and the activation state of several cellular signaling pathways known to modulate AR activity and commonly activated in castration resistant prostate cancer. Relative expression of AR, Akt, phosphorylated Akt (Ser473), p44/42 MAPK (Erk1/2), phosphorylated p44/42 MAPK (Erk1/2) (Thr202/Tyr204), tubulin and actin were determined.

For Western analysis, cells were grown in RPMI 1640 supplemented with 5% charcoal stripped serum for 3 days. Cells were lysed in modified radioimmunoprecipitation buffer (mRIPA; 10 mM Tris, 150 mM NaCl, 1% (v/v) NP-40, 0.5% deoxycholate, 0.1% SDS, 5 mM EDTA, pH 7.4) containing Halt™ Protease and Phosphatase Inhibitor Cocktail (Thermo Scientific). Total protein of the clarified lysates was quantitated by Lowry Assay (Biorad DC protein assay). NuPAGE® LDS Sample Buffer and Sample Reducing Agent were added to the lysates and heated to 70° C. for 10 minutes. 20 μg of total cell protein was separated on a NuPAGE 4-12% Bis Tris Acrylamide Gel and transferred to a nitrocellulose membrane using an Xcell II™ blot module (Invitrogen). Membranes were incubated in Blocking Buffer (LI-COR, Lincoln, Nebr.) for 30 minutes at room temperature, followed by 60 minute incubations with primary antibodies against Androgen Receptor (Santa Cruz Biotechnology cat. No. SC-816), Akt and Phospho-Akt (Ser473) (Cell Signaling cat. Nos. 9272 and 4058 respectively), p44/42 MAPK (Erk1/2) and Phospho-p44/42 MAPK (Erk1/2) (Thr202/Tyr204) (Cell Signaling cat. Nos. 4695 and 4376s respectively) and tubulin or actin (Sigma cat. No T6199 and A4700 respectively). Following incubation with an IRDye® Conjugated Goat Anti Mouse or Rabbit IgG (LI-COR), protein bands were quantified using an Odyssey® Infrared Imaging System.

Figure 2:
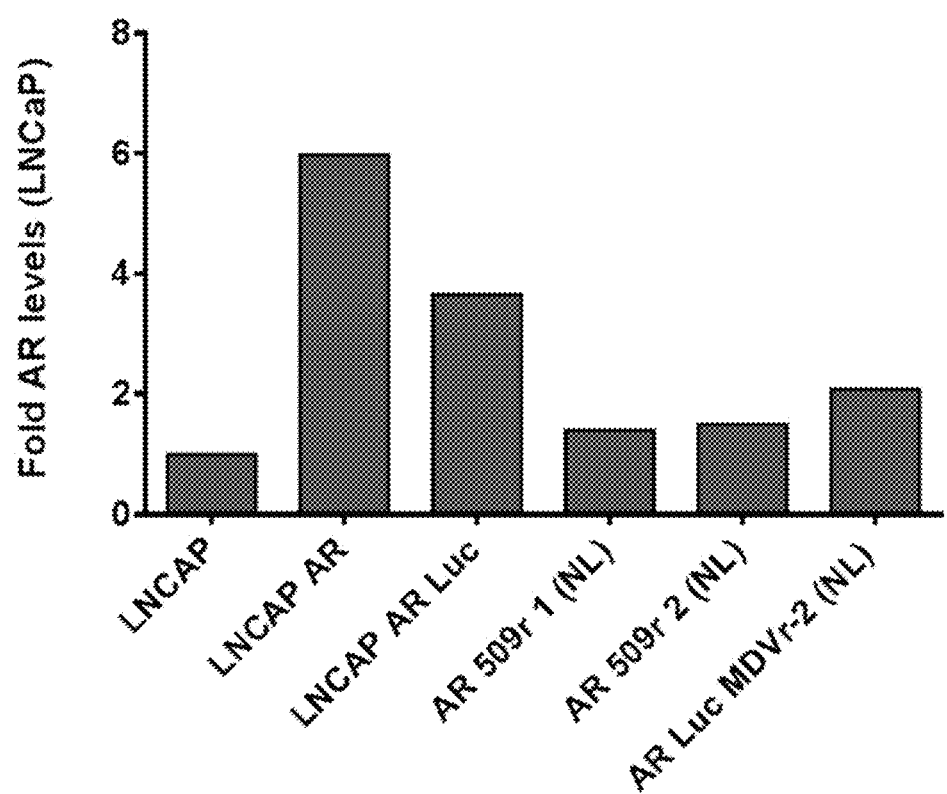
FIG. 2 illustrates AR levels in parental and 2nd generation anti-androgen resistant cell lines. Protein extracts were generated from cells cultured in hormone depleted medium for 3 days. AR protein levels were analyzed and by western blot. AR levels were quantified and normalized to α-tubulin and expressed relative to LNCaP cells.
Figure 3A:
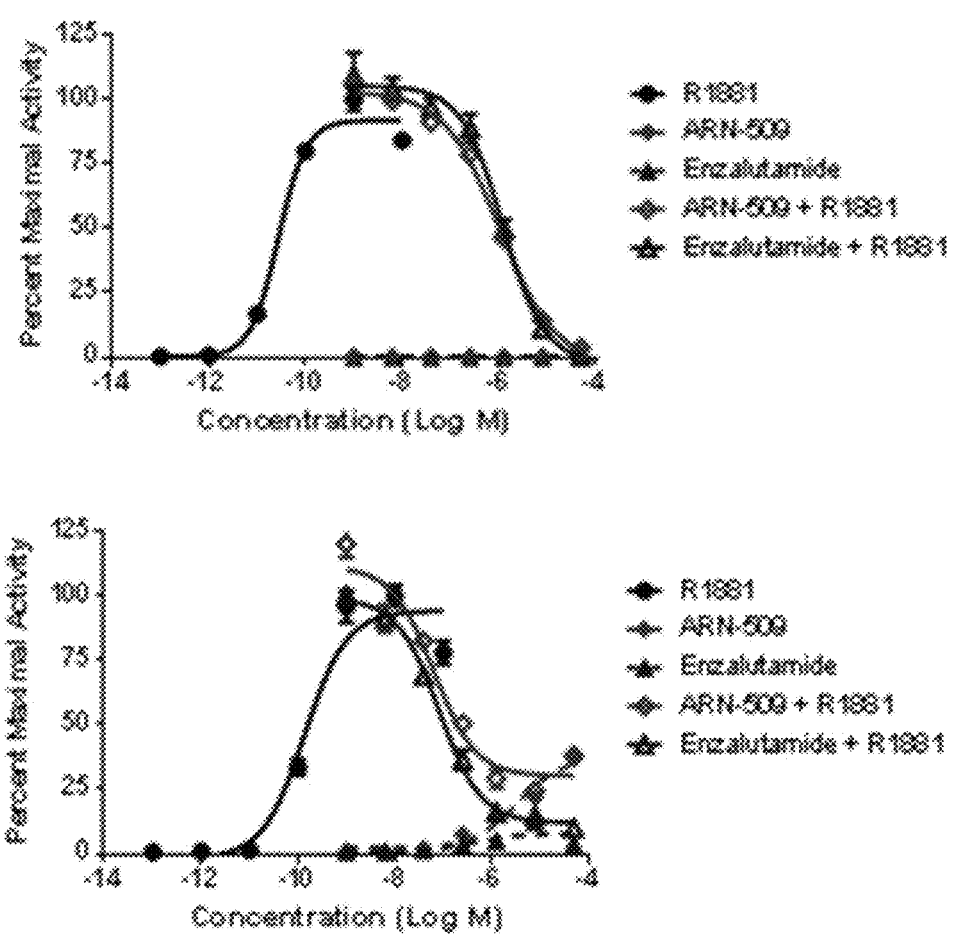
FIG. 3 illustrates ARN-509 and enzalutamide are partial agonists of AR F876L. (A) Transcriptional agonist and antagonist activity of ARN-509 and enzalutamide on wild-type or F876L AR. Transcriptional activation of a 4×ARE-luciferase reporter was measured in the presence of increasing compound concentration in the absence or presence of 1 nM R1881 (for wild-type AR) or 5 nM R1881 (for F876L AR). (B) Transcriptional agonist activity of $1^{st}$ and $2^{nd}$ generation anti-androgens and prednisone on wild-type, F876L, T877A, F876L/T877A, L701H, H874Y and W741C AR dependent activation of 4×ARE-Luciferase reporter was measured in transiently transfected HepG2 cells.

By Western blot, the AR levels in the class 1 resistant cell lines were approximately 2 to 4-fold higher than observed in the LNCaP/AR(cs) cell line (FIG. 2). Analogous to an approximate 3-fold increase in AR levels being sufficient to support growth of LNCaP cells in a castrate setting in vivo, the further 2 to 4-fold elevation in AR levels may be sufficient to promote proliferation in the absence of androgens in vitro. In contrast, the AR levels of the class 2 resistant lines were similar to that observed in the parental cell lines. Thus, the conversion of enzalutamide and ARN-509 to partial agonists in the class 2 cell lines was not due to AR overexpression. Minor differences in total and phosphorylated Akt and Erk were observed with no consistent changes seen in either class of resistant cell lines.

Example 7

Determination of Mutant AR Sequence

MDV3100 and ARN-509 are transcriptional and proliferative agonists in the class 2 resistant cell lines, while bicalutamide remains an antagonist. AR expression in class 2 resistant cells was similar to the parental cell line (Example 6). Thus, the sequence of AR in class 2 resistant cells was determined to ascertain whether a mutation of the AR ligand binding domain promotes the gain of function activity.

cDNA generated by reverse transcription of RNA isolated from class 1 and class 2 cells (see Example 5) was used as a template to sequence AR. Using a series of oligonucleotides, overlapping segments encompassing the AR ligand binding domain (c.2013-2757) were generated by PCR using Phusion® polymerase (New England Biolabs) using the manufacturer's protocol. The PCR products were gel purified to remove non-specific bands as well as unincorporated oligonucleotides. The purified PCR products were sequenced using internal oligonucleotides.

A single nucleic acid mutation was identified within the AR ligand binding domain at nucleotide position 2626 in three independently derived cell lines. The missense mutation identified in all lines was Thymine (T) to Cytosine (C) that converts Phenylalanine (F) at amino acid position 876 of the encoded polypeptide to Leucine (L) (SEQ ID NO: 19). Additionally, sequencing of individual subcloned PCR products from the LNCaP/AR-Luc ENZr2 cell line indicated that in all cell lines the F876L mutation arose in the endogenous AR allele.

Figure 1D:
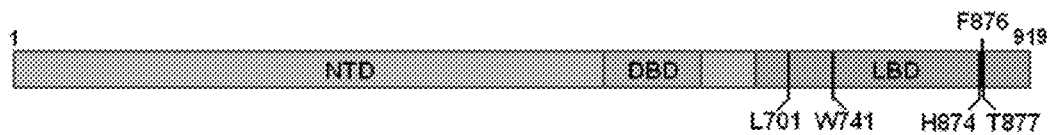

F876 lies in helix 11 in a region of AR ligand binding pocket that is a hotspot for CRPC AR mutations (FIG. 1D). However, unlike T877 and L701, which coordinate hydrogen bonding to the 17α-OH group of dihydrotestosterone, F876 contributes to a small hydrophobic core formed by residues in helix 11 (F786, L880), the loop between helices 11 and 12 (F891) and helix 3 (F697, L701). While similar residues and hydrophobic ligand interactions are conserved in the estrogen and progesterone receptor, F876 has not been implicated in high affinity binding or steroid selectivity. Consistent with the relatively minor role F876 is predicted to play in steroid binding, the AR-F876L mutation has not been reported in prostate cancer or androgen insensitive populations.

Example 8

Expression of the Mutant AR in AR-Deficient Cells

To confirm that the F876L mutation confers agonist activities to ARN-509 and MDV3100, the point mutation was generated in the context of the full-length wild-type AR and the LNCaP T877A mutant receptor. The F876L and F876L/T877A mutants were generated in the plasmid pcDNA3-AR using the QuickChange II Site-Directed Mutagenesis Kit (Agilent Technologies, Santa Clara, Calif.) according to the manufacturer's protocol.

Transcriptional reporter assays using an ARE response element operatively linked to a reporter gene were performed to test the transcriptional activity of the mutant AR in response to ARN-509, MDV3100 and bicalutamide treatment.

Transcriptional reporter assays were performed by seeding 100 μL of HEPG2 cells at a density of 250,000 cells/mL into 96-well cell culture plates in MEM supplemented with 10% charcoal stripped serum and allowed to attach overnight at 37° C.

Cells were transiently transfected using Lipofectin® (Life Technologies) according to the manufacturer's protocol. Triplicate transfections were performed using 378 ng reporter vector (4×ARE-Luciferase or pGL4 Pb-Luciferase (the rat probasin promoter in pGL4 (Promega, Madison, Wis.)), 50 ng pcDNA-AR (wild-type or mutant) 50 ng pRL-CMV (normalization vector) and 0.7 μL Lipofectin®. Following transfection, the cells were incubated for 4 hours.

Following the incubation, the cells were treated with the test compounds ARN-509, MDV3100 and bicalutamide. For agonist assays, the compounds were diluted 1:6 and 50 μL of compound in MEM plus 5% charcoal stripped FBS was added to the cells for a final concentration range of 30 μM to 0.64 nM. For antagonist assays, the compounds were serially diluted with 1 nM R1881 (for wild-type AR) or 5 nM R1881 (for F876L AR).

Following 48 hour incubation the medium was removed and the cells were lysed in 40 μL of lysis buffer (25 mM Tris Phosphate, 2 mM CDTA, 10% Glycerol, 0.5% Triton X-100, 2 mM DTT). Firefly luciferase activity was measured immediately following the addition of 40 μL luciferase buffer (20 mM tricine, 0.1 mM EDTA, 1.07 mM $(MgCo_3)_4$ $Mg(OH)_2.5H_2O$, 2.67 mM $MgSO_4$, 33.3 mM DTT, 270 μM Coenzyme A, 470 μM luciferin, 530 μM ATP). Renilla luciferase was measured following the addition of 40 μL coelenterazine buffer (1.1 M NaCl, 2.2 mM $Na_2EDTA$, 0.22 M $K_xPO_4$ (pH 5.1), 0.44 mg/mL BSA, 1.3 mM $NaN_3$, 1.43 μM coelenterazine, final pH adjusted to 5.0).

In transient transfection assays, second-generation AR antagonists ARN-509 and MDV3100 induced AR dependent transcriptional activity in the context of the F876L or F876L/T877A mutant AR, while induction from bicalutamide was minimal (Table 5). For example, in HepG2 cells using either a 4×ARE-luciferase or Pb-luciferase reporter, ARN-509 and MDV3100, but not bicalutamide, induced AR dependent transcriptional activity in the context of the F876L or F876L/T877A mutant AR. This indicates that mechanism of resistance in the class 2 cell lines is the AR F876L mutation.

TABLE 5

AR Transcriptional Activity (Fold DMSO)

| | R1881 | Bicalutamide | MDV3100 (enzalutamide) | ARN509 |
|---|---|---|---|---|
| AR WT | +++ | + | + | + |
| AR F876F | +++ | + | ++ | ++ |

+ = <20,
++ = 10-200,
+++ > 200
[R1881] = 100 nM,
[Antagonists] = 6.3 μM

A second experiment was performed 4x-ARE-Luciferease report to confirm the above results. In this experiment, first generation anti-androgens nilutamide and hydroxyflutamide were also compared along with bicalutamide, ARN-509 and enzalutamide. The AR transcriptional reporter assays were performed essentially as described above with minor modifications. Triplicate transfections were performed using 50 ng pCDNA3-AR or pCDNA3-AR mutant, 65 ng 4xARE-Luciferase, 20 ng pRL (Promega), and 25 ng pCMX. For agonist assays, compounds were serially diluted, and 50 μL of compound plus RPMI 1640 supplemented with charcoal stripped serum was added to the cells. For antagonist assays, the compounds were serially diluted, and 50 μL of compound with RPMI supplemented with charcoal stripped serum plus methyltrienolone (R1881) were added to the cells. The final R1881 concentration used in the antagonist assays was 1 nM with the exception of F876L for which 5 nM R1881 was used.

Figure 4:
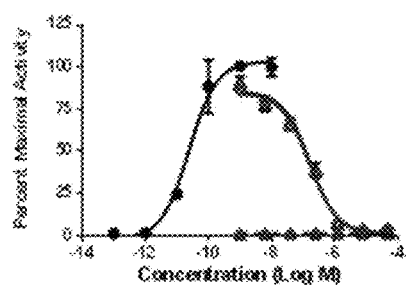
FIG. 4 illustrates VP16-AR (A) and F876L VP16-AR (B) agonist and antagonist activity of ARN-509 and enzalutamide. 4×ARE-luciferase reporter activity was monitored in the presence of increasing compound concentration in the absence or presence of 90 pM R1881 (for wild-type VP16-AR) or 1 nM R1881 (for F876L VP16-AR).
Figure 4:
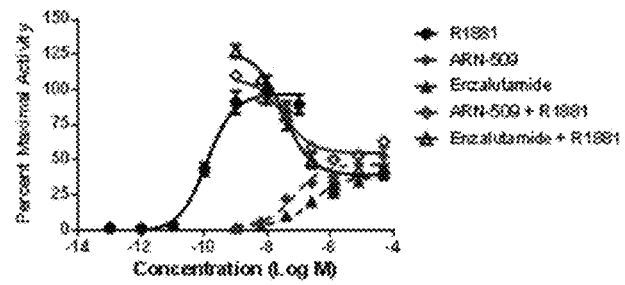

As shown in FIG. 4, in the context of wild-type AR, ARN-509 and enzalutamide were full antagonists and with minimal agonist activity in 4x-ARE androgen responsive transcriptional reporter assays. However, in cells expressing AR-F876L or AR F876L/T877A, enzalutamide and ARN-509 were partial transcriptional agonists (FIG. 4A). Conversely, the first generation anti-androgens bicalutamide, nilutamide and hydroxyflutamide displayed minimal agonist activity on the F876L mutant (Table 6, FIG. 4) (Emax=percent maximal R1881 response). Enzalutamide and ARN-509 were full antagonists on AR mutants T877A, L701H, H874Y and W741C that either confer resistance to first generation AR antagonists or broaden steroidal ligand specificities in CRPC patients.

TABLE 6

4X ARE Reporter Assay

| Compound | WT IC$_{50}$ (μM) | WT Emax | F876L IC$_{50}$ (μM) | F876L Emax |
|---|---|---|---|---|
| ARN-509 | 0.79 ± 0.15 | 1.3 ± 0.3 | 0.09 ± 0.06 | 49.7 ± 11.1 |
| Enzalutamide | 1.12 ± 0.17 | 0.4 ± 0.1 | 0.13 ± 0.04 | 20.2 ± 5.2 |
| Bicalutamide | 1.65 ± 0.93 | 10.0 ± 2.9 | 3.63 ± 0.04 | 0.7 ± 0.3 |
| Hydroxy-flutamide | 0.36 ± 0.04 | 28.9 ± 5.0 | 2.60 ± 6.61 | 0.8 ± 0.2 |
| Nilutamide | 1.11 ± 0.17 | 5.1 ± 2.1 | 7.59 ± 1.18 | 0.6 ± 0.1 |

To test DNA binding competency of the F876L mutants VP16-AR fusion constructs were generated. pVP16-AR was generated by subloning full-length human AR into pVP16 (Clontech). AR point mutations were generated in VP16-AR using the QuickChange II Site-Directed Mutagenesis Kit (Agilent Technologies, Santa Clara, Calif.) according to the manufacturer's protocol.

Transcription assays were performed essentially as described above. Triplicate transfections were performed using 35 ng pVP16-AR or pVP16-F876L, 70 ng 4xARE-Luciferase, 20 ng pRL (Promega), and 35 ng pCMX. 4xARE-luciferase reporter activity was monitored in the presence of increasing compound concentrations in the absence or presence of 90 pM R1881 (for wild-type VP16-AR) or 1 nM R1881 (for F876L VP16-AR). Luciferase activity was measured as described above.

Reflective of the transcriptional reporter assay, in the wild-type VP16-AR assay, which monitors the DNA binding competency of the receptor, enzalutamide and ARN-509 were full antagonists (Table 7, FIG. 4) (Emax=percent maximal R1881 response). However, in the context of the VP16-AR-F876L, ARN-509 and enzalutamide stimulated AR DNA binding. Thus, the mutation of AR F876 to L was sufficient to convert the 2nd generation anti-androgens, enzalutamide and ARN-509, to partial agonists.

TABLE 7

| | AR-VP16 | | | |
|---|---|---|---|---|
| Compound | WT IC$_{50}$ (μM) | WT Emax | F876L IC$_{50}$ (μM) | F876L Emax |
| ARN-509 | 0.16 ± 0.06 | 3.98 ± 0.27 | 0.03 ± 0.02 | 53.98 ± 1.45 |
| Enzalutamide | 0.21 ± 0.07 | 2.65 ± 0.73 | 0.05 ± 0.01 | 34.32 ± 5.38 |
| Bicalutamide | 0.18 ± 0.10 | 32.77 ± 5.76 | 2.51 ± 1.11 | 2.20 ± 1.35 |
| Hydroxy-flutamide | 0.03 ± 0.01 | 42.28 ± 4.44 | 0.97 ± 0.27 | 5.36 ± 5.35 |
| Nilutamide | 0.13 ± 0.08 | 33.53 ± 9.75 | 2.12 ± 0.68 | 2.90 ± 1.80 |

Example 9

Stable Cell Line Generation

In this example, cell lines were generated with stable expression of AR F876L mutant. pSRαF876L, pQCXIN-AR and pQCXIN-F876L retroviruses were first generated by co-transfecting GP2-293 cells with pVSV-G (Clontech) according to the manufacturer's protocol.

PC3 cells stably expressing wild-type or AR-F876L were generated by transducing PC3 cells with either pQXIN-AR or pQXIN-F876L retrovirus and selection in RPMI 1640 medium containing 500 μg/mL gentamycin.

LNCaP cells stably expressing AR-F876L were generated by either transfecting LNCaP cells with pCDNA-F876L or transducing LNCaP cells with SRαF876L retrovirus. Individual clones of LNCaP/pCDNA-F876L were isolated following selection in 400 μg/mL gentamycin. LNCaP/SRαF876L cell pools were selected 400 mg/mL gentamycin.

AR protein expression of all cell lines was validated by western analysis using AR N-20 antibody (Santa Cruz Biotechnology).

Example 10

Equilibrium AR Binding Assays

Competitive binding assays of wild-type AR vs. F876L AR were performed as described in Clegg et al. (2012) Cancer Research 72:1494-503 using PC3 cells stably expressing wild-type human AR or AR-F876L as described above. Ki was calculated as Ki=IC50/(1+([$^3$H-R1881]/Kd)), [$^3$H-R1881]=0.6 nM.

Figure 5:
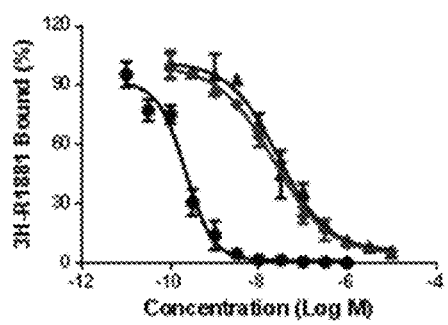
FIG. 5 illustrates a competitive binding assay of wild-type AR (A) vs. F876L AR (B). $^3$H-R1881 binding performed in PC3 cell extracts expressing wild-type or F876L AR. Data is representative of 3 independent experiments. Error bars, SEM; n=2.
Figure 5:
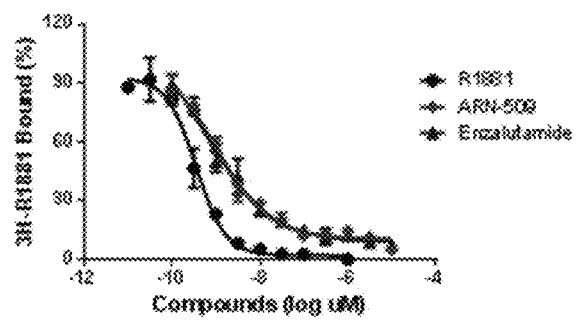

In equilibrium AR binding assays, ARN-509 and enzalutamide bound the mutant with 30 and 48-fold higher affinity, respectively (Table 8, FIG. 5) (Kd for R1881: AR=0.5 nM;

AR-F877L=0.64 nM). Thus, increased agonist activity on AR is associated with increased binding affinity to both wild-type and F876L receptor, suggesting that the agonist confirmation enables higher affinity through decreased dissociation constant.

TABLE 8

| Compound | AR binding, WT $K_i$ (nM) | AR binding, F876L $K_i$ (nM) |
|---|---|---|
| ARN-509 | 18.07 ± 7.46 | 0.68 ± 0.15 |
| Enzalutamide | 26.30 ± 12.77 | 0.60 ± 0.17 |
| Bicalutamide | 26.56 ± 12.51 | 360.36 ± 283.85 |
| Hydroxyflutamide | 14.56 ± 8.25 | 150.57 ± 55.10 |
| Nilutamide | 17.74 ± 5.65 | 197.42 ± 9.26 |

Example 11

Expression of AR Target Genes in and Proliferation of F876L Stable Prostate Cancer Cell Lines As shown above, expression of AR-F876L was sufficient to confer enzalutamide and ARN-509 resistance in transient reporter based assays. In this example, the effects of F876L on endogenous AR target genes and proliferation in prostate cancer cells stably expressing the mutant was examined. Two LNCaP cell lines (LNCaP/SRαF876L and LNCaP/pCDNAF876L) were engineered as described in Example 9 to overexpress AR-F876L at levels comparable to the LNCaP/AR(cs) model.

Figure 6:
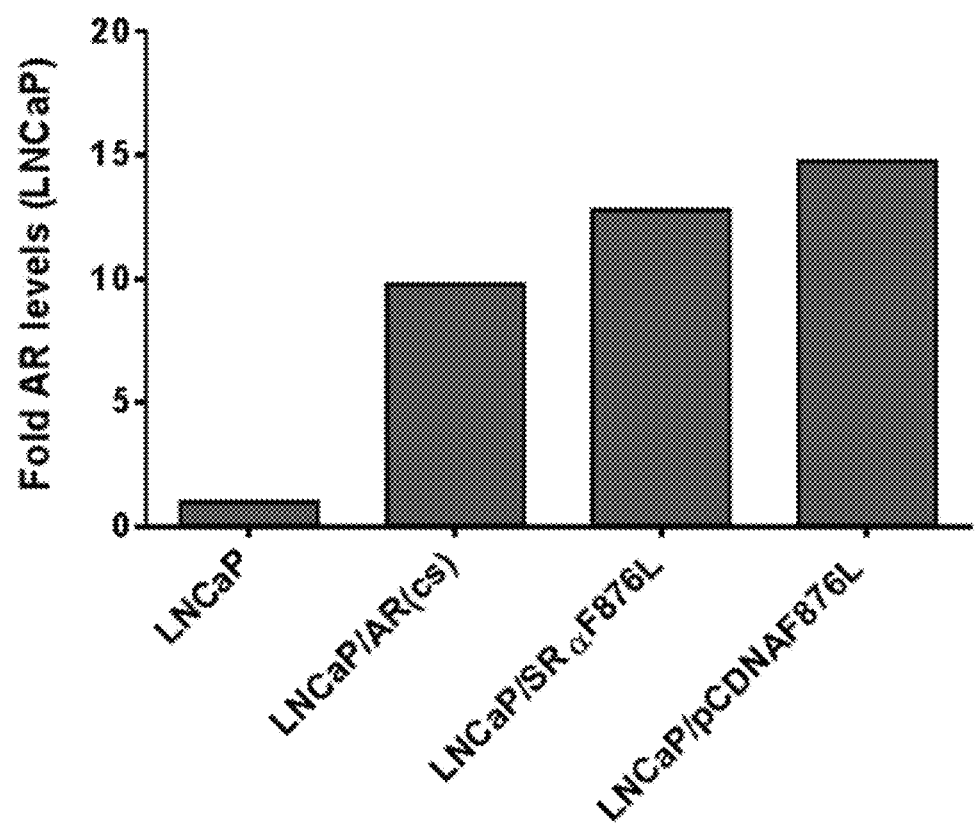
FIG. 6 illustrates AR levels in AR overexpressing cell lines. Protein extracts were generated from LNCaP, LNCap/AR(cs), LNCaP/SRαF876L and LNCaP/pCDNAF876L cells cultured in hormone depleted medium for 3 days. AR protein levels were analyzed and by Western blot. AR levels were quantified and normalized to actin and expressed relative to LNCaP cells.

To measure AR levels in the cells, protein extracts were generated from LNCaP, LNCap/AR(cs), LNCaP/SRαF876L and LNCaP/pCDNAF876L cells cultured in hormone depleted medium for 3 days. AR protein levels were analyzed by western blot. AR levels were quantified and normalized to actin and expressed relative to AR expression in LNCaP cells (FIG. 6)

For endogenous target gene analysis, LNCaP/AR(cs), LNCaP SRαF876L, and LNCaP/pCDNAF876L cells were cultured for 3 days in hormone depleted medium followed by treatment with vehicle, 1 nM R1881 or 1, 3, 10 and 30 μM ARN-509 or enzalutamide in the presence or absence on 1 nM R1881.

For the proliferation assays, LNCaP/AR(cs), LNCaP SRαF876L, and LNCaP/pCDNAF876L cells were cultured in the presence of hormone depleted medium for 2 days followed by ligand treatment for 7 days as described above. For antagonist assays, ARN-509 or enzalutamide were added in the presence of 200 pM R1881 (100 pM final concentration). Proliferation was quantified by CellTiter-Glo luminescence based viability assay as described above.

Figure 7:
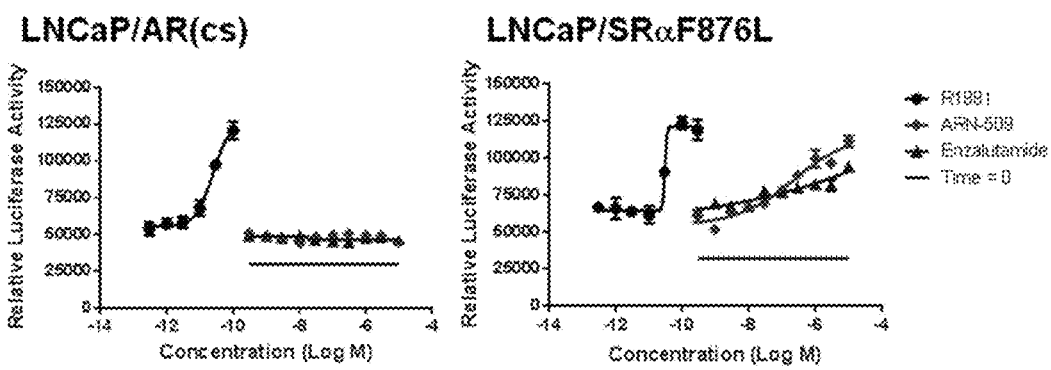
FIG. 7 illustrates F876L AR mutation confers partial agonist activity to ARN-509 and enzalutamide. (A) LNCaP/AR(cs) and LNCaP/SRαF876L cell proliferation. Cells were cultured in the presence of hormone depleted medium for 2 days followed by ligand treatment for 7 days. Proliferation is quantified by CellTiter-Glo luminescence based viability assay. (B) LNCaP/AR(cs), LNCaP/SRαF876L and LNCaP/pCDNAF876L cell proliferation. Cells were cultured in hormone depleted medium for 2 days followed by ligand treatment for 7 days. For antagonist assays, compounds were added in the presence of 200 pM R1881 (100 pM final concentration). Proliferation was quantified using the luminescence based CellTiter-Glo® assay.
Figure 7:
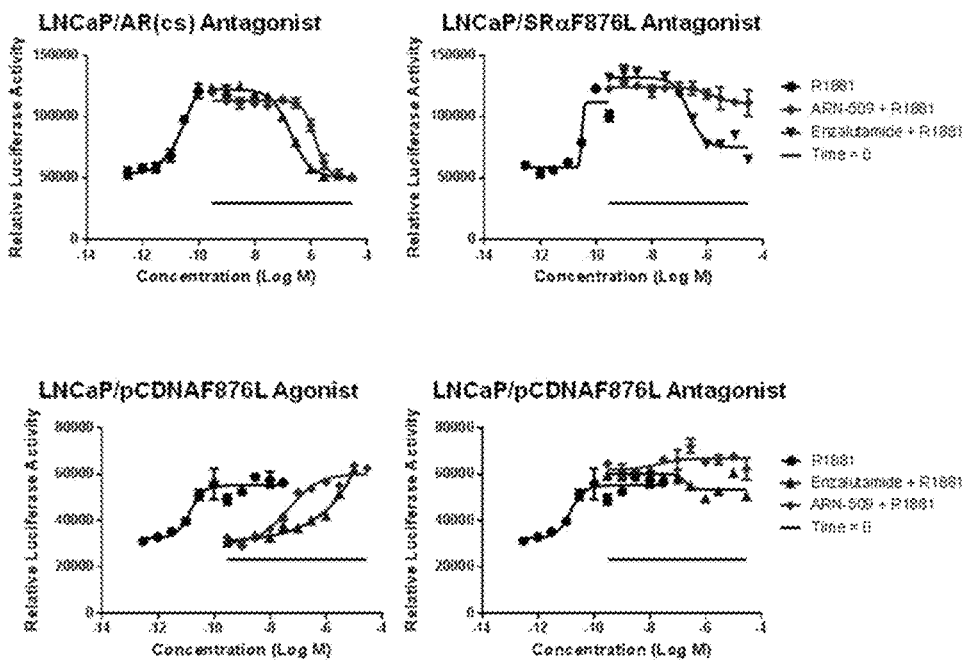

In LNCaP/AR(cs) cells, ARN-509 and enzalutamide had little effect on the induction of AR target genes or proliferative activity (FIG. 7A, Table 9A). Both antagonists blocked R1881 induced transcription and proliferation to levels consistent with their agonist activity at the highest concentration (FIG. 7B, Table 9B). In contrast, in F876L-AR expressing cells, both enzalutamide and ARN-509 demonstrated robust transcriptional and proliferative agonist activity (FIGS. 7A and 7B, Tables 9C-F).

TABLE 9A

LNCaP/AR(cs) Agonist Transcription

| | | | −R1881 | | | | | | | | | |
|---|---|---|---|---|---|---|---|---|---|---|---|---|
| | | | Enzalutamide | | | | | ARN-509 | | | | |
| Gene | Vehicle | 1 nM R1881 | 0.3 μM | 1 μM | 3 μM | 10 μM | 30 μM | 0.3 μM | 1 μM | 3 μM | 10 μM | 30 μM |
| AMIGO2 | 1.00 | 0.98 | 0.68 | 0.61 | 0.62 | 0.66 | 1.22 | 1.14 | 0.69 | 0.89 | 0.65 | 2.41 |
| BDNF | 1.00 | 0.86 | 1.04 | 0.92 | 0.88 | 0.95 | 0.98 | 1.15 | 0.93 | 1.03 | 1.03 | 1.80 |
| CAM2KN1 | 1.00 | 0.04 | 0.80 | 0.70 | 0.71 | 0.64 | 0.64 | 0.90 | 0.76 | 0.99 | 0.78 | 1.56 |
| FASN | 1.00 | 4.12 | 0.47 | 0.32 | 0.29 | 0.31 | 0.58 | 0.46 | 0.40 | 0.42 | 0.41 | 1.30 |
| FKBP5 | 1.00 | 100.51 | 0.91 | 0.62 | 0.75 | 0.61 | 0.85 | 0.99 | 0.71 | 0.91 | 0.75 | 1.87 |
| HPGD | 1.00 | 324.60 | 0.74 | 0.57 | 0.61 | 0.63 | 1.29 | 0.81 | 0.56 | 0.78 | 0.61 | 1.86 |
| NCAPD3 | 1.00 | 95.54 | 0.66 | 0.57 | 0.47 | 0.56 | 0.79 | 0.72 | 0.74 | 0.73 | 0.74 | 1.34 |
| NKX3.1 | 1.00 | 12.72 | 0.71 | 0.52 | 0.51 | 0.86 | 1.63 | 1.11 | 0.68 | 0.73 | 0.85 | 2.24 |
| NOV | 1.00 | 0.05 | 1.12 | 0.91 | 0.80 | 1.02 | 1.01 | 1.12 | 1.00 | 1.11 | 0.98 | 2.07 |
| ORM1 | 1.00 | 6987.01 | 0.92 | 0.90 | 1.06 | 0.71 | 2.02 | 1.37 | 1.79 | 1.20 | 0.97 | 1.35 |
| PLD1 | 1.00 | 0.03 | 0.77 | 0.62 | 0.63 | 0.56 | 0.56 | 1.28 | 0.66 | 0.88 | 0.65 | 1.33 |
| PSA | 1.00 | 22.14 | 0.42 | 0.32 | 0.38 | 0.74 | 1.60 | 0.44 | 0.49 | 0.58 | 0.61 | 1.13 |
| SLUG | 1.00 | 91.84 | 0.53 | 0.55 | 0.31 | 0.51 | 0.91 | 0.38 | 0.42 | 0.52 | 0.56 | 1.36 |
| STEAP4 | 1.00 | 1498.46 | 0.75 | 0.73 | 0.52 | 1.16 | 1.28 | 0.94 | 0.77 | 1.05 | 0.56 | 1.01 |
| TMPRSS2 | 1.00 | 35.42 | 0.75 | 0.53 | 0.63 | 0.89 | 1.45 | 0.99 | 0.64 | 1.04 | 0.62 | 2.78 |

TABLE 9B

LNCaP/AR(cs) Antagonist Transcription

| | | | +1 nM R1881 | | | | | | | | | |
|---|---|---|---|---|---|---|---|---|---|---|---|---|
| | | | Enzalutamide | | | | | ARN-509 | | | | |
| Gene | Vehicle | 1 nM R1881 | 0.3 μM | 1 μM | 3 μM | 10 μM | 30 μM | 0.3 μM | 1 μM | 3 μM | 10 μM | 30 μM |
| AMIGO2 | 1.00 | 0.98 | 0.49 | 0.19 | 0.48 | 0.78 | 0.92 | 0.30 | 0.31 | 0.52 | 0.60 | 0.76 |
| BDNF | 1.00 | 0.86 | 0.61 | 0.28 | 0.63 | 0.99 | 1.12 | 0.43 | 0.35 | 0.67 | 0.74 | 0.88 |
| CAM2KN1 | 1.00 | 0.04 | 0.04 | 0.06 | 0.27 | 0.50 | 0.56 | 0.04 | 0.06 | 0.19 | 0.43 | 0.42 |
| FASN | 1.00 | 4.12 | 1.30 | 0.42 | 0.71 | 0.46 | 0.59 | 1.92 | 1.52 | 1.08 | 0.60 | 0.64 |
| FKBP5 | 1.00 | 100.51 | 23.51 | 5.64 | 3.32 | 1.41 | 1.50 | 33.14 | 22.49 | 12.56 | 2.74 | 1.08 |

TABLE 9B-continued

LNCaP/AR(cs) Antagonist Transcription

+1 nM R1881

| Gene | Vehicle | 1 nM R1881 | Enzalutamide | | | | | ARN-509 | | | | |
|---|---|---|---|---|---|---|---|---|---|---|---|---|
| | | | 0.3 μM | 1 μM | 3 μM | 10 μM | 30 μM | 0.3 μM | 1 μM | 3 μM | 10 μM | 30 μM |
| HPGD | 1.00 | 324.60 | 99.16 | 16.30 | 13.19 | 3.85 | 4.25 | 105.97 | 76.25 | 32.19 | 8.36 | 2.78 |
| NCAPD3 | 1.00 | 95.54 | 23.74 | 4.35 | 3.14 | 1.29 | 1.27 | 43.93 | 32.00 | 15.57 | 2.39 | 0.96 |
| NKX3.1 | 1.00 | 12.72 | 7.70 | 3.77 | 6.72 | 4.70 | 5.03 | 8.32 | 9.92 | 12.01 | 7.22 | 5.49 |
| NOV | 1.00 | 0.05 | 0.11 | 0.14 | 0.61 | 1.00 | 0.92 | 0.03 | 0.09 | 0.31 | 0.86 | 0.82 |
| ORM1 | 1.00 | 6987.01 | 3521.95 | 503.02 | 257.85 | 43.91 | 22.70 | 5100.90 | 2679.73 | 1031.40 | 156.90 | 16.42 |
| PLD1 | 1.00 | 0.03 | 0.02 | 0.02 | 0.13 | 0.42 | 0.54 | 0.02 | 0.02 | 0.04 | 0.11 | 0.32 |
| PSA | 1.00 | 22.14 | 22.76 | 8.82 | 11.75 | 6.59 | 5.65 | 19.09 | 21.75 | 23.57 | 12.90 | 7.20 |
| SLUG | 1.00 | 91.84 | 50.08 | 10.20 | 10.56 | 5.26 | 5.22 | 71.33 | 62.00 | 50.70 | 11.15 | 5.49 |
| STEAP4 | 1.00 | 1498.46 | 585.81 | 109.37 | 74.44 | 13.61 | 7.79 | 1019.98 | 742.61 | 256.89 | 32.98 | 6.86 |
| TMPRSS2 | 1.00 | 35.42 | 19.88 | 7.72 | 10.51 | 3.58 | 4.62 | 19.07 | 24.11 | 23.38 | 11.45 | 5.94 |

TABLE 9C

LNCaP/SRαF876L Agonist Transcription

−R1881

| Gene | Vehicle | 1 nM R1881 | Enzalutamide | | | | | ARN-509 | | | | |
|---|---|---|---|---|---|---|---|---|---|---|---|---|
| | | | 0.3 μM | 1 μM | 3 μM | 10 μM | 30 μM | 0.3 μM | 1 μM | 3 μM | 10 μM | 30 μM |
| AMIGO2 | 1.00 | 0.29 | 0.58 | 0.32 | 0.47 | 0.40 | 0.31 | 0.27 | 0.47 | 0.23 | 0.34 | 0.27 |
| BDNF | 1.00 | 1.65 | 1.04 | 1.30 | 1.01 | 0.99 | 1.55 | 0.79 | 1.07 | 0.75 | 0.84 | 0.94 |
| CAM2KN1 | 1.00 | 0.03 | 0.52 | 0.48 | 0.38 | 0.23 | 0.37 | 0.30 | 0.24 | 0.17 | 0.21 | 0.18 |
| FASN | 1.00 | 3.76 | 0.50 | 0.64 | 0.58 | 1.09 | 1.34 | 0.64 | 1.01 | 0.93 | 1.50 | 2.77 |
| FKBP5 | 1.00 | 66.89 | 1.38 | 1.14 | 2.54 | 9.61 | 23.67 | 2.66 | 5.95 | 5.56 | 13.02 | 27.89 |
| HPGD | 1.00 | 182.19 | 0.68 | 0.96 | 2.79 | 18.98 | 55.76 | 4.18 | 7.90 | 10.12 | 25.79 | 69.22 |
| NCAPD3 | 1.00 | 31.69 | 0.77 | 1.01 | 1.09 | 3.56 | 8.83 | 1.39 | 1.58 | 1.69 | 3.53 | 9.35 |
| NKX3.1 | 1.00 | 10.80 | 4.26 | 5.54 | 7.05 | 11.94 | 14.20 | 7.12 | 9.47 | 7.96 | 9.85 | 12.67 |
| NOV | 1.00 | 0.06 | 0.55 | 0.28 | 0.53 | 0.42 | 0.21 | 0.27 | 0.51 | 0.31 | 0.29 | 0.17 |
| ORM1 | 1.00 | 6535.38 | 2.17 | 4.85 | 18.77 | 242.08 | 2114.41 | 44.44 | 58.96 | 101.45 | 459.30 | 1357.12 |
| PLD1 | 1.00 | 0.02 | 0.67 | 0.76 | 0.60 | 0.42 | 0.41 | 0.49 | 0.44 | 0.30 | 0.45 | 0.36 |
| PSA | 1.00 | 3.43 | 1.95 | 2.25 | 3.02 | 4.05 | 5.02 | 3.71 | 3.26 | 3.00 | 5.07 | 5.16 |
| SLUG | 1.00 | 99.20 | 1.21 | 1.55 | 3.28 | 16.87 | 107.64 | 5.56 | 5.91 | 8.15 | 26.35 | 56.48 |
| STEAP4 | 1.00 | 1706.02 | 1.13 | 2.15 | 9.98 | 96.53 | 343.81 | 20.36 | 27.49 | 46.06 | 187.24 | 479.64 |
| TMPRSS2 | 1.00 | 25.55 | 3.11 | 3.85 | 5.39 | 9.20 | 18.61 | 6.36 | 6.29 | 5.84 | 10.90 | 14.20 |

TABLE 9D

LNCaP/SRαF876L Antagonist Transcription

+1 nM R1881

| Gene | Vehicle | 1 nM R1881 | Enzalutamide | | | | | ARN-509 | | | | |
|---|---|---|---|---|---|---|---|---|---|---|---|---|
| | | | 0.3 μM | 1 μM | 3 μM | 10 μM | 30 μM | 0.3 μM | 1 μM | 3 μM | 10 μM | 30 μM |
| AMIGO2 | 1.00 | 0.29 | 0.23 | 0.29 | 0.33 | 0.39 | 0.40 | 0.17 | 0.22 | 0.14 | 0.18 | 0.18 |
| BDNF | 1.00 | 1.65 | 0.53 | 0.64 | 0.62 | 0.51 | 0.71 | 0.74 | 0.76 | 0.57 | 0.50 | 0.63 |
| CAM2KN1 | 1.00 | 0.03 | 0.08 | 0.12 | 0.19 | 0.24 | 0.32 | 0.03 | 0.03 | 0.06 | 0.11 | 0.17 |
| FASN | 1.00 | 3.76 | 1.29 | 1.22 | 0.85 | 0.94 | 1.58 | 2.23 | 2.03 | 1.39 | 1.30 | 2.66 |
| FKBP5 | 1.00 | 66.89 | 17.90 | 14.89 | 10.21 | 17.33 | 40.52 | 36.57 | 39.48 | 26.46 | 29.94 | 22.71 |
| HPGD | 1.00 | 182.19 | 49.66 | 30.03 | 21.62 | 34.77 | 93.52 | 149.34 | 134.70 | 79.93 | 70.80 | 131.79 |
| NCAPD3 | 1.00 | 31.69 | 6.34 | 4.28 | 2.21 | 3.44 | 13.64 | 19.83 | 15.47 | 8.71 | 6.50 | 11.82 |
| NKX3.1 | 1.00 | 10.80 | 21.66 | 20.78 | 16.19 | 11.84 | 15.26 | 12.63 | 14.12 | 11.34 | 10.15 | 13.64 |
| NOV | 1.00 | 0.06 | 0.12 | 0.28 | 0.25 | 0.33 | 0.26 | 0.05 | 0.06 | 0.09 | 0.11 | 0.09 |
| ORM1 | 1.00 | 6535.38 | 386.40 | 216.67 | 137.73 | 661.51 | 3496.87 | 3335.14 | 2343.29 | 1469.18 | 1608.16 | 3440.86 |
| PLD1 | 1.00 | 0.02 | 0.04 | 0.08 | 0.14 | 0.37 | 0.48 | 0.01 | 0.01 | 0.02 | 0.08 | 0.20 |
| PSA | 1.00 | 3.43 | 5.84 | 5.63 | 4.47 | 4.54 | 4.64 | 4.93 | 4.38 | 4.59 | 5.28 | 4.17 |
| SLUG | 1.00 | 99.20 | 85.97 | 64.63 | 35.50 | 48.80 | 161.58 | 85.97 | 64.63 | 35.50 | 48.80 | 161.58 |
| STEAP4 | 1.00 | 1706.02 | 259.94 | 147.25 | 83.20 | 275.88 | 645.04 | 259.94 | 147.25 | 83.20 | 275.88 | 645.04 |
| TMPRSS2 | 1.00 | 25.55 | 14.05 | 13.81 | 11.78 | 12.92 | 20.19 | 14.05 | 13.81 | 11.78 | 12.92 | 20.19 |

TABLE 9E

LNCaP/pCDNAF876L Agonist Transcription

−R1881

| | | | Enzalutamide | | | | | ARN-509 | | | | |
|---|---|---|---|---|---|---|---|---|---|---|---|---|
| Gene | Vehicle | 1 nM R1881 | 0.3 μM | 1 μM | 3 μM | 10 μM | 30 μM | 0.3 μM | 1 μM | 3 μM | 10 μM | 30 μM |
| AMIGO2 | 1.00 | 0.92 | 1.28 | 0.82 | 0.87 | 0.72 | 0.91 | 1.07 | 0.86 | 1.25 | 0.60 | 1.55 |
| BDNF | 1.00 | 1.01 | 1.54 | 1.04 | 1.11 | 0.82 | 0.64 | 1.01 | 0.76 | 0.87 | 0.85 | 1.16 |
| CAM2KN1 | 1.00 | 0.02 | 0.55 | 0.96 | 0.51 | 0.37 | 0.23 | 0.47 | 0.55 | 0.34 | 0.41 | 0.27 |
| FASN | 1.00 | 22.20 | 0.91 | 0.72 | 0.48 | 1.27 | 3.66 | 1.16 | 1.42 | 1.59 | 1.79 | 7.86 |
| FKBP5 | 1.00 | 145.63 | 2.18 | 2.91 | 4.28 | 10.54 | 42.25 | 7.24 | 7.82 | 9.52 | 17.39 | 55.55 |
| HPGD | 1.00 | 854.42 | 4.70 | 6.32 | 13.26 | 26.78 | 105.81 | 15.36 | 19.27 | 29.25 | 47.33 | 173.82 |
| NCAPD3 | 1.00 | 169.67 | 1.95 | 1.94 | 3.68 | 9.41 | 35.36 | 5.83 | 6.52 | 8.28 | 20.42 | 51.13 |
| NKX3.1 | 1.00 | 9.67 | 3.76 | 3.71 | 3.57 | 4.69 | 8.12 | 6.07 | 5.72 | 5.93 | 7.05 | 11.69 |
| NOV | 1.00 | 0.08 | 1.73 | 1.62 | 2.19 | 0.88 | 0.49 | 1.24 | 1.01 | 0.82 | 0.86 | 0.72 |
| ORM1 | 1.00 | 12816.69 | 116.91 | 195.36 | 659.73 | 2530.13 | 4760.77 | 932.41 | 1371.33 | 2307.29 | 3322.63 | 5541.08 |
| PLD1 | 1.00 | 0.75 | 1.37 | 0.80 | 0.69 | 0.29 | 0.45 | 0.78 | 0.69 | 1.01 | 0.68 | 0.48 |
| PSA | 1.00 | 12.17 | 3.56 | 4.04 | 5.29 | 9.53 | 11.70 | 6.74 | 7.19 | 8.25 | 10.06 | 12.99 |
| SLUG | 1.00 | 268.77 | 1.99 | 3.53 | 4.74 | 14.91 | 55.93 | 7.84 | 8.70 | 10.91 | 21.21 | 71.08 |
| STEAP4 | 1.00 | 3084.81 | 10.38 | 15.58 | 46.50 | 240.68 | 520.15 | 113.39 | 113.29 | 173.77 | 317.80 | 597.09 |
| TMPRSS2 | 1.00 | 26.85 | 4.98 | 6.46 | 6.09 | 8.51 | 21.78 | 9.49 | 8.51 | 9.70 | 11.09 | 23.01 |

TABLE 9F

LNCaP/pCDNAF876L Antagonist Transcription

+1 nM R1881

| | | | Enzalutamide | | | | | ARN-509 | | | | |
|---|---|---|---|---|---|---|---|---|---|---|---|---|
| Gene | Vehicle | 1 nM R1881 | 0.3 μM | 1 μM | 3 μM | 10 μM | 30 μM | 0.3 μM | 1 μM | 3 μM | 10 μM | 30 μM |
| AMIGO2 | 1.00 | 0.92 | 0.51 | 0.43 | 0.39 | 0.49 | 0.52 | 0.24 | 0.31 | 0.43 | 0.41 | 0.40 |
| BDNF | 1.00 | 1.01 | 0.59 | 0.71 | 0.53 | 0.50 | 0.41 | 0.28 | 0.41 | 0.42 | 0.45 | 0.34 |
| CAM2KN1 | 1.00 | 0.02 | 0.05 | 0.16 | 0.17 | 0.21 | 0.14 | 0.01 | 0.02 | 0.06 | 0.11 | 0.06 |
| FASN | 1.00 | 22.20 | 5.29 | 2.44 | 1.55 | 2.08 | 4.22 | 3.89 | 5.52 | 3.22 | 2.10 | 3.98 |
| FKBP5 | 1.00 | 145.63 | 53.18 | 26.29 | 10.03 | 14.22 | 32.97 | 45.69 | 48.95 | 38.89 | 24.82 | 30.26 |
| HPGD | 1.00 | 854.42 | 149.44 | 59.67 | 21.66 | 35.90 | 96.55 | 192.05 | 170.69 | 107.79 | 73.28 | 87.03 |
| NCAPD3 | 1.00 | 169.67 | 101.65 | 31.49 | 14.34 | 16.69 | 42.06 | 68.41 | 90.52 | 62.27 | 22.96 | 44.10 |
| NKX3.1 | 1.00 | 9.67 | 8.53 | 7.05 | 5.69 | 5.54 | 7.61 | 3.08 | 5.95 | 5.42 | 4.81 | 5.24 |
| NOV | 1.00 | 0.08 | 0.08 | 0.17 | 0.32 | 0.49 | 0.39 | 0.02 | 0.10 | 0.12 | 0.26 | 0.18 |
| ORM1 | 1.00 | 12816.69 | 4375.20 | 1581.76 | 587.00 | 1377.92 | 3765.54 | 4802.10 | 4943.10 | 3366.19 | 2576.38 | 2470.99 |
| PLD1 | 1.00 | 0.75 | 0.08 | 0.12 | 0.09 | 0.11 | 0.12 | 0.04 | 0.12 | 0.05 | 0.06 | 0.04 |
| PSA | 1.00 | 12.17 | 16.08 | 12.73 | 7.92 | 8.12 | 14.27 | 10.36 | 14.01 | 12.21 | 10.27 | 13.14 |
| SLUG | 1.00 | 268.77 | 166.04 | 86.01 | 30.23 | 36.56 | 98.34 | 112.06 | 134.56 | 113.34 | 69.55 | 85.38 |
| STEAP4 | 1.00 | 3084.81 | 524.97 | 156.24 | 47.11 | 92.80 | 214.69 | 633.57 | 587.91 | 376.66 | 195.78 | 232.63 |
| TMPRSS2 | 1.00 | 26.85 | 19.03 | 16.05 | 8.14 | 8.92 | 15.32 | 12.13 | 15.75 | 14.19 | 12.99 | 12.67 |

Example 12

Interaction of N and C Expression of AR Target Genes in and Proliferation of F876L Stable Prostate Cancer Cell Lines Interaction of the AR amino-terminus with the AR carboxy-terminus is important for the full AR transactivation capacity. Many AR full and partial agonists stimulate the AF2 dependent N-C interaction. A N-C two hybrid interaction assay was performed to assess the interaction of the AR N- and C-termini in the F87L mutant in the presence of ARN-509 and enzalutamide.

pM-AR1-660, pVP16-AR507-919 and pVP16-F876L507-919 were generated by subcloning appropriate PCR products from pCDNA3-AR and pCDNA3-F876L into pM and pVP16 (Clontech). For N-C terminal interaction assays, triplicate transfections were performed using 50 ng pM-AR1-660, 75 ng pVP16-AR507-919 or pVP16-F876L507-919, 25 ng pMH100-Luc and 10 ng pRL (Promega). Transfected cells were incubated 4 hours then treated with ligand. ARN-509 and enzalutamide were assayed at 8 μM and R1881 at 1 nM.

Figure 8:
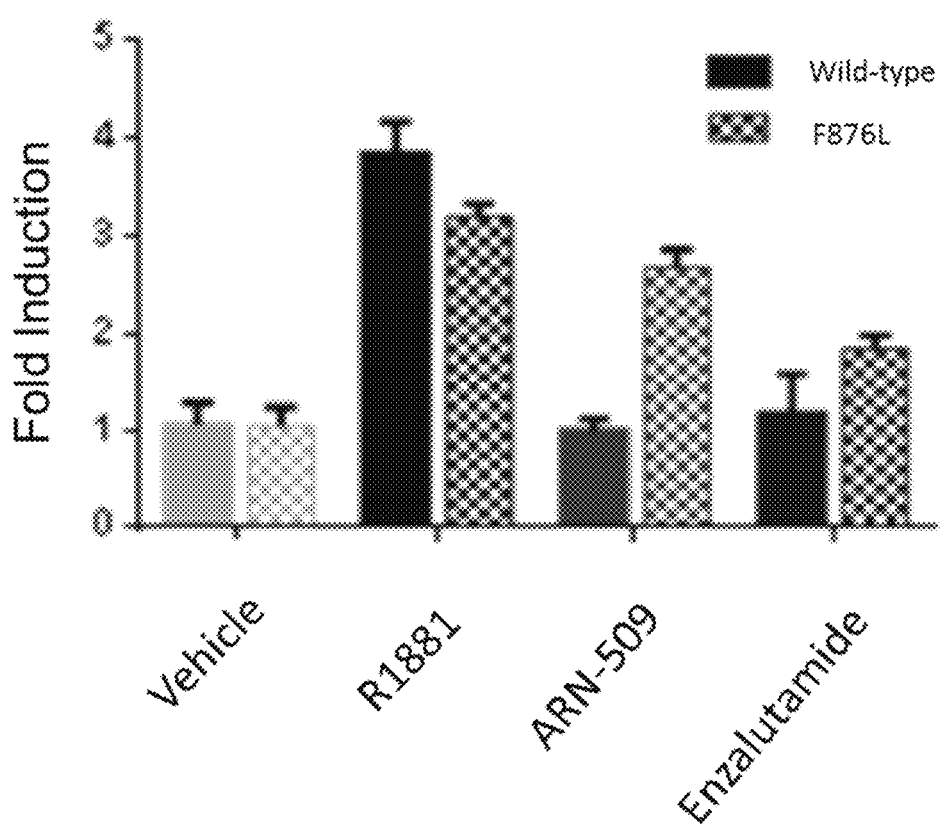
FIG. 8 illustrates AR N/C interaction assay. Ligand induced N/C interaction was monitored via mammalian two hybrid assay in HepG2 cells. Antagonists were assayed at 8 µM, R1881 at 1 nM.

Consistent with their transcriptional activities, enzalutamide and ARN-509 promoted the N-C interaction of AR-F876L but not wild-type AR (FIG. 8). Thus, the agonist activity of ARN-509 and enzalutamide on AF-F876L is associated with an agonist-like AF-2 conformation.

Example 13

Chromatin Immunoprecipitation Assay of AR

Transcriptional activation of androgen regulated AR target genes requires agonist-induced DNA binding and subsequent recruitment of transcriptional coregulators. To confirm the VP16-AR reporter results indicating ARN-509 and enzalutamide stimulate AR-F876L DNA binding, we performed chromatin immunoprecipitation (ChIP) analysis of 6 AR target genes from cells treated with R1881 and/or each antagonist was performed.

ChIP assays were performed as described in Joseph et al. (2009) PNAS USA 106:12178-83]. Briefly, LNCaP/AR(cs) and LNCaP SRαF876L cells were plated in 150 mm dishes (7×10⁶ cells in 20 mL) in RPMI 1640 supplemented with 10% CSS for 3 days. Cells were treated with 10 µM antagonist in the presence or absence of 1 nM R1881 for 4 hours. Following ligand treatment, formaldehyde was added to the media to a final concentration of 1%, incubated for 10 min and quenched with glycine (125 mM final concentration) for 5 minutes. Cells were washed 3× with PBS containing 1× Halt™ Protease & Phosphatase Single-Use Inhibitor Cocktail (1×PI, Thermo Scientific), pelleted, lysed in 1 mL RIPA buffer (50 mM Tris pH7.5, 0.15 M NaCl, 1% NP-40, 0.5% Na-deoxycholate, 0.05% SDS, 1 mM EDTA, 1×PI) and sonicated until the average DNA size fragment was ≈500 bp. The sonicated cross-linked chromatin was diluted into 3.3 mL RIPA and precleared with 100 mL 50% protein A/G agarose slurry (SC-2003, Santa Cruz Biotechnology) containing 200 mg per mL sonicated salmon sperm DNA and 500 mg per mL of BSA. One mL of precleared chromatin was then immunoprecipitated with 15 µg anti-AR (SC-816, Santa Cruz Biotechnology) or normal rabbit IgG (SC-2027, Santa Cruz Biotechnology), for 2 hours at 4° C. and 100 mL of a 50% slurry of protein A/G agarose beads were added and incubated overnight at 4° C. Beads were washed 2 times sequentially in low-salt buffer (50 mM HEPES pH 7.8, 140 mM NaCl, 1 mM EDTA, 1% Triton X-100, 0.1% Na-deoxycholate, 0.1% SDS), high-salt buffer (same as low-salt with 500 mM NaCl), LiCl buffer (20 mM Tris pH 8.0, 1 mM EDTA, 250 mM LiCl, 0.5% NP-40, 0.5% Na-deoxycholate), and TE buffer (50 mM Tris pH 8.0, 1 mM EDTA). All washing steps were performed in the presence of 1×PI. Protein-DNA complexes were eluted in 225 mL Elution buffer (50 mM Tris pH 8.0, 1 mM EDTA, 1% SDS) at 65° C. twice for 15 minutes. Eluted protein-DNA complexes were reverse cross-linked in the presence of NaCl overnight at 65° C. and further treated with EDTA and proteinase K at 42° C. for 1 hour. The DNA fragments were purified in 10 mM Tris pH 8.5 using the QIAquick PCR purification kit (Qiagen), diluted and analyzed by real-time PCR using iTaq SYBR Green Supermix with ROX (Bio-Rad). The samples were amplified on the ABI 7900HT instrument. Oligonucleotide primer sequences are listed in Table 8.

TABLE 8

ChIP Real-time PCR Oligonucleotide Sequence

| Gene | Forward Primer Sequence | Reverse Primer Sequence |
|---|---|---|
| PSA E2 | ACCTGCTCAGCCTTTGTCT CTGAT (SEQ ID NO: 50) | AGATCCAGGCTTGCTTACTG TCCT (SEQ ID NO: 51) |
| PSA D1 | ATTCTGGGTTGGGAGTGCA AGGAA (SEQ ID NO: 52) | AGGAGACATGCCCAGGATGA AACA (SEQ ID NO: 53) |
| STEAP4 | ACTAGGCAGGACATTGACA TCCCA (SEQ ID NO: 54) | ACAGTAAACCTCTCCACACA TGGC (SEQ ID NO: 55) |
| FASN | TATGACACCCAGGGCTTT CGTTCA (SEQ ID NO: 56) | TAACGTTCCCTGCGCGTTTA CAGA (SEQ ID NO: 57) |
| TMPRSS2 | TCCCAAATCCTGACCCCA (SEQ ID NO: 58) | ACCACACAGCCCCTAGGAGA (SEQ ID NO: 59) |

TABLE 8 -continued

ChIP Real-time PCR Oligonucleotide Sequence

| Gene | Forward Primer Sequence | Reverse Primer Sequence |
|---|---|---|
| NKX3.1 | ACAGGGTGGCCCAAATAG AAC (SEQ ID NO: 60) | CCTGTCTTGGACAAGCGGAG A (SEQ ID NO: 61) |
| ORM1 | GGGTCATTTCCACCACCT CAAACA (SEQ ID NO: 62) | GGAGAAAGGCCTTACAGTAG TCTC (SEQ ID NO: 63) |

Figure 9:
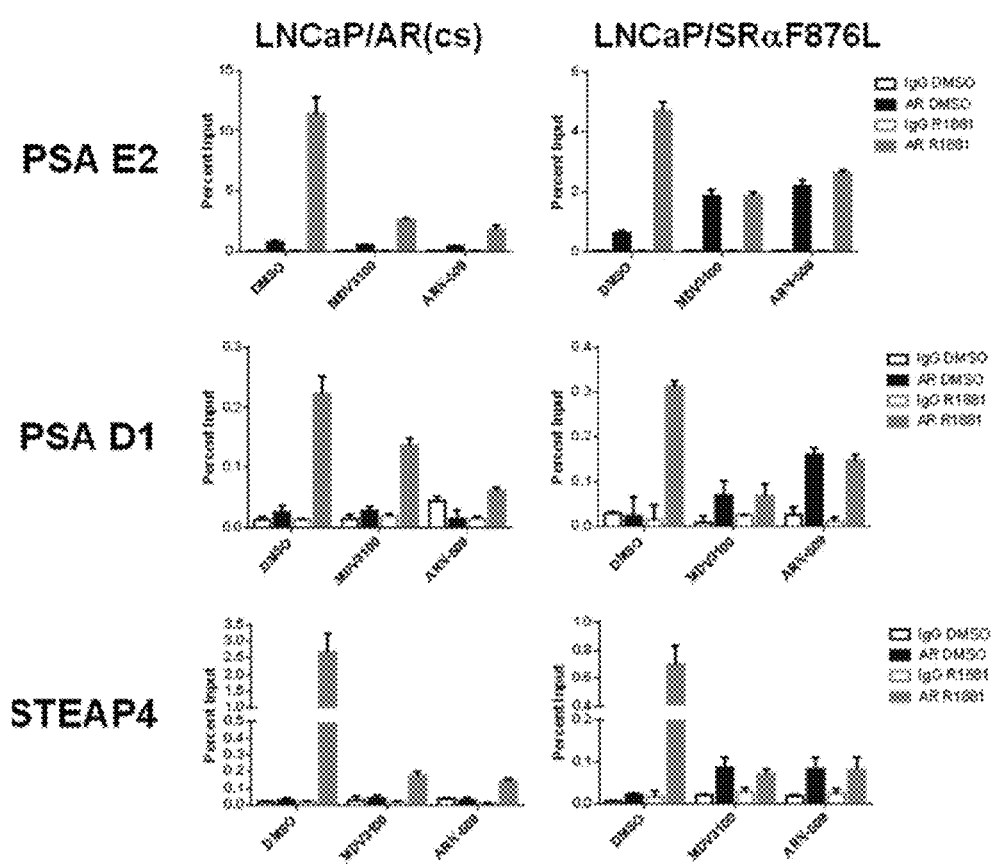
FIG. 9 illustrates AR ChIP analysis of AR target genes. ChIP assays were performed on LNCaP/AR(cs) and LNCaP/SRαF876L cells incubated for 3 days in hormone depleted medium followed by 4 hour ligand treatment. Cells were treated in with 10 µM antagonist in the presence or absence of 1 nM R1881. Data for AR and non-specific IgG control is presented as percent input.

In the LNCaP/AR(cs) cells, R1881 promoted AR DNA (FIG. 9). Consistent with the VP16-AR reporter data, both ARN-509 and enzalutamide promoted AR DNA binding LNCaP/SRαF876L cells. In the presence of R1881, all antagonists inhibited R1881-stimulated AR DNA binding to levels consistent with their partial agonist or antagonist activity in both cell lines (Supplementary Figure S9).

Example 14

In Vivo Effects of AR F876L

To determine whether the F876L alteration conveys resistance to enzalutamide and ARN-509 in vivo, LNCaP cell lines stably expressing F876L AR were injected (s.c.) into castrated immune-deficient mice and tumors established.

All animal studies were carried out under protocols approved by the Institutional Animal Care and Use Committees and institutional guidelines for the proper, humane use of animals in research were followed. In vivo xenograft experiments were carried out in SCID Hairless Outbred (SHO) male mice (Charles River Laboratories). Mice were orchiectomized under isoflorane anesthesia and were given 7-10 days to recover. LNCaP/AR(cs) or LNCaP/SRαF876L cells (as described above) were suspended in 50% RPMI, 50% Matrigel (BD Biosciences), and 3×10⁶ cells/xenograft were injected in a volume of 100 µL. Animals were observed weekly until tumor growth was apparent. After 40-60 days post-injection, animals were randomized into cohorts of equivalent tumor burden mean (150-250 mm³) and range. All compounds were administered daily by oral gavage at a dose of 30 mg/kg/day compound. For all LNCaP/AR(cs) xenograft studies ARN-509 and enzalutamide drug stocks were prepared in 18% PEG-400, 1% Tween-80 and 1% povidone, and were formulated for dosing in 15% Vitamin E-TPGS and 65% of a 0.5% w/v CMC solution in 20 mM citrate buffer (pH 4.0). ARN-509 and enzalutamide pharmacokinetics were assessed at the end of study as described previously (Clegg et al. (2012) Cancer Research 72:1494-503).

Figure 10:
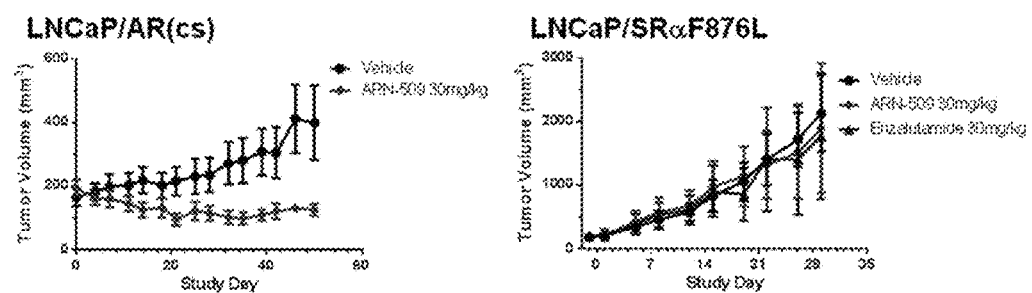
FIG. 10 illustrates AR F876L mutation confers ARN-509 and enzalutamide resistance in vivo. LNCaP/AR(cs) and LNCaP/SRαF876L tumor xenografts. Castrate male mice bearing tumors were treated daily with vehicle or 30 mg/kg/day compound. Tumor growth for each group is presented as the average tumor volume±SEM.

Consistent with the in vitro data, neither ARN-509 nor enzalutamide 30 mg/kg/day impacted the growth of LNCaP/AR/SRαF876L tumors (FIG. 10). This lack of activity was not a function of unexpectedly low compound exposure as day 28 plasma drug levels were quantified and were consistent with previous LNCaP/AR xenograft studies (Table 9). In addition, in a parallel experiment, ARN-509 30 mg/kg/day exhibited robust anti-tumor activity in the LNCaP/AR(cs) model, consistent with previous results (FIG. 10).

TABLE 9

LNCaP/SRαF876L Xenograft Pharmacokinetics

| Compound | Dose | $C_{24}$ (μg/mL) | $T_{1/2}$ (hr) | $AUC_{0-24}$ (μg · hr/mL) | $C_{max}$ (μg/mL) | $T_{max}$ (hr) |
|---|---|---|---|---|---|---|
| Enzalutamide | 30 mg/kg | 9.14 | 9.9 | 527.3 | 33.5 | 1.0 |
| ARN-509 | 30 mg/kg | 1.02 | 7.1 | 98.9 | 9.11 | 1.0 |

Example 15

An Open-Label, Phase 1/2 Safety, Pharmacokinetic, and Proof-of-Concept Study of ARN-509 in Patients with Progressive Advanced Castration-Resistant Prostate Cancer (CRPC)

In this study, DNA was isolated from 29 patient plasma samples patients participating in a Phase 1/2 clinical study ARN-509 treatment for prostate cancer. These were analyzed using the emulsion PCR-based BEAMing Technology method (Dressman et al. (2003) PNAS USA 100:8817-22). BEAMing has been successfully used to detect a variety of tumor derived mutations in driver oncogenes such as PIKC3a and K-ras in ctDNA derived from human plasma (Diehl et al. (2008) *Nature Medicine* 14:985-90). The AR F876L mutation was identified in 3 of the 29 patient samples tested.

The clinical study performed was multi-institution, first in man, Phase 1/2, dose-escalation and proof-of-concept study across 9 dose levels in which eligible patients with progressive advanced CRPC received oral doses of ARN-509 on an outpatient basis to determine the safety, pharmacokinetics (PK) and preliminary evidence of the anti-tumor effects of ARN-509.

Patients with mCRPC were assigned sequentially to dose levels in cohorts of 3 to 6 patients per dose level using standard 3×3 dose-escalation criteria.

Figure 11:
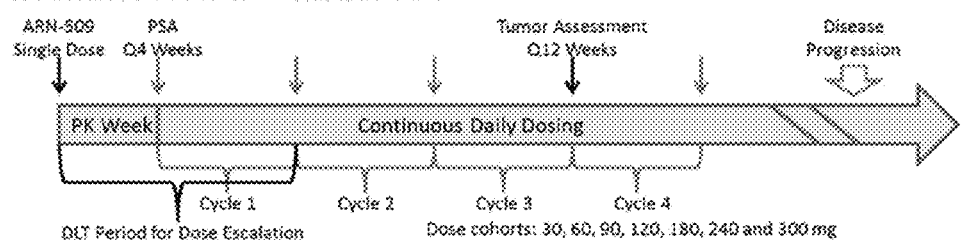
FIG. 11 illustrates the dosing schedule for the open-label phase 1/2 safety, pharmacokinetic, and proof-of-concept study of ARN-509 in patients with progressive advanced, metastatic Castration-Resistant Prostate Cancer.
Figure 11:
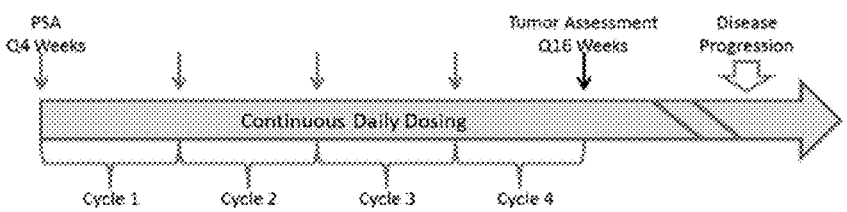
Figure 11:
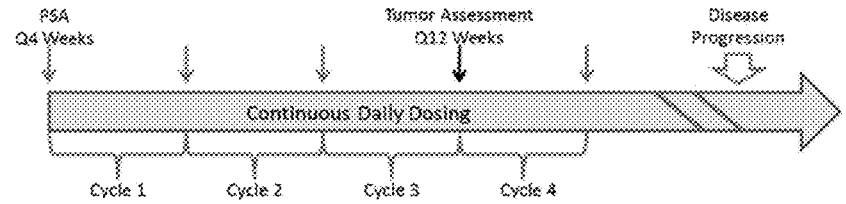

The objective was to determine the maximum tolerated dose (MTD) and/or recommended Phase 2 dose (RP2D) of ARN-509 that leads to a dose-limiting toxicity (DLT) in a maximum of 30% of patients. A DLT is generally defined as any Grade 1 or higher seizure, any Grade 3-4 non-hematologic toxicity (GI toxicities must persist at Grade 3-4 despite maximal medical therapy) and/or grade 4 hematologic toxicity of more than 5 days duration, defined by CTCAE V4.0, and that is assessed as related to ARN-509 treatment. A schematic of the study design is provided in FIG. 11.

Eligible patients who signed informed consent documents were initially enrolled into a dose escalation cohort where they will receive a single oral dose of ARN-509 followed by a one-week observation period (PK Week). Continuous dosing began on Cycle 1 Day 1 assuming no unacceptable toxicities were observed.

A minimum of 3 subjects at each dose level were monitored for a DLT through day 28 of Cycle 1. If no DLTs were observed in the first 3 patients at each dose level, subsequent enrollment proceeded at the next dose level. If 2 or more patients experienced a DLT at a given dose level or a single episode of seizure of any grade was observed at a given dose level, dose escalation was stopped and the MTD was defined as the previous dose level. If no DLTs were observed, RP2D was based on the overall pharmacokinetic and safety profile of ARN-509 and the optimal biological dose determined from preclinical data, and not necessarily the MTD.

The starting dose was 30 mg/day, with escalations to 60 mg, 90 mg, 120 mg, 180 mg, 240 mg, 300 mg, 390 mg, and 480 mg daily. It was anticipated that these dose levels span the anticipated pharmacologically active dose range and be within the safety margin indicated by the preclinical toxicology results.

Following the selection of 240 mg as the RP2D, additional eligible patients were enrolled in the Phase 2 portion of the study, consisting of 3 concurrent expansion cohorts at the MTD and/or RP2D to gather additional safety information and provide an initial signal of anti-tumor activity. The three expansion cohorts included:

1. Non-metastatic CRPC treatment naïve (50 patients with non-metastatic CRPC who are chemotherapy and abiraterone treatment naïve);
2. Metastatic CRPC treatment-naïve (20 patients with mCRPC who are chemotherapy and abiraterone naïve); and
3. Metastatic CRPC abiraterone treated (10-20 patients).

It was expected that each patient with mCRPC would receive at least 3 cycles (12 weeks) of continuous treatment and each patient with non-metastatic CRPC will receive at least 4 cycles (16 weeks) of continuous treatment. Treatment was discontinued at any time for protocol-defined disease progression or unacceptable toxicity. Tumor evaluations were performed every 3 cycles (12 weeks) for patients with mCRPC and every 4 cycles (16 weeks) for patients with non-metastatic CRPC. Safety was assessed from the first dose through at least four weeks after the last dose or until resolution of drug-related toxicity, or when toxicity is deemed irreversible, whichever was longer. The effect of food on the absorption of ARN-509 and the effect of ARN-509 on ventricular repolarization was evaluated in the Phase 2 expansion phase at selected clinical sites.

Analysis of the samples using BEAMing technology in the current ARN-509 clinical study was carried out by Inostics GMBH. Blood was collected in K2-EDTA evacuated tubes and mix thoroughly by slowly inverting several times. Within 30 minutes of collection tubes were spun at 2000×g for 15 minutes. Plasma was decanted, transferred to cryo storage tubes. Within 90 minutes of decantation, plasma was stored at −70° C. or lower until analysis. DNA was purified from 300-500 μl plasma aliquots and extracted as described in Diehl et al. (2008) *Nature medicine* 14:985-90. Mutation detection was performed according to BEAMing technology as described in Diehl et al. Briefly, in the initial PCR step, the target region (~100 bp) was amplified using gene-specific primers with tag sequences and subjected to an emulsion PCR containing primer coated magnetic beads. After emulsion PCR discrimination of wildtype and mutant beads was performed by allele-specific hybridization followed flow cytometry. Flow cytometry results were analyzed using FCS Express (De Novo Software, Los Angeles, Calif.) resulting in the quantification of the ratio of the mutant allele over the wild type alleles.

Samples were analyzed for the presence of wild type AR or 3 single point mutant alleles that could result in F876L (T2988C, C2990A, and C2990G). Analyzed mutations and the technical sensitivity of the BEAMing Method are shown in Table 10. For detection, the frequency has to be above the total amount of genome equivalent used per assay. For example, if in a sample, 1,000 genomic equivalent are present, yet the calculated fraction of mutant DNA molecules is 0.02% (1 mutant allele in 5,000 wild-type alleles), the samples is scored as wild type.

TABLE 10

AR nucleotide changes monitored by BEAMing assay

| Nucleotide Position | Nucleotide Change | Amino Acid Position | Amino Acid Change |
|---|---|---|---|
| c.2626 | T > C | 876 | F > L |
| c.2628 | C > A | 876 | F > L |
| c.2628 | C > G | 876 | F > L |

Results

Figure 12:
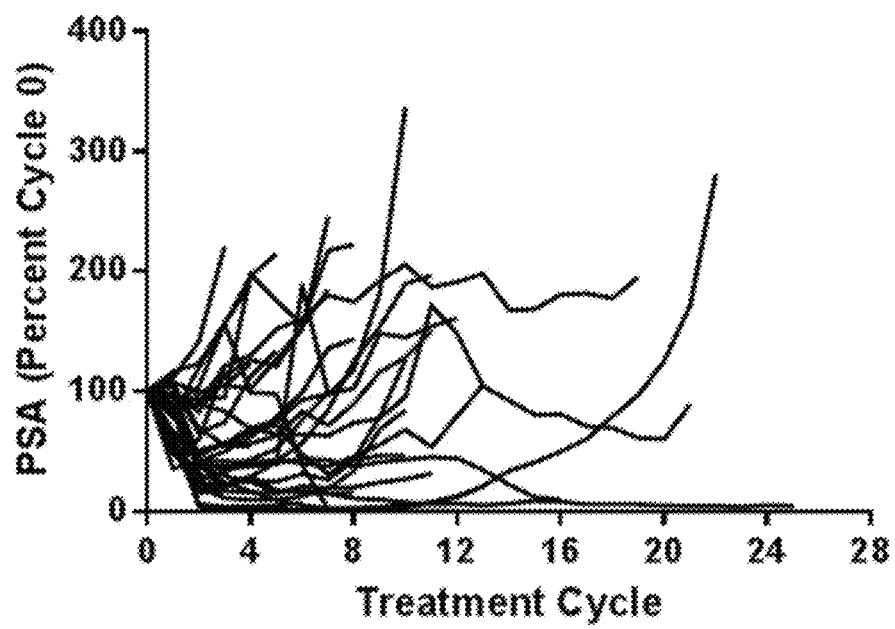
FIG. 12 illustrates Identification of AR-F876L in ARN-509 treated patients. (A) PSA response of 29 patients analyzed for F876L mutation. Terminal end of PSA response line is time at which the patient plasma was screened for F876L mutation using BEAMing analysis. The plasma used in this study was initially collected to determine pharmacokinetics of ARN-509 and as such the samples were not prepared using methodology to maximize ratio of ctDNA to lymphocyte DNA. (B) PSA response of patient positive for F876L. PSA response of patient 7 at indicated treatment cycle. Circulating plasma was analysed for the F876L at times indicated with arrows. The plasma samples with no detectable mutant are notated as "w.t.", the presence of the F876L mutation is represented by "m". A plasma sample was called positive for the mutant if the percent of mutant beads was above the cut-off (0.02%) and the number of mutant copies estimated to be ≥0.5 (number of genome equivalents in the plasma sample×mutant bead fraction=≥0.5).
Figure 12:
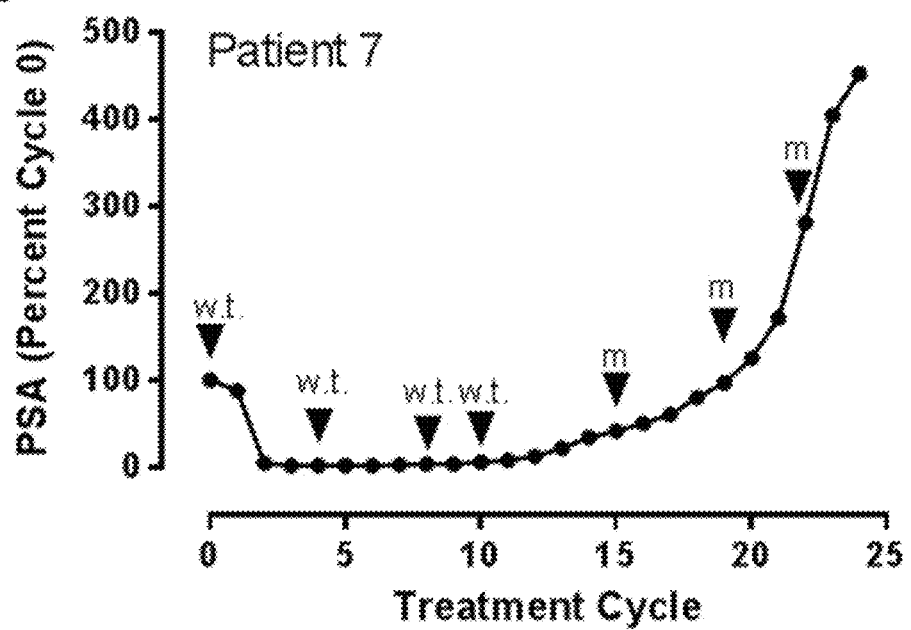

A subset of patients across all dose groups exhibited PSA response with 14/30 patients exhibiting a 12 week ≥50% decline in PSA compared to baseline. The PSA response for the 29 patients screened is depicted in FIG. 12. Pre-treatment and during treatment plasma samples were analyzed. Time of BEAMing analysis is indicated by the terminal end of the PSA response line. Eighteen out of the 29 patients had PSA above of baseline at time of analysis indicating either intrinsic or acquired resistance to ARN-509.

Figure 13:
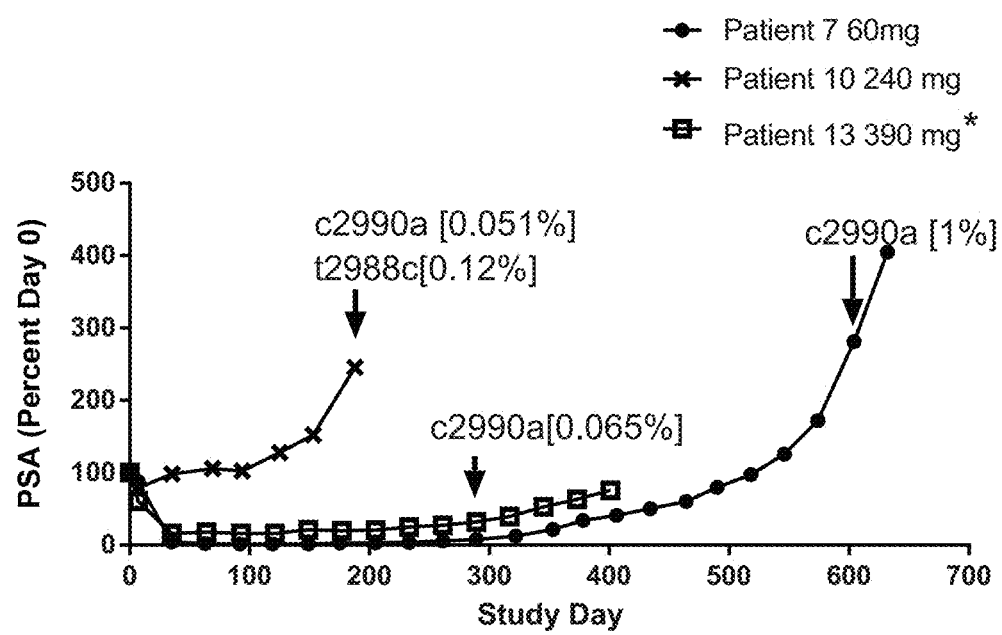
FIG. 13 illustrates the relative amount of prostate specific antigen (PSA) detected over the course of the Phase 1/2 ARN-509 clinical study in each of the three patients (7, 10, and 13) bearing detectable somatic F876L mutations in AR. Arrow indicates sample in which the mutation(s) were detected.

Three probes were designed to monitor the 3 nucleotide changes that can encode for the F876L amino acid substitution. Dilution mixing experiments with the mutant sequence and wild-type DNA indicated a technical sensitivity of 0.02% (potential to detect 1 mutant sequence among 5000 wild-type). In an initial screen of plasma samples of 29 ARN-509 treated patients, evidence of the mutation was detected in 3 patients (Tables 11 and 12). At time of BEAMing analysis, Patient 7 and 10 had PSA levels above baseline, whereas Patient 13 has evidence of rising PSA above the treatment nadir (FIG. 13). In all 3 patients, the nucleotide change c2628a was detected. In one of these 3 patients (Patient 10) the t2626c mutant was also detected, indicative of polyclonal disease. F876L encoding mutations were not detected in any of pre-treatment samples (0/29) suggesting that if present prior to ARN-509 treatment they were below the limit of detection or that the mutations arose de novo during ARN-509 treatment. In either scenario, the data support the hypothesis that the selective outgrowth of lesions bearing the mutant allele to levels sufficient to detect in ctDNA is dependent on chronic exposure to ARN-509 and is associated with rising PSA. To further establish the association of F876L with progressive disease, we analyzed plasma samples taken at additional timepoints from the 3 patients scored positive during the initial screen (Table 12) In patient 10, the mutation was not detected at the one other timepoint analyzed (Cycle 4; PSA 102% of T0). In Patient 13, the mutation was not detected at Cycle 4 (PSA 16.2% of baseline) or at Cycle 12 (patient was scored positive at Cycle 11). The mutant sequence at Cycle 11 was at the limit of detection and is estimated to arise via amplification of a single mutant molecule. Although PSA of Patient 13 was slowly rising from the treatment nadir at Cycle 11 and 12, at both time points PSA was still >60% below study start, and thus frank resistance had not yet emerged. Identification of the mutant sequence at the limit of detection likely reflects presence of a relatively rare, mutant clone that has potential to expand under continued selective pressure and eventually drive progressive disease.

Given the relatively long duration of treatment of Patient 7, plasma from additional time points during evident PSA reduction; (>90% decline from baseline; Cycle 4, 8 and 10) and at initial PSA rise from its nadir (Cycle 15 and 19) (FIG. 13) was analyzed. Interestingly, mutations were not detected in the 3 samples from treatment cycle 4, 8 and 10 whereas the c2628a mutation was detected in the 2 samples analyzed from initial PSA rise (Cycle 15 and 19). These clinical data are consistent with the preclinical data indicating that the F876L amino acid change is sufficient to convey resistance to ARN-509.

TABLE 11

BEAMing Results from F876L Positive Patients

| Patient | Treatment Cycle* | PSA [Percent of Day 0] | Genotypic Call | Mutant Frequency [mutant/w.t. beads x 100] | | |
|---|---|---|---|---|---|---|
| | | | | c2990a | c2990g | t2988c |
| 7 | 0 | 100 | Wild-type | — | — | — |
| 7 | 4 | 1.4 | Wild-type | — | — | — |
| 7 | 8 | 3.3 | Wild-type | — | — | — |
| 7 | 10 | 5.6 | Wild-type | — | — | — |
| 7 | 15 | 41.2 | Mutant | 0.162 | — | — |
| 7 | 19 | 97.2 | Mutant | 5.005 | — | — |
| 7 | 22 | 281.0 | Mutant | 1.002 | — | — |
| 10 | 0 | 100 | Wild-type | — | — | — |
| 10 | 4 | 102 | Wild-type | — | — | — |
| 10 | 7 | 245 | Mutant | 0.051 | — | 0.12 |
| 13 | 0 | 100 | Wild-type | — | — | — |
| 13 | 4 | 16.2 | Wild-type | — | — | — |
| 13 | 11 | 31.7 | Mutant | 0.065 | — | — |
| 13 | 12 | 39.5 | Wild-type | — | — | — |

*Treatment cycle was 4 weeks; Cycle 0 is pre-treatment timepoint.

TABLE 12

Primary F876L BEAMing of ARN-509-001 Patients

| Patient | 12 week PSA Response | BEAMing Analysis Treatment Cycle* | PSA at Time of BEAMing Analysis [Percent of Baseline] | Baseline Genotypic Call# | During Treatment Genotypic Call |
|---|---|---|---|---|---|
| 1 | 30.49 | 19 | 195.4 | w.t. | w.t. |
| 2 | −61.8 | 10 | 337.08 | w.t. | w.t. |
| 3 | 22.7 | 4 | 122 | w.t. | w.t. |
| 4 | 12.4 | 5 | 134 | w.t. | w.t. |
| 5 | −70.65 | 8 | 16 | w.t. | w.t. |
| 6 | −90.02 | 10 | 84.6 | w.t. | w.t. |
| 7 | −98.6 | 22 | 281 | w.t. | Mutant |
| 8 | −62.2 | 16 | 10.2 | w.t. | w.t. |
| 9 | 26.38 | 7 | 185 | w.t. | w.t. |
| 10 | 2.33 | 7 | 245 | w.t. | Mutant |
| 11 | −49.76 | 8 | 143.88 | w.t. | w.t. |
| 12 | −56.65 | 7 | 99.47 | w.t. | w.t. |
| 13 | −83.79 | 11 | 31.7 | w.t. | Mutant |
| 14 | −43.21 | 11 | 150.5 | w.t. | w.t. |
| 15 | 164.14 | 3 | 220 | w.t. | w.t. |
| 16 | 89.09 | 4 | 189 | w.t. | w.t. |
| 17 | −45.86 | 4 | 54.14 | w.t. | w.t. |
| 18 | −95.65 | 6 | 7.34 | w.t. | w.t. |
| 19 | −71.19 | 11 | 196.86 | w.t. | w.t. |
| 20 | −30.88 | 21 | 89.3 | w.t. | w.t. |
| 21 | −74.43 | 10 | 46.91 | w.t. | w.t. |
| 22 | −82.7 | 25 | 0.19 | w.t. | w.t. |
| 23 | 97.78 | 8 | 222.46 | w.t. | w.t. |
| 24 | −74.86 | 25 | 4.89 | w.t. | w.t. |
| 25 | −30.07 | 12 | 161 | w.t. | w.t. |
| 26 | 96.51 | 5 | 214.85 | w.t. | w.t. |
| 27 | −0.89 | 13 | 20.69 | w.t. | w.t. |
| 28 | −33.59 | 10 | 126 | w.t. | w.t. |
| 29 | −58.44 | 13 | 105 | w.t. | w.t. |

Example 16

Method for Generation of Cell Lines for Drug Screening

To identify compounds that retain AR antagonist activity in the context of the F876L mutation of the androgen receptor, a number of in vitro and in vivo assays as described above are adapted.

In an in vitro setting, a transient transfection transcription assays similar to that described in Example 8 is used to identify compounds that are devoid of agonist activity and fully antagonize both the wild-type as well as F876L mutant AR transcriptional activity. HEPG2 cells or any eukaryotic cell in which AR transcriptional activity can be monitored is employed for this screen.

As an alternative to transient transfection, the transcriptional reporter and F876L AR is stably integrated in a number of cell lines and used for screening compounds. The stable integration of the mutant F876L AR into an androgen sensitive prostate cancer cell line such as LNCaP, LaPC4 or VCaP through the use of plasmid (i.e. pCDNA3.1) or viral based integration allows the screening and evaluation of compounds in transcriptional, proliferation and xenograft setting. Briefly, the F876L AR is cloned into a retroviral expression vector such as pQCXIP (Clontech, Mountain View, Calif.). The resultant plasmid is then used to generate high titer viral stocks for use in the generation of stably transduced cell lines according to the manufacturer's protocol. The resulting cell lines are used in transient transfection transcriptional assays as described in Example 4, endogenous gene transcriptional assays as described in Example 5, proliferation assays as described in Example 3 or xenograft studies as described in Example 1.

Alternatively the cells are further modified by the stable integration of an AR responsive reporter such as Cignal Lenti AR Reporter (Qiagen, Valencia, Calif.) allowing reporter based compound screening without the need for transient transfection.

The examples and embodiments described herein are for illustrative purposes only and various modifications or changes suggested to persons skilled in the art are to be included within the spirit and purview of this application and scope of the appended claims.

What is claimed is:

1. A fusion protein comprising an androgen receptor (AR) polypeptide comprising at least 95% sequence identity to a ligand binding domain having the amino acid sequence of amino acid positions 554 to 919 in SEQ ID NO: 1 and comprising an F876L amino acid substitution in SEQ ID NO: 1, wherein said AR polypeptide is fused to a heterologous polypeptide, a secretion signal sequence, an epitope tag, or an affinity tag.

2. The fusion protein of claim 1, wherein the AR polypeptide has at least 96% sequence identity to the ligand binding domain.

3. The fusion protein of claim 1, wherein the AR polypeptide has at least 97% sequence identity to the ligand binding domain.

4. The fusion protein of claim 1, wherein the AR polypeptide has at least 98% sequence identity to the ligand binding domain.

5. The fusion protein of claim 1, wherein the AR polypeptide comprises the sequence of amino acids set forth in SEQ ID NO: 5.

6. The fusion protein of claim 1, wherein the AR polypeptide further comprises one or more amino acid substitutions in addition to the F876L amino acid substitution.

7. The fusion protein of claim 6, wherein the one or more additional amino acid substitutions is T877A, W741C, W741L, W741R, L701H, or H874Y.

8. The fusion protein of claim 1, wherein the AR polypeptide further comprises at least one of:
   (a) a substitution of the threonine at amino acid position 877 in SEQ ID NO: 1 by leucine, isoleucine, valine, alanine, phenylalanine, glycine, methionine, serine, cysteine, tryptophan, lysine, arginine, histidine, praline, tyrosine, asparagine, glutamine, aspartic acid or glutamic acid;
   (b) a substitution of the tryptophan at amino acid position 741 in SEQ ID NO: 1 by leucine, isoleucine, valine, alanine, phenylalanine, glycine, methionine, serine, threonine, cysteine, lysine, arginine, histidine, praline, tyrosine, asparagine, glutamine, aspartic acid or glutamic acid;
   (c) a substitution of the leucine at amino acid position 701 in SEQ ID NO: 1 by isoleucine, valine, alanine, phenylalanine, glycine, methionine, histidine, serine, threonine, cysteine, lysine, arginine, tryptophan, praline, tyrosine, asparagine, glutamine, aspartic acid, or glutamic acid; and
   (d) a substitution of the histidine at amino acid position 874 in SEQ ID NO: 1 by leucine, isoleucine, valine, alanine, phenylalanine, glycine, methionine, serine, threonine, cysteine, lysine, arginine, tryptophan, praline, tyrosine, asparagine, glutamine, aspartic acid or glutamic acid.

9. The fusion protein of claim 1, wherein the heterologous polypeptide is a heterologous DNA binding domain, a fluorescent protein, or a bioluminescent protein.

10. The fusion protein of claim 9, wherein the heterologous DNA binding domain is selected from the group consisting of GAL4 and LexA.

11. The fusion protein of claim 9, wherein the AR polypeptide is linked to the heterologous DNA binding domain via a peptide linker.

12. The fusion protein of claim 9, wherein the fluorescent protein is selected from the group consisting of green fluorescent protein (GFP), red fluorescent protein (RFP), cyan fluorescent protein (CFP), yellow fluorescence protein (YFP), and blue fluorescent protein (BFP).

13. The fusion protein of claim 1, wherein the epitope tag is selected from the group consisting of c-myc, V-5, hemagglutinin (HA), and FLAG.

14. The fusion protein of claim 1, wherein the affinity tag is selected from the group consisting of biotin, strep-tag, chitin binding protein (CBP), maltose binding protein (MBP), glutathione-S-transferase (GST), and a poly(His) tag.

15. A cDNA molecule encoding an androgen receptor (AR) polypeptide comprising at least 95% sequence identity to a ligand binding domain having the amino acid sequence of amino acid positions 554 to 919 of SEQ ID NO:1 and comprising an F876L amino acid substitution in SEQ ID NO:1.

16. The cDNA molecule of claim 15, wherein the AR polypeptide has at least 96% sequence identity to the ligand binding domain.

17. The cDNA molecule of claim 15, wherein the AR polypeptide has at least 97% sequence identity to the ligand binding domain.

18. The cDNA molecule of claim 15, wherein the AR polypeptide has at least 98% sequence identity to the ligand binding domain.

19. The cDNA molecule of claim 15, wherein the cDNA molecule comprises the nucleotide sequence set forth in SEQ ID NO: 19.

20. A vector, comprising the cDNA molecule of claim 15.

21. The vector of claim 20, wherein the vector is a viral or plasmid vector.

22. The vector of claim 20, wherein the cDNA molecule is operably linked to a promoter.

23. The vector of claim 22, wherein the promoter is a constitutive or an inducible promoter.

24. An isolated host cell, comprising the vector of claim 20.

25. The isolated host cell of claim 24, wherein the isolated host cell is a prokaryotic cell.

26. The isolated host cell of claim 25, wherein the isolated host cell is a bacterial cell.

27. The isolated host cell of claim 24, wherein the isolated host cell is a eukaryotic cell.

28. The isolated host cell of claim 27, wherein the isolated host cell is a mammalian cell, a yeast cell, an insect cell, a plant cell, or an amphibian cell.

29. A microchip comprising the fusion protein of claim 1 or the cDNA molecule of claim 15.

30. A system for detecting a modified AR that is resistant to inhibition with a first- or second-generation AR antagonist in a subject, comprising:
 (a) a sample containing a nucleic acid molecule encoding an AR polypeptide from the subject; and
 (b) a microarray comprising the cDNA molecule of claim 15.

31. The system of claim 30, wherein the microarray is contained on a microchip.

\* \* \* \* \*

UNITED STATES PATENT AND TRADEMARK OFFICE
CERTIFICATE OF CORRECTION

PATENT NO. : 9,617,602 B2  
APPLICATION NO. : 14/417515  
DATED : April 11, 2017  
INVENTOR(S) : James David Joseph et al.

Page 1 of 1

It is certified that error appears in the above-identified patent and that said Letters Patent is hereby corrected as shown below:

On the Title Page

At (56) References Cited, Other Publications, please insert the following publication:
--Joseph et al., "Inhibition of prostate cancer cell growth by second-site androgen receptor antagonists", 2009, PNAS, 106(29), 12178-12183--

Signed and Sealed this
First Day of August, 2017

Joseph Matal
*Performing the Functions and Duties of the*
*Under Secretary of Commerce for Intellectual Property and*
*Director of the United States Patent and Trademark Office*